US 12,162,910 B2

(12) United States Patent
Franchini et al.

(10) Patent No.: US 12,162,910 B2
(45) Date of Patent: Dec. 10, 2024

(54) RECOMBINANT GP120 PROTEIN WITH V1-LOOP DELETION

(71) Applicants: The United States of America, as represented by the Secretary, Department of Health and Human Services, Bethesda, MD (US); New York University, New York, NY (US)

(72) Inventors: Genoveffa Franchini, Washington, DC (US); Timothy Cardozo, New York, NY (US); Manuel Becerra-Flores, Brooklyn, NY (US); Isabela Silva de Castro, Bethesda, MD (US); Giacomo Gorini, Bethesda, MD (US); Massimiliano Bissa, Washington, DC (US)

(73) Assignees: The United States of America, as represented by the Secretary, Department of Health and Human Services, Bethesda, MD (US); New York University, New York, NY (US)

( * ) Notice: Subject to any disclaimer, the term of this patent is extended or adjusted under 35 U.S.C. 154(b) by 555 days.

(21) Appl. No.: 17/285,453

(22) PCT Filed: Oct. 21, 2019

(86) PCT No.: PCT/US2019/057268
§ 371 (c)(1),
(2) Date: Apr. 14, 2021

(87) PCT Pub. No.: WO2020/086483
PCT Pub. Date: Apr. 30, 2020

(65) Prior Publication Data
US 2021/0340188 A1    Nov. 4, 2021

Related U.S. Application Data

(60) Provisional application No. 62/748,905, filed on Oct. 22, 2018.

(51) Int. Cl.
| | | |
|---|---|---|
| *C07K 14/16* | (2006.01) | |
| *A61K 38/00* | (2006.01) | |
| *A61K 39/21* | (2006.01) | |
| *A61P 31/18* | (2006.01) | |
| *C12N 15/86* | (2006.01) | |
| *G01N 33/569* | (2006.01) | |

(52) U.S. Cl.
CPC ............ *C07K 14/162* (2013.01); *A61K 39/21* (2013.01); *A61P 31/18* (2018.01); *C12N 15/86* (2013.01); *G01N 33/56988* (2013.01); *A61K 38/00* (2013.01); *G01N 2333/16* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,602,705 B1 | 8/2003 | Barnett et al. |
| 6,710,173 B1 | 3/2004 | Binley et al. |
| 6,815,201 B2 | 11/2004 | Pinter |
| 7,524,927 B2 | 4/2009 | Hoxie et al. |

FOREIGN PATENT DOCUMENTS

| | | | |
|---|---|---|---|
| EP | 1433851 A2 | 6/2004 | |
| WO | WO-2004053100 A2 * | 6/2004 | ............ C07K 14/005 |

OTHER PUBLICATIONS

Sullivan et al., Journal of Virology, Jun. 1998, 72(6):4694-4703. (Year: 1998).*
Yang et al., Journal of Virology, Jun. 2000, 74(12):5716-5725. (Year: 2000).*
Tighe et al., Eur. J. Immunol., 2000, 30:1939-1947. (Year: 2000).*
Gonelli et al., Viruses, Jun. 2, 2019, 11:507. (Year: 2019).*
Barnett et al., Vaccine, 1997, 15(8):869-873. (Year: 1997).*
Abagyan and Totrov, "Biased probability Monte Carlo conformational searches and electrostatic calculations for peptides and proteins," *J Mol Biol.* 235.3: 983-1002, Jan. 1994.
Aiyegbo et al., "Peptide Targeted by Human Antibodies Associated with HIV Vaccine-Associated Protection Assumes a Dynamic α-Helical Structure," *PLoS One* 12.1: e0170530, Jan. 2017 (14 pages).
Auwerx et al., "Glycan deletions in the HIV-1 gp120 V1/V2 domain compromise viral infectivity, sensitize the mutant virus strains to carbohydrate-binding agents and represent a specific target for therapeutic intervention," *Virology* 382.1: 10-19, Dec. 2008.
Balzarini et al., "Mutational pathways, resistance profile, and side effects of cyanovirin relative to human immunodeficiency virus type 1 strains with N-glycan deletions in their gp120 envelopes," *J Virol.* 80.17: 8411-8421, Sep. 2006.
Basmaciogullari et al., "Identification of Conserved and Variable Structures in the Human Immunodeficiency Virus gp120 Glycoprotein of Importance for CXCR4 Binding," *J Virol.* 76.21: 10791-10800, Nov. 2002.
Bontjer et al., "Optimization of Human Immunodeficiency Virus Type 1 Envelope Glycoproteins with V1/V2 Deleted, Using Virus Evolution," *J Virol.* 83.1: 368-383, Jan. 2009.

(Continued)

*Primary Examiner* — Nicole Kinsey White
(74) *Attorney, Agent, or Firm* — Klarquist Sparkman, LLP

(57) ABSTRACT

Embodiments of recombinant HIV-1 gp120 proteins that contain a V1 deletion are disclosed. Also provided are gp140, gp145, and gp160 proteins containing the V1 deletion, as well as HIV-1 Env ectodomain trimers containing protomers containing the V1 deletion. Nucleic acid molecules encoding these proteins are also provided. In several embodiments, the disclosed recombinant HIV-1 proteins and/or nucleic acid molecules can be used to generate an immune response to HIV-1 in a subject, for example, to treat or prevent an HIV-1 infection in the subject.

19 Claims, 48 Drawing Sheets

Specification includes a Sequence Listing.

(56) References Cited

OTHER PUBLICATIONS

Ching and Stamatatos, "Alterations in the Immunogenic Properties of Soluble Trimeric Human Immunodeficiency Virus Type 1 Envelope Proteins Induced by Deletion or Heterologous Substitutions of the V1 Loop," *J Virol.* 84.19: 9932-9946, Oct. 2010.

Gordon et al., "Antibody to the gp120 V1/V2 loops and CD4+ and CD8+ T cell responses in protection from SIVmac251 vaginal acquisition and persistent viremia," *J Immunol.* 193.12: 6172-6183, Dec. 2014.

Gottardo et al., "Plasma IgG to Linear Epitopes in the V2 and V3 Regions of HIV-1 gp120 Correlate with a Reduced Risk of Infection in the RV144 Vaccine Efficacy Trial," *PLoS One* 8.9: e75665, Sep. 2013 (16 pages).

Gzyl et al., "Effect of Partial and Complete Variable Loop Deletions of the Human Immunodeficiency Virus Type 1 Envelope Glycoprotein on the Breadth of gp160-specific Immune Responses," *Virology* 318.2: 493-506, Jan. 2004.

Haynes et al., "Immune-Correlates Analysis of an HIV-1 Vaccine Efficacy Trial," *N Engl J Med.* 366.14: 1275-1286, Apr. 2012.

Julien et al., "Crystal Structure of a Soluble Cleaved HIV-1 Envelope Trimer," *Science* 342.6165: 1245625, Dec. 2013 (19 pages).

Klionsky et al., "Guidelines for the Use and Interpretation of Assays for Monitoring Autophagy," *Autophagy* 12.1: 1-222, 2016.

Liao et al., "Vaccine Induction of Antibodies Against a Structurally Heterogeneous Site of Immune Pressure within HIV-1 Envelope Protein Variable Regions 1 and 2," *Immunity* 38.1: 176-186, Jan. 2013.

Li et al., "The V1 Region of gp120 is Preferentially Selected during SIV/HIV Transmission and is Indispensable for Envelope Function and Virus Infection." *Virologica Sinica* 31.3: 207-218, Jun. 2016.

McLellan et al., "Structure of HIV-1 gp120 V1/V2 Domain with Broadly Neutralizing Antibody PG9," *Nature* 480.7377: 336-343, Nov. 2011.

Pegu et al., "Antibodies with high avidity to the gp120 envelope protein in protection from simian immunodeficiency virus SIV(mac251) acquisition in an immunization regimen that mimics the RV-144 Thai trial," *J Virol.* 87.3: 1708-1719, Feb. 2013.

Rerks-Ngarm et al., "Vaccination with ALVAC and AIDSVAX to Prevent HIV-1 Infection in Thailand," *N Engl J Med.* 361.23: 2209-2220, Dec. 2009 (w/Supplementary Appendix).

Rolland et al., "Increased HIV-1 Vaccine Efficacy Against Viruses with Genetic Signatures in Env-V2," *Nature* 490.7420: 417-420, Oct. 2012.

Sautto et al., "Anti-Hepatitis C Virus E2 (HCV/E2) Glycoprotein Monoclonal Antibodies and Neutralization Interference," *Antiviral Res.* 96.1: 82-89, Oct. 2012.

Silva de Castro et al., "Anti-V2 antibodies virus vulnerability revealed by envelope V1 deletion in HIV vaccine candidates," *iScience* 24.2: 102047, Jan. 2021 (83 pages).

Vaccari et al., "Adjuvant-dependent innate and adaptive immune signatures of risk of SIVmac251 acquisition," *Nat Med.* 22.7: 762-770, Jul. 2016.

Vaccari et al., "HIV vaccine candidate activation of hypoxia and the inflammasome in CD14 + monocytes is associated with a decreased risk of SIV mac251 acquisition," *Nat Med.* 24.6: 847-856, Jun. 2018.

Verrier et al., "Additive Effects Characterize the Interaction of Antibodies Involved in Neutralization of the Primary Dualtropic Human Immunodeficiency Virus Type 1 Isolate 89.6," *J Virol.* 75.19: 9177-9186, Oct. 2001.

Yuan et al., "HIV-1 envelope glycoprotein variable loops are indispensable for envelope structural integrity and virus entry," *PLoS One* 8.8: e69789, Aug. 2013 (9 pages).

Zolla-Pazner et al., "Vaccine-induced IgG antibodies to V1V2 regions of multiple HIV-1 subtypes correlate with decreased risk of HIV-1 infection," *PLoS One* 9.2: e87572, Feb. 2014 (14 pages).

\* cited by examiner

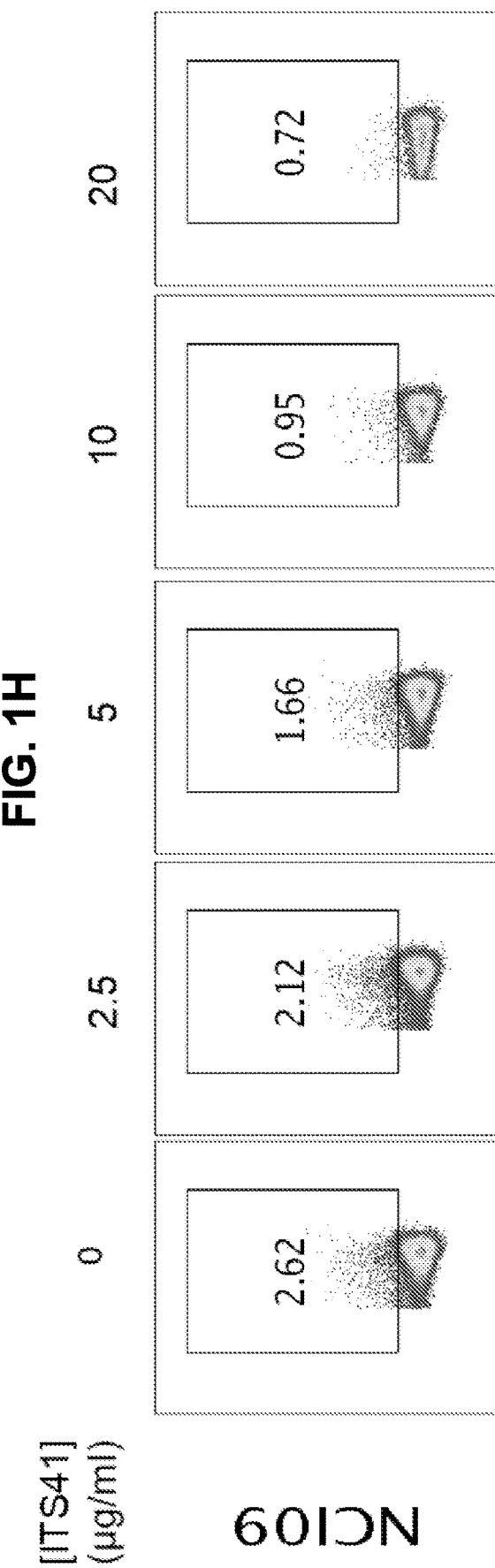

Side view

Top view (zoomed)

gp120 ΔV1 (α-helix)

gp120 ΔV1$_{gpg}$ (β-strand)

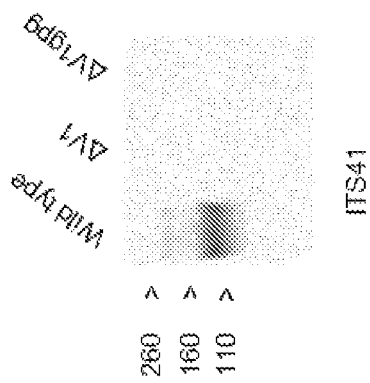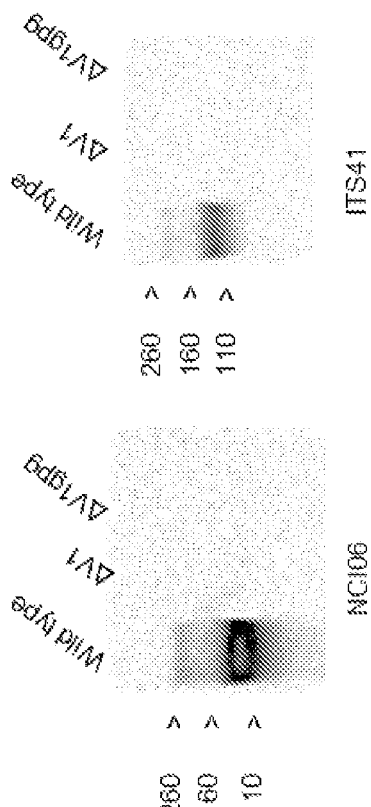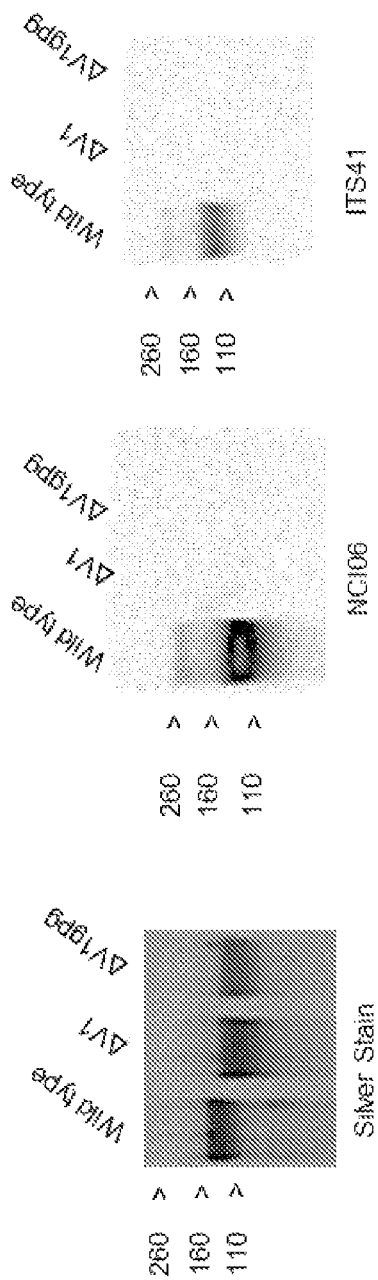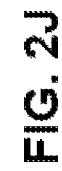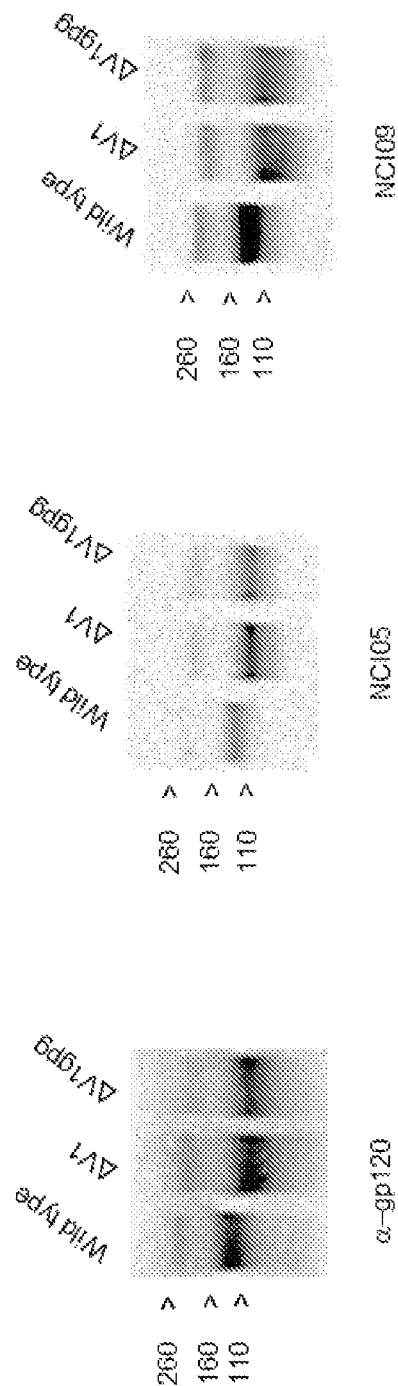

FIG. 2M gp120 ΔV1$_{gpg}$
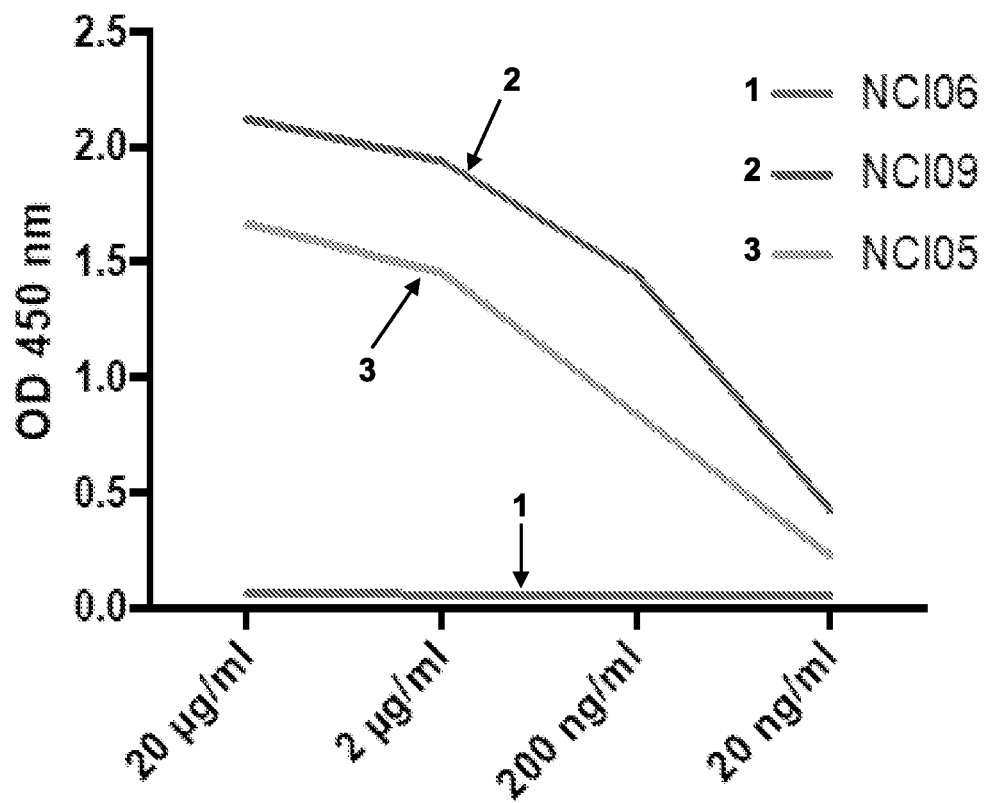
FIG. 2N
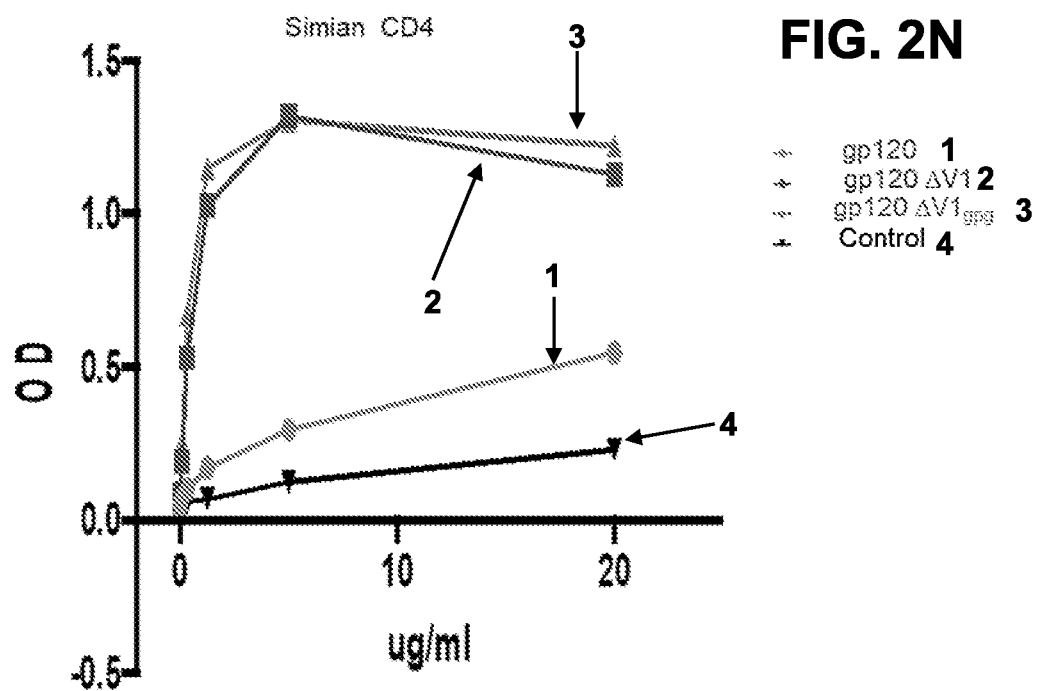

FIG. 3D V1⁻ gpg X Ctr
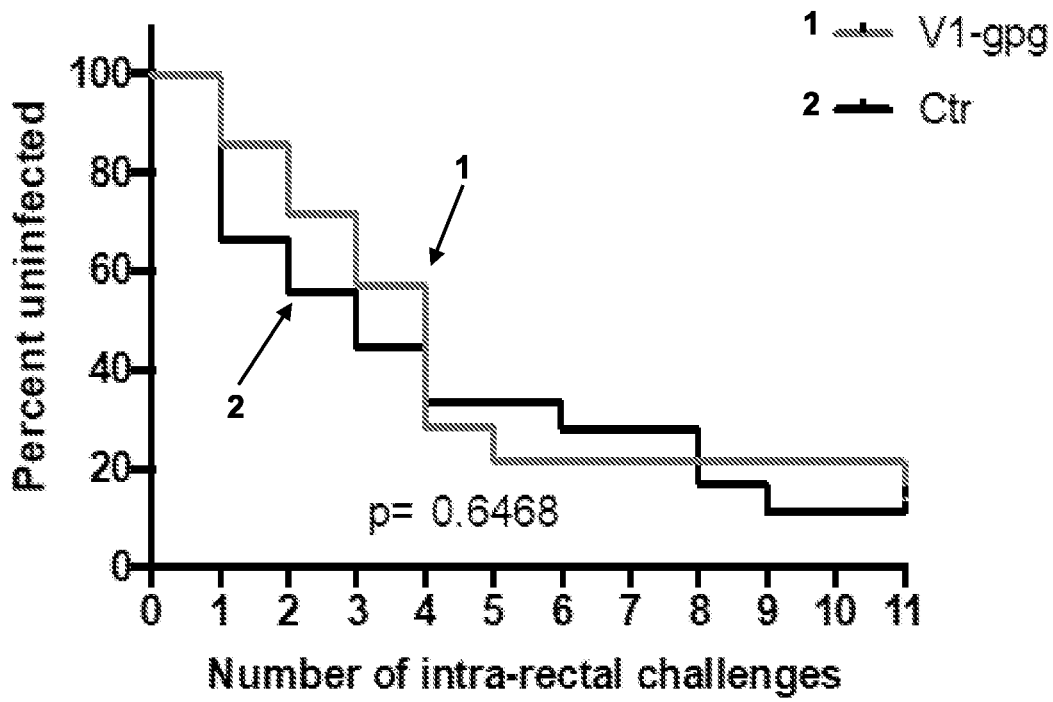
FIG. 3E
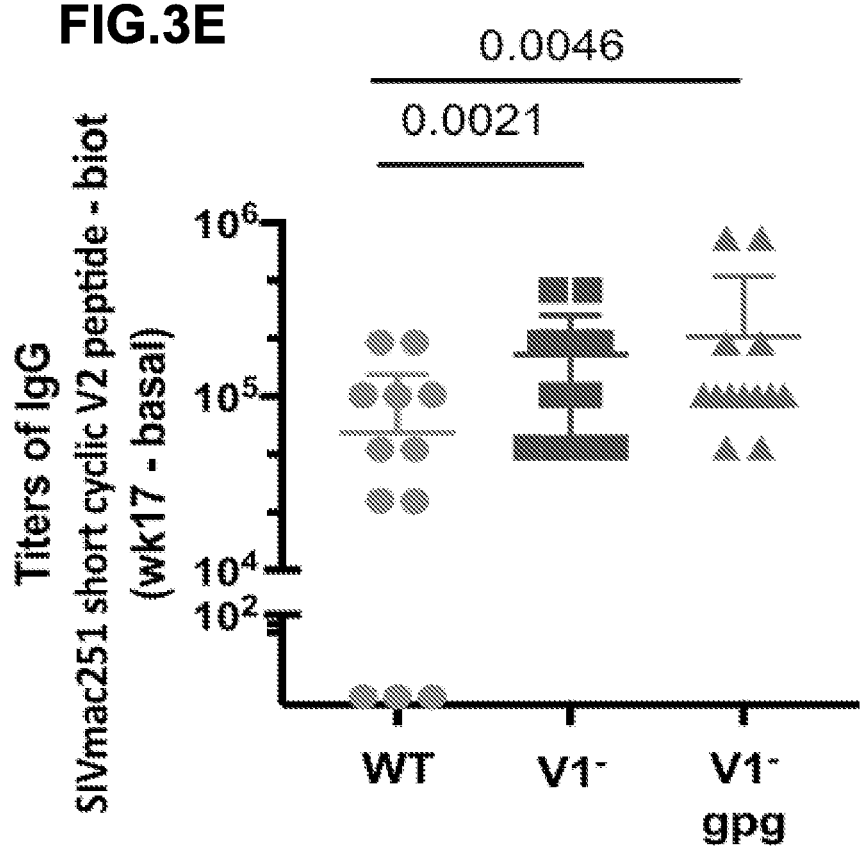

| | | | |
|---|---|---|---|
| DP2α4β7$_{251}$ | | DKTK EYNETWYSTD | SIV$_{mac251}$ |
| DP2α4β7$_{E543}$ | | DKKI EYNETWYSRD | SIV$_{E543}$ |
| NCI09 | KFTMTGLKR | DKTK EYN | |
| NCI05 | R | DKKK EYNETWYSAD | |

NCI05

1 — V2 SIV251
2 — V2 SIV543

| Group | Relative VE | P = |
|---|---|---|
| ALVAC-SIV+ gp120 alum | 44% | 0.025 |
| DNA-SIV + ALVAC-SIV + gp120 alum | 52% | 0.029 |
| ALVAC-SIV+ gp120 MF59 | 9% | ns |
| Ad26 + ALVAC-SIV + gp120 alum | 13% | ns |

FIG. 5A

V2 OVERLAPPING PEPTIDES

```
    N-ter   NETSSCIAQNNCTGLEQEQMISCKFTMTGLKRDKTKEYNETWYSTDLVCEQGNSTDC-OOH
Peptide 25           TGLEQEQMISCKFTMTGLKR
Peptide 26              QMISCKFTMTGLKRDKTKEY
Peptide 27                  FTMTGLKRDKTKEYNETWYS
Peptide 28                       KRDKTKEYNETWYSTDLVCE
Peptide 29                           EYNETWYSTDLVCEQGNSTD
```

FIG. 5B

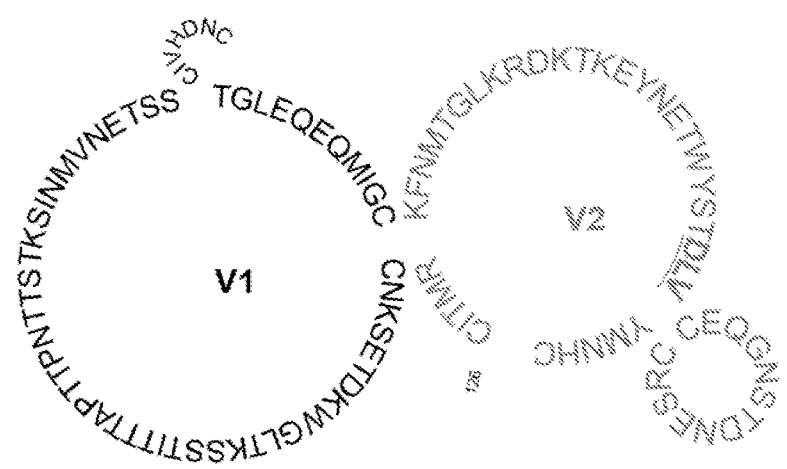

PROTECTIVE VACCINES

NON PROTECTIVE VACCINES

PROTECTIVE VACCINES

NON PROTECTIVE VACCINES

FIG. 5G  PROTECTIVE VACCINES
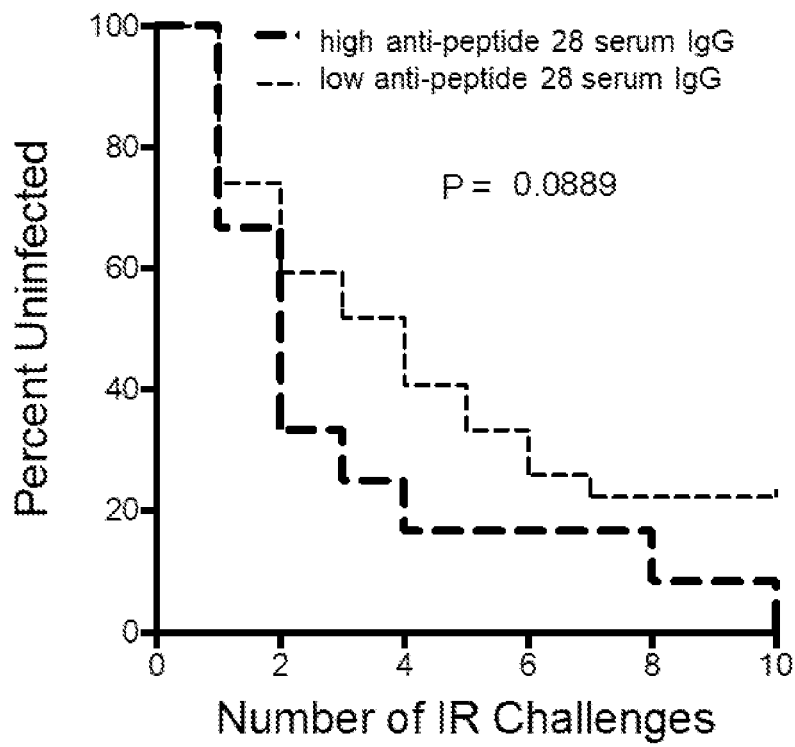
NON PROTECTIVE VACCINES
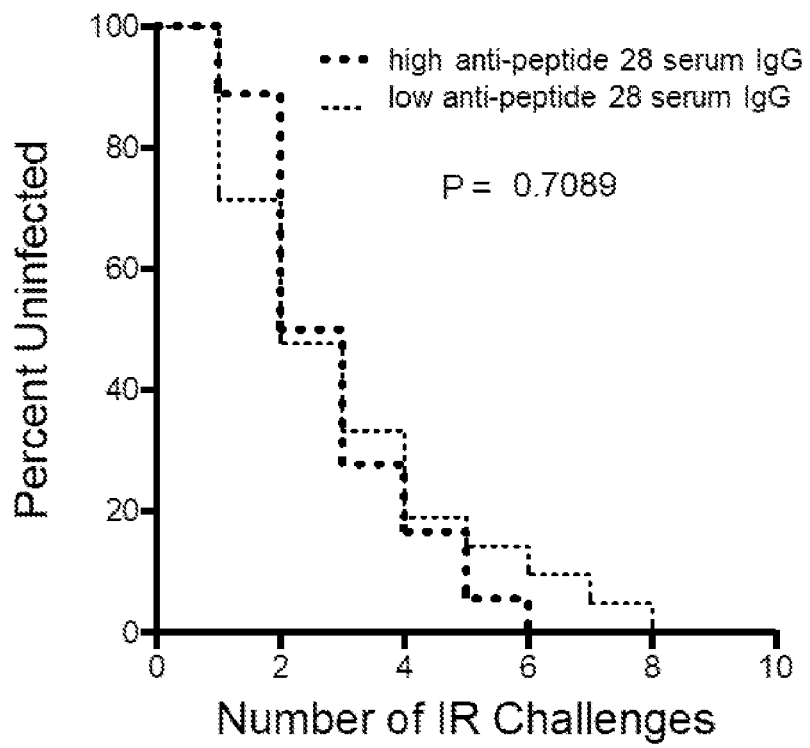

PROTECTIVE VACCINES

NON PROTECTIVE VACCINES

FIG. 6A

V1 OVERLAPPING PEPTIDES

NH₂-NKSETDRWGLTKSSTTITTAAPTSAPVSEKIDMVNETSS-COOH

| Peptide 15 | PCVKLSPLCITMRCNKSETD |
| Peptide 16 | PLCITMRCNKSETDRWGLTK |
| Peptide 17 | RCNKSETDRWGLTKSSTTIT |
| Peptide 18 | TDRWGLTKSSTTITTAAPTS |
| Peptide 19 | TKSSTTITTAAPTSAPVSEK |
| Peptide 20 | ITTAAPTSAPVSEKIDMVNE |
| Peptide 21 | TSAPVSEKIDMVNETSSCIA |
| Peptide 22 | EKIDMVNETSSCIAQNNCTG |
| Peptide 23 | NETSSCIAQNNCTGLEQEQM |
| Peptide 24 | IAQNNCTGLEQEQMISCKFT |

FIG. 6B

V1(peptide 15-24)
Anti-V1 serum
P = 0.4352 peptides 15-24

PROTECTIVE VACCINES

FIG. 8A

Monoclonal Antibody Binding

| | NCI05 | NCI09 | NCI04 | NCI06 | ITS09 | ITS41 |
|---|---|---|---|---|---|---|
| SIVmac251 M766 gp120 | ++ | ++ | ++ | ++ | ++ | ++ |
| SIVsmE660.CR54 gp140 | ++ | ++ | - | ++ | ++ | - |
| SIVsmE543 1J08 V1V2 | ++ | ++ | - | ++ | ND | ND |
| SIVmac251 1J08 V1V2 | ++ | ++ | ++ | ++ | ND | ND |
| SIVmac239 1J08 V1V2 | ++ | ++ | + | ++ | ND | ND |
| SIVsmE543 cV2 | ++ | ++ | - | - | ND | ND |
| SIVmac251 cV2 | ~¶ | ++ | - | - | ND | ND |
| V1 peptide | - | - | PLCITMRCNKSE TDRWGLTK (SEQ ID NO: 54) | RCNKSETDRWGLTK (SEQ ID NO: 20) | ND | ND |
| V2 peptide | - | TGLKRDKTKEY (SEQ ID NO: 53) | - | - | TGLKRDKKKEY (SEQ ID NO: 55) | EQEQMISCKFN MTGL (SEQ ID NO: 56) |

| | |
|---|---|
| ++ | OD450 ≥ 2 |
| + | 1 ≤ OD450 < 2 |
| - | OD450 < 0.5 |

¶ borderline 0.5 ≤ OD450 < 1

SIV$_{mac239}$ Peptides

```
p41--  EQEQMISCKFNMTGL
p42--      MISCKFNMTGLKRDK
p43--          KFNMTGLKRDKKKEY
p44--              TGLKRDKKKEYNETW
p45--                  RDKKKEYNETWYSAD
p46--                      KEYNETWYSADLVCE
p47--                          ETWYSADLVCEQGNN
p48--                              SADLVCEQGNNTGNE
``` cV2 binding inhibition (NCI09)

| | NCI05 | | NCI09 | |
|---|---|---|---|---|
| | KA | KD | KA | KD |
| SIVmac251-M766 gp120 | 1.78E+08 | 5.60E-09 | 8.19E+09 | 1.22E-10 |
| SIVsmE660.CR54 gp140 | 9.60E+10 | 1.04E-11 | N/A | N/A |
| SIVmac251-M766 cV2 | 5.12E+06 | 1.97E-07 | 9.13E+11 | 1.10E-12 |

FIG. 9C

| | ITS41 | | NCI05 | | NCI09 | |
|---|---|---|---|---|---|---|
| | KA | KD | KA | KD | KA | KD |
| SIVmac251-M766 gp120 | 3.90E+04 | 2.57E-05 | 1.78E+08 | 5.60E-09 | 8.19E+09 | 1.22E-10 |
| SIVsmE660.CR54 gp140 | N/A | N/A | 9.60E+10 | 1.04E-11 | N/A | N/A |
| SIVmac251-M766 cV2 | 1.06E+08 | 9.46E-09 | 5.12E+06 | 1.97E-07 | 9.13E+11 | 1.10E-12 |

FIG. 9D

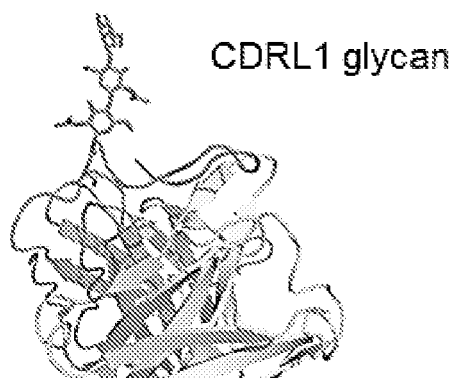
FIG. 10B
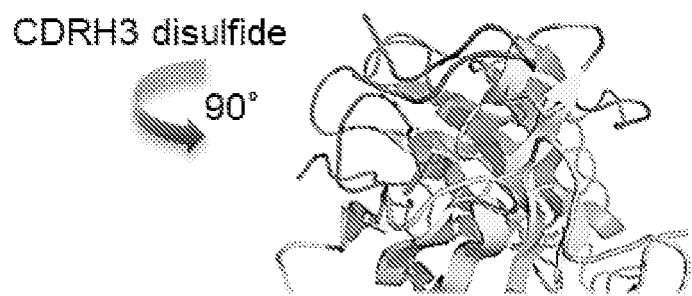
FIG. 10C
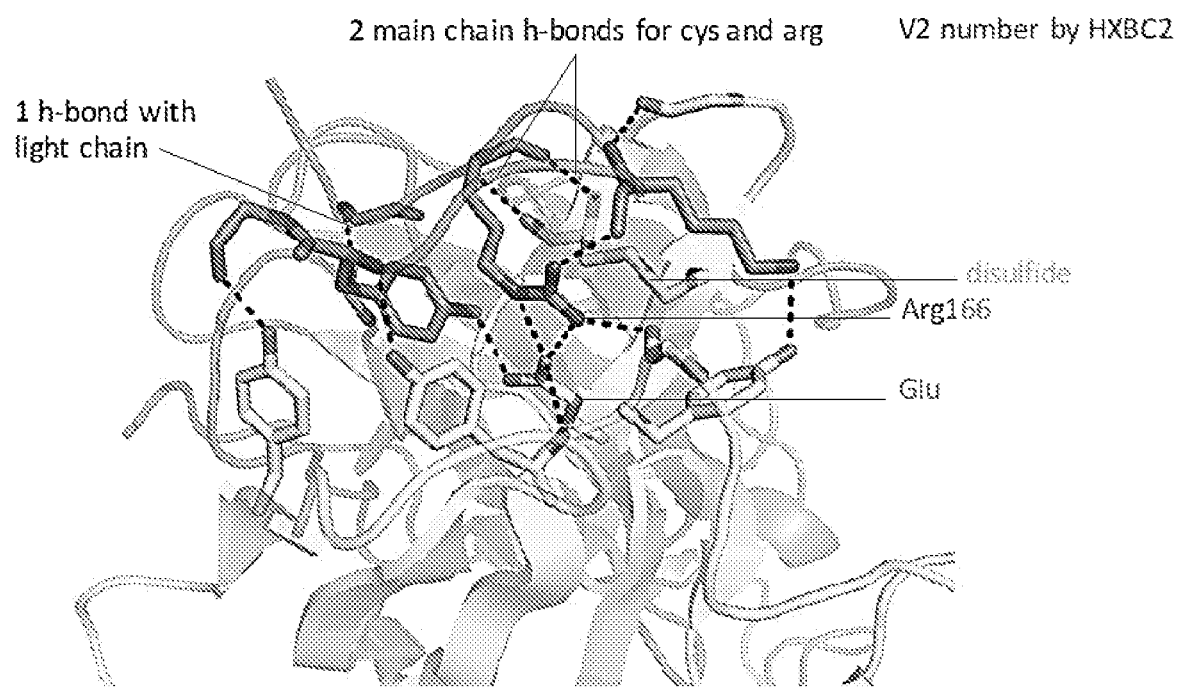

Monoclonal Antibody Neutralization

|  | NCI05 | NCI09 | NCI04 | NCI06 |
|---|---|---|---|---|
| SIVsmE660.CP3C (Tier 1) | 4.449 * | >50† | >50† | >50† |
| SIVsmE660.CR54 (Tier 2) | >50† | >50† | >50† | >50† |
| SIVmac251.H9 (Tier 1) | >50 | 0.412 ** | >50 | 0.024 *** |
| SIVmac251.30 (Tier 2) | >50† | >50† | >50† | >50† |

\* 1 - 9.99 µg/ml
\*\* 0.01 - 0.099 µg/ml
\*\*\* 0.1 - 0.99 µg/ml
† curve plateaued below 50%

Week 17

V2(ΔV1) domain p=0.000004

RECOMBINANT GP120 PROTEIN WITH V1-LOOP DELETION

CROSS REFERENCE TO RELATED APPLICATIONS

This is the U.S. National Stage of International Application No. PCT/US2019/057268, filed on Oct. 21, 2019, which was published in English under PCT Article 21 (2), which in turn claims priority to U.S. Provisional Application No. 62/748,905, filed Oct. 22, 2018. The provisional application is incorporated by reference in its entirety.

STATEMENT REGARDING FEDERALLY SPONSORED RESEARCH AND DEVELOPMENT

This invention was made with Government Support under project number ZIA BC 011126 awarded by the National Institutes of Health, National Cancer Institute. The Government has certain rights in this invention.

FIELD

This disclosure relates to recombinant Human immunodeficiency virus type 1 (HIV-1) gp120 proteins and HIV-1 Envelope (Env) ectodomain trimers including the recombinant gp120 proteins for treatment and inhibition of HIV-1 infection and disease.

BACKGROUND

Millions of people are infected with HIV-1 worldwide, and 2.5 to 3 million new infections have been estimated to occur yearly. Although effective antiretroviral therapies are available, millions succumb to AIDS every year, especially in sub-Saharan Africa, underscoring the need to develop measures to prevent the spread of this disease.

An enveloped virus, HIV-1 hides from humoral recognition behind a wide array of protective mechanisms. The major envelope protein of HIV-1 is a glycoprotein of approximately 160 kD (gp160). During infection, proteases of the host cell cleave gp160 into gp120 and gp41. Gp41 is an integral membrane protein, while gp120 protrudes from the mature virus. Together gp120 and gp41 make up the HIV-1 envelope spike, which is a target for neutralizing antibodies.

It is believed that immunization with an effective immunogen based on HIV-1 Env can elicit a neutralizing response, which may be protective against HIV-1 infection. However, despite extensive effort, a need remains for agents capable of such action.

SUMMARY

This disclosure provides recombinant HIV-1 gp120 proteins that include a novel V1 domain deletion that unmasks epitopes targeted by protective immune responses, and which are shown to elicit a surprisingly effective immune response for viral inhibition in a primate model. The recombinant gp120 proteins and related embodiments, such as HIV-1 Env ectodomain trimers containing the recombinant gp120 proteins, can be used to elicit an immune response in a subject that inhibits HIV-1 infection.

In some embodiments, a recombinant gp120 protein comprising a deletion of HIV-1 Env residues 137-152 according to the HXBc2 numbering system is provided. The recombinant gp120 protein elicits an immune response that inhibits HIV-1 infection in a subject. In some embodiments, the recombinant gp120 protein comprises or consists of HIV-1 Env residues 31-507 containing the deletion of residues 137-152 (HXBc2 numbering). In some embodiments, the recombinant gp120 protein comprises or consists the amino acid sequence set forth as any one of SEQ ID NOs: 1-3, or an amino acid sequence at least 90% identical thereto.

In some embodiments, the recombinant gp120 protein is included in a recombinant gp140 protein, a recombinant gp145 protein, or a recombinant gp160 protein.

In some embodiments, a recombinant HIV-1 Env ectodomain trimer is provided that comprises protomers comprising the recombinant gp120 protein and a gp41 ectodomain. The recombinant HIV-1 Env ectodomain trimer elicits an immune response that inhibits HIV-1 infection in a subject. In some embodiments, the recombinant gp120 protein in the protomer comprises or consists of HIV-1 Env residues 31-507 containing the deletion of residues 137-152 (HXBc2 numbering), and the gp41 ectodomain in the protomer comprises or consists of HIV-1 Env residues 512-664 (HXBc2 numbering). In some embodiments, the protomers of the HIV-1 Env ectodomain trimer comprise or consist of the amino acid sequence set forth as any one of SEQ ID NOs: 4-5 and 66, or an amino acid sequence at least 90% identical thereto.

In some embodiments, a recombinant V1V2 domain of a gp120 protein is provided that comprises a deletion of HIV-1 Env residues 137-152 according to the HXBc2 numbering system. In some embodiments, the recombinant V1V2 domain of the gp120 protein comprises or consists of HIV-1 Env residues 126-196 or 119-205 with the deletion of residues 137-152 (HXBc2 numbering). In some embodiments, the recombinant V1V2 domain comprises or consists of the amino acid sequence set forth as SEQ ID NO: 8 or an amino acid sequence at least 90% identical thereto. In some embodiments, the recombinant V1V2 domain can be fused to a scaffold protein, such as a gp70 protein, a typhoid toxin protein, and an antibody Fc domain Nucleic acid molecules encoding the disclosed recombinant gp120, gp140, gp160, or HIV-1 Env ectodomain trimer, or V1V2 domain are also provided. In some embodiments, the nucleic acid molecule can encode a precursor protein of a gp120-gp41 protomer of a disclosed recombinant HIV-1 Env trimer. Expression vectors (such as an inactivated or attenuated viral vector) including the nucleic acid molecules are also provided.

Immunogenic compositions including one or more of the disclosed recombinant gp120, gp140, gp160, or HIV-1 Env ectodomain trimer or V1V2 domain are also provided. The composition may be contained in a unit dosage form. The composition can further include an adjuvant.

Methods of eliciting an immune response to HIV-1 envelope protein in a subject are disclosed, as are methods of treating, inhibiting or preventing an HIV-1 infection in a subject. In such methods a subject, such as a human subject, is administered an effective amount of a disclosed recombinant gp120, gp140, gp160, or HIV-1 Env ectodomain trimer or V1V2 domain to elicit the immune response. The subject can be, for example, a human subject at risk of or having an HIV-1 infection.

In additional embodiments, a method for prognosis of an immune response to HIV-1 in a subject is provided. The method comprises contacting a biological sample from a subject with one or more peptides comprising or consisting of the amino acid sequence of HIV Env residues 141-154 (V1a), HIV Env residues 157-173 (V2b), or HIV Env residues 166-180 (V2c) according to the HXBc2 numbering system, and detecting specific binding activity of antibodies in the biological sample to the one or more peptides. Detecting specific binding activity of antibodies in the biological sample to the V2b peptide or to the V2c peptide identifies the immune response to HIV-1 in the subject as an immune response that inhibits HIV-1 infection. Detecting specific binding activity of antibodies in the biological sample to the V1a peptide identifies the immune response to HIV-1 in the subject as an immune response that does not inhibit HIV-1 infection.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1K. (FIGS. 1A and 1B) Correlation of SIV DNA level in rectal mucosa obtained 2 weeks after infection in vaccinated macaques with serum recognition (detected by ELISA, optical density) of peptide 27 and 29 respectively. (FIG. 1C) Schematic representation of the V1 and V2 $SIV_{mac251}$ loops. The amino acids shown are not a linear sequence. (FIG. 1D) Serum level (detected by ELISA, optical density) of antibodies against peptide 23 and 24 in animals vaccinated with protective and non-protective vaccines following immunization (week 27). (FIG. 1E) Correlation of antibodies to V1 and time of $SIV_{mac251}$ acquisition. (FIG. 1F-1G) Inhibition of binding to gp120 SIVsmE660/V1/V2 scaffold using combinations of the mAbs NCI09 or NCI05 as probe and as competitors together with ITS101 and ITS41. (FIG. 1H) Competition of increasing amount (0, 2, 5, 5, 10, and 20 µg/ml of ITS41) with binding of NCI09 to $SIV_{mac251}$ infected CD4+ cells. (FIG. 1I) Binding to human α4β7 of native $SIV_{mac251}$ M766 gp120 and of deglycosylated $SIV_{mac251}$ M766 gp120 alone, in presence of non-relevant mAb ELN3 at 2.5 µg/ml or NCI09 at 1.25 µg/ml. (FIG. 1J) ITS41-mediated inhibition of gp120 binding to α4β7 at the concentrations tested in the competition experiment presented in FIG. 1K. (FIG. 1K) NCI09-mediated inhibition of binding of α4β7 to deglycosylated $SIV_{mac251}$ gp120 preincubated with serial dilutions of competitor ITS41 NCI09-mediated 81% inhibitory activity is calculated as a ratio of percent binding of native gp120 to α4β7: percent binding of deglycosylated gp120 to α4β7 in presence of NCI09.

FIGS. 2A-2N. (FIGS. 2A and 2B) Spatial relationship of the V1 and V2 loops. (FIGS. 2E-2J) Western blot of the purified $gp120_{WT}$, $gp120_{\Delta V1}$ and $gp120_{\Delta V1gpg}$ with the α-V1 monoclonal antibodies NCI06 and ITS41, the polyclonal α-gp120 rabbit serum and the α-V2 mAbs NCI05 and NCI09. ELISA binding of the α-V2 mAbs MCI05 and NCI09 and the α-V1 mAb NCI06 to (FIG. 22) $gp120_{WT}$. (FIG. 2I) the $gp120_{\Delta V1}$ and (FIG. 2M) the $gp120_{\Delta V1gpg}$. (FIG. 2N) Binding of simian soluble CD4 to the $gp120_{WT}$, the $gp120_{\Delta V1}$, the $gp120_{\Delta V1gpg}$ and the recombinant protein IGF-1 as control.

(FIG. 3A) Schematic representation of the study design. Each vaccinated group included 14 young male macaques and the control group consisted of 18 naïve young male macaques. All animals were exposed beginning at week 17 to weekly low doses of $SIV_{mac251}$ by the intrarectal route. Risk of $SIV_{mac251}$ acquisition in animals immunized with WT (FIG. 3B), ΔV1 (FIG. 3C), or ΔV1gpg (FIG. 3D) envelope immunogens.

FIGS. 4A and 4B. (FIG. 4A) Vaccine efficacy in the 78 animals cohort. Acquisition curves in animal vaccinated with ALVAC-SIV/gp120/alum (27 animals), ALVAC-SIV/gp120/MF9 (27 animals), DNA/ALVAC-SIV/gp120/alum (12 animals) and Ad26 ALVAC-SIV/gp120/alum (12 animals) compared to controls (53 animals). (FIG. 4B) Average per exposure risk of $SIV_{mac251}$ acquisition (VE).

FIGS. 5A-5H. (FIG. 5A) V2 overlapping peptides encompassing the sequence of $SIV_{mac251\ K6W}$. A portion of the V2 sequence (NETSSCIAQNNCTGLEQEQMIS-CKFTMTGLKRDKTKEYNETWYSTDLVCEQGNSTD, SEQ ID NO: 36) is shown, as are Peptides 25 (SEQ ID NO: 37), Peptide 26 (SEQ ID NO: 38), Peptide 27 (SEQ ID NO: 39), Peptide 28 (SEQ ID NO: 40), and Peptide 29 (SEQ ID NO: 41). (FIG. 5B) Simplified schematic representation of the V1 (black) and V2 (red) loops. The amino acids shown are not a linear sequence. (FIG. 5C) Average serum antibody levels at week 27 to peptide 25-29 in vaccines. (FIG. 5D-5H) Correlation between serum response at week 27 to each peptide and virus acquisition in vaccines.

FIGS. 6A-6D. (FIG. 6A) V2 overlapping peptides encompassing the sequence of $SIV_{mac251\ K6W}$. A portion of the V1 sequence (NKSETDRWGLTKSSTTITTAAPT-SAPVSEKIDMVNETSS, SEQ ID NO: 42) is shown, as are Peptide 15 (SEQ ID NO: 43), Peptide 16 (SEQ ID NO: 44), Peptide 17 (SEQ ID NO: 45), Peptide 18 (SEQ ID NO: 46), Peptide 19 (SEQ ID NO: 47), Peptide 20 (SEQ ID NO: 48), Peptide 21 (SEQ ID NO: 49), Peptide 22 (SEQ ID NO: 50), Peptide 23 (SEQ ID NO: 51), and Peptide 24 (SEQ ID NO: 52). (FIG. 6B) Simplified schematic representation of the V1 (black) and V2 (red) loops. The amino acids shown are not a linear sequence. (FIG. 6C) Average serum antibody levels at week 27 to peptide 15-24 in animal vaccinated with protective or non-protective vaccine. (FIG. 6D) No difference in the correlation with $SIV_{mac251}$ acquisition with high or low (above or below average) serum response (week 27) to V1 peptides in animal immunized with protective vaccine.

(FIG. 7A) Serum antibody level to SIV gp120 in animals immunized and challenged protected against the first $SIV_{mac251}$ challenge exposure (week 28) and subsequently immunized 9 times with ALVAC-SIV/gp120/alum. The titers of antibodies thereafter remain stable at $10^4$ 1 up to 4 years. (FIG. 7B) Vaccine efficacy following the second exposure to $SIV_{mac251}$. Animal 770 remained uninfected. (FIG. 7C) Staining strategy on PBMCs to identify B cells from animal P770 positive for either or both the 1J08 $SIV_{smE543}$ and the $SIV_{smE543}$ V1V2 scaffolds. (FIG. 7D)

Retrospective color identification of B-cells that produced the mAbs NCI04, NCI06, NCI05 and NCI09 isolated by cloning in animal 770.

Figure 8B:
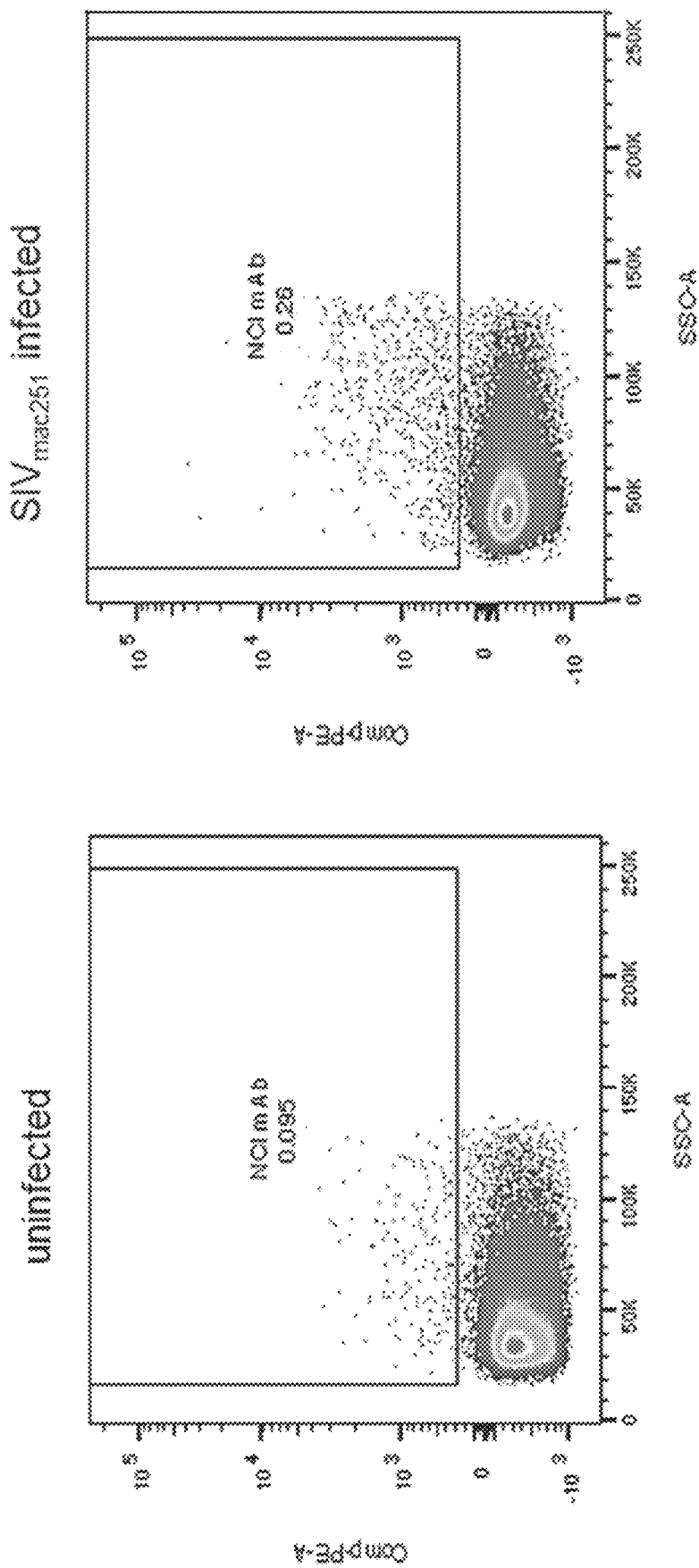
Figures 8C, 8D:
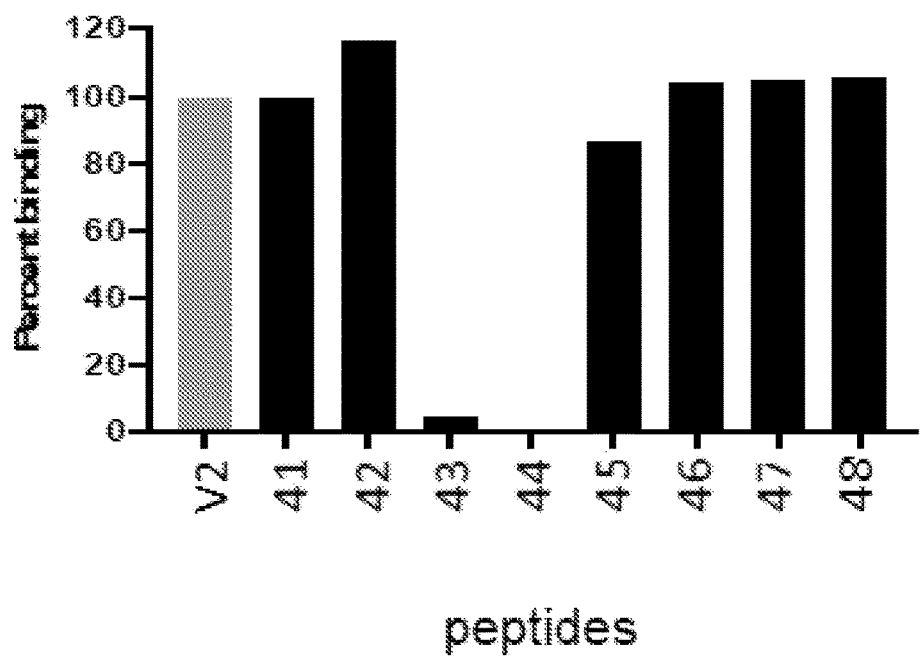

FIGS. 8A-8D. (FIG. 8A) Summary of binding in ELISA of monoclonal antibodies NCI04, NCI06, NCI05, and NCI09. SEQ ID NOs: 20, 53, 54, 55, and 56 are shown in the table. (FIG. 8B) NCI09 binding to $SIV_{mac251}$ infected CD4+ cells. (FIG. 8C) Overlapping peptides used to compete NCI09 binding to cyclic V2 in (FIG. 8D). In FIG. 8C, the sequences of Peptide p41 (SEQ ID NO: 57), Peptide p42 (SEQ ID NO: 58), Peptide p43 (SEQ ID NO: 59), Peptide p44 (SEQ ID NO: 60), Peptide p45 (SEQ ID NO: 61), Peptide p46 (SEQ ID NO: 62), Peptide p47 (SEQ ID NO: 63), and Peptide p48 (SEQ ID NO: 64) are shown.

FIGS. 9A-9E. (FIG. 9A) NCI05 binding to $SIV_{mac251}$ infected CD4-cells. (FIGS. 9B-9D) $K_A$ and $K_D$ of NCI05 and NCI09 binding to $SIV_{mac251}$ cyclic V2. (FIG. 9E) Competition of NCI05 binding with the overlapping peptide depicted in FIG. 8C.

Figure 10A:
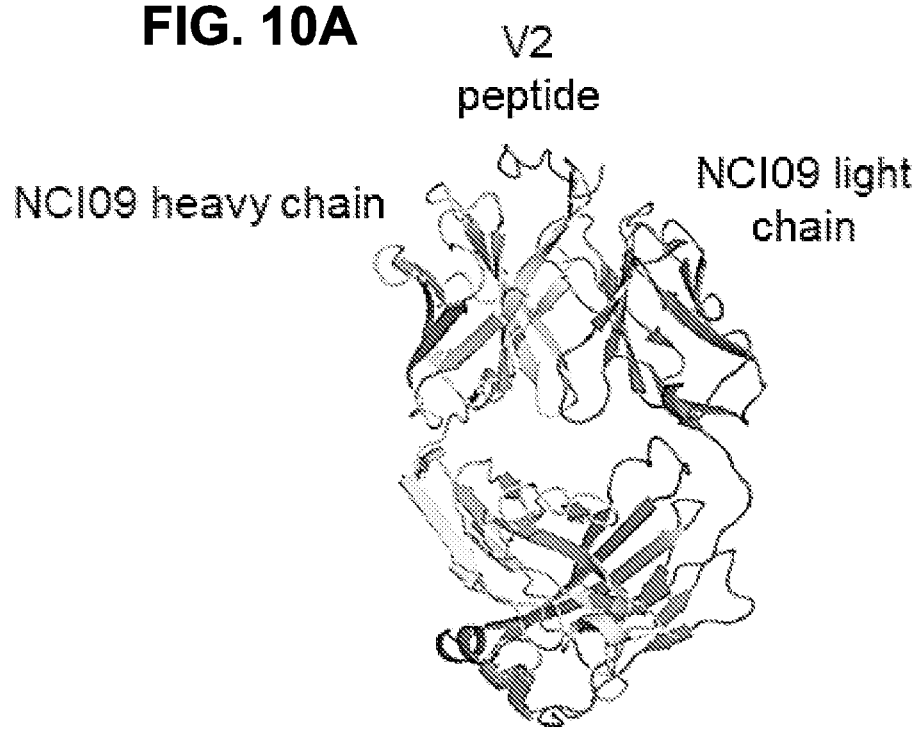

FIG. 10A-10C. (FIGS. 10A and 10B) Overall structure of NCI09 in complex with a $SIV_{mac251}$ linear peptide. The peptide sequence (KFTMTGLKRDKTKEYN, SEQ ID NO: 18) is that of consensus $SIV_{mac251}$, in complex with Fab of antibody NCI09. The N-terminal 4 residues were not ordered in the structure. The NCI09 heavy and light chains are displayed as yellow and blue ribbons, respectively. (FIG. 10C) Side chains in peptide making most of the contact with NCI09 are shown in red space filling spheres with sizes proportional to the area of contact with NCI09: these key contacts, and therefore the NCI09-targeted epitope may be precisely represented by the sequence motif RxKxxEY (SEQ ID NO: 68).

FIGS. 11A-11D (FIG. 11A) α-V1 and α-V2 monloclonal antibodies neutralizing activity against Tier 1 and Tier 2 $SIV_{mac251}$ and SIVsmE660 pseudoviruses. >50: no neutralization. (FIG. 11B) Dose dependent inhibition of α4β7 binding of mildly deglycosylated $SIV_{M766}$ (adhesion assay) by NCI09. (FIG. 11C) Inhibition of α4β7 binding of mildly deglycosylated $SIV_{M766}$ (adhesion assay) by sera of immunized (p770, p842, p888, p897) or naïve animals (MAE, MGM, MT3). The mAb 2B4 serves as positive control. (FIG. 11D) Titration of the inhibitory α4β7 binding activity of the sera from two of the immunized macaques presented in FIGS. 4 and S4a.

FIGS. 12A-12D. (FIG. 12A) ELISA profiles of anti-V1 ITS41probe competed by NCI09, ITS41, ITS01, and BSA. (FIG. 12B) ELISA profiles of anti-V1 ITS41probe competed by NCI05, ITS41, ITS01, and BSA. (FIG. 12C) ELISA profiles of anti-V1 NCI06 probe competed by NCI09, ITS01, NCI06, and BSA. (FIG. 12D) ELISA profiles of anti-V2 NCI09 probe competed by NCI06, NCI09, ITS01 and BSA.

Figure 13A:
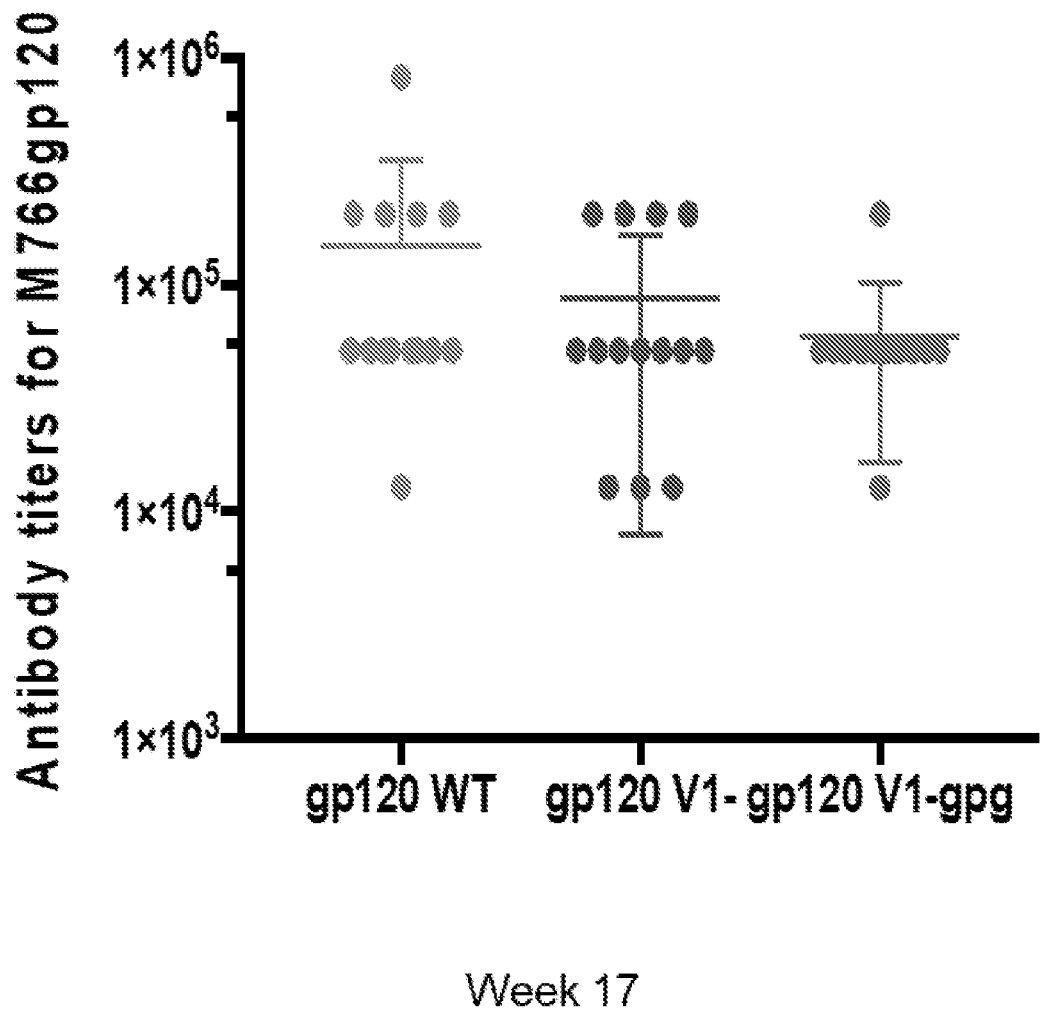
Figure 13B:
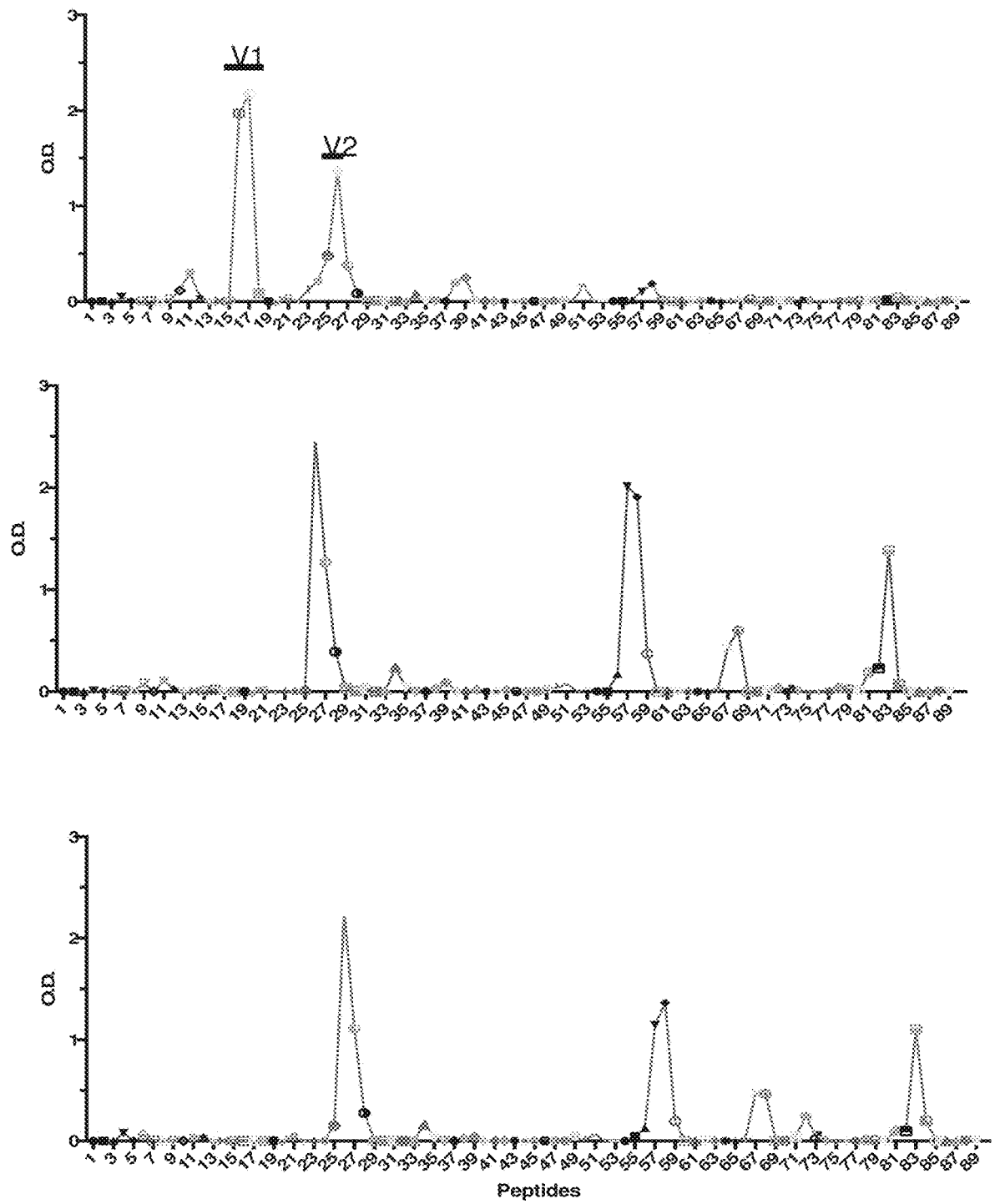

FIGS. 13A-13B. (FIG. 13A) ELISA titers of serum antibodies against $SIV_{mac251766}$ five weeks post immunizations. (FIG. 13B) ELISA peptide array on the entire gp120 with sera collected five weeks post immunization.

Figure 14A:
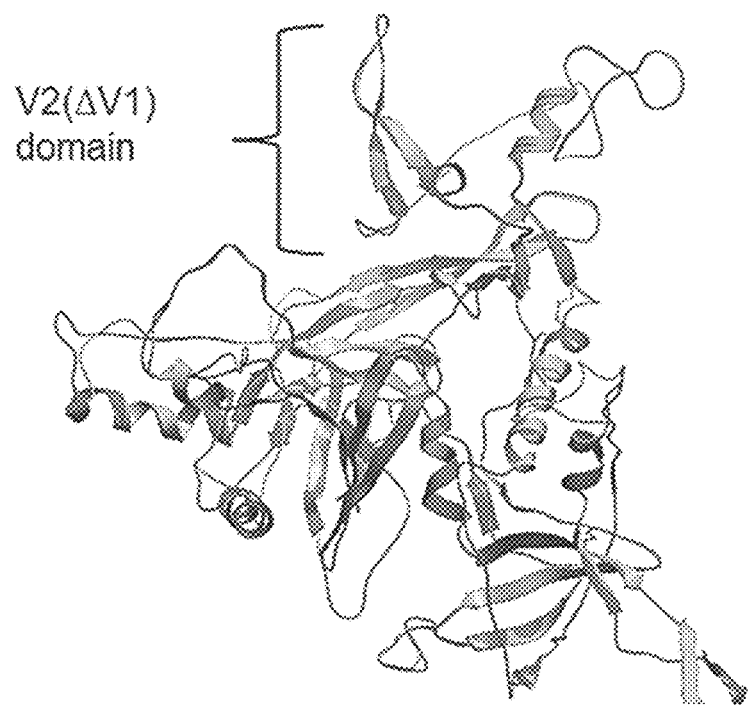
Figure 14B:
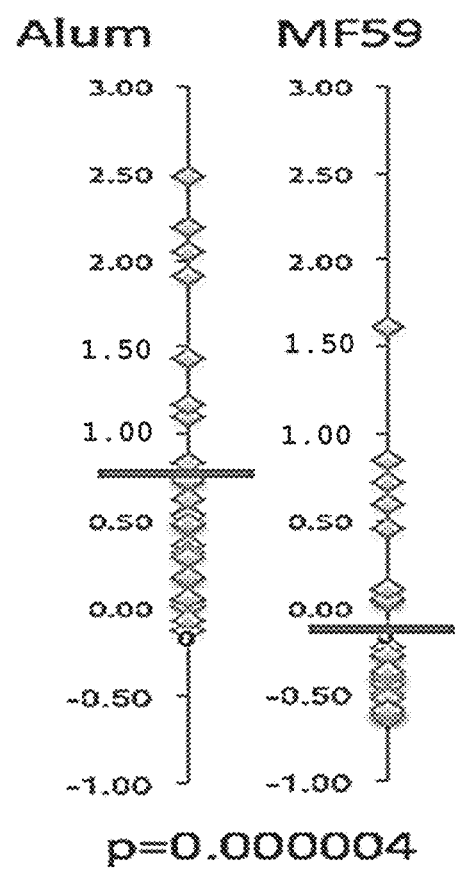

FIGS. 14A and 14B. (FIG. 14A) Ribbon diagram showing a superimposed models of the SIVmac251 gp120 with the 137-152 ΔV1 deletion (red) and HIV-1 A244 gp120 with the 137-152 ΔV1 deletion (green) that illustrates the identical conformation of each mutated gp120. The structure shown is gp120 of the HIV-1 Env trimer in the prefusion mature closed conformation. (FIG. 14B) Binding values (OD) of macaque serum from macaque sera from an animal vaccinated with a protective vaccine compared to A244 HIV V2b probe.

Figure 15:
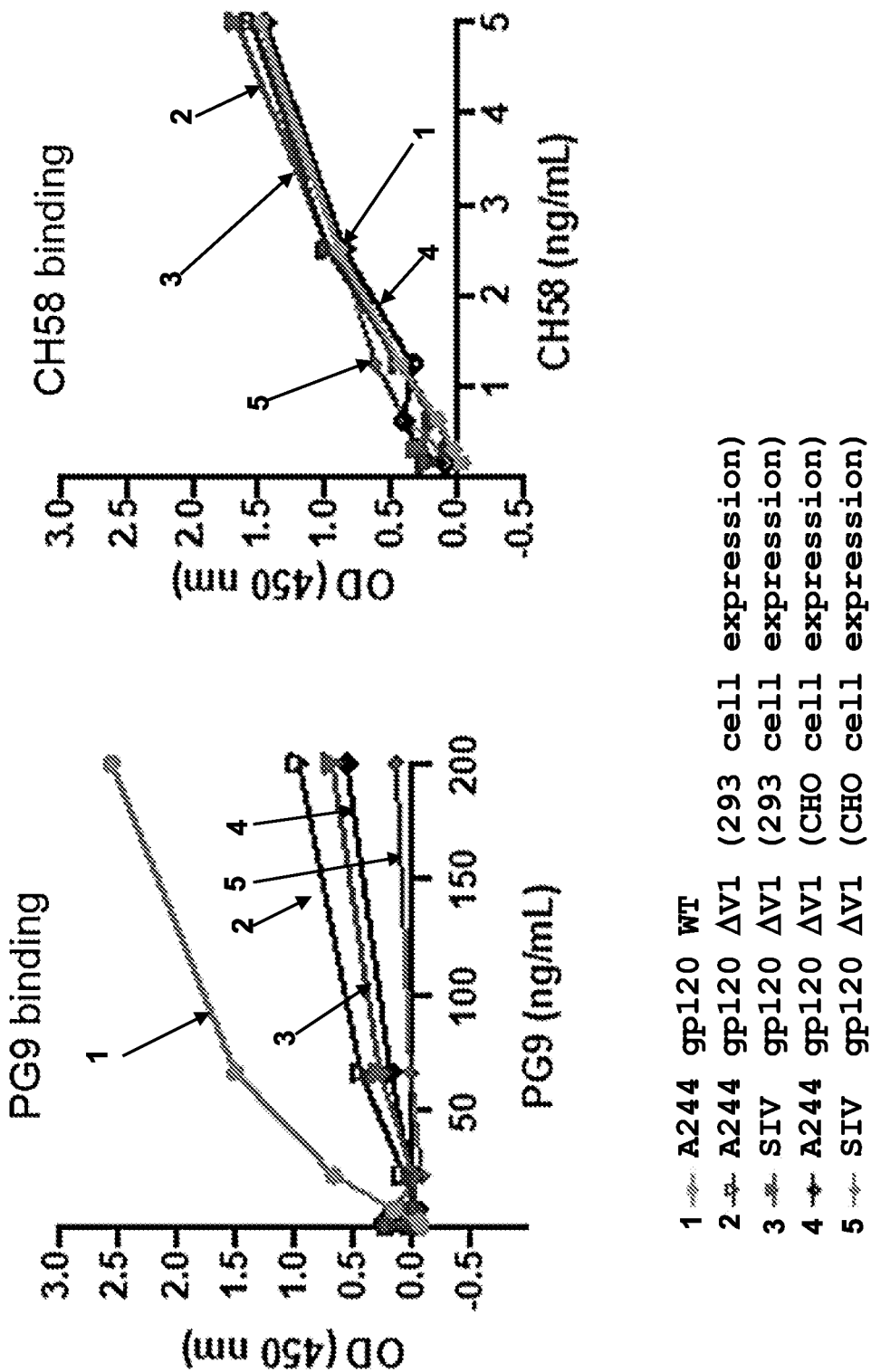

FIG. 15. ELISA binding of the V1/V2 specific antibody PG9 and the V2 specific antibody CH58 to gp120 from HIV-1 strain A244 with (ΔV1) and without (WT) deletion of V1 residues 137-152 (HXBc2 numbering), or SIV gp120 with the corresponding V1 deletion. The sequence of the A244 gp120 ΔV1 is provided as SEQ ID NO: 1. The gp120 proteins were produced in 293 cells or CHO cells.

SEQUENCES

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~84 kb), which was created on Apr. 7, 2021 which is incorporated by reference herein.

DETAILED DESCRIPTION

A major obstacle to the development of a protective HIV-1 vaccine is the antigenic variation of the viral envelope protein, which varies epitopes that could be targeted by the human or other host immune system from strain to strain and also conceals conserved epitopes via glycosylation and conformational masking. This remarkable variation and plasticity of the viral envelope spike underlies the belated and inconsistent appearance of protective and/or broadly neutralizing antibodies in HIV-infected individuals, as well as the failure of experimental vaccines to elicit such antibodies.

Variable region 1 and Variable Region 2 (V1/V2) of the gp120 component of the viral spike are believed to both harbor key epitopes that could be targeted by the host immune system to reduce the risk of viral acquisition and contribute greatly to the antigenic variation and conformational masking that facilitates evasion of host antibody responses, including but not limited to neutralizing antibody responses. Localized to a membrane-distal, apical "cap," which holds the spike in a neutralization-resistant conformation, V1/V2 is not essential for host cell entry, but removal in its entirety renders the virus sensitive to antibody-mediated neutralization. The ~50-90 residues that comprise V1/V2 contain two of the most sequence-variable portions of the virus, and one in ten residues of V1/V2 are N-glycosylated. Despite the diversity and glycosylation of V1/V2, a number of broadly neutralizing and non-neutralizing, cross-reactive human antibodies have been identified that target this region. As discussed in the examples, the majority of these antibodies share specificity for the V2 portion of the V1V2 domain. However, despite extensive effort, immunogens embodying intact V1V2 have proven ineffective at eliciting a V2-based immune response that is protective against HIV-1 infection.

In the current disclosure, the V1 was assessed as responsible for conformational masking of the key epitopes in V2 targeted by the host immune system to reduce the risk of viral acquisition. Structure-guided design was used to identify deletions of V1 residues that exposes V2 epitopes. Surprisingly, immunogens containing a particular V1 deletion (HXBc2 residues 137-152) elicited higher responses to V2 (suggesting that V2 is masked in the presence of V1) than the corresponding wild type immunogen (V1 replete) or immunogens with deletion of different V1 residues. In addition, the V1-deleted immunogen (HXBc2 residues 137-152) exhibited increased binding to soluble CD4 and V2 antibodies relative to the corresponding wild-type control and other V1-deleted immunogens, suggesting that these areas are more exposed in the V1-deleted immunogens. Even more surprisingly, the V1-deletion yielded an immunogen that elicits a protective immune response in animal models. These results are particularly unexpected in view of prior observations that V1-deleted HIV-1 immunogens fail to elicit a V2-directed antibody response.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particularly suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A component of an immunogenic composition used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJUPLEX™ adjuvant available from Advanced BioAdjuvants, LLC, see also Wegmann, Clin Vaccine Immunol, 22 (9): 1004-1012, 2015). Additional adjuvants for use in the disclosed immunogenic compositions include the QS21 purified plant extract, Matrix M, AS01, MF59, and ALFQ adjuvants. Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, β7-1, β7-2, OX-40L, 4-1BBL and toll-like receptor (TLR) agonists, such as TLR-9 agonists. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed immunogens.

Administration: The introduction of a composition into a subject by a chosen route. Administration can be local or systemic. For example, if the chosen route is intravenous, the composition (such as a composition including a disclosed immunogen) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid. In some examples, an amino acid in a polypeptide is substituted with an amino acid from a homologous polypeptide, for example, an amino acid in a recombinant Clade A HIV-1 Env polypeptide can be substituted with the corresponding amino acid from a Clade B HIV-1 Env polypeptide.

Antibody: An immunoglobulin, antigen-binding fragment, or derivative thereof, that specifically binds and recognizes an analyte (antigen), such as HIV-1 Env. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, F (ab') 2; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010). Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The framework region of an antibody, that is the combined framework regions of the constituent light and heavy chains, serves to position and align the CDRs in three-dimensional space. The CDRs are primarily responsible for binding to an epitope of an antigen.

Biological sample: A sample of biological material obtained from a subject. Biological samples include all clinical samples useful for detection of disease or infection (e.g., HIV infection) in subjects. Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, cerebrospinal fluid (CSF), etc.), tissue biopsies or autopsies, fine-needle aspirates, and/or tissue sections. In a particular example, a biological sample is obtained from a subject having, suspected of having or at risk of having HIV infection.

Carrier: An immunogenic molecule to which an antigen (such as gp120) can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Conservative variants: "Conservative" amino acid substitutions are those substitutions that do not substantially affect or decrease a function of a protein, such as the ability of the protein to elicit an immune response when administered to a subject. The term conservative variation also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:
1) Alanine (A), Serine(S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the recombinant Env protein, such as the ability to elicit an immune response when administered to a subject. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form. Contacting includes contact between one molecule and another molecule, for example the amino acid on the surface of one polypeptide, such as an antigen, that contact another polypeptide, such as an antibody. Contacting also includes administration, such as administration of a disclosed antigen to a subject by a chosen route.

Control: A reference standard. In some embodiments, the control is a negative control sample obtained from a healthy patient. In other embodiments, the control is a positive control sample obtained from a patient diagnosed with HIV-1 infection. In still other embodiments, the control is a historical control or standard reference value or range of values (such as a previously tested control sample, such as a group of HIV-1 patients with known prognosis or outcome, or group of samples that represent baseline or normal values).

A difference between a test sample and a control can be an increase or conversely a decrease. The difference can be a qualitative difference or a quantitative difference, for example, a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a polypeptide (such as a disclosed immunogen) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detectable marker: A detectable molecule (also known as a label) that is conjugated directly or indirectly to a second molecule, such as a V1a, V2b, or V2c peptide as disclosed herein, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, fluorescent proteins, chemiluminescent agents, enzymatic linkages, radioactive isotopes and heavy metals or compounds (for example super paramagnetic iron oxide nanocrystals for detection by MRI). In some embodiments, the detectable marker a radiolabeled amino acid incorporated into the peptide, or attachment of the peptide to biotinyl moieties that can be detected by marked avidin (for example, streptavidin containing a fluorescent marker or enzymatic activity that can be detected by optical or colorimetric methods). Any suitable method of labeling peptides and may be used. Examples of labels for peptides include, but are not limited to: radioisotopes or radionuclides (such as 35S or 131I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, 4th ed, Cold Spring Harbor, New York, 2012) and Ausubel et al. (In Current Protocols in Molecular Biology, John Wiley & Sons, New York, 2013).

Detecting: To identify the existence, presence, or fact of something. General methods of detecting are known to the skilled artisan and may be supplemented with the protocols and reagents disclosed herein. Detection can include a physical readout, such as fluorescence or a reaction output, or the results of a PCR assay.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Effective amount: An amount of agent, such as an immunogen, that is sufficient to elicit a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to inhibit or reduce or prevent HIV-1 infection. The HIV-1 infection does not need to be completely eliminated or reduced or prevented for the method to be effective. For example, administration of an effective amount of the agent can decrease the HIV-1 infection (for example, as measured by infection of cells, or by number or percentage of subjects infected by HIV-1) by a desired amount, for example by at least 50%, at least 60%, at least 70%, at least 80%, at least 90%, at least 95%, at least 98%, or even at least 100% (elimination or prevention of detectable HIV-1 infection), as compared to a suitable control.

Epitope-Scaffold Protein: A chimeric protein that includes an epitope sequence fused to a heterologous "acceptor" scaffold protein. Design of the epitope-scaffold is performed, for example, computationally in a manner that preserves the native structure and conformation of the epitope when it is fused onto the heterologous scaffold protein. Several embodiments include an epitope scaffold protein with a recombinant V1V2 domain included on a heterologous scaffold protein. When linked to the heterologous scaffold, the recombinant V1V2 domain a conformation similar to that of the recombinant V1V2 domain in the context of the HIV-1 Env ectodomain trimer.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Non-limiting examples of expression vectors include cosmids, plasmids (e.g., naked or contained in liposomes) and viruses (e.g., lentiviruses, retroviruses, adenoviruses, and adeno-associated viruses) that incorporate the recombinant polynucleotide.

Heterologous: A heterologous polypeptide or polynucleotide refers to a polypeptide or polynucleotide derived from a different source or species.

Human Immunodeficiency Virus Type 1 (HIV-1): A retrovirus that causes immunosuppression in humans (HIV-1 disease), and leads to a disease complex known as the acquired immunodeficiency syndrome (AIDS). "HIV-1 disease" refers to a well-recognized constellation of signs and symptoms (including the development of opportunistic infections) in persons who are infected by an HIV-1 virus, as determined by antibody or western blot studies. Laboratory findings associated with this disease include a progressive decline in T cells. Related viruses that are used as animal models include simian immunodeficiency virus (SIV), and feline immunodeficiency virus (FIV). Treatment of HIV-1 with HAART has been effective in reducing the viral burden and ameliorating the effects of HIV-1 infection in infected individuals.

HIV-1 broadly neutralizing antibody: An antibody that reduces the infectious titer of HIV-1 by binding to HIV-1 Envelope protein and inhibiting HIV-1 function. In some embodiments, broadly neutralizing antibodies to HIV are distinct from other antibodies to HIV in that they neutralize a high percentage (such as at least 50% or at least 80%) of the many types of HIV in circulation. Non-limiting examples of HIV-1 broadly neutralizing antibodies include PG9 and VRC01.

HIV-1 envelope protein (Env): The HIV-1 Env protein is initially synthesized as a precursor protein of 845-870 amino acids in size. Individual precursor polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp120-gp41 protomers within the homotrimer. The ectodomain (that is, the extracellular portion) of the HIV-1 Env trimer undergoes several structural rearrangements from a prefusion closed conformation that evades antibody recognition, through intermediate conformations that bind to receptors CD4 and co-receptor (either CCR5 or CXCR4), to a postfusion conformation. The HIV-1 Env ectodomain comprises the gp120 protein (approximately HIV-1 Env positions 31-511) and the gp41 ectodomain (approximately HIV-1 Env positions 512-664). An HIV-1 Env ectodomain trimer comprises a protein complex of three HIV-1 Env ectodomains. As used herein "HIV-1 Env ectodomain trimer" includes both soluble trimers (that is, trimers without gp41 transmembrane domain or cytoplasmic tail) and membrane anchored trimers (for example, trimers including a full-length gp41).

Mature gp120 includes approximately HIV-1 Env residues 31-511, contains most of the external, surface-exposed, domains of the HIV-1 Env trimer, and it is gp120 which binds both to cellular CD4 receptors and to cellular chemokine receptors (such as CCR5). The mature gp120 wild-type polypeptide is heavily N-glycosylated, giving rise to an apparent molecular weight of 120 kD. Native gp120 includes five conserved regions (C1-C5) and five regions of high variability (V1-V5).

Variable region 1 and Variable Region 2 (V1/V2 domain) of gp120 include ~50-90 residues which contain two of the most variable portions of HIV-1 (the V1 loop and the V2 loop), and one in ten residues of the V1/V2 domain are N-glycosylated. Despite the diversity and glycosylation of the V1/V2 domain, a number of broadly neutralizing human antibodies have been identified that target this region, including the somatically related antibodies PG9 and PG16 (Walker et al., Science, 326:285-289, 2009). In certain examples the V1/V2 domain includes gp120 position 126-196.

Mature gp41 includes approximately HIV-1 Env residues 512-860, and includes cytosolic-, transmembrane-, and ectodomains. The gp41 ectodomain (including approximately HIV-1 Env residues 512-644) can interact with gp120 to form an HIV-1 Env protomer that trimerizes to form the HIV-1 Env trimer.

A standardized numbering scheme for HIV-1 Env proteins (the HXBc2 numbering system) is set forth in *Numbering Positions in HIV Relative to HXB20G* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, NM, which is incorporated by reference herein in its entirety. For reference, the amino acid sequence of HIV-1 Env of HXB2 is set forth as SEQ ID NO: 10 (GENBANK® GI: 1906382, incorporated by reference herein).

```
HXBc2 (Clade B, SEQ ID NO: 10):
MRVKEKYQHLWRWGWRWGTMLLGMLMICSATEKLWVTVYYGVPVWKEAT

TTLFCASDAKAYDTEVHNVWATHACVPTDPNPQEVVLVNVTENFNMWKN

DMVEQMHEDIISLWDQSLKPCVKLTPLCVSLKCTDLKNDTNTNSSSGRM

IMEKGEIKNCSFNISTSIRGKVQKEYAFFYKLDIIPIDNDTTSYKLTSC

NTSVITQACPKVSFEPIPIHYCAPAGFAILKCNNKTFNGTGPCTNVSTV

QCTHGIRPVVSTQLLINGSLAEEEVVIRSVNFTDNAKTIIVQLNTSVEI

NCTRPNNNTRKRIRIQRGPGRAFVTIGKIGNMRQAHCNISRAKWNNTLK

QIASKLREQFGNNKTIIFKQSSGGDPEIVTHSFNCGGEFFYCNSTQLFN

STWENSTWSTEGSNNTEGSDTITLPCRIKQIINMWQKVGKAMYAPPISG
```

-continued
```
QIRCSSNITGLLLTRDGGNSNNESEIFRPGGGDMRDNWRSELYKYKVVK

IEPLGVAPTKAKRRVVQREKRAVGIGALFLGFLGAAGSTMGAASMTLTV

QARQLLSGIVQQQNNLLRAIEAQQHLLQLTVWGIKQLQARILAVERYLK

DQQLLGIWGCSGKLICTTAVPWNASWSNKSLEQIWNHTTWMEWDREINN

YTSLIHSLIEESQNQQEKNEQELLELDKWASLWNWFNITNWLWYIKLFI

MIVGGLVGLRIVFAVLSIVNRVRQGYSPLSFQTHLPTPRGPDRPEGIEE

EGGERDRDRSIRLVNGSLALIWDDLRSLCLFSYHRLRDLLLIVTRIVEL

LGRRGWEALKYWWNLLQYWSQELKNSAVSLLNATAIAVAEGTDRVIEVV

QGACRAIRHIPRRIRQGLERILL
```

HIV-1 gp140: A recombinant HIV Env polypeptide including gp120 and the gp41 ectodomain, but not the gp41 transmembrane or cytosolic domains. HIV-1 gp140 polypeptides can trimerize to form a soluble HIV-1 Env ectodomain trimer.

HIV-1 gp145: A recombinant HIV Env polypeptide including gp120, the gp41 ectodomain, and the gp41 transmembrane domain. HIV-1 gp145 polypeptides can trimerize to form a membrane-anchored HIV-1 Env ectodomain trimers.

HIV-1 gp160: A recombinant HIV Env polypeptide including gp120 and the entire gp41 protein (ectodomain, transmembrane domain, and cytosolic tail).

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immunogenic conjugate: A composition composed of at least two heterologous molecules (such as an HIV-1 Env trimer and a carrier, such as a protein carrier) linked together that stimulates or elicits an immune response to a molecule in the conjugate in a vertebrate. In some embodiments where the conjugate include a viral antigen, the immune response is protective in that it enables the vertebrate animal to better resist infection from the virus from which the antigen is derived.

Immune response: A response of a cell of the immune system, such as a B cell, T cell, or monocyte, to a stimulus, such as a vaccination or an infection. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to treatment of a subject with a "prime" immunogen to induce an immune response that is subsequently "boosted" with a boost immunogen. Together, the prime and boost immunizations produce the desired immune response in the subject. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogen: A protein or a portion thereof that is capable of inducing an immune response in a mammal, such as a mammal infected or at risk of infection with a pathogen.

Immunogenic composition: A composition comprising a disclosed immunogen, or a nucleic acid molecule or vector encoding a disclosed immunogen, that elicits a measurable CTL response against the immunogen, or elicits a measurable B cell response (such as production of antibodies) against the immunogen, when administered to a subject. It further refers to isolated nucleic acids encoding an immunogen, such as a nucleic acid that can be used to express the immunogen (and thus be used to elicit an immune response against this immunogen). For in vivo use, the immunogenic composition will typically include the protein or nucleic acid molecule in a pharmaceutically acceptable carrier and may also include other agents, such as an adjuvant.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g. electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker". In several embodiments, linked components are associated in a chemical or physical manner so that the components are not freely dispersible from one another, at least until contacting a cell, such as an immune cell.

Linker: One or more molecules or groups of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In several embodiments, a peptide linker can be used to link the C-terminus of a first protein to the N-terminus of a second protein. Non-limiting examples of peptide linkers include glycine-serine peptide linkers, which are typically not more than 10 amino acids in length. Typically, such linkage is accomplished using molecular biology techniques to genetically manipulate DNA encoding the first polypeptide linked to the second polypeptide by the peptide linker.

Native protein, sequence, or disulfide bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Peptide: A polymer in which the monomers are amino acid residues that are joined together through amide bonds. The amino acids included in a peptide may be subject to post-translational modification (e.g., glycosylation or phosphorylation). In some embodiments, a peptide can be between 10 and 30 amino acids in length, such as from 10 to 20 amino acids in length. In several embodiments, a polypeptide or peptide is at most 50 amino acids in length, such as at most 40, at most 30, or at most 20 amino acids in length. Peptides for use in the method embodiments disclosed herein can be linked to heterologous moieties, such as tags and labels.

Peptides include analogs (non-peptide organic molecules), derivatives (chemically functionalized peptide molecules obtained starting with the disclosed peptide sequences) and variants (homologs) that can be utilized in the methods described herein.

Peptides can be modified by a variety of chemical techniques to produce derivatives having essentially the same activity as the unmodified peptides, and optionally having other desirable properties. For example, carboxylic acid groups of the peptide, whether carboxyl-terminal or side chain, can be provided in the form of a salt of a pharmaceutically-acceptable cation or esterified to form a C1-C16 ester, or converted to an amide of formula $NR_1R_2$ wherein $R_1$ and $R_2$ are each independently H or C1-C16 alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide for the incorporation of certain functionalities of linkage of ligand molecules, such as an adjuvant.

Hydroxyl groups of the peptide side chains may be converted to $C_1$-$C_{16}$ alkoxy or to a $C_1$-$C_{16}$ ester using well-recognized techniques to introduce hydrophobic characteristics to the peptide. Alternatively, the hydroxyl groups may be sulfated or phosphorylated to introduce negative charge and increase water solubility. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Thiols may be reacted with maleimides or disulfides. Those skilled in the art will also recognize methods for introducing cyclic structures into the peptides of this invention to select and provide conformational constraints to the structure that result in enhanced stability.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate. In particular embodiments, suitable for administration to a subject the carrier may be sterile, and/or suspended or otherwise contained in a unit dosage form containing one or more measured doses of the composition suitable to elicit the desired anti-HIV-1 immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with protein, and is used herein to refer to a polymer of amino acid residues.

Prime-boost immunization: An immunotherapy including administration of multiple immunogens over a period of time to elicit the desired immune response.

Prognosis of an immune response to HIV-1 in a subject: A prediction of the likelihood that an immune response in a subject will (or will not) inhibit HIV-1 infection in the subject. For example, the prediction can include determining the likelihood that an immune response in a subject will (or will not) prevent HIV-1 infection in the subject. In some embodiments, the prediction includes determining the likelihood that an immune response in a subject will (or will not) inhibit signs or symptoms of HIV-1 in a subject already infected with HIV-1, such as full development of HIV-1 in the subject, a delayed onset of clinical symptoms of the HIV-1 infection, a reduction in severity of some or all clinical symptoms of the HIV-1 infection, a slower progression of the HIV-1 disease (such as a slower progression to AIDS).

Recombinant: A recombinant nucleic acid is one that has a sequence that is not naturally occurring or has a sequence that is made by an artificial combination of two otherwise separated segments of sequence. This artificial combination can be accomplished, for example, the artificial manipulation of isolated segments of nucleic acids, for example, using genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

RV144 Trial: A phase III clinical trial of a prime-boost HIV-1 vaccine that was carried out in Thailand. The immunization protocol consisted of four injections of ALVAC HIV (vCP1521) followed by two injections of AIDSVAX B/E. ALVAC HIV (vCP1521) is a canarypox vector genetically engineered to express HIV-1 Gag and Pro (subtype B LAI strain) and CRF01_AE (subtype E) HIV-1 gp120 (92TH023) linked to the transmembrane anchoring portion of gp41 (LAI). AIDSVAX B/E is a bivalent HIV gp120 envelope glycoprotein vaccine containing a subtype E envelope from the HIV-1 strain A244 (CM244) and a subtype B envelope from the HIV-1 MN each produced in Chinese hamster ovary cell lines. The envelope glycoproteins, 300 μg of each, were co-formulated with 600 μg of alum adjuvant. The RV144 trial, ALVAC HIV (vCP1521), and AIDSVAX B/E are described in Rerks-Ngarm et al. (New Eng J Med. 361 (23): 2209-2220, 2009, incorporated by reference herein). In some embodiments, the Env ectodomain encoding portion of ALVAC HIV (vCP1521) and the gp120 proteins of AIDSVAX B/E can be modified to encode or contain the V1 deletion provided herein (deletion of residues 137-152 according to HXBc2 numbering) and administered to a subject using the rv 144 prime-boost protocol (or any other suitable protocol).

Sensitivity and specificity: Statistical measurements of the performance of a binary classification test. Sensitivity measures the proportion of actual positives which are correctly identified (e.g., the percentage of samples that are identified as including nucleic acid from a particular virus). Specificity measures the proportion of negatives which are correctly identified (e.g., the percentage of samples that are identified as not including nucleic acid from a particular virus).

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-30 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). Exemplary signal peptide sequences are set forth as residues 1-11 of SEQ ID NOs: 10, 6, and 7.

Specifically bind: When referring to the formation of an antibody: antigen protein complex, or a protein: protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example, gp120) and does not bind in a significant amount to other proteins or polysaccharides present in the sample or subject. Specific binding can be determined by standard methods. A first protein or antibody specifically binds to a target protein when the interaction has a $K_D$ of less than $10^{-7}$ Molar, such as less than $10^{-8}$ Molar, less than $10^{-9}$, or even less than $10^{-10}$ Molar.

Subject: Living multicellular vertebrate organisms, a category that includes human and non-human mammals. In an example, a subject is a human. In an additional example, a subject is selected that is in need of inhibiting of an HIV-1 infection. For example, the subject is either uninfected and at risk of HIV-1 infection or is infected in need of treatment.

Transmembrane domain: An amino acid sequence that inserts into a lipid bilayer, such as the lipid bilayer of a cell or virus or virus-like particle. A transmembrane domain can be used to anchor an antigen to a membrane.

Treating or inhibiting HIV-1: Inhibiting the full development of HIV-1 in a subject who is at risk for or has an HIV-1 infection or acquired immunodeficiency syndrome (AIDS). "Treatment" refers to a therapeutic intervention that ameliorates a sign or symptom of HIV-1 infection in an infected subject. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Inhibiting HIV-1 in an uninfected subject refers to a reduction in infection rate or likelihood of infection. In this context, the term "reduces" is a relative term. An immunogenic composition that induces an immune response that inhibits HIV-1, can, but does not necessarily completely, inhibit HIV-1 infection of a subject (or group of subjects), so long as the infection is measurably diminished, for example, by at least about 50%, such as by at least about 70%, or about 80%, or even by about 90% of (that is to 10% or less than) the infection or response in the absence of the agent, or in comparison to a reference agent.

Under conditions sufficient for: A phrase that is used to describe any environment that permits a desired activity. In one example the desired activity is formation of an immune complex.

Vaccine: A pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine reduces the severity of the symptoms associated with HIV-1 infection and/or decreases the viral load compared to a control. In another non-limiting example, a vaccine reduces HIV-1 infection compared to a control.

Vector: An entity containing a DNA or RNA molecule bearing a promoter(s) that is operationally linked to the coding sequence of an immunogenic protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses.

A non-limiting example of a DNA-based expression vector is pCDNA3.1, which can include includes a mammalian expression enhancer and promoter (such as a CMV promoter). Non-limiting examples of viral vectors include adeno-associated virus (AAV) vectors as well as Poxvirus vector (e.g., Vaccinia, MVA, avian Pox, or Adenovirus).

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. The presence of VLPs following recombinant expression of viral proteins can be detected using conventional techniques, such as by electron microscopy, biophysical characterization, and the like. Further, VLPs can be isolated by known techniques, e.g., density gradient centrifugation and identified by characteristic density banding. See, for example, Baker et al. (1991) Biophys. J. 60:1445-1456; and Hagensee et al. (1994) J. Virol. 68:4503-4505; Vincente, J Invertebr Pathol., 2011; Schneider-Ohrum and Ross, Curr. Top. Microbiol. Immunol., 354:53073, 2012).

II. Immunogens

Embodiments of immunogens comprising a recombinant gp120 protein that is modified to expose V2 epitopes are provided herein. The modification comprises deletion of HXBc2 residues 137-152 from the gp120 protein, which, as discussed in the examples, exposes V2 epitopes and is shown to produce a protective immune response in an animal model. Additionally provided are isolated V1V2 domain proteins that contain the V1 deletion, as well as HIV-1 Env trimers containing the recombinant gp120 protein with the V1 deletion.

A. Recombinant Gp120 and HIV-1 Env Proteins Containing Same

Isolated immunogens are disclosed that include a recombinant gp120 protein that is modified to include a deletion of V1 residues 137-152 according to the HXBc2 numbering system. As described herein, deletion of these V1 residues exposes V2 epitopes on the gp120 protein, and immunogens including this modification are shown to elicit a protective immune response that targets the V2 epitopes. Also provided are HIV-1 Env ectodomain trimers comprising protomers including the deletion of V1 residues 137-152, as well as gp140 proteins, gp145 proteins, and gp160 proteins including this deletion.

In several embodiments, the recombinant gp120, gp140, gp145, gp160, or the protomers of the recombinant HIV-1 Env ectodomain trimer specifically bind to an antibody that targets the V2 portion of the V1V2 domain such as the human monoclonal antibody CH58 and/or CH59. The determination of specific binding may readily be made by using or adapting routine procedures, such as ELISA, immunocompetition, surface plasmon resonance, or other immunosorbant assays (described in many standard texts, including Harlow and Lane, Using Antibodies: A Laboratory Manual, CSHL, New York, 1999).

HIV-1 can be classified into four groups: the "major" group M, the "outlier" group O, group N, and group P. Within group M, there are several genetically distinct clades (or subtypes) of HIV-1. The disclosed recombinant HIV-1 Env proteins can be derived from any type of HIV, such as groups M, N, O, or P, or clade, such as clade A, B, C, D, F, G, H, J, or K, and the like. HIV-1 Env proteins from the different HIV-1 clades, as well as nucleic acid sequences encoding such proteins and methods for the manipulation and insertion of such nucleic acid sequences into vectors, are known (see, e.g., HIV Sequence Compendium, Division of AIDS, National Institute of Allergy and Infectious Diseases (2013); HIV Sequence Database (hiv-web.lanl.gov/content/hiv-db/mainpage.html); see, e.g., Sambrook et al. (Molecular Cloning: A Laboratory Manual, 4th ed, Cold Spring Harbor, New York, 2012) and Ausubel et al. (In Current Protocols in Molecular Biology, John Wiley & Sons, New York, through supplement 104, 2013). Exemplary native HIV-1 Env protein sequences are available in the HIV Sequence Database (hiv-web.lanl.gov/content/hiv-db/mainpage.html).

In some embodiments, any of the recombinant gp120, gp140, gp145, gp160, or the protomers of the recombinant HIV-1 Env ectodomain trimer can include the corresponding amino acid sequence from a native HIV-1 Env protein, for example, from genetic subtype A-F as available in the HIV Sequence Database (hiv-web.lanl.gov/content/hiv-db/mainpage.html), or an amino acid sequence at least 90% (such as at least 95%, at least 96%, at least 97%, at least 98% or at least 99%) identical thereto that has been modified to include a deletion of HXBc2 residues 137-152.

In some embodiments, the recombinant gp120 protein comprises or consists essentially of the amino acid sequence set forth as any one of:

SEQ ID NO: 1. gp120 of HIV-1 Env circulating recombinant form AE, strain A244 (GenBank: KU562843.1, incorporated by reference herein in its entirety) with V1 137-152 deletion. Deletion boundaries are underlined.

```
NLWKWGTLILGLVIICSASDNLWVTVYYGVPVWRDADTTLFCASDAKAQ

ETEAHNVWATHACVPTDPNPQELHLENVTENFNMWKNNMVEQMQEDVIS

LWDQSLKPCVKLTPLCVTLNCTNANLEVRNCSFNMTTELRDKKQKVHAL

FYKLDIVPIEDNTSSSKYRLINCNTSVIKQACPKISFDPIPIHYCTPAG

YAILKCNDKNFNGTGPCKNVSSVQCTHGIKPAVSTQLLLNGSLAEEEII

IRSENLTNNAKTIIVHLNKSVEINCTRPSNNTRTSINIGPGQVFYRTGD

IIGDIRKAYCEINGAKWNEVLKKVTEKLKEHFNNKTIIFQPPSGGDLEI

TMHHFNCRGEFFYCNTTRLENNTCMENETMEGCNGTIILPCKIKQIINM

WQRAGQAMYAPPISGRINCVSNITGILLTRDGGLNNTNETFRPGGGNIK

DNWRSELYKYKVVQIEPLGIAPTRAKRRVVEREKR
```

SEQ ID NO: 2. gp120 of HIV-1 Env clade B strain MN (GenBank: AAL66251.1, incorporated by reference herein in its entirety) with V1 137-152 deletion. Deletion boundaries are underlined.

HWWGWGTMLLGLLMICSATEKLWVTVYYGVPVWKEATTTLFCASDAKAY

DTEVHNVWATHACVPTDPNPQEVQLVNVTEDFNMWKNNMVEQMHEDIIS

LWDQSLKPCVKLTPLCVTLNCTDLR<u>N</u>EMKNCSFNITTSIRDKMQKEYAL

LYKLDIVAIDKDNTSYRLISCNTSVITQACPKVSFEPIPIHYCAPAGFA

ILKCNDKNFTGKGPCKNVSTVQCTHGIRPVVSTQLLLNGSLAEEEVVIR

SENFTNNAKTIIVHLNESVQINCTRPYNNRRTRIHIGPGRAFYTTKNIK

GTIRQAHCTISSAKWNDTLRQIVSKLKEQFKNKTIVFKQSSGGDPEIVM

HSFNCGGEFFYCNTSSLENSTWNGNNTWNNTTGSNSNITLQCKIKQIIN

MWQEVGKAMYAPPIEGQIRCSSNITGLLLTRDGGNDTDTNNTEIFRPGG

GDMRDNWRSELYKYKVVTIEPLGVAPTKAKRRVVQREKR

SEQ ID NO: 3. gp120 of HIV-1 Env clade C strain 96ZM651 (GenBank: AAK30970.1, incorporated by reference herein in its entirety) with V1 137-152 deletion. Deletion boundaries are underlined.

RWWTWGILGFWMLMICNVWGNLWVTVYYGVPVWKEAKTTLFCASDAKSY
EKEVHNVWATHACVPTDPNPQEIVLGNVTENFNMWKNDMVDQMHEDIIS
LWDQSLKPCVKLTPLCVTLNCTEVNVDMKNCSENITTELKDKKKNVYAL
FYKLDIVSINETDDSETGNSSKYYRLINCNTSALTQACPKVSFDPIPIH
YCAPAGYAILKCNNKTENGTGPCHNVSTVQCTHGIKPVVSTQLLINGSL
AEEGIIIRSENLINNVKTIIVHLNRSIEIVCVRPNNNTRQSIRIGPGQT
FYATGDIIGDIRQAHCNISRTNWTKTLREVRNKLREHFPNKNITFKPSS
GGDLEITTHSENCRGEFFYCNTSGLESINYTENNTDGTPITLPCRIRQI
INMWQEVGRAMYAPPIEGNIACKSDITGLLLVRDGGSTNDSTNNNTEIF
RPAGGDMRDNWRSELYKYKVVEIKPLGIAPTEAKRRVVEREKR

In some embodiments, the recombinant gp120 protein comprises or consists essentially of an amino acid sequence at least 90% (such as at least 95%, at least 96%, at least 97%, at least 98% or at least 99%) identical to any one of SEQ ID NOs: 1-3 that comprises the V1 deletion of residues 137-152 (HXBc2 numbering).

In some embodiments, the immunogen comprises a gp160 or a HIV-1 Env trimer comprising the recombinant gp120 protein with the deletion of residues 137-152 (HXBc2 numbering. In some embodiments, the gp160 or the protomers of the HIV-1 Env trimer comprise or consist essentially of the amino acid sequence set forth as any one of:

SEQ ID NO: 4. HIV-1 A244 Env with V1 137-152 deletion and without signal peptide. Deletion boundaries are underlined.

NLWKWGTLILGLVIICSASDNLWVTVYYGVPVWRDADTTLFCASDAKAQ
ETEAHNVWATHACVPTDPNPQELHLENVTENFNMWKNNMVEQMQEDVIS
LWDQSLKPCVKLTPLCVTLNCTNANLEVRNCSFNMTTELRDKKQKVHAL
FYKLDIVPIEDNTSSSKYRLINCNTSVIKQACPKISFDPIPIHYCTPAG
YAILKCNDKNFNGTGPCKNVSSVQCTHGIKPAVSTQLLLNGSLAEEEII
IRSENLINNAKTIIVHLNKSVEINCTRPSNNTRTSINIGPGQVFYRTGD

-continued

IIGDIRKAYCEINGAKWNEVLKKVTEKLKEHFNNKTIIFQPPSGGDLEI
TMHHFNCRGEFFYCNTTRLFNNTCMENETMEGCNGTIILPCKIKQIINM
WQRAGQAMYAPPISGRINCVSNITGILLTRDGGLNNTNETFRPGGGNIK
DNWRSELYKYKVVQIEPLGIAPTRAKRRVVEREKRAVGIGAMIFGFLGA
AGSTMGAASITLTVQARQLLSGIVQQQSNLLRAIEAQQHLLQLTVWGIK
QLQARVLAVERYLKDQKLLGLWGCSGKIICTTAVPWNSTWSNRSFEEIW
NNMTWIEWEREISNYTNQIYEILTQSQNQQDRNEKDLLELDKWASLWKW
FDITNWLWYIKIFIMIVGGLIGLRIIFAVLSIVNRVRQGYSPLSLQIPT
HHQREPDRPERIEEGGGEQGRDKSVRLVSGFLALTWDDLRSLCLFSYHR
LRDFISIAARTVELLGHSSLKGLRRGWEGLKYLGNLILYWGQELKISAI
SLLNATAIAVAGWTDRVIEVAQGAWRAILHIPRRIRQGLERTLL

SEQ ID NO: 5. HIV-1 MN Env with V1 137-152 deletion and without signal peptide. Deletion boundaries are underlined.

HWWGWGTMLLGLLMICSATEKLWVTVYYGVPVWKEATTTLFCASDAKAY
DTEVHNVWATHACVPTDPNPQEVQLVNVTEDFNMWKNNMVEQMHEDIIS
LWDQSLKPCVKLTPLCVTLNCTDLRNEMKNCSFNITTSIRDKMQKEYAL
LYKLDIVAIDKDNTSYRLISCNTSVITQACPKVSFEPIPIHYCAPAGFA
ILKCNDKNFTGKGPCKNVSTVQCTHGIRPVVSTQLLLNGSLAEEEVVIR
SENFTNNAKTIIVHLNESVQINCTRPYNNRRTRIHIGPGRAFYTTKNIK
GTIRQAHCTISSAKWNDTLRQIVSKLKEQFKNKTIVFKQSSGGDPEIVM
HSFNCGGEFFYCNTSSLENSTWNGNNTWNNTTGSNSNITLQCKIKQIIN
MWQEVGKAMYAPPIEGQIRCSSNITGLLLTRDGGNDTDTNNTEIFRPGG
GDMRDNWRSELYKYKVVTIEPLGVAPTKAKRRVVQREKRAAIGALFLGF
LGAAGSTMGAASMMLTVQARQLLSGIVQQQNNLLRAIEAQQHMLQLTVW
GIKQLQARVLAVERYLRDQQLLGIWGCSGKLICTTTVPWNASWSNKSQE
DIWNNMTWMQWEREIDNYTSTIYELLEKSQNQQEKNEQELLELDKWASL
WNWFDITNWLWYIKIFIMIVGGLIGLRIVFAVLSIVNRVRQGYSPLSLQ
TRPPVPRGPDRPEGTEEEGGERDRDTSGRLVDGFLAIIWVDLRSLLLES
YHRLRDLLLIAARIVELLGRRGWEILKYWWNLLQYWSQELKNSAVSLLN
ATAVAVAEGTDRVIEVLQRAGRAILHIPTRIRQGLERALL

SEQ ID NO: 66. HIV-1 96ZM651 Env with V1 137-152 deletion and without signal peptide. Deletion boundaries are underlined.

RWWTWGILGFWMLMICNVWGNLWVTVYYGVPVWKEAKTTLFCASDAKSY
EKEVHNVWATHACVPTDPNPQEIVLGNVTENFNMWKNDMVDQMHEDIIS
LWDQSLKPCVKLTPLCVTLNCTEVNVDMKNCSFNITTELKDKKKNVYAL
FYKLDIVSLNETDDSETGNSSKYYRLINCNTSALTQACPKVSFDPIPIH
YCAPAGYAILKCNNKTENGTGPCHNVSTVQCTHGIKPVVSTQLLINGSL
AEEGIIIRSENLTNNVKTIIVHLNRSIEIVCVRPNNNTRQSIRIGPGQT
FYATGDIIGDIRQAHCNISRTNWTKTLREVRNKLREHFPNKNITFKPSS

```
GGDLEITTHSENCRGEFFYCNTSGLESINYTENNTDGTPITLPCRIRQI

INMWQEVGRAMYAPPIEGNIACKSDITGLLLVRDGGSTNDSTNNNTEIF

RPAGGDMRDNWRSELYKYKVVEIKPLGIAPTEAKRRVVEREKRAVGIGA

VFLGFLGAAGSTMGAASITLTAQARQVLSGIVQQQSNLLRAIEAQQHLL

QLTVWGIKQLQTRVLAIERYLKDQQLLGLWGCSGKLICTTAVPWNISWS

NKSKTDIWDNMTWMQWDREISNYTNTIYRLLEDSQSQQEQNEKDLLALD

SWNNLWNWFDITKWLWYIKIFIMIVGGLIGLRIIFAVLSIVNRVRQGYS

PLSFQTLIPNPREPDRPGRIEEEGGEQDKERSVRLVSGFLALAWDDLRS

LCLFSYHRLRDFILVTARAVELLRRSSLKGLQRGWEALKYLGSLVQYWG

LELKKSAISLLDTIAIAVAEGTDRIIELIQGICRAIRNVPRRIRQGFET
ALL
```

In some embodiments, the recombinant gp160 or the protomers of the HIV-1 Env trimer comprise or consist essentially of an amino acid sequence at least 90% (such as at least 95%, at least 96%, at least 97%, at least 98% or at least 99%) identical to any one of SEQ ID NOs: 4-5 and 66 that comprises the V1 deletion of residues 137-152 (HXBc2 numbering).

The full-length sequences of A244 Env and HIV-1 Env clade B with the V1 137-152 deletion are provided as:

SEQ ID NO: 6. HIV-1 A244 Env with the V1 137-152 deletion. Deletion boundaries are underlined.

MRVKETQMTWPNLWKWGTLILGLVIICSASDNLWVTVYYGVPVWRDADT
TLFCASDAKAQETEAHNVWATHACVPTDPNPQELHLENVTENFNMWKNN
MVEQMQEDVISLWDQSLKPCVKLTPLCVTLNCTNANLEVRNCSFNMTTE
LRDKKQKVHALFYKLDIVPIEDNTSSSKYRLINCNTSVIKQACPKISFD
PIPIHYCTPAGYAILKCNDKNFNGTGPCKNVSSVQCTHGIKPAVSTQLL
INGSLAEEEIIIRSENLINNAKTIIVHLNKSVEINCTRPSNNTRTSINI
GPGQVFYRTGDIIGDIRKAYCEINGAKWNEVLKKVTEKLKEHFNNKTII
FQPPSGGDLEITMHHFNCRGEFFYCNTTRLENNTCMENETMEGCNGTII
LPCKIKQIINMWQRAGQAMYAPPISGRINCVSNITGILLTRDGGLNNTN
ETFRPGGGNIKDNWRSELYKYKVVQIEPLGIAPTRAKRRVVEREKRAVG
IGAMIFGFLGAAGSTMGAASITLTVQARQLLSGIVQQQSNLLRAIEAQQ
HLLQLTVWGIKQLQARVLAVERYLKDQKLLGLWGCSGKIICTTAVPWNS
TWSNRSFEEIWNNMTWIEWEREISNYTNQIYEILTQSQNQQDRNEKDLL
ELDKWASLWKWFDITNWLWYIKIFIMIVGGLIGLRIIFAVLSIVNRVRQ
GYSPLSLQIPTHHQREPDRPERIEEGGGEQGRDKSVRLVSGFLALTWDD
LRSLCLESYHRLRDFISIAARTVELLGHSSLKGLRRGWEGLKYLGNLIL
YWGQELKISAISLLNATAIAVAGWTDRVIEVAQGAWRAILHIPRRIRQG
LERTLL

SEQ ID NO: 7. HIV-1 MN Env with the V1 137-152 deletion. Deletion boundaries are underlined.

MRVKGIRRNYQHWWGWGTMLLGLLMICSATEKLWVTVYYGVPVWKEATT
TLFCASDAKAYDTEVHNVWATHACVPTDPNPQEVQLVNVTEDFNMWKNN

-continued

MVEQMHEDIISLWDQSLKPCVKLTPLCVTLNCTDLRNEMKNCSFNITTS
IRDKMQKEYALLYKLDIVAIDKDNTSYRLISCNTSVITQACPKVSFEPI
PIHYCAPAGFAILKCNDKNFTGKGPCKNVSTVQCTHGIRPVVSTQLLIN
GSLAEEEVVIRSENFTNNAKTIIVHLNESVQINCTRPYNNRRTRIHIGP
GRAFYTTKNIKGTIRQAHCTISSAKWNDTLRQIVSKLKEQFKNKTIVFK
QSSGGDPEIVMHSFNCGGEFFYCNTSSLENSTWNGNNTWNNTTGSNSNI
TLQCKIKQIINMWQEVGKAMYAPPIEGQIRCSSNITGLLLTRDGGNDTD
TNNTEIFRPGGGDMRDNWRSELYKYKVVTIEPLGVAPTKAKRRVVQREK
RAAIGALFLGFLGAAGSTMGAASMMLTVQARQLLSGIVQQQNNLLRAIE
AQQHMLQLTVWGIKQLQARVLAVERYLRDQQLLGIWGCSGKLICTTTVP
WNASWSNKSQEDIWNNMTWMQWEREIDNYTSTIYELLEKSQNQQEKNEQ
ELLELDKWASLWNWFDITNWLWYIKIFIMIVGGLIGLRIVFAVLSIVNR
VRQGYSPLSLQTRPPVPRGPDRPEGTEEEGGERDRDTSGRLVDGFLAII
WVDLRSLLLFSYHRLRDLLLIAARIVELLGRRGWEILKYWWNLLQYWSQ
ELKNSAVSLLNATAVAVAEGTDRVIEVLQRAGRAILHIPTRIRQGLERA
LL

SEQ ID NO: 67. HIV-1 96ZM651 Env strain with V1 137-152 deletion. Deletion boundaries are underlined.

MRVREILRNWQRWWTWGILGFWMLMICNVWGNLWVTVYYGVPVWKEAKT
TLFCASDAKSYEKEVHNVWATHACVPTDPNPQEIVLGNVTENFNMWKND
MVDQMHEDIISLWDQSLKPCVKLTPLCVTLNCTEVNVDMKNCSFNITTE
LKDKKKNVYALFYKLDIVSLNETDDSETGNSSKYYRLINCNTSALTQAC
PKVSFDPIPIHYCAPAGYAILKCNNKTENGTGPCHNVSTVQCTHGIKPV
VSTQLLINGSLAEEGIIIRSENLTNNVKTIIVHLNRSIEIVCVRPNNNT
RQSIRIGPGQTFYATGDIIGDIRQAHCNISRTNWTKTLREVRNKLREHF
PNKNITFKPSSGGDLEITTHSFNCRGEFFYCNTSGLFSINYTENNTDGT
PITLPCRIRQIINMWQEVGRAMYAPPIEGNIACKSDITGLLLVRDGGST
NDSTNNNTEIFRPAGGDMRDNWRSELYKYKVVEIKPLGIAPTEAKRRVV
EREKRAVGIGAVFLGFLGAAGSTMGAASITLTAQARQVLSGIVQQQSNL
LRAIEAQQHLLQLTVWGIKQLQTRVLAIERYLKDQQLLGLWGCSGKLIC
TTAVPWNISWSNKSKTDIWDNMTWMQWDREISNYTNTIYRLLEDSQSQQ
EQNEKDLLALDSWNNLWNWFDITKWLWYIKIFIMIVGGLIGLRIIFAVL
SIVNRVRQGYSPLSFQTLIPNPREPDRPGRIEEEGGEQDKERSVRLVSG
FLALAWDDLRSLCLFSYHRLRDFILVTARAVELLRRSSLKGLQRGWEAL
KYLGSLVQYWGLELKKSAISLLDTIAIAVAEGTDRIIELIQGICRAIRN
VPRRIRQGFETALL

In some embodiments, the recombinant gp120, gp140, gp145, gp160, or the protomers of the recombinant HIV-1 Env ectodomain trimer can further include a non-natural disulfide bond between HIV-1 Env positions 201 and 433. For example, the non-natural disulfide bond can be introduced by including cysteine substitutions at positions 201 and 433 (e.g., I201C and A433C substitutions). The presence of the non-natural disulfide bond between residues 201 and 433 contributes to the stabilization of the HIV-1 Env protein in its prefusion mature closed conformation.

In some embodiments, the protomers of the recombinant HIV-1 Env ectodomain trimer can include gp120-gp41 ectodomain protomers further including the "SOSIP" substitutions, which include a non-natural disulfide bond between cysteine residues introduced at HIV-1 Env positions 501 and 605 (for example, by A501C and T605C substitutions), and a proline residue introduced at HIV-1 Env positions 559 (for example, by an I559P substitution). The presence of the non-natural disulfide bond between positions 501 and 605 and the proline residue at position 559 contributes to the stabilization of the HIV-1 Env ectodomain in the prefusion mature closed conformation. In several embodiments, the protomers of the recombinant HIV-1 Env ectodomain trimer can further include a non-natural disulfide bond between HIV-1 Env positions 201 and 433 (e.g., by introduction of I201C and A433C substitutions) and the HIV-1 Env ectodomain trimer can further included the SOSIP mutations.

In some embodiments, the recombinant gp120, gp140, gp145, gp160, or the protomers of the recombinant HIV-1 Env ectodomain trimer can further include an N-linked glycosylation site at HIV-1 Env position 332 (if not already present on the ectodomain). For example, by T332N substitution in the case of BG505-based immunogens. The presence of the glycosylation site at N332 allows for binding by 2G12 antibody.

In some embodiments, the recombinant gp120, gp140, gp145, gp160, or the protomers of the recombinant HIV-1 Env ectodomain trimer can include a lysine residue at HIV-1 Env position 168 (if not already present on the ectodomain). For example, the lysine residue can be added by amino acid substitution (such as an E168K substitution in the case of the JR-FL based immunogens). The presence of the lysine residue at position 168 allows for binding of particular broadly neutralizing antibodies to the V1V2 loops of gp120.

In some embodiments, the protomers of the recombinant HIV-1 Env ectodomain trimer can further include mutations to add an N-linked glycan sequon at position 504, position 661, or positions 504 and 661, to increase glycosylation of the membrane proximal region of the ectodomain.

Native HIV-1 Env sequences include a furin cleavage site between positions 508 and 512 (HXBc2 numbering), that separates gp120 and gp41. Any of the disclosed recombinant gp160 proteins and HIV-1 Env ectodomains can further include an enhanced cleavage site between gp120 and gp41 proteins. The enhanced cleavage cite can include, for example, substitution of six arginine resides for the four residues of the native cleavage site (e.g., REKR, SEQ ID NO: 11) to RRRRRR (SEQ ID NO: 12). It will be understood that protease cleavage of the furin or enhanced cleavage site separating gp120 and gp41 can remove a few amino acids from either end of the cleavage site.

The recombinant HIV-1 Env ectodomain trimer includes a protein complex of gp120-gp41 ectodomain protomers. The gp120-gp41 ectodomain protomer can include separate gp120 and gp41 polypeptide chains, or can include gp120 and gp41 polypeptide chains that are linked (e.g., by a peptide linker) to form a single polypeptide chain (e.g., a "single chain"). In several embodiments, the recombinant HIV-1 Env ectodomain trimer is membrane anchored and can include a trimeric complex of recombinant HIV-1 Env ectodomains that are linked to a transmembrane domain (e.g., a gp145 protein including a gp120 protein and a gp41 ectodomain and transmembrane domain).

In several embodiments, the N-terminal residue of the recombinant gp120 protein is one of HIV-1 Env positions 1-35, and the C-terminal residue of the recombinant gp120 protein is one of HIV-1 Env positions 503-511. In some embodiments, the N-terminal residue of the recombinant gp120 protein is HIV-1 Env position 31 and the C-terminal residue of the recombinant gp120 protein is HIV-1 Env position 511 or position 507. In some embodiments, the recombinant gp120 protein comprises or consists of HIV-1 Env positions 31-507 (HXBc2 numbering).

The purified proteins provided herein typically do not include a signal peptide (for example, the purified recombinant gp120 protein typically does not include HIV-1 Env positions 1-30), as the signal peptide is proteolytically cleaved during cellular processing.

In embodiments including a soluble recombinant HIV-1 Env ectodomain, the gp41 ectodomain is not linked to a transmembrane domain or other membrane anchor. However, in embodiments including a membrane anchored recombinant HIV-1 Env ectodomain trimer the gp41 ectodomain can be linked to a transmembrane domain (such as, but not limited to, an HIV-1 Env transmembrane domain).

In some embodiments, the HIV-1 Env ectodomain trimer includes the recombinant gp120 protein and the gp41 ectodomain, wherein the N-terminal residue of the recombinant gp120 protein is HIV-1 Env position 31; the C-terminal residue of the recombinant gp120 protein is HIV-1 Env position 507 or 511; the N-terminal residue of the gp41 ectodomain is HIV-1 Env position 512; and the C-terminal residue of the gp41 ectodomain is HIV-1 Env position 664. In some embodiments, the HIV-1 Env ectodomain trimer includes the recombinant gp120 protein and the gp41 ectodomain, wherein the N-terminal residue of the recombinant gp120 protein is HIV-1 Env position 31; the C-terminal residue of the recombinant gp120 protein is HIV-1 Env position 507; the N-terminal residue of the gp41 ectodomain is HIV-1 Env position 512; and the C-terminal residue of the gp41 ectodomain is HIV-1 Env position 664. In some embodiments, the C-terminal residue of the recombinant HIV-1 Env ectodomain is position 683 (the entire ectodomain, terminating just before the transmembrane domain). In additional embodiments, the C-terminal residue of the recombinant HIV-1 Env ectodomain is position 707 (the entire ectodomain, terminating just after the transmembrane domain).

In view of the conservation and breadth of knowledge of HIV-1 Env sequences, the person of ordinary skill in the art can easily identify corresponding HIV-1 Env amino acid positions between different HIV-1 Env strains and subtypes. The HXBc2 numbering system has been developed to assist comparison between different HIV-1 amino acid and nucleic acid sequences. The numbering of amino acid substitutions disclosed herein is made according to the HXBc2 numbering system, unless context indicates otherwise.

It is understood in the art that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering technique known to those skilled in the art. Examples of such techniques are found in see, e.g., Sambrook et al. (Molecular Cloning: A Laboratory Manual, 4$^{th}$ ed, Cold Spring Harbor, New York, 2012) and Ausubel et al. (In Current Protocols in Molecular Biology, John Wiley &

Sons, New York, 2013, both of which are incorporated herein by reference in their entirety.

The recombinant gp120, gp140, gp145, gp160, or the protomers of the recombinant HIV-1 Env ectodomain trimer can be derivatized or linked to another molecule (such as another peptide or protein). In general, the derivatization is such that the binding of antibodies that bind to the V2 domain (or of the V2b or V2c peptides disclosed herein) is not affected adversely by the derivatization or labeling. In some embodiments, the recombinant gp120, gp140, gp145, gp160, or the protomers of the recombinant HIV-1 Env ectodomain trimer can be functionally linked (by chemical coupling, genetic fusion, noncovalent association or otherwise) to one or more other molecular entities, such as an antibody or protein or detection tag.

Membrane Anchored Embodiments

In some embodiments, the HIV-1 Env ectodomain trimer including the recombinant gp120 protein can be a membrane anchored HIV-1 Env ectodomain trimer, for example, the HIV-1 Env ectodomains in the trimer can each be linked to a transmembrane domain. The transmembrane domain can be linked to any portion of the HIV-1 Env ectodomain, as long as the presence of the transmembrane domain does not disrupt the structure of the HIV-1 Env ectodomain, or its ability to induce an immune response to HIV-1. In non-limiting examples, the transmembrane domain can be linked to the N- or C-terminal residue of a gp120 polypeptide, or the C-terminal residue of a gp41 ectodomain included in the HIV-1 Env ectodomain. One or more peptide linkers (such as a gly-ser linker, for example, a 10 amino acid glycine-serine peptide linker, such as a peptide linker comprising the amino acid sequence set forth as SEQ ID NO: 13 (GGSGGGGSGG) can be used to link the transmembrane domain and the gp120 or gp41 protein. In some embodiments a native HIV-1 Env MPER sequence can be used to link the transmembrane domain and the gp120 or gp41 protein.

Non-limiting examples of transmembrane domains for use with the disclosed embodiments include the BG505 TM domain (KIFIMIVGGLIGLRIVFAVLSVIHRVR, SEQ ID NO: 14), the Influenza A Hemagglutinin™ domain (ILAIYSTVASSLVLLVSLGAISF, SEQ ID NO: 15), and the Influenza A Neuraminidase™ domain (IIT-IGSICMVVGIISLILQIGNIISIWVS, SEQ ID NO: 16).

The recombinant HIV-1 Env ectodomain linked to the transmembrane domain can include any of the mutations provided herein (or combinations thereof) as long as the recombinant HIV-1 Env ectodomain linked to the transmembrane domain retains the desired properties.

Linkage to a Trimerization Domain

In several embodiments, the HIV-1 Env ectodomain trimer including the recombinant gp120 protein can be linked to a trimerization domain, for example, the C-terminus of the gp41 ectodomains included in the HIV-1 Env ectodomain trimer can be linked to the trimerization domain. The trimerization domain can promote trimerization of the three protomers of the recombinant HIV-1 Env protein. Non-limiting examples of exogenous multimerization domains that promote stable trimers of soluble recombinant proteins include: the GCN4 leucine zipper (Harbury et al. 1993 *Science* 262:1401-1407), the trimerization motif from the lung surfactant protein (Hoppe et al. 1994 *FEBS Lett* 344:191-195), collagen (McAlinden et al. 2003 *J Biol Chem* 278:42200-42207), and the phage T4 fibritin Foldon (Miroshnikov et al. 1998 *Protein Eng* 11:329-414), any of which can be linked to the recombinant HIV-1 Env ectodomain (e.g., by linkage to the C-terminus of the gp41 polypeptide to promote trimerization of the recombinant HIV-1 protein.

In some examples, the recombinant HIV-1 Env ectodomain can be linked to a T4 fibritin Foldon domain, for example, the recombinant HIV-1 Env ectodomain can include a gp41 polypeptide with a Foldon domain linked to its C-terminus. In specific examples, the T4 fibritin Foldon domain can include the amino acid sequence GYIPEAPRDGQAYVRKDGEWVLLSTF (SEQ ID NO: 17), which adopts a β-propeller conformation, and can fold and trimerize in an autonomous way (Tao et al. 1997 *Structure* 5:789-798).

Typically, the heterologous trimerization domain is positioned C-terminal to the gp41 protein. Optionally, the heterologous trimerization is connected to the recombinant HIV-1 Env ectodomain via a linker, such as an amino acid linker. Exemplary linkers include Gly or Gly-Ser linkers, such as SEQ ID NO: 13 (GGSGGGGSGG). Some embodiments include a protease cleavage site for removing the trimerization domain from the HIV-1 polypeptide, such as, but not limited to, a thrombin site between the recombinant HIV-1 Env ectodomain and the trimerization domain.

Carrier Molecules

In some embodiments, a disclosed the recombinant gp120, gp140, gp145, gp160, or recombinant HIV-1 Env ectodomain trimer can be linked to a carrier protein by a linker (such as a peptide linker) or can be directly linked to the carrier protein (for example, by conjugation, or synthesis as a fusion protein) too form an immunogenic conjugate.

Suitable linkers are well known to those of skill in the art and include, but are not limited to, straight or branched-chain carbon linkers, heterocyclic carbon linkers or peptide linkers. One skilled in the art will recognize, for an immunogenic conjugate from two or more constituents, each of the constituents will contain the necessary reactive groups. Representative combinations of such groups are amino with carboxyl to form amide linkages or carboxy with hydroxyl to form ester linkages or amino with alkyl halides to form alkylamino linkages or thiols with thiols to form disulfides or thiols with maleimides or alkylhalides to form thioethers. Hydroxyl, carboxyl, amino and other functionalities, where not present may be introduced by known methods. Likewise, as those skilled in the art will recognize, a wide variety of linking groups may be employed. In some cases, the linking group can be designed to be either hydrophilic or hydrophobic in order to enhance the desired binding characteristics of the HIV-1 Env protein and the carrier. The covalent linkages should be stable relative to the solution conditions under which the conjugate is subjected.

In some embodiments, the linkers may be joined to the constituent amino acids through their side groups (such as through a disulfide linkage to cysteine) or to the alpha carbon amino and carboxyl groups of the terminal amino acids. In some embodiments, the recombinant gp120, gp140, gp145, gp160, or the protomers of the recombinant HIV-1 Env ectodomain trimer, the linker, and the carrier can be encoded as a single fusion polypeptide such that the recombinant gp120, gp140, gp145, gp160, or the protomers of the recombinant HIV-1 Env ectodomain trimer and the carrier are joined by peptide bonds.

The procedure for attaching a molecule to a polypeptide varies according to the chemical structure of the molecule. Polypeptides typically contain a variety of functional groups; for example, carboxylic acid (COOH), free amine (—NH$_2$) or sulfhydryl (—SH) groups, which are available for reaction with a suitable functional group on a polypeptide. Alternatively, the polypeptide is derivatized to expose or attach additional reactive functional groups. The derivatization may involve attachment of any of a number of linker molecules such as those available from Pierce Chemical Company, Rockford, IL.

It can be advantageous to produce conjugates in which more than one recombinant gp120, gp140, gp145, gp160, or HIV-1 Env ectodomain trimer is conjugated to a single carrier protein. In several embodiments, the conjugation of multiple recombinant gp120, gp140, gp145, gp160, or HIV-1 Env ectodomain trimers to a single carrier protein is possible because the carrier protein has multiple lysine or cysteine side-chains that can serve as sites of attachment.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, recombinantly produced, semi-synthetic or synthetic materials containing one or more amino groups, such as those present in a lysine amino acid residue present in the carrier, to which a reactant moiety can be attached. Carriers that fulfill these criteria are generally known in the art (see, for example, Fattom et al., Infect. Immun. 58:2309-12, 1990; Devi et al., PNAS 88:7175-79, 1991; Szu et al., Infect. Immun. 59:4555-61, 1991; Szu et al., J. Exp. Med. 166:1510-24, 1987; and Pavliakova et al., Infect. Immun. 68:2161-66, 2000). A carrier can be useful even if the antibody that it elicits is not of benefit by itself.

Specific, non-limiting examples of suitable polypeptide carriers include, but are not limited to, natural, semi-synthetic or synthetic polypeptides or proteins from bacteria or viruses. In one embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322); *B. anthracis* LF (for example, as encoded by the complement of bases 149357 to 151786 of GENBANK® Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065), such as tetanus toxin heavy chain C fragment; *P. aeruginosa* exotoxin/toxoid (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094) *C. difficile* toxin B or A, or analogs or mimetics of and combinations of two or more thereof. Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin (KLH), horseshoe crab hemocyanin, Concholepas Concholepas Hemocyanin (CCH), Ovalbumin (OVA), edestin, mammalian serum albumins (such as bovine serum albumin), and mammalian immunoglobulins. In some examples, the carrier is bovine serum albumin.

In some embodiments, the carrier is selected from one of: Keyhole Limpet Hemocyanin (KLH), tetanus toxoid, tetanus toxin heavy chain C fragment, diphtheria toxoid, diphtheria toxin variant CRM197, or H influenza protein D (HiD). CRM197 is a genetically detoxified form of diphtheria toxin; a single mutation at position 52, substituting glutamic acid for glycine, causes the ADP-ribosyltransferase activity of the native diphtheria toxin to be lost. For description of protein carriers for vaccines, see Pichichero, Protein carriers of conjugate vaccines: characteristics, development, and clinical trials, Hum Vaccin Immunother., 9:2505-2523, 2013, which is incorporated by reference herein in its entirety).

Following conjugation of the recombinant gp120, gp140, gp145, gp160, or HIV-1 Env ectodomain trimer to the carrier protein, the conjugate can be purified by a variety of techniques well known to one of skill in the art. The conjugates can be purified away from unconjugated material by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry, for example.

In several embodiments, the disclosed immunogenic conjugates can be formulated into immunogenic composition (such as vaccines), for example by the addition of a pharmaceutically acceptable carrier and/or adjuvant.

B. Recombinant V1V2 Domain and Epitope Scaffold Proteins

In additional embodiments, a recombinant V1V2 domain that comprises the deletion of HIV-1 Env residues 137-152 (HXBc2 numbering) is provided as an isolated protein. The recombinant V1V2 domain elicits an immune response to HIV-1.

The minimal residues of the V1V2 domain are typically understood to be set by the disulfide bridge between cysteine-119 and cysteine-205 of HIV-1 Env (HXBc2 numbering). In some embodiments, the recombinant V1V2 domain comprises or consists essentially of residues 119-205 with the 137-152 V1 deletion (HXBc2 numbering). However, the N- and C-terminal residues of the recombinant V1V2 domain can be any HIV-1 Env position that maintains the structure of the recombinant V1V2 domain with the V1 deletion as described in the examples. In some embodiments, the recombinant V1V2 domain comprises or consists essentially of residues 126-196 with the 137-152 V1 deletion (HXBc2 numbering).

In some embodiments, the recombinant V1V2 domain can be included on an epitope scaffold protein. The recombinant V1V2 domain with the V1 deletion may be scaffolded onto other proteins using a variety of start and stop points, including but not limited to those noted above.

In some embodiments, the scaffold protein is a gp70 protein. For example, the epitope-scaffold protein including a recombinant V1V2 from the clade B CaseA2 strain on the gp70 scaffold comprises or consists of the amino acid sequence set forth as:

```
SEQ ID NO: 8, gp70-ΔV1-V1/V2 CaseA2
QVYNITWEVTNGDRETVWAISGNHPLWTWWPVLTPDLCMLALSGPPHWG

LEYQAPYSSPPGPPCCSGSSGSSAGCSRDCDEPLTSLTPRCNTAWNRLK

LDQVTHKSSEGFYVCPGSHRPREAKSCGGPDSFYCASWGCETTGRVYWK

PSSSWDYITVDNNLTTSQAVQVCKDNKWCNPLAIQFTNAGKQVTSWTTG

HYWGLRLYVSGRDPGLTFGIRLRYQNLGPRVPIGPNPVLADQLSLPRPN
```

-continued

PLPKPAKSPPASVKLTPLCVTLNCIDLR<u>NE</u>IKNCSFNITTSIRDKVQKE

YALFYKLDIVPIDNPKNSTNYRLISCNTSVITQA

However, any protein with a beta-hairpin joining point superimposable on the original disulfide bridge of the V1V2 domain of the HIV-1 Env protein in native prefusion closed conformation may be a scaffold for the recombinant V1V2 domain. Non-limiting examples include typhoid toxin, and antibody Fc domains (PMID: 27707920).

In additional embodiments, the epitope-scaffold protein is any one of the V1V2 scaffolds disclosed in PCT Pub. No. 2013/039792, which is incorporated by reference herein in its entirety.

Suitable methods for identifying and selecting appropriate scaffolds are available and include (but are not limited to) superposition-, grafting-, and de novo-based methods disclosed herein and known to the person of ordinary skill in the art. For example, methods for superposition, grafting and de novo design of epitope-scaffolds are disclosed in U.S. Patent Application Publication No. 2010/0068217, incorporated by reference herein in its entirety.

"Superposition" epitope-scaffolds are based on scaffold proteins having an exposed segment with similar conformation as the target epitope—the backbone atoms in this "superposition-region" can be structurally superposed onto the target epitope with minimal root mean square deviation (RMSD) of their coordinates. Suitable scaffolds are identified by computationally searching through a library of protein crystal structures; epitope-scaffolds are designed by putting the epitope residues in the superposition region and making additional mutations on the surrounding surface of the scaffold to prevent clash or other interactions with the antibody.

"Grafting" epitope-scaffolds utilize scaffold proteins that can accommodate replacement of an exposed segment with the crystallized conformation of the target epitope. For each suitable scaffold identified by computationally searching through all protein crystal structures, an exposed segment is replaced by the target epitope and the surrounding side-chains are redesigned (mutated) to accommodate and stabilize the inserted epitope. Finally, as with superposition epitope-scaffolds, mutations are made on the surface of the scaffold and outside the epitope, to prevent clash or other interactions with the antibody. Grafting scaffolds require that the replaced segment and inserted epitope have similar translation and rotation transformations between their N- and C-termini, and that the surrounding peptide backbone does not clash with the inserted epitope. One difference between grafting and superposition is that grafting attempts to mimic the epitope conformation exactly, whereas superposition allows for small structural deviations.

"De novo" epitope-scaffolds are computationally designed from scratch to optimally present the crystallized conformation of the epitope. This method is based on computational design of a novel fold (Kuhlman, B. et al. 2003 Science 302:1364-1368). The de novo allows design of immunogens that are both minimal in size, so they do not present unwanted epitopes, and also highly stable against thermal or chemical denaturation.

In several embodiments, the native scaffold protein (without epitope insertion) is not a viral envelope protein. In additional embodiments, the scaffold protein is not an HIV protein. In still further embodiments, the scaffold protein is not a viral protein.

C. Polynucleotides and Expression

Polynucleotides encoding a disclosed immunogen are also provided. These polynucleotides include DNA, cDNA and RNA sequences which encode the antigen. One of skill in the art can readily use the genetic code to construct a variety of functionally equivalent nucleic acids, such as nucleic acids which differ in sequence but which encode the same protein sequence, or encode a conjugate or fusion protein including the nucleic acid sequence.

For example, in some embodiments, the polynucleotide encodes a V1 deleted HIV-1 Env sequence such as any one of SEQ ID NOs: 4-7 and 66-67; for example, the polynucleotide comprises the DNA sequence set forth as:

A244 gp160 V1 deleted
(SEQ ID NO: 9)
ATGAGAGTGAAGGAGACACAGATGAATTGGCCAAACTTGTGGAAATGGG

GGACTTTGATCCTTGGGTTGGTGATAATTTGTAGTGCCTCAGACAACTT

GTGGGTTACAGTTTATTATGGGGTTCCTGTGTGGAGAGATGCAGATACC

ACCCTATTTTGTGCATCAGATGCCAAAGCACATGAGACAGAAGTGCACA

ATGTCTGGGCCACACATGCCTGTGTACCCACAGACCCCAACCCACAAGA

AATAGACCTGGAAAATGTAACAGAAAATTTTAACATGTGGAAAAATAAC

ATGGTAGAGCAGATGCAGGAGGATGTAATCAGTTTATGGGATCAAAGTC

TAAAGCCATGTGTAAAGTTAACTCCTCTCTGCGTTACTTTACATTGTAC

TAATGCTAATTTGGAAGTAAGAAACTGTTCTTTTAATATGACCACAGAA

CTAAGAGATAAGAAGCAGAAGGTCCATGCACTTTTTTATAAGCTTGATA

TAGTACCAATTGAAGATAATAACGATAATAGTAAGTATAGGTTAATAAA

TTGTAATACTTCAGTCATTAAGCAGGCTTGTCCAAAGATATCCTTTGAT

CCAATTCCTATACATTATTGTACTCCAGCTGGTTATGCGATTTTAAAGT

GTAATGATAAGAATTTCAATGGGACAGGGCCATGTAAAAACGTCAGCTC

AGTACAATGCACACATGGAATTAAGCCAGTGGTATCAACTCAATTGCTG

TTAAATGGCAGTCTAGCAGAAGAAGAGATAATAATCAGATCTGAAGATC

TCACAAACAATGCCAAAACCATAATAGTGCACCTTAATAAATCTGTAGT

AATCAATTGTACCAGACCCTCCAACAATACAAGAACAAGTATAACTATA

GGACCAGGACAAGTATTCTATAGAACAGGAGACATAATAGGAGATATAA

GAAAAGCATATTGTGAGATTAATGGAACAGAATGGAATAAAGCTTTAAA

ACAGGTAACTGAAAAGTTAAAAGAGCACTTTAATAATAAGCCAATAATC

TTTCAACCACCCTCAGGAGGAGATCTAGAAATTACAATGCATCATTTTA

ATTGTAGAGGAGAATTTTTCTATTGCAATACAACACGACTGTTTAATAA

TACTTGCATAGCAAATGGAACCATAGAGGGGTGTAATGGCAATATCACA

CTTCCATGCAAGATAAAACAAATTATAAACATGTGGCAGGGAGCAGGAC

AAGCAATGTATGCTCCTCCCATCAGTGGAACAATTAATTGTGTATCAAA

TATTACAGGAATACTATTGACAAGAGATGGTGGTGCTACTAATAATACG

AATAACGAGACCTTCAGACCTGGAGGAGGAAATATAAAGGACAATTGGA

GAAATGAATTATATAAATATAAAGTAGTACAAATTGAACCACTAGGAGC

AGCACCCACCAGGGCAAAGAGAAGAGTGGTGGAGAGAGAAAAAAGAGCA

GTGGGAATAGGAGCTATGATCTTTGGGTTCTTAGGAGCAGCAGGAAGCA

-continued

```
CTATGGGCGCGGCGTCAATAACGCTGACGGTACAGGCCAGACAATTATT

GTCTGGTATAGTGCAACAGCAAAGCAATTTGCTGAGGGCTATAGAGGCG

CAGCAGCATCTGTTGCAACTCACAGTCTGGGGCATTAAACAGCTCCAGG

CAAGAGTCCTGGCTGTGGAAAGATACCTAAAGGATCAAAAGTTCCTAGG

ACTTTGGGGCTGCTCTGGAAAAATCATCTGCACCACTGCAGTGCCCTGG

AACTCCACTTGGAGTAATAAATCTCTTGAAGAGATTTGGAACAACATGA

CATGGATAGAATGGGAGAGAGAAATTAGCAATTACACAAACCAAATATA

TGAGATACTTACAAAATCGCAGGACCAGCAGGACAGGAATGAAAAGGAT

TTGTTAGAATTGGATAAATGGGCAAGTCTGTGGACTTGGTTTGACATAA

CAAATTGGCTGTGGTATATAAAAATATTTATAATGATAGTGGGAGGTTT

AATAGGATTAAGAATAATTTTTGCTGTGCTTTCTATAGTGAATAGAGTT

AGGCAGGGATACTCACCTTTGTCTTTCCAGACCCCTTGCCATCATCAGA

GGGAACCCGACAGACCCGAAAGAATCGAAGAAGAAGGTGGCGAGCAAGG

CAGAGACAGATCCGTGCGATTAGTGAGCGGATTCTTAGCTCTTGCATGG

GACGATCTACGGAGCCTGTGCCTCTTCAGCTACCACCGCTTGAGAGACT

TCATCTTGATTGCAGCGAGGACTGTGGAACTTCTGGGACGCAGCAGTCT

CAAGGGACTGAGACGGGGGTGGGAAGGCCTCAAATATCTGGGGAATCTT

CTGTTATATTGGGGTCAGGAACTAAAAATTAGTGCTATTTCTTTGCTTG

ATGCTACAGCAATAGCAGTAGCGGGGTGGACAGATAGGGTTATAGAAGT

AGCACAAGGAGCTTGGAAAGCCATTCTCCACATACCTAGAAGAATCAGA

CAGGGCTTAGAAAGGGCTTTGCAATAA
```

In several embodiments, the nucleic acid molecule encodes a precursor of a protomer of a disclosed HIV-1 Env trimer, that, when expressed in cells under appropriate conditions, forms HIV-1 Env trimers and is processed into the mature form of the HIV-1 Env protein.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4$^{th}$ ed., Cold Spring Harbor, New York, 2012) and Ausubel et al. (In Current Protocols in Molecular Biology, John Wiley & Sons, New York, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed immunogen can include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed immunogen can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the disclosed immunogen can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), 4th Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022), or HEK-293F cells.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., *J. Virol*, 79, 8828-8834, 2005, which is incorporated by reference herein).

Modifications can be made to a nucleic acid encoding a disclosed immunogen without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

D. Viral Vectors

A nucleic acid molecule encoding a disclosed immunogen (e.g., a recombinant gp120 protein or a HIV-1 Env ectodomain trimer comprising the recombinant gp120 protein) can be included in a viral vector, for example, for expression of the immunogen in a host cell, or for immunization of a subject as disclosed herein. In some embodiments, the viral vectors are administered to a subject as part of a prime-boost vaccination. In several embodiments, the viral vectors are included in a vaccine, such as a primer vaccine or a booster vaccine for use in a prime-boost vaccination.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed, that can be used to express the disclosed antigens, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158: 67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a disclosed recombinant HIV-1 Env ectodomain or immunogenic fragment thereof. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Replication competent and deficient adenoviral vectors (including singly and multiply replication deficient adenoviral vectors) can be used with the disclosed embodiments. Examples of replication-deficient adenoviral vectors, including multiply replication-deficient adenoviral vectors, are disclosed in U.S. Pat. Nos. 5,837,511; 5,851,806; 5,994, 106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/02231 1.

E. Virus-Like Particles

In some embodiments, a virus-like particle (VLP) is provided that includes a disclosed immunogen (e.g., a recombinant HIV-1 Env ectodomain or immunogenic fragment thereof). VLPs lack the viral components that are required for virus replication and thus represent a highly attenuated, replication-incompetent form of a virus. However, the VLP can display a polypeptide (e.g., a recombinant HIV-1 Env protein) that is analogous to that expressed on infectious virus particles and should be equally capable of eliciting an immune response to HIV when administered to a subject. Virus like particles and methods of their production are known, and viral proteins from several viruses are known to form VLPs, including human papillomavirus, HIV (Kang et al., Biol. Chem. 380:353-64 (1999)), Semliki-Forest virus (Notka et al., Biol. Chem. 380:341-52 (1999)), human polyomavirus (Goldmann et al., J. Virol. 73:4465-9 (1999)), rotavirus (Jiang et al., Vaccine 17:1005-13 (1999)), parvovirus (Casal, Biotechnology and Applied Biochemistry, Vol 29, Part 2, pp 141-150 (1999)), canine parvovirus (Hurtado et al., J. Virol. 70:5422-9 (1996)), hepatitis E virus (Li et al., J. Virol. 71:7207-13 (1997)), and Newcastle disease virus. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

The virus like particle can include any of the recombinant gp120 proteins or recombinant HIV-1 Env ectodomain trimers or an immunogenic fragments thereof, that are disclosed herein.

III. Immunogenic Compositions

Immunogenic compositions comprising a disclosed immunogen and a pharmaceutically acceptable carrier are also provided. Such compositions can be administered to subjects by a variety of administration modes, for example, intramuscular, subcutaneous, intravenous, intra-arterial, intra-articular, intraperitoneal, or parenteral routes. Methods for preparing administrable compositions are described in more detail in such publications as *Remingtons Pharmaceutical Sciences*, 19$^{th}$ Ed., Mack Publishing Company, Easton, Pennsylvania, 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The pharmaceutical composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the composition can be provided as a sterile composition. The pharmaceutical composition typically contains an effective amount of a disclosed immunogen and can be prepared by conventional techniques. Typically, the amount of immunogen in each dose of the immunogenic composition is selected as an amount which elicits an immune response without significant, adverse side effects. In some embodiments, the composition can be provided in unit dosage form for use to elicit an immune response in a subject, for example, to prevent HIV-1 infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

IV. Methods of Inducing an Immune Response

The disclosed immunogens (e.g., a recombinant gp120 protein comprising a V1-deletion or HIV-1 Env trimer containing the recombinant gp120 protein), polynucleotides and vectors encoding the disclosed immunogens, and compositions including same, can be used in methods of inducing an immune response to HIV-1 to treat or inhibit (including prevent) an HIV-1 infection.

When inhibiting or treating HIV-1 infection, the methods can be used either to avoid infection in an HIV-1 seronegative subject (e.g., by inducing an immune response that protects against HIV-1 infection), or to treat existing infection in an HIV-1 seropositive subject. The HIV-1 seropositive subject may or may not carry a diagnosis of AIDS. Hence in some embodiments the methods involve selecting a subject at risk for contracting HIV-1 infection, or a subject at risk of developing AIDS (such as a subject with HIV-1 infection), and administering a disclosed immunogen to the subject to elicit an immune response to HIV-1 in the subject.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize HIV-1 infection. These and other routine methods allow the clinician to select patients in need of therapy using the methods and pharmaceutical compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The disclosed immunogens can be used in coordinate (or prime-boost) immunization protocols or combinatorial formulations. In certain embodiments, novel combinatorial immunogenic compositions and coordinate immunization protocols employ separate immunogens or formulations, each directed toward eliciting an anti-HIV-1 immune response, such as an immune response to HIV-1 Env protein. Separate immunogenic compositions that elicit the anti-HIV-1 immune response can be combined in a polyvalent immunogenic composition administered to a subject in a single immunization step, or they can be administered separately (in monovalent immunogenic compositions) in a coordinate immunization protocol.

In one embodiment, a suitable immunization regimen includes at least two separate inoculations with one or more immunogenic compositions including a disclosed immunogen, with a second inoculation being administered more than about two, about three to eight, or about four, weeks following the first inoculation. A third inoculation can be administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. Alternatively, the T cell populations can be monitored by conventional methods. In addition, the clinical condition of the subject can be monitored for the desired effect, e.g., prevention of HIV-1 infection or progression to AIDS, improvement in disease state (e.g., reduction in viral load), or reduction in transmission frequency to an uninfected partner. If such monitoring indicates that vaccination is sub-optimal, the subject can be boosted with an additional dose of immunogenic composition, and the vaccination parameters can be modified in a fashion expected to potentiate the immune response. Thus, for example, a dose of a disclosed immunogen can be increased or the route of administration can be changed.

It is contemplated that there can be several boosts, and that each boost can be a different immunogen. It is also contemplated in some examples that the boost may be the same immunogen as another boost, or the prime.

The prime and the boost can be administered as a single dose or multiple doses, for example, two doses, three doses, four doses, five doses, six doses or more can be administered to a subject over days, weeks or months. Multiple boosts can also be given, such one to five, or more. Different dosages can be used in a series of sequential inoculations. For example, a relatively large dose in a primary inoculation and then a boost with relatively smaller doses. The immune response against the selected antigenic surface can be elicited by one or more inoculations of a subject.

In several embodiments, a disclosed immunogen can be administered to the subject simultaneously with the administration of an adjuvant. In other embodiments, the immunogen can be administered to the subject after the administration of an adjuvant and within a sufficient amount of time to elicit the immune response.

Determination of effective dosages in this context is typically based on animal model studies followed up by human clinical trials and is guided by administration protocols that significantly reduce the occurrence or severity of targeted disease symptoms or conditions in the subject, or that elicit a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer an effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Dosage can be varied by the attending clinician to maintain a desired concentration at a target site (for example, systemic circulation). Higher or lower concentrations can be selected based on the mode of delivery, for example, transepidermal, rectal, oral, pulmonary, or intranasal delivery versus intravenous or subcutaneous delivery. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

A non-limiting range for an effective amount of the disclosed immunogen within the methods and immunogenic compositions of the disclosure is about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example, 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight. In some embodiments, the dosage includes a set amount of a disclosed immunogen such as from about 1-300 µg, for example, a dosage of about 1, 2, 3, 4, 5, 6, 7, 8, 9, 10, 15, 20, 30, 40, 50, 60, 70, 80, 90, 100, 150, 200, 250, or about 300 µg.

The dosage and number of doses will depend on the setting, for example, in an adult or anyone primed by prior HIV-1 infection or immunization, a single dose may be a sufficient booster. In naïve subjects, in some examples, at least two doses would be given, for example, at least three doses. In some embodiments, an annual boost is given, for example, along with an annual influenza vaccination.

HIV-1 infection does not need to be completely inhibited for the methods to be effective. For example, elicitation of an immune response to HIV-1 with one or more of the disclosed immunogens can reduce or inhibit HIV-1 infection by a desired amount, for example, by at least 10%, at least 20%, at least 50%, at least 60%, at least 70%, at least 80%, at least 90%, at least 95%, at least 98%, or even at least 100% (elimination or prevention of detectable HIV-1 infected cells), as compared to HIV-1 infection in the absence of the therapeutic agent. In additional examples, HIV-1 replication can be reduced or inhibited by the disclosed methods. HIV-1 replication does not need to be completely eliminated for the method to be effective. For example, the immune response elicited using one or more of the disclosed immunogens can reduce HIV-1 replication by a desired amount, for example, by at least 10%, at least 20%, at least 50%, at least 60%, at least 70%, at least 80%, at least 90%, at least 95%, at least 98%, or even at least 100% (elimination or prevention of detectable HIV-1 replication), as compared to HIV-1 replication in the absence of the immune response.

To successfully reproduce itself, HIV-1 must convert its RNA genome to DNA, which is then imported into the host cell's nucleus and inserted into the host genome through the action of HIV-1 integrase. Because HIV-1's primary cellular target, CD4+ T-Cells, can function as the memory cells of the immune system, integrated HIV-1 can remain dormant for the duration of these cells' lifetime. Memory T-Cells may survive for many years and possibly for decades. This latent HIV-1 reservoir can be measured by co-culturing CD4+ T-Cells from infected patients with CD4+ T-Cells from uninfected donors and measuring HIV-1 protein or RNA (See, e.g., Archin et al., *AIDS,* 22:1131-1135, 2008). In some embodiments, the provided methods of treating or inhibiting HIV-1 infection include reduction or elimination of the latent reservoir of HIV-1 infected cells in a subject. For example, a reduction of at least 10%, at least 20%, at least 50%, at least 60%, at least 70%, at least 80%, at least 90%, at least 95%, at least 98%, or even at least 100% (elimination of detectable HIV-1) of the latent reservoir of HIV-1 infected cells in a subject, as compared to the latent reservoir of HIV-1 infected cells in a subject in the absence of the treatment with one or more of the provided immunogens.

Following immunization of a subject, serum can be collected from the subject at appropriate time points, frozen, and stored for neutralization testing. Methods to assay for neutralization activity, and include, but are not limited to, plaque reduction neutralization (PRNT) assays, microneutralization assays, flow cytometry based assays, single-cycle infection assays (e.g., as described in Martin et al. (2003) *Nature Biotechnology* 21:71-76), and pseudovirus neutralization assays (e.g., as described in Georgiev et al. (*Science,* 340, 751-756, 2013), Seaman et al. (*J. Virol.,* 84, 1439-1452, 2005), and Mascola et al. (*J. Virol.,* 79, 10103-10107, 2005), each of which is incorporated by reference herein in its entirety. In some embodiments, the serum neutralization activity can be assayed using a panel of HIV-1 pseudoviruses as described in Georgiev et al., Science, 340, 751-756, 2013 or Seaman et al. J. Virol., 84, 1439-1452, 2005. Briefly, pseudovirus stocks are prepared by co-transfection of 293T cells with an HIV-1 Env-deficient backbone and an expression plasmid encoding the Env gene of interest. The serum to be assayed is diluted in Dulbecco's modified Eagle medium-10% FCS (Gibco) and mixed with pseudovirus. After 30 min, 10,000 TZM-bl cells are added, and the plates are incubated for 48 hours. Assays are developed with a luciferase assay system (Promega, Madison, WI), and the relative light units (RLU) are read on a luminometer (Perkin-Elmer, Waltham, MA). To account for background, a cutoff of $ID_{50} \geq 40$ can be used as a criterion for the presence of serum neutralization activity against a given pseudovirus.

In some embodiments, administration of an effective amount of one or more of the disclosed immunogens to a subject (e.g., by a prime-boost administration of a DNA vector encoding a disclosed immunogen followed by a protein boost) elicits a neutralizing immune response in the subject, wherein serum from the subject neutralizes, with an $ID_{50} \geq 40$, at least 10% (such as at least 15%, at least 20%, at least 30%, at least 40%, at least 50%, or at least 70%) of pseudoviruses is a panel of pseudoviruses including the HIV-1 Env proteins listed in Table S5 or Table S6 of Georgiev et al. (Science, 340, 751-756, 2013), or Table 1 of Seaman et al. (J. Virol., 84, 1439-1452, 2005).

One approach to administration of nucleic acids is direct immunization with plasmid DNA, such as with a mammalian expression plasmid. Immunization by nucleic acid constructs is taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil ATM (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a disclosed immunogen can be administered to a subject to elicit an immune response to HIV-1 gp120. In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed immunogen (such as a protomer of a HIV-1 Env ectodomain trimer) can be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding a disclosed immunogen (such as a protomer of a HIV-1 Env ectodomain trimer) is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

In some embodiments, an immunization protocol that mirrors the "rv144" trial is used with the immunogens provided herein. As discussed in Rerks-Ngarm et al. (New Eng J Med. 361 (23): 2209-2220, 2009, incorporated by reference herein) rv144 was a phase III trial of a prime-boost HIV-1 vaccine consisting of four injections of ALVAC HIV (vCP1521) followed by two injections of AIDSVAX B/E. ALVAC HIV (vCP1521) is a canarypox vector containing HIV-1 env, gag, and pol genes, and AIDSVAX B/E is a genetically engineered form of gp120. The env gene of ALVAC HIV (vCP1521) and the AIDSVAX B/E gp120 can be modified to encode or contain the V1 deletion provided herein (deletion of residues 137-152 according to HXBc2 numbering) and administered to a subject using the rv144 prime-boost protocol (or any other suitable protocol).

In some embodiments, a modified form of the "rv144" immunization protocol can be used. For example, there can be additional (or fewer) prime or boost administrations, and the initial prime can be a DNA based immunization including a plasmid vector encoding HIV-1 Env with or without the V1 deletion as disclosed herein.

V. Prognosis of an Immune Response to HIV-1

Also provided herein is a method of interrogating an immune response to HIV-1 in a subject (such as a human subject) to predict if the immune response is or is not likely to inhibit HIV-1 infection in the subject. In some embodiments, the method provides a prognosis of an immune response to HIV-1 in a subject. In some embodiments, the method comprises contacting a biological sample from a subject with one or more peptides comprising or consisting of the amino acid sequence of HIV Env residues 141-154 (V1a), HIV Env residues 157-173 (V2b), or HIV Env residues 166-180 (V2c) according to the HXBc2 numbering system, and detecting specific binding activity of antibodies in the biological sample to the one or more peptides. As described in the examples, subjects who received an HIV-1 vaccine and subsequently exhibit antibody binding activity for the V2b or V2c peptide are less likely to become infected with HIV-1 subsequent to viral challenge relative to unvaccinated controls. Further, subjects who received an HIV-1 vaccine and subsequently exhibit antibody binding activity for the V1a peptide are more likely to become infected with HIV-1 subsequent to viral challenge relative to unvaccinated controls. Accordingly, detecting specific binding activity of antibodies in the biological sample to the V2b peptide or to the V2c peptide identifies the biological sample as originating from a subject with an immune response that inhibits HIV-1 infection, and detecting specific binding activity of antibodies in the biological sample to the V1a peptide identifies the biological sample as originating from a subject with an immune response that does not inhibit HIV-1 infection, The V1a, V2b, and V2c peptides for use in the disclosed methods can include any HIV-1 Env peptide sequence containing the relevant HXBc2 residues, that is residues 141-154 for the V1a peptide, residues 157-173 for the V2b, and residues 166-180 for the V2c peptide. Exemplary peptide sequences for use in the disclosed methods are provided in the following table.

TABLE 1

Exemplary V1a, V2b, and V2c peptide sequences

| SEQ ID NO | Sequence | HIV Strain (isolate) | Subtype |
|---|---|---|---|
| Exemplary V1a peptide sequences (Hxbc2 numbering 127-140) | | | |
| 26 | VTLHCTNANLTNAN | 90TH_CM235 | CRF01_AE |
| 27 | VTLNCTDLRNTTNT | 84US_MNp | B.MN |
| 28 | VTLNCTEVNVTRNV | 96ZM651 gp120-TM | C |
| Exemplary V2b peptide sequences (Hxbc2 numbering 157-173) | | | |
| 29 | CSFNMTTELRDKKQKVH | 90TH_CM235 | CRF01 AE |
| 30 | CSFNITTSIRDKMQKEY | 84US_MNp | B.MN |
| 31 | CSFNITTELKDKKKNVY | 96ZM651 gp120-TM | C |
| Exemplary V2c peptide sequences (Hxbc2 numbering 167-180) | | | |
| 32 | DKKQKVHALFYKLD | 90TH_CM235 | CRF01_AE |
| 33 | DKMQKEYALLYKLD | 84US_MNp | B.MN |
| 34 | DKKKNVYALFYKLD | 96ZM651 gp120-TM | C |

The peptides for use in the disclosed methods comprise, consist essentially of, or consist of the V1a, V2b, or V2c sequence. In some embodiments, the V1a, V2b, and/or V2c peptide used in the assay is a cocktail of V1a, V2b, or V2c peptides from different HIV-1 strains. The V1a, V2b, and V2c peptides can be from HIV-1 Env from any HIV-1 strain, for example as listed in the Los Alamos HIV sequence database (hiv.lanl.gov).

In some embodiments, the peptide comprises, consists essentially of, or consists of the V1a, V2b, or V2c sequence and further comprises additional heterologous amino acids, such as a peptide tag. The peptides for use in the disclosed methods can be any suitable length of amino acids. In some embodiments, the peptides are no more than 50 amino acids in length, such as no more than 40 amino acids in length, or no more than 30 amino acids in length, or no more than 20 amino acids in length. In some embodiments, the peptides for use in the disclosed embodiments are from 10 to 30 amino acids in length, such as from 10 to 20 amino acids in length.

The biological sample can be any sample from a subject containing antibodies, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. In some embodiments, the biological sample is obtained from a subject prior to assessment using the methods disclosed herein.

In one embodiment, the peptide is labeled with a detectable marker. Non-limiting examples of suitable labels are known and include various enzymes, prosthetic groups, fluorescent materials, luminescent materials, magnetic agents, and radioactive materials.

In some embodiments, a subject is selected for assessment using the method of prognosis of the immune response to HIV-1. Suitable subjects include, for example, individuals exposed to HIV-1 virus, or who have an HIV-1 infection, as well as subjects with or with an HIV-1 infection who have been administered an HIV-1 vaccine. For example, a biological sample from a subject with a known HIV-1 infection can be tested for specific binding activity to the V1a, V2b, and V2c peptides as described above to determine if the subject has produced an immune response to HIV-1 that is or is not likely to inhibit the HIV-1 infection. In another example, a biological sample from a subject without an HIV-1 infection who has been administered an HIV-1 vaccine can be tested for specific binding activity to the V1a, V2b, and V2c peptides as described above to determine if the vaccination elicited production of an immune response to HIV-1 in the subject that is or is not likely to inhibit a subsequent HIV-1 infection. In another example, a biological sample from a subject with an HIV-1 infection who has been administered an HIV-1 vaccine can be tested for specific binding activity to the V1a, V2b, and V2c peptides as described above to determine if the vaccination elicited production of an immune response to HIV-1 in the subject that is or is not likely to inhibit the HIV-1 infection.

In several embodiments, detection of specific binding activity for the V2b or V2c peptides indicates that the immune response to HIV-1 in the subject is likely to inhibit HIV-1 infection, for example, the immune response is likely to prevent or reduce subsequent infection of the subject with HIV-1, or is likely to inhibit progression of HIV-1 disease in a subject already infected with HIV-1. Detecting specific binding activity for the V2b or V2c peptides includes, for example, detecting a positive signal in an appropriate assay as well as detecting an increase in binding activity relative to a suitable control.

In some embodiments, detection of specific binding activity for the V2b or V2c peptides indicates that the immune response to HIV-1 in the subject has a good prognosis.

The good prognosis can refer to any positive clinical outcome, such as, but not limited to, an increase in likelihood of survival (such as overall survival or AIDS-free survival), an increase in the time of survival (e.g., more than 5 years, more than one year, or more than two months), absence or reduction of HIV-1 replication, likelihood of benefit of the subject to therapy (e.g., HAART therapy), an increase in response to therapy (e.g., HAART therapy), or the like. The relative "goodness" of a prognosis, in various examples, may be in comparison to historical measure of other subjects with the same or similar infection, or similar presentation of symptoms of HIV-1 infection, for example.

In several embodiments, detection of specific binding activity for the V1a peptide indicates that the immune response to HIV-1 in the subject is not likely to inhibit HIV-1 infection, for example, the immune response is not likely to prevent or reduce subsequent infection of the subject with HIV-1, or is not likely to inhibit progression of HIV-1 disease in a subject already infected with HIV-1. Detecting specific binding activity for the V1a peptide includes, for example, detecting a positive signal in an appropriate assay as well as detecting an increase in binding activity relative to a suitable control.

In some embodiments, detection of specific binding activity for the V1a peptide indicates that the immune response to HIV-1 in the subject has a poor prognosis.

The poor prognosis can refer to any negative clinical outcome, such as, but not limited to, a decrease in likelihood of survival (such as overall survival or AIDS-free survival), a decrease in the time of survival (e.g., less than 5 years, less than one year, or less than two months), presence or increase in HIV-1 replication, an increase in the severity of disease, resistance to therapy (e.g., HAART therapy), an decrease in response to therapy (e.g., HAART therapy), or the like. The relative "poorness" of a prognosis, in various examples, may be in comparison to historical measure of other subjects with the same or similar infection, or similar presentation of symptoms of HIV-1 infection, for example.

Antibodies in the biological sample specific for the V1a, V2b, and/or V2c peptides can be detected by any suitable assay, including, but not limited to, ELISA, immunoprecipitation, generic binding to solid supports, surface plasmon resonance. In some embodiments, antibodies in the biological sample specific for the V1a, V2b, and V2c peptides can be detected by any suitable immunoassay one of a number of immunoassay, such as those presented in Harlow and Lane, *Using Antibodies: A Laboratory Manual*, CSHL, New York, 1999). In some embodiments, a standard immunoassay format (such as ELISA, Western blot, or RIA assay) can be used to measure antibody levels. Immunohistochemical techniques can also be utilized for antibody detection and quantification, for example using formalin-fixed, paraffin embedded (FFPE) slides coupled with an automated slide stainer. General guidance regarding such techniques can be found in Bancroft et al. (*Theory and Practice of Histological Techniques*, 8$^{th}$ ed., Elsevier, 2018) and Ausubel et al. (In Current Protocols in Molecular Biology, John Wiley & Sons, New York, through supplement 104, 2013).

For the purposes of quantitating the disclosed proteins, a sample that includes antibodies can be used. Quantitation of antibodies can be achieved by immunoassay. In some embodiments, a level of specific binding antivity for the V1a, V2b, and/or V2c peptides can be assessed in the sample and optionally in a corresponding control sample, such as a sample from a subject known to have a protective or non-protective immune response to HIV-1 or other control (such as a standard value or reference value). A significant increase or decrease in the amount can be evaluated using statistical methods known in the art.

In some embodiments, the method of detection can include contacting a cell or sample, with the V1a, V2b, and/or V2c peptide or conjugate thereof (e.g. a conjugate including a detectable marker) under conditions sufficient to form an immune complex, and detecting the immune complex (e.g., by detecting a detectable marker conjugated to the peptide.

EXAMPLES

The following examples are provided to illustrate particular features of certain embodiments, but the scope of the claims should not be limited to those features exemplified.

Example 1

Unmasking the α-Helix Conformation of V2 by V1 Deletion Augments HIV-1 Vaccine Efficacy ALVAC-gp120/alum HIV vaccine candidates decrease the risk of virus acquisition in both humans and macaques. Antibodies to the envelope variable V2 region 2 (V2) is the primary correlate of risk in both species. This example shows that serum antibodies to the envelope variable region 1 (V1) from macaques vaccinated with these vaccine modalities interfere in vitro with binding of V2-specific antibodies. Furthermore, the α-V1 antibody levels in vaccinated macaques correlated with an increased risk of $SIV_{mac251}$ acquisition. Accordingly, V1-deleted envelope immunogens elicited higher titers of antibodies to V2 in macaques. Strikingly, however, only the V1-deleted immunogen engineered to maintain a V2 α-helix conformation was associated with a decreased risk of $SIV_{mac251}$ acquisition correlating with serum levels of antibodies to a V2 α-helix diagnostic peptide. These data confirm V2 as a viral vulnerability site and support the development and testing of V1-deleted HIV immunogens in humans.

The HIV recombinant Canarypox-derived vector (AL-VAC) in combination with two gp120-envelope proteins formulated in alum afforded limited but significant efficacy (31.2%) in the RV144 HIV vaccine trial (Rerks-Ngarm et al., N Engl J Med, 361, 2209-2220, 2009). This vaccine regimen induced high titers of binding antibodies to the HIV-1 envelope proteins and envelope-specific $CD4^+$ T cells in nearly all vaccines and negligible $CD8^+$ T cell responses (Rerks-Ngarm et al., N Engl J Med, 361, 2209-2220, 2009). The primary correlates of risk of HIV acquisition were the titers of serum IgG to the gp70-V1/V2 scaffold (Haynes et al., N Engl J Med, 366, 1275-1286, 2012) and to linear V2 peptides (Zolla-Pazner et al., PLOS One, 9, e87572, 2014; Gottardo et al., PLOS One, 8, e75665, 2013). Sieve analysis demonstrated genetic markers of immunologic pressure at positions 169 and 181 in the more conserved carboxyl-terminus region of V2 (Rolland et al., Nature, 490, 417-420, 2012), corresponding to sites comprising, or allosterically influencing, gp120 binding to the α4β7 integrin receptor. In the macaque model, vaccination with a similar SIV-based vaccine platform also significantly decreased the risk of virus acquisition (44% efficacy) following mucosal exposure of immunized macaques to repeated low doses of $SIV_{mac251}$ (Pegu et al., J Virol, 87, 1708-1719, 2013; Gordon et al., J Immunol, 193, 6172-6183, 2014; Klionsky et al., Autophagy, 12, 1-222, 2016). In this example, linear peptide arrays encompassing the entire gp120 of $SIV_{K6W}$ were used to characterize the serum antibody response to V1 and V2 in a cohort of 78 vaccinated macaques immunized with ALVAC-SIV/gp120 based vaccines whereby the alum adjuvant was substituted with the more immunogenic MF59 (Vaccari et al., Nat Med, 22, 762-770, 2016) or the ALVAC-SIV prime was substituted with either the DNA-SIV or Ad26-SIVprime (Vaccari et al., Nat Med, 24, 847-856, 2018). The efficacy of these vaccine regimens was evaluated as the average risk of virus acquisition following intrarectal exposure to low repeated doses of the identical $SIV_{mac251}$ and ranged between 9% and 52%. For simplicity, these vaccine regimens are referred to as protective (39 animals; vaccine efficacy ranges from 44 to 52%; p=0. <0.05) or non-protective (39 animals, vaccine efficacy range 9 to 13%, p>0.05) when compared to controls (FIGS. 4A-4B) (Vaccari et al., Nat Med, 22, 762-770, 2016; Vaccari et al., Nat Med, 24, 847-856, 2018).

Figure 1A:
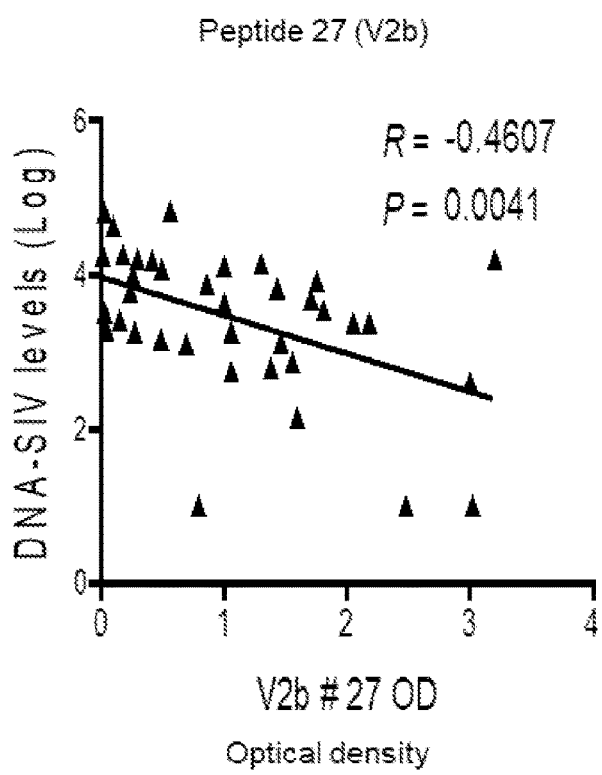
Figure 1B:
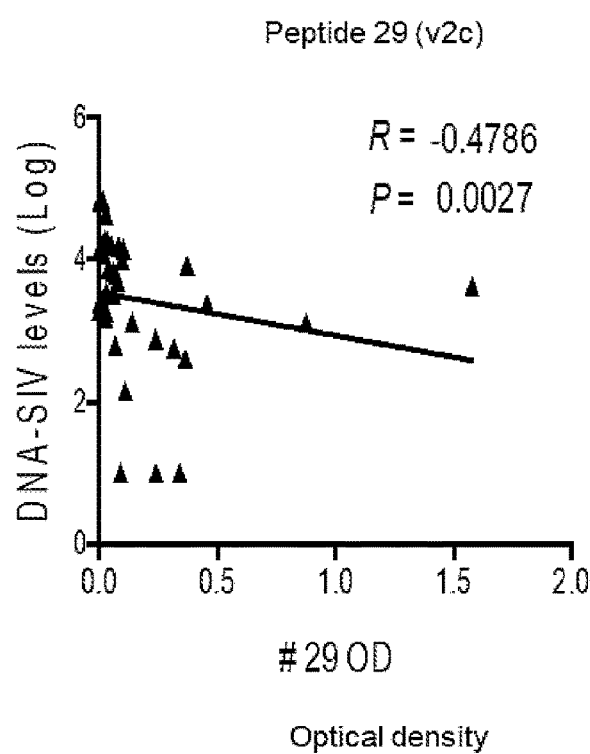
Figure 1C:
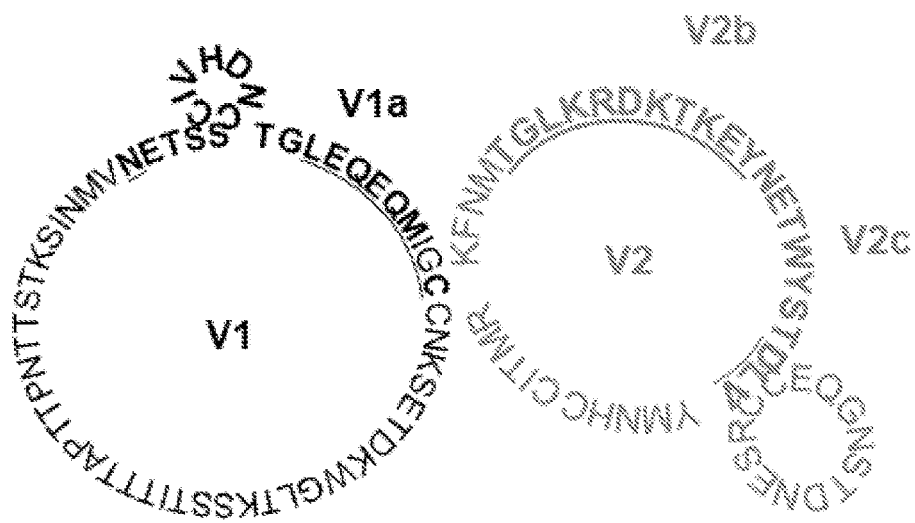
Figure 5C:
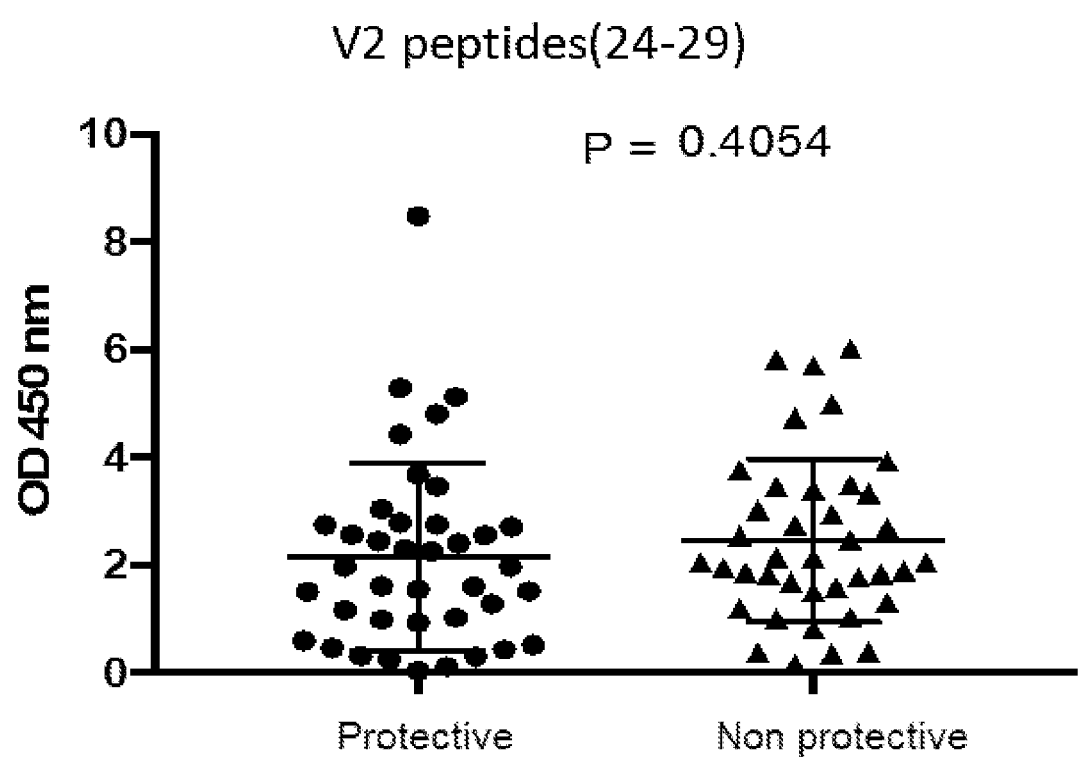
Figure 5D:
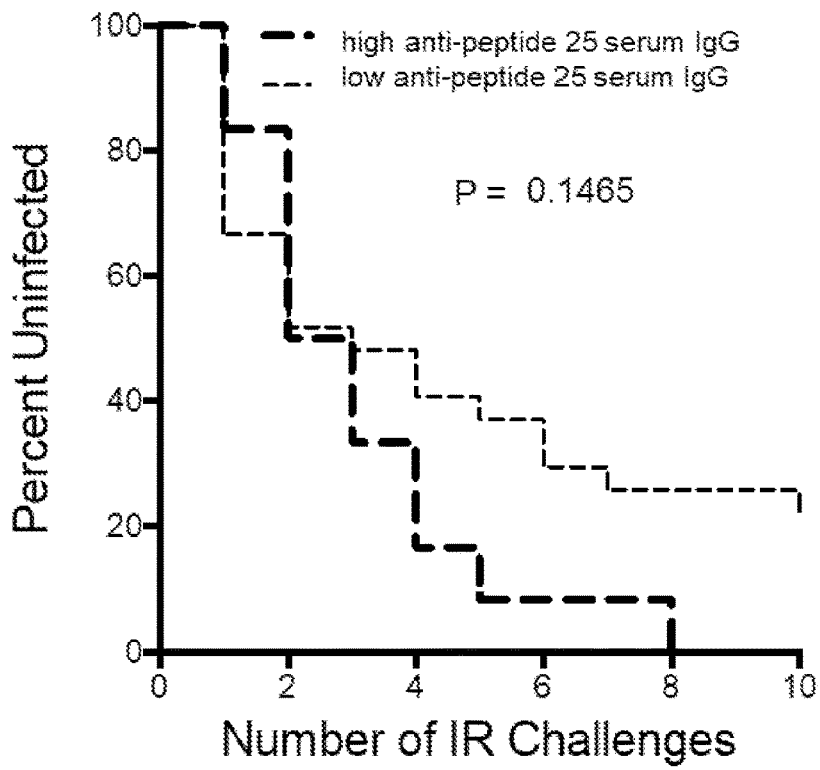
Figure 5D:
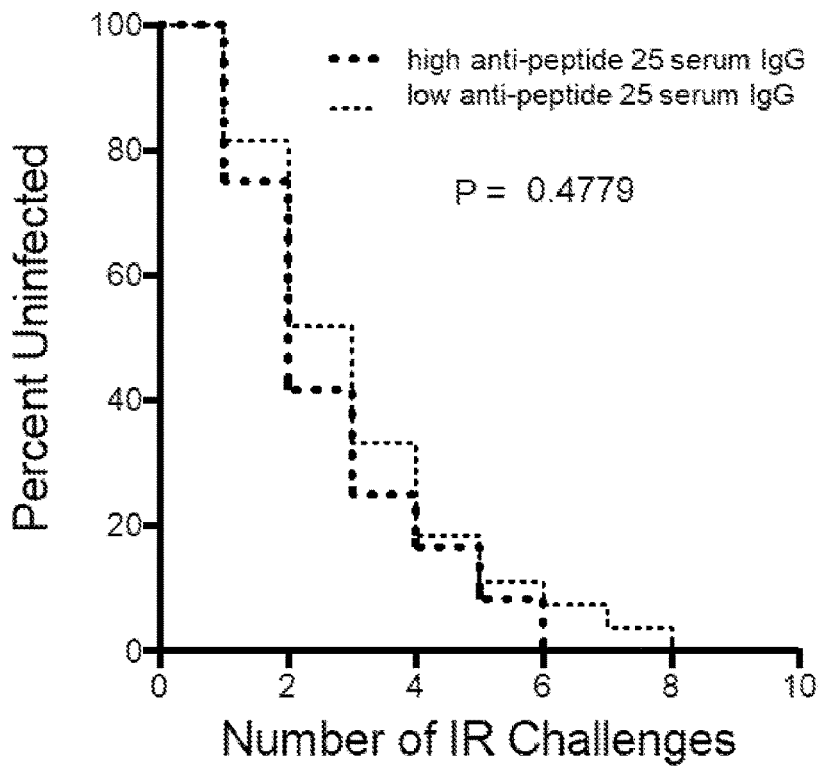
Figure 5E:
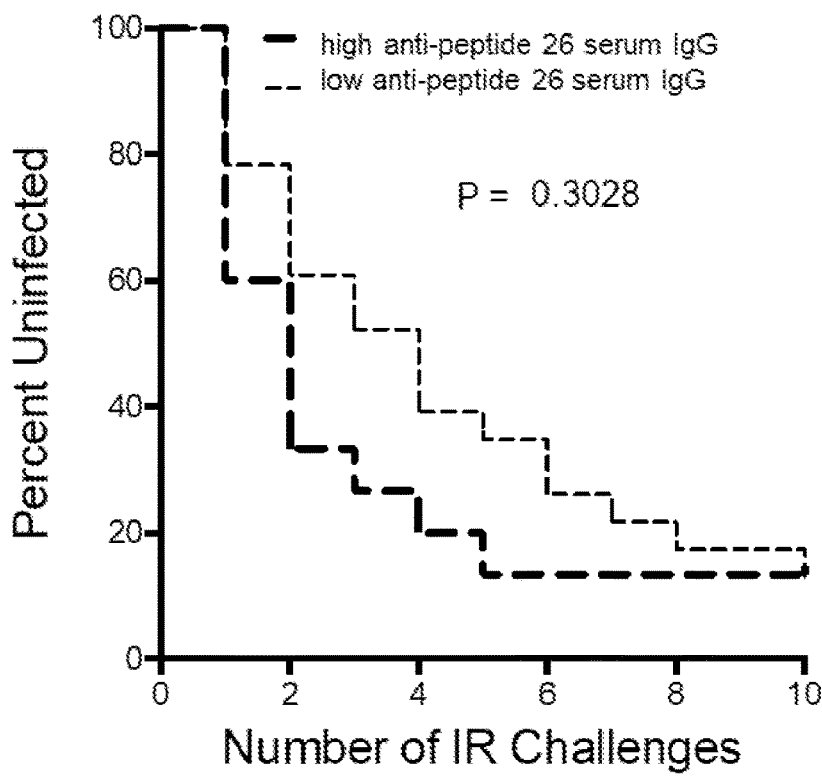
Figure 5E:
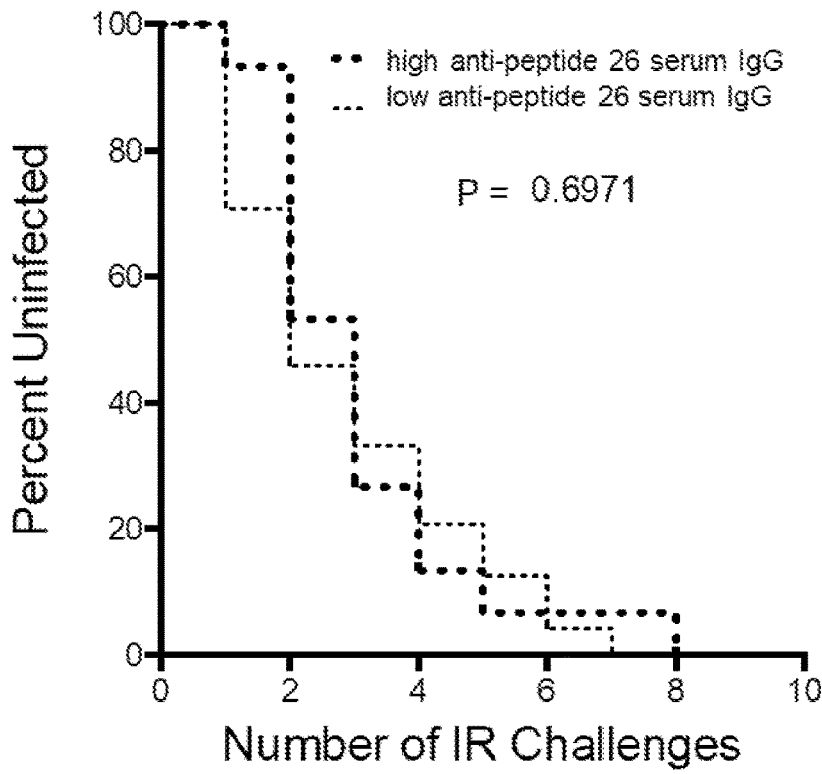
Figure 5F:
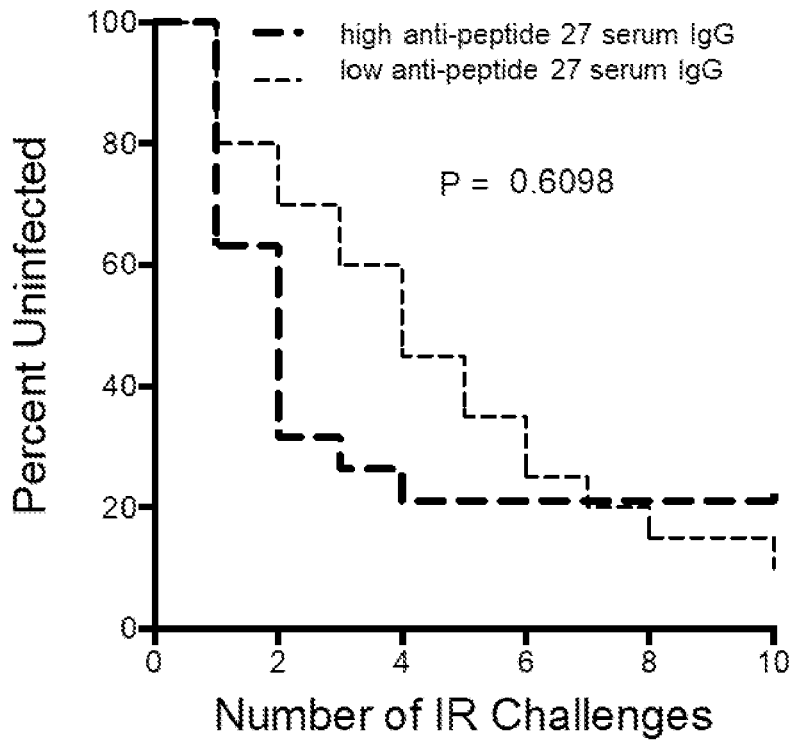
Figure 5F:
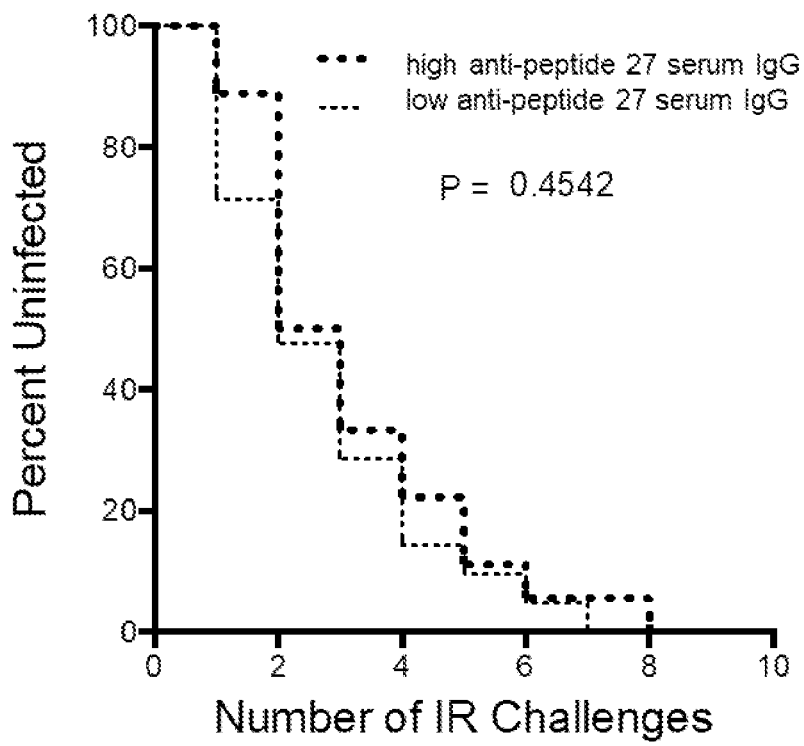
Figure 5H:
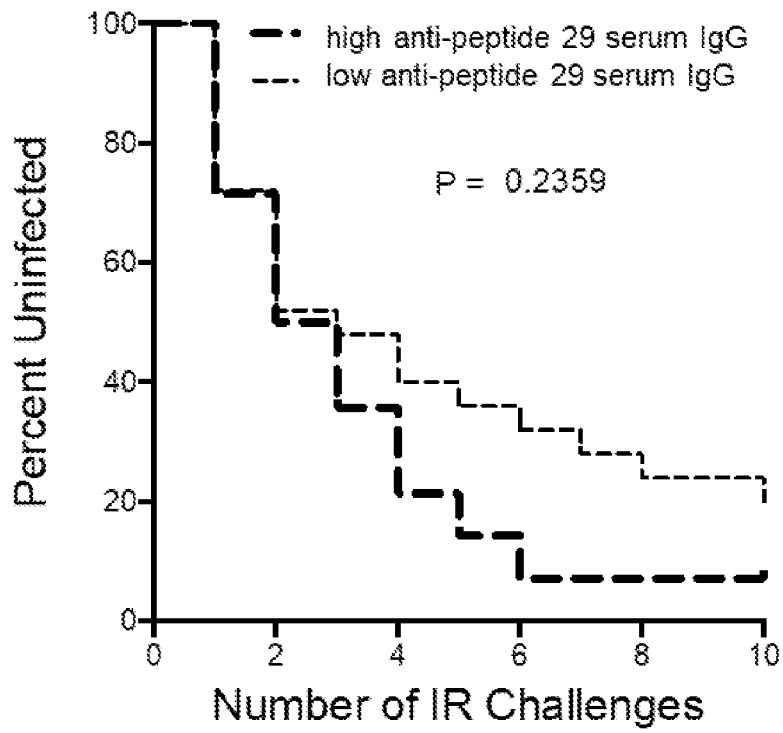
Figure 5H:
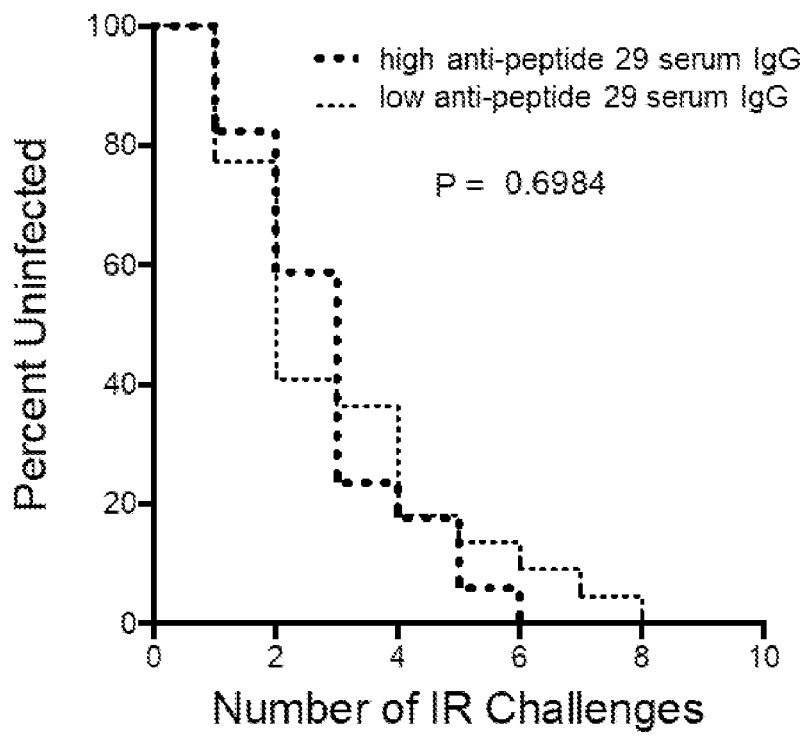

It was shown previously that mucosal antibody levels to conformational cyclic V2 correlated with decreased $SIV_{mac251}$ acquisition in animals immunized with protective vaccines (Vaccari et al., Nat Med, 24, 847-856, 2018). Here it is shown that the levels of serum antibodies to all linear peptides encompassing V2 (FIGS. 5A-5B) did not differ between the animals immunized with protective and non protective vaccines (FIG. 5C), and none of the individual linear V2 peptides correlated with $SIV_{mac251}$ acquisition (FIG. 5D). The levels of serum recognition of the V2 peptides 27 and 29 (hereafter referred as to V2b and V2c), however, was associated with a decreased amount of SIV DNA in the mucosa of the vaccinated animals that became infected following immunization (FIG. 1A-1B). Notably, V2b and V2c (FIG. 1C) correspond to the allosteric and actual binding sites of gp120 to the α4β7 integin respectively. Thus, antibodies to specific V2 epitopes may play a role not only in preventing acquisition but also in post-infection control of local virus spreading.

Figure 1D:
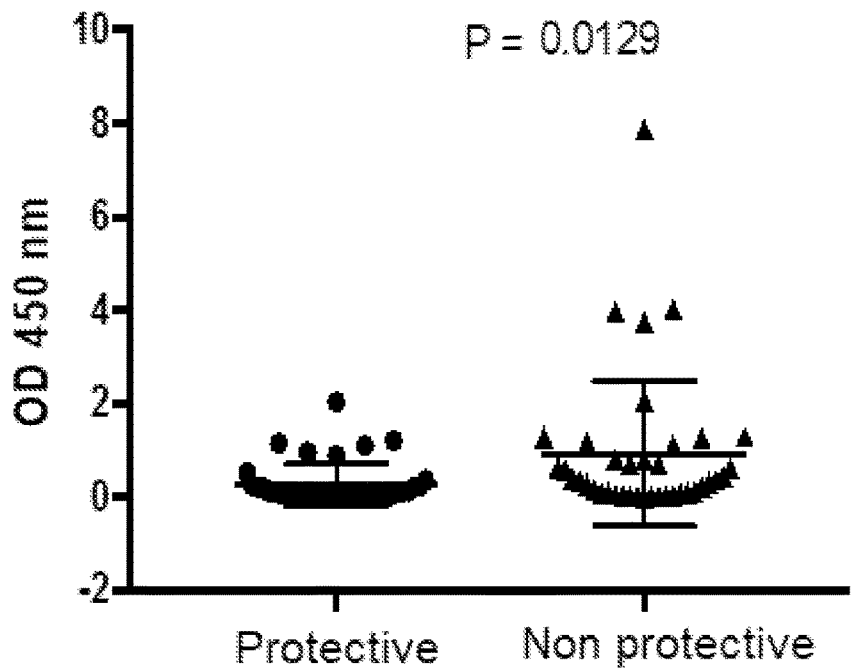
Figure 1E:
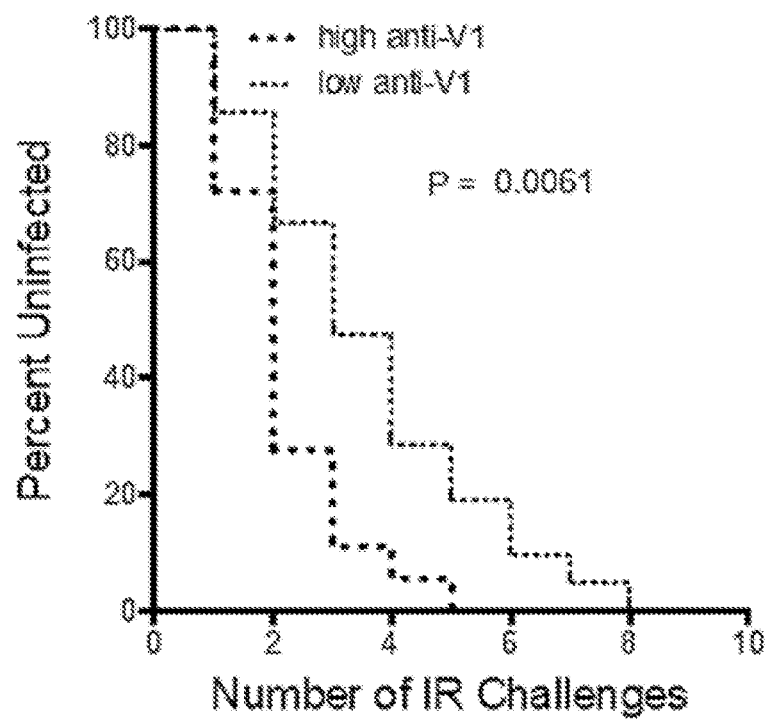
Figure 2A:
Figure 2B:
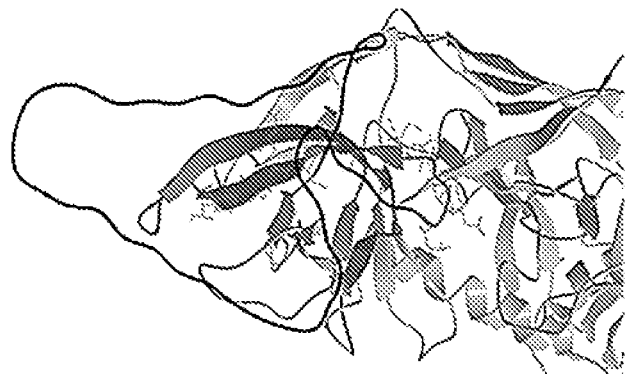
Figure 6C:
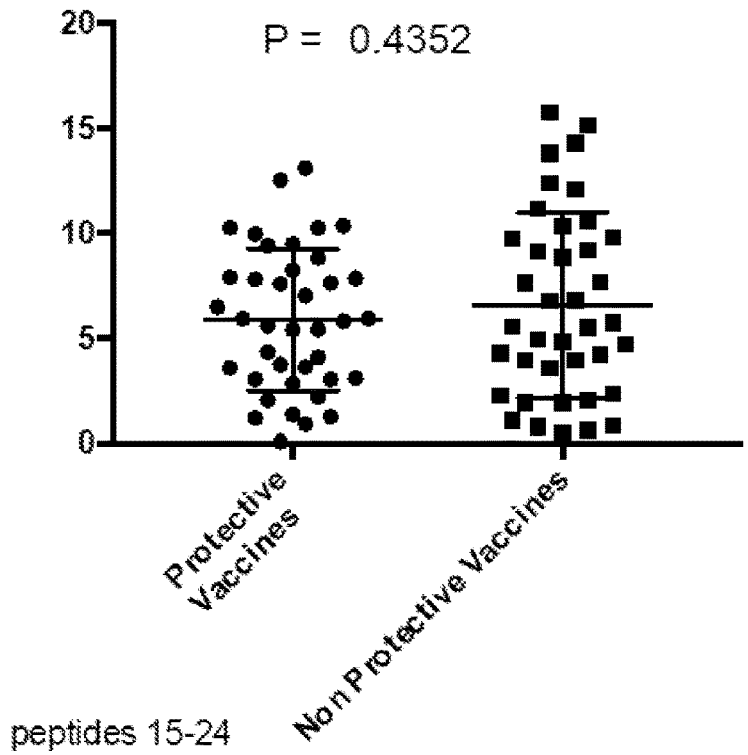
Figure 6D:
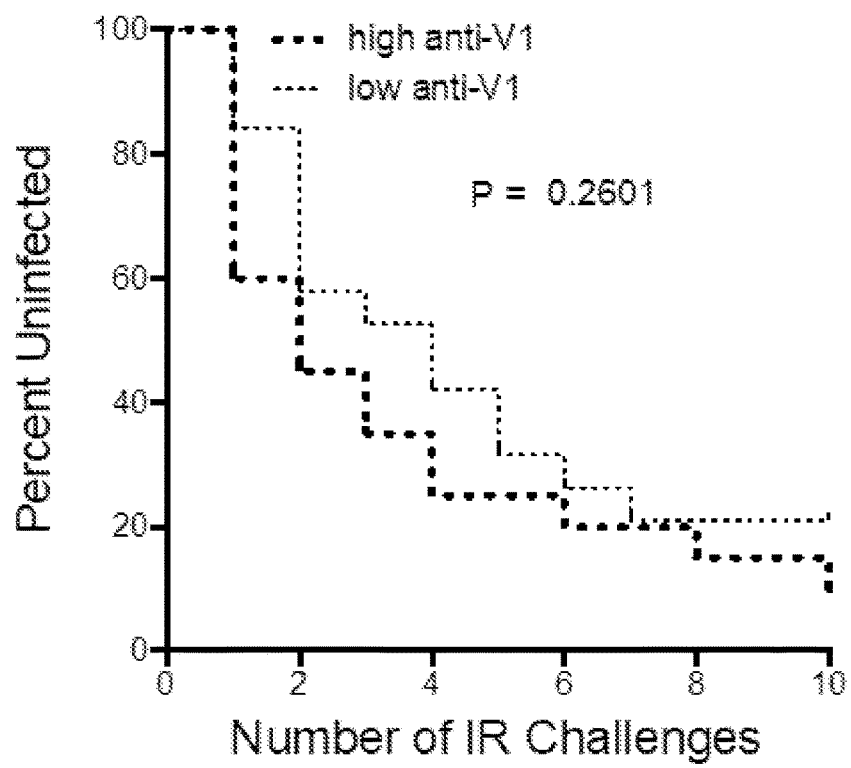

Analyses of serum reactivity to overlapping V1 peptides 15-24 (FIGS. 6A-6B) revealed no differences between the immunized groups (FIG. 6C), nor a correlation with $SIV_{mac251}$ acquisition in animal immunized with protective vaccines (FIG. 6D). However, in animals immunized with non-protective vaccines, we found a significantly higher response to peptides 23 and 24 encompassing amino acids IAQNNCTGLEQEQM (SEQ ID NO: 19, designated as V1a), than those immunized with protective vaccines and this response, was associated with an increased risk of $SIV_{mac251}$ acquisition (FIG. 1D-1E). V1a is directly N-terminal to V2b and both V1a and V2b are part of a continuous, exposed area at the very apex of the envelope trimer, while V1a also is superficial to, directly buries and contacts V2c (FIG. 2A-2B). Thus, the three biochemical sites found to influence risk of $SIV_{mac251}$ acquisition are consistent with the crystallographic 3D structural architecture of the V1V2 domain in the viral envelope, with immunologic RV144 correlates and with α4β7r functional sites. This suggests that V1a interferes with host recognition of vulnerable V2b and V2c sites.

Figure 7A:
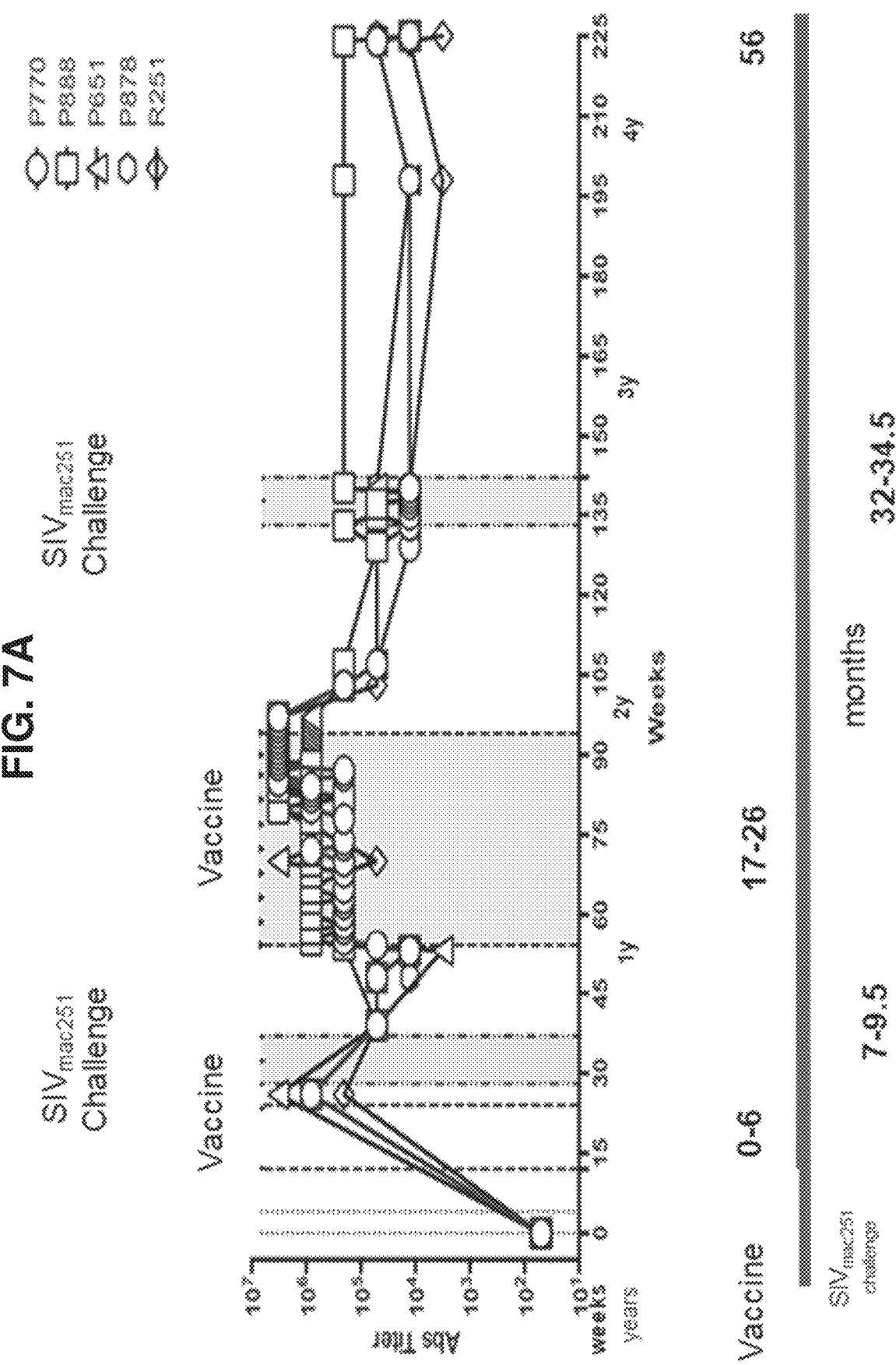
FIGS. 7A-7D.
Figure 7B:
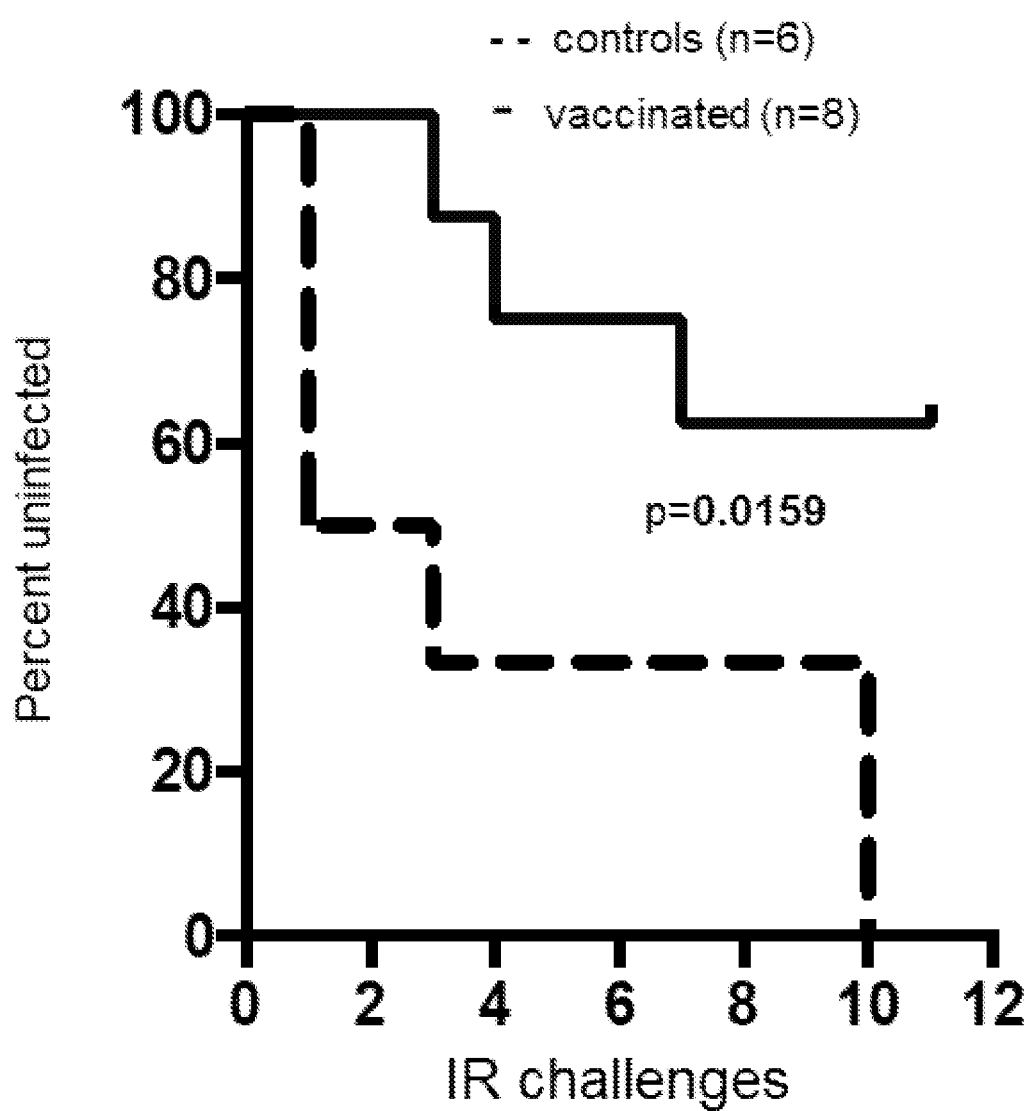
Figure 7C:
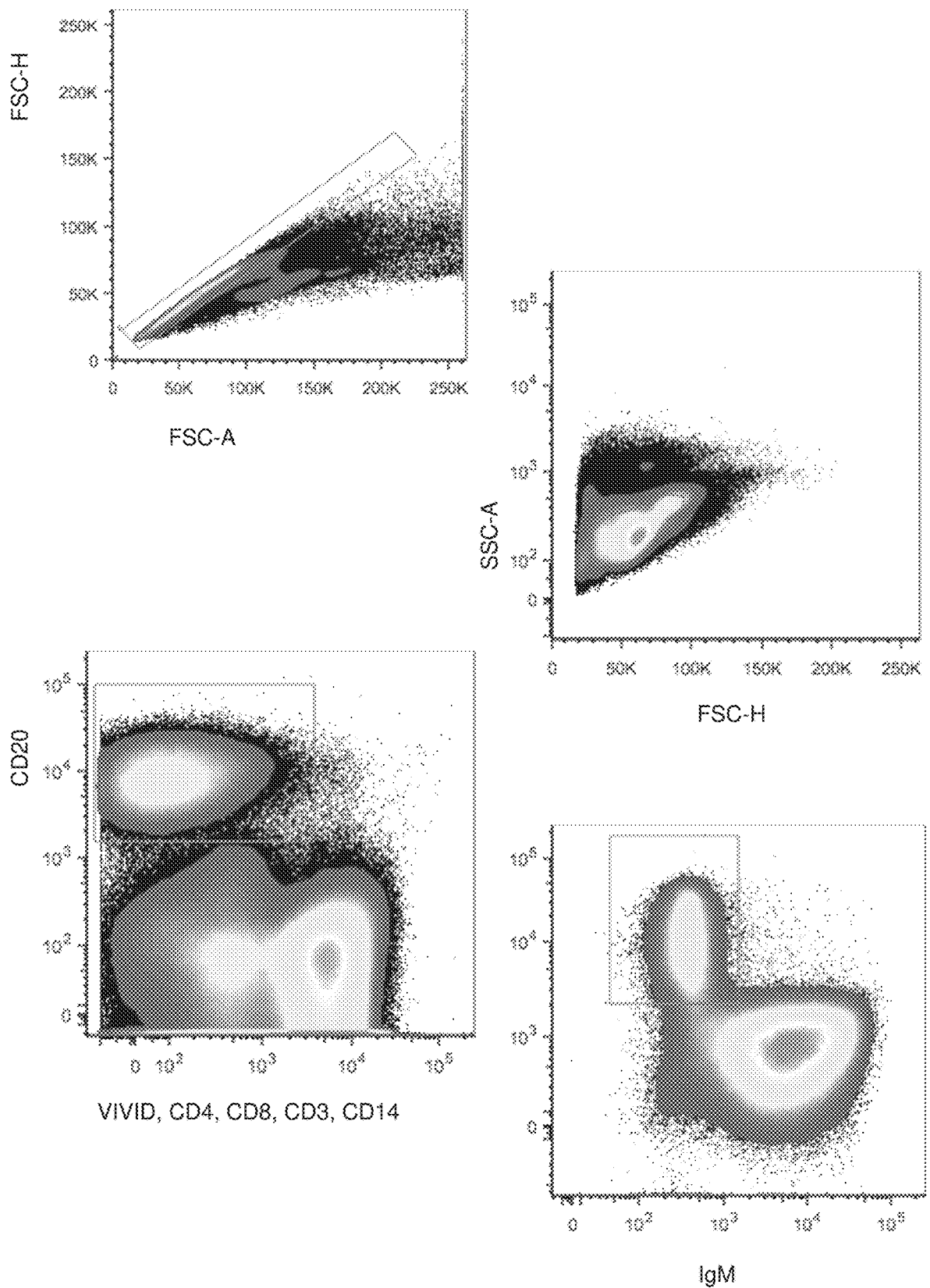
Figure 7D:
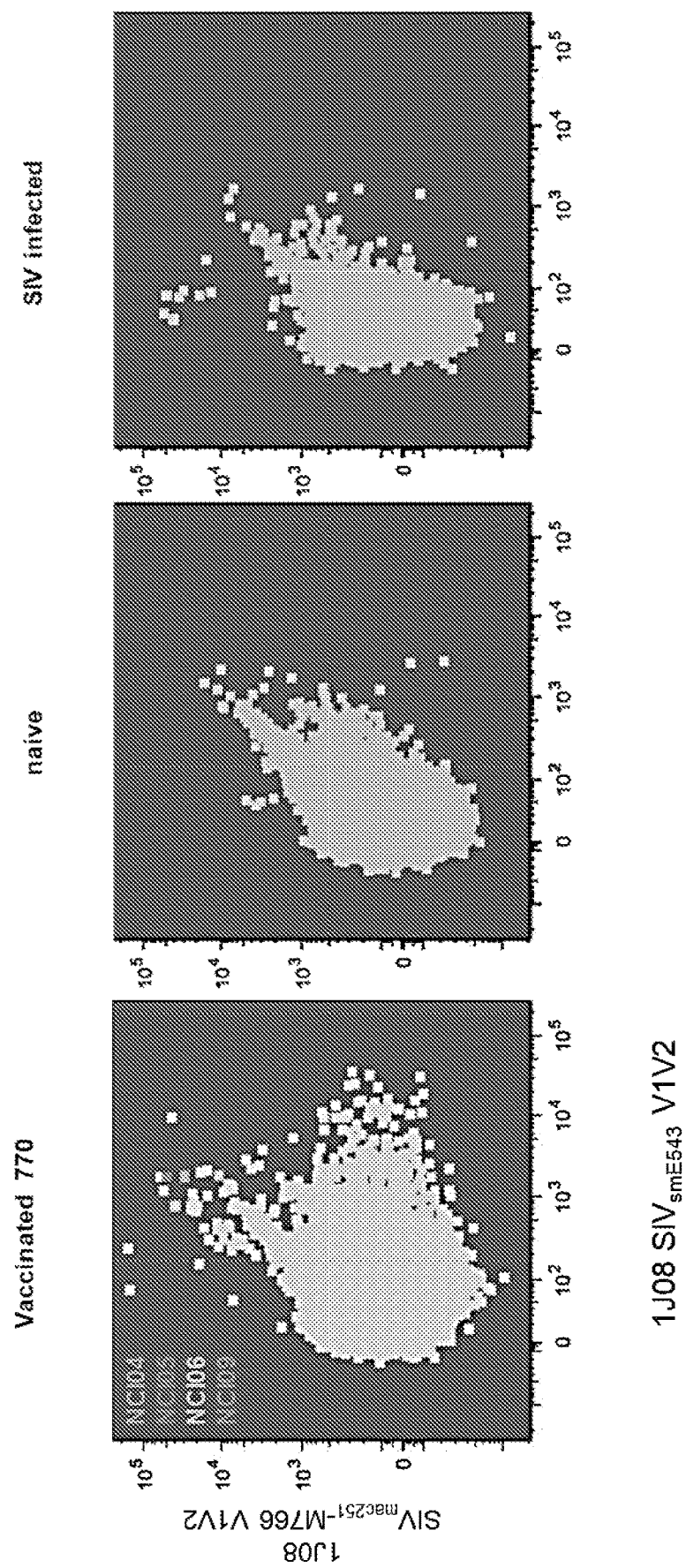
Figure 9A:
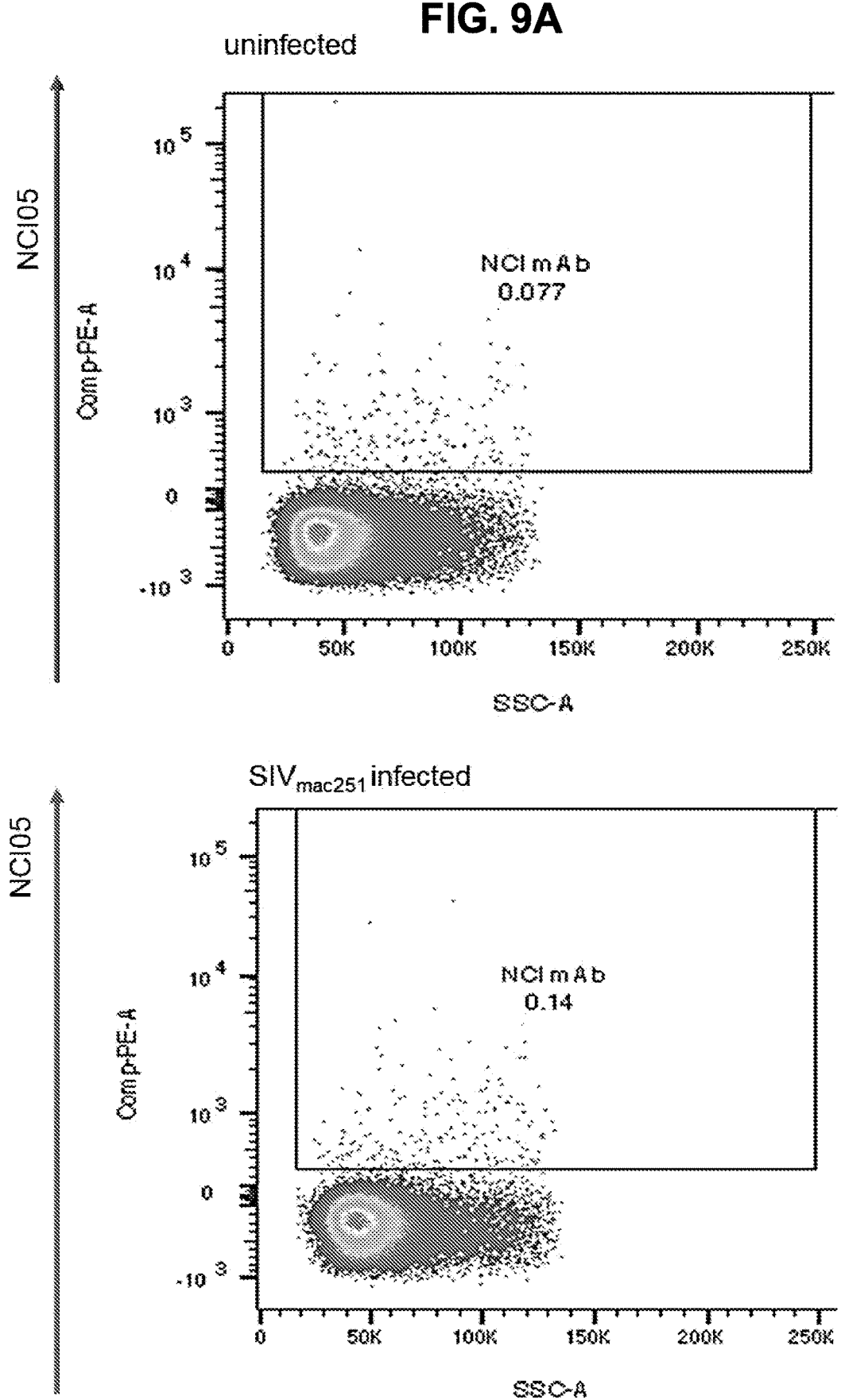
Figure 9B:
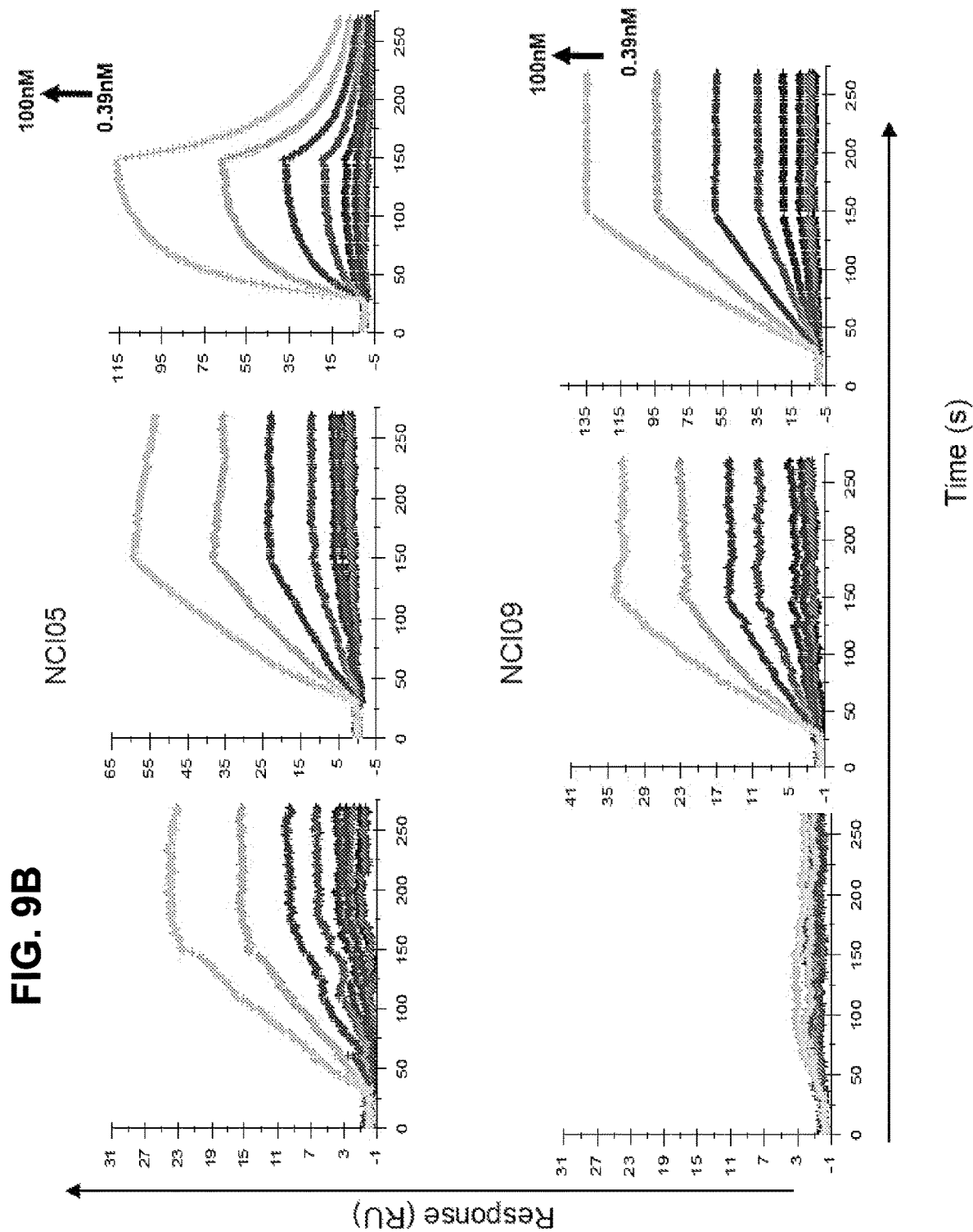
Figure 9E:
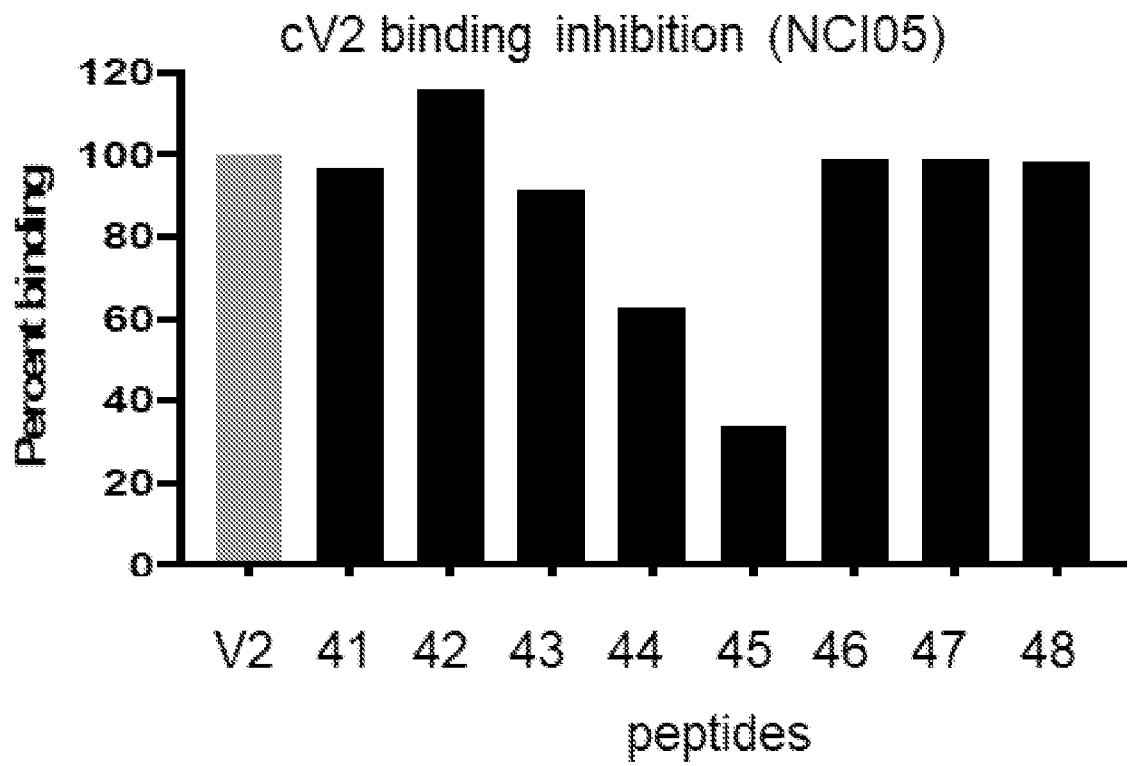
Figures 11A, 11B:
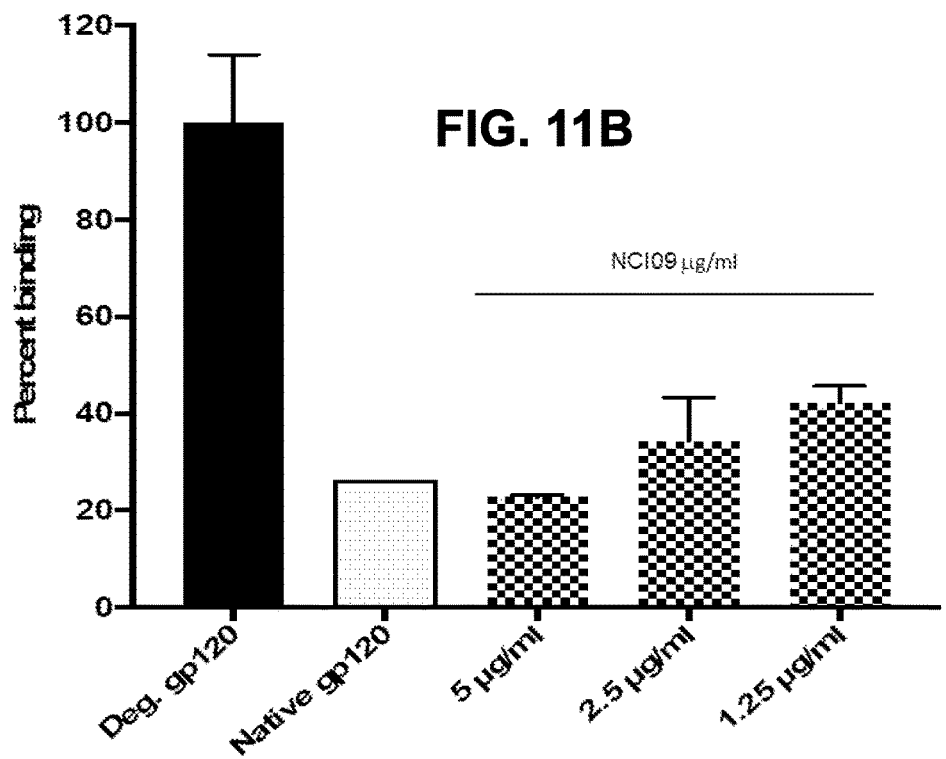
Figure 11C:
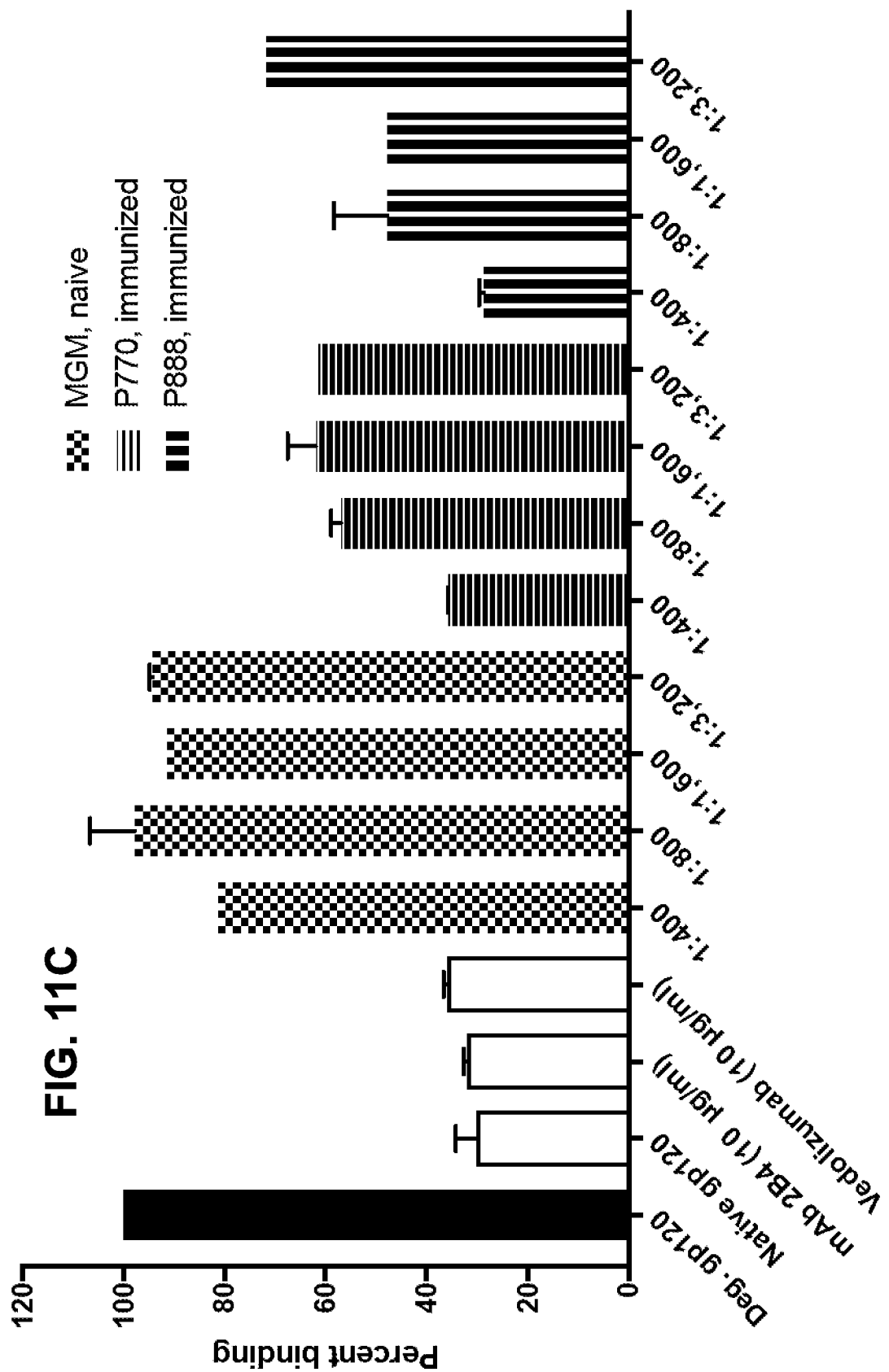
Figure 11D:
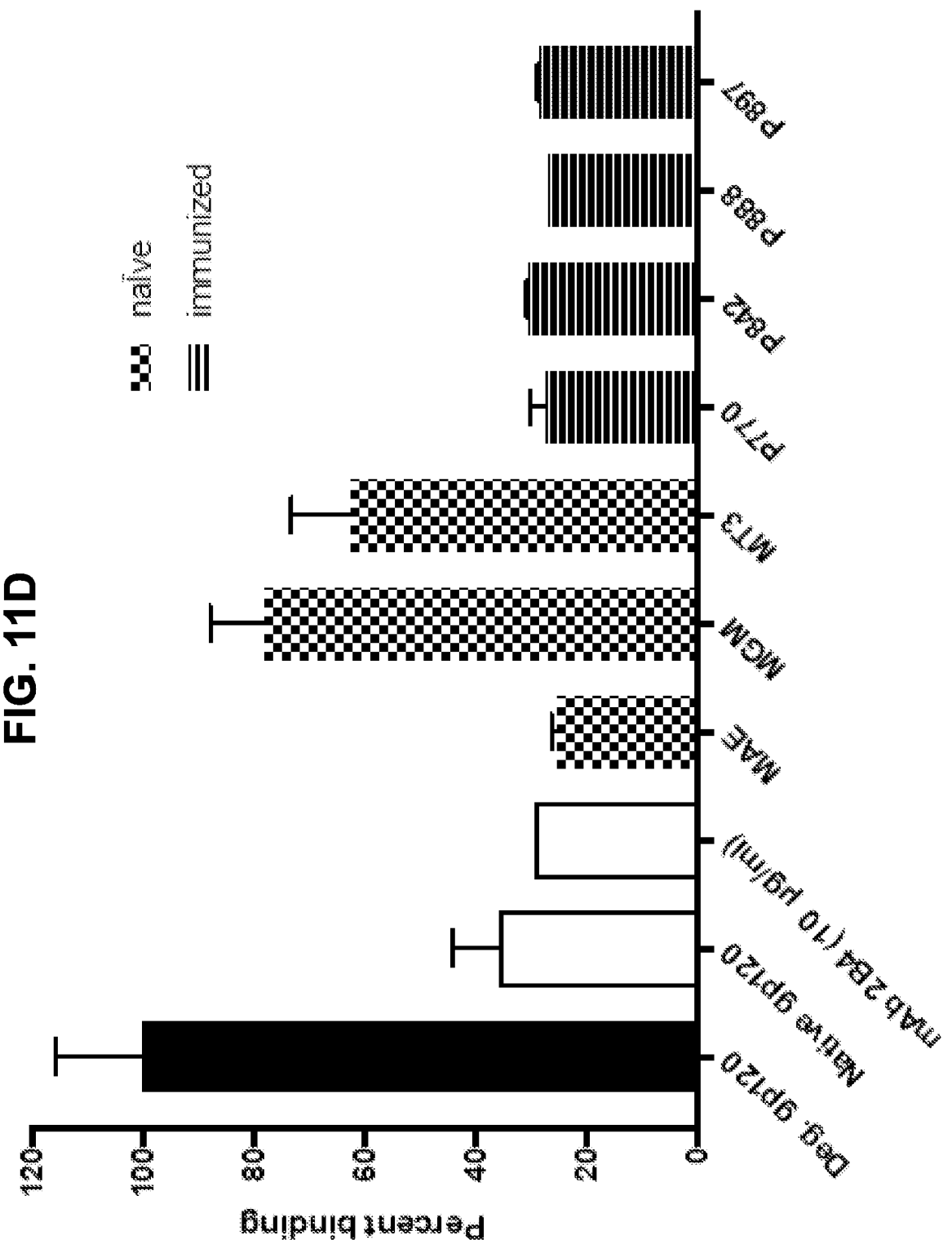
Figure 12A:
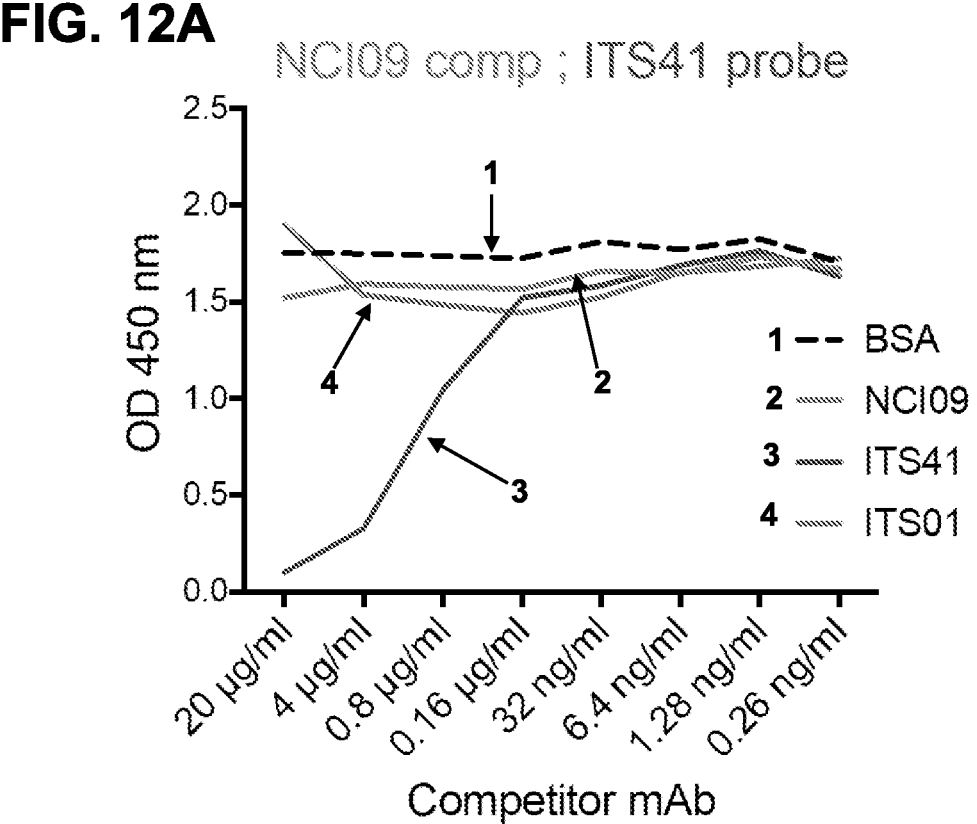
Figure 12B:
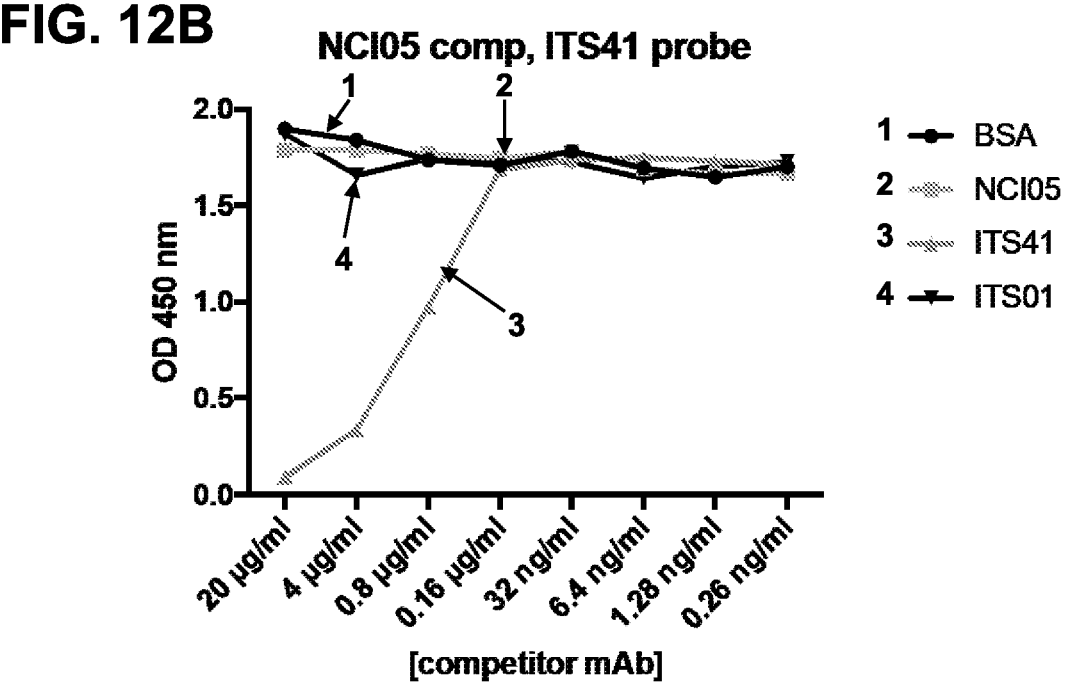
Figure 12C:
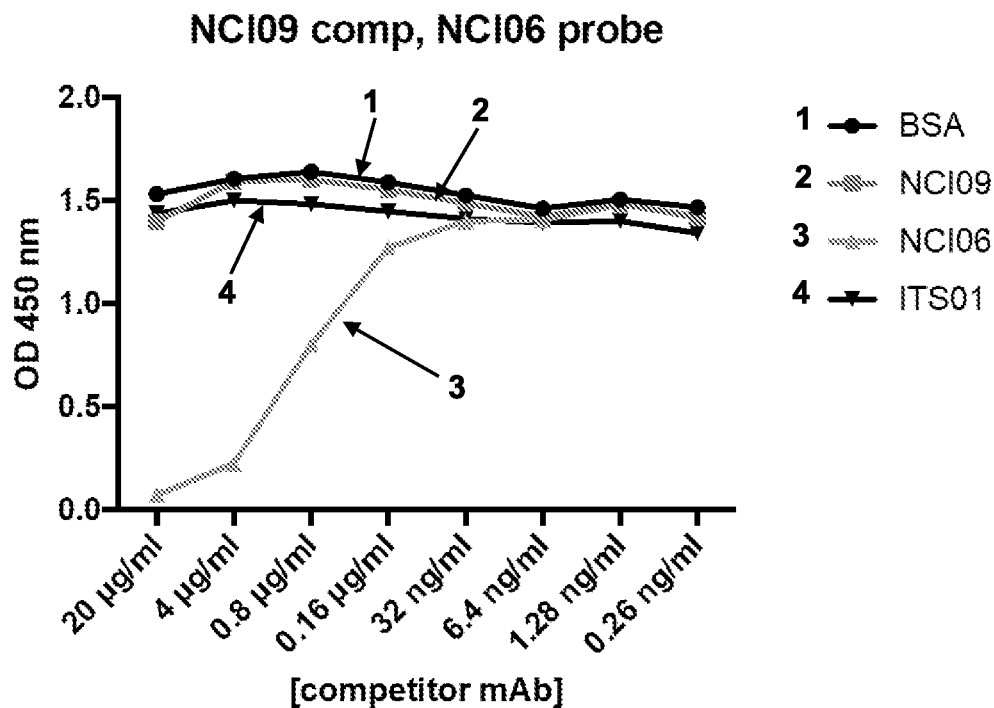
Figure 12D:
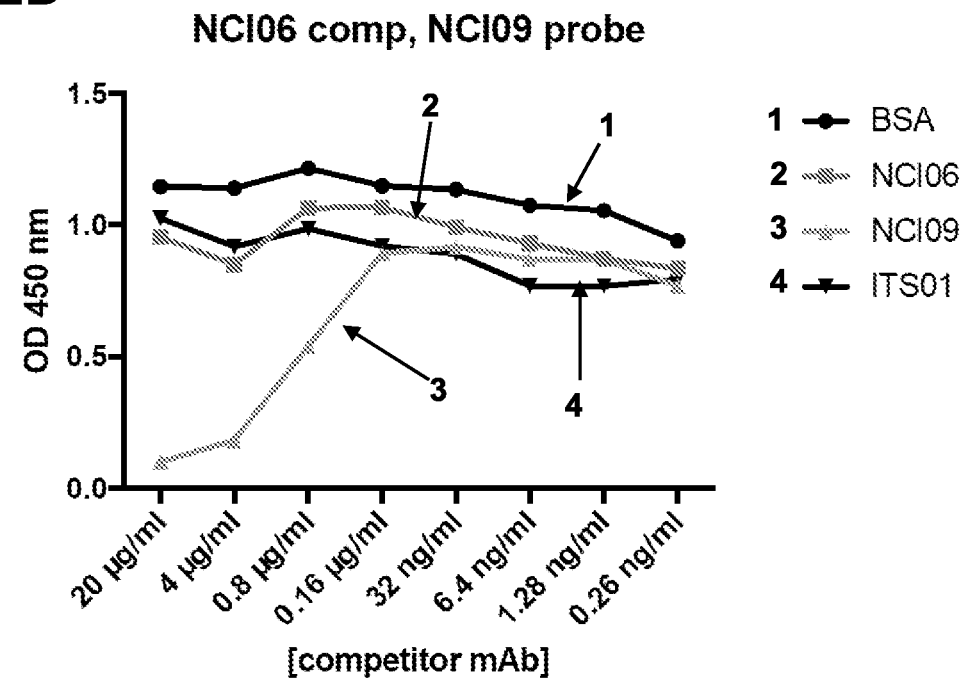

To assess this conclusion monoclonal antibodies recognizing V1a and V2b and V2c were cloned from the B-cells of an animal, P770, that was vaccinated with ALVAC-SIV/gp120/alum (Vaccari et al., Nat Med, 22, 762-770, 2016), resisted 10 $SIV_{mac251}$ challenges, was subsequently immunized and challenged again with 10 additional $SIV_{mac251}$ challenges years later and remained uninfected (FIGS. 7A and 7B). Memory B cells were identified and sorted from animal P770 that stained with either the 1J08 $SIV_{smE543}$ V1/V2 scaffold alone or in combination with the 1J08 $SIV_{mac251}$ V1/V2 scaffold and accounted for 0.78% of the memory cells and 0.13% of the total B cells in blood (FIGS. 7C and 7D). two α-V2 mAbs, NCI05 and NCI09, were isolated that recognized both $SIV_{mac251}$ and $SIV_{smE543}$ gp120 and their respective 1J08 V1/V2 scaffolds (FIG. 8A). NCI09 recognized the V2 linear peptide TGLKRDKTKEY (SEQ ID NO: 53), corresponding to the center of V2b, the $SIV_{mac251}$ and $SIV_{smE543}$ cyclic V2 peptides, native gp120 on the surface of $SIV_{mac251}$ infected cells (FIG. 8B), and its target epitope was confirmed by peptides competition assay (FIG. 8C-8D) as well as by crystallography (FIG. 1). NCI05 also bound to native gp120 on the surface of $SIV_{mac251}$ infected cells (FIG. 9A) and its binding to cyclic V2 was competed by peptides 43 and 44 corresponding loosely to V2c (FIG. 9E). Additionally, two α-V1 antibodies, NCI04 and NCI06, were characterized from animal P770, both of which recognize the V1 RCNKSETDRWGLTK (SEQ ID NO: 20) region that is N terminal to V1a (FIG. 8A). None of the NCI mAbs demonstrated potent neutralization properties as tested against a panel of Tier 1 and Tier 2 $SIV_{mac251}$ and $SIV_{smE660}$ (FIG. 11A). NCI09 inhibited mildly deglycosylated SIV gp120 binding α4β7 in a dose-dependent manner in a cell adhesion assay (FIG. 11B), but NCI05 did not (data not shown), consistent with the exposure and burial of the two targets, respectively. This inhibitory activity was also observed in the sera of animal P770 as well in other immunized animals' sera and tittered to a 60% activity at a 1:3,200 serum dilution (FIG. 11D).

Figure 1F:
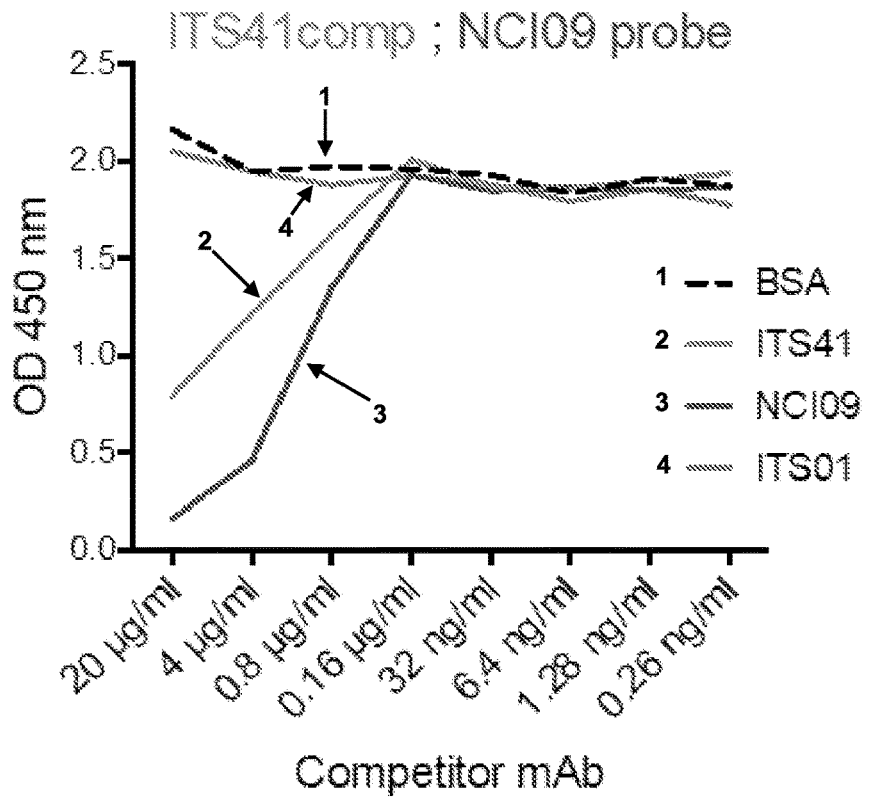
Figure 1G:
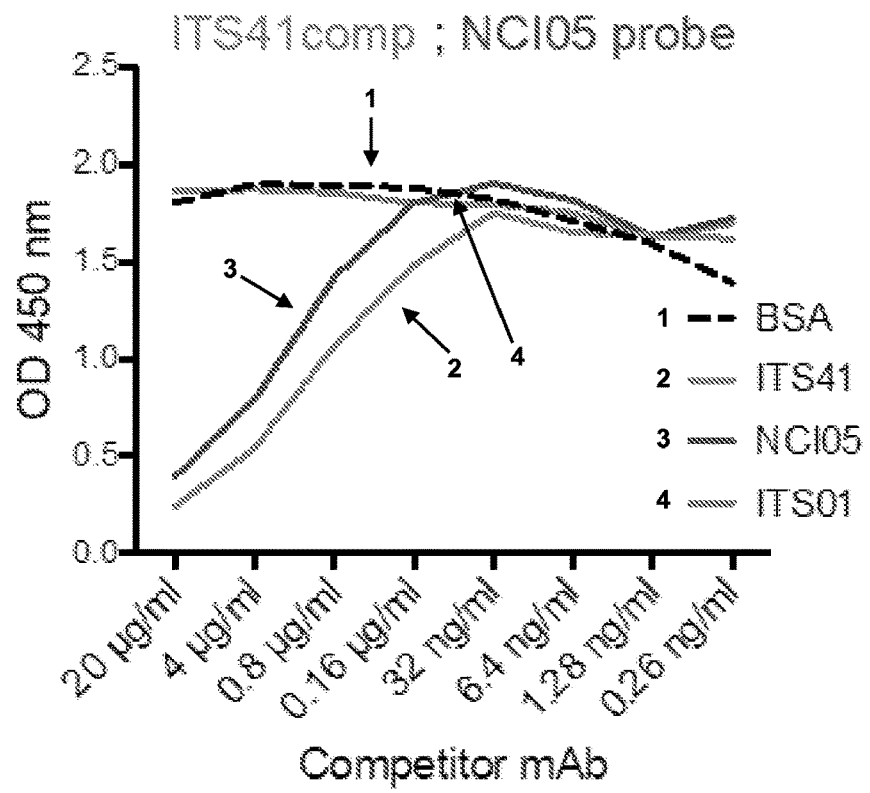
Figure 1I:
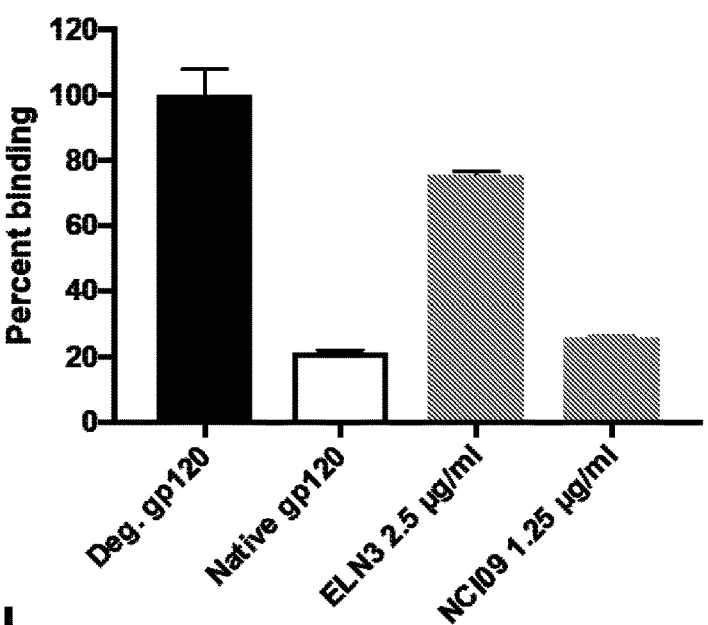
Figure 1J:
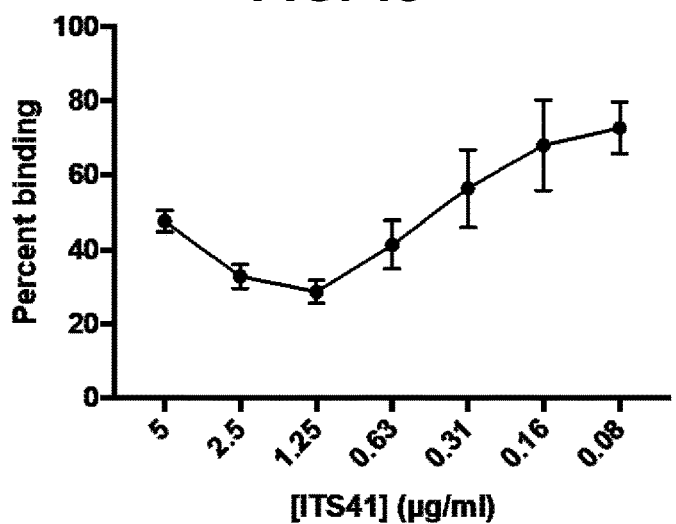
Figure 1K:
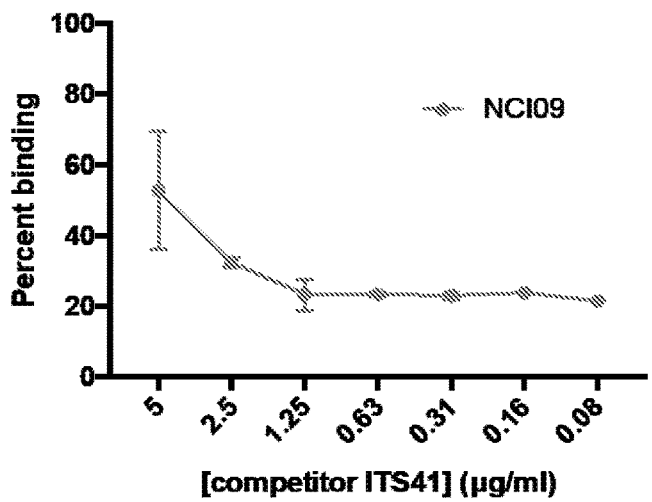

Next, in vitro binding competition assays were performed using soluble SIV gp120 and mAb ITS41, which recognizes V1a and was isolated from a vaccinated macaques that was not protected from SIV infection (FIG. 8A). ITS41 inhibited the binding to soluble gp120 of both the mAb NCI09 and NCI05 when pre-bound to soluble gp120 (FIGS. 1F and 1G). Conversely, binding of mAb NCI09 or NCI05 to gp120 was not affected by the later addition of ITS-41 demonstrating asymmetric competition (FIGS. 12A and 12B), which is consistent with proximal interference of V1a with the V2 sites. The α-V1 mAbs NCI04 and NCI06 did not interfere with NCI05 or NCI09 binding to gp120 (FIGS. 12C and 12D), likely because their common target epitope is distant from V1a. The NCI09 binding to the surface of $SIV_{mac251}$ infected cells was also inhibited in a dose dependent manner by pre-treatment of cells with ITS41 (FIG. 1H). NCI09 at a 1.25 µg/ml concentration inhibits by 80% gp120 binding to α4β7 (FIG. 1I) and by tittering in increasing amount of ITS41 (FIG. 1J), it was found that ITS41 reversed the inhibitory activity of NCI09 (FIG. 1K). Taken together these data suggest that ITS41 interferes with V2b and V2c binding by NCI09 and NCI05 either via steric hindrance or allosteric competition, which is consistent with the 3D structural locations of these sites on the SIV envelope trimer (FIGS. 2A and 2B).

Figure 2C:
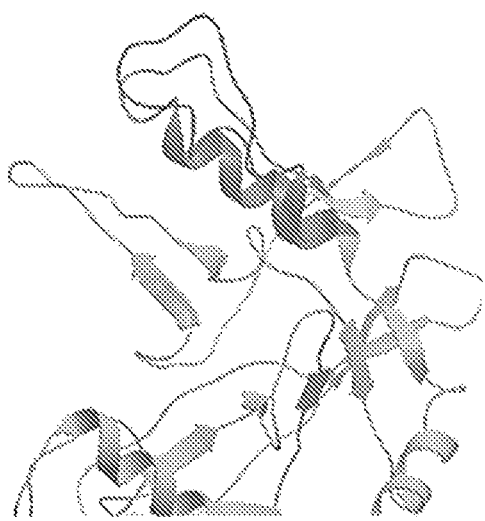
(FIG. 2C) Modeling of the gp120 ΔV1 α-helix V2 (in blue).
Figure 2D:
(FIG. 2D) Modeling of the $gp120_{\Delta V1gpg}$ β-strand.
Figure 2K:
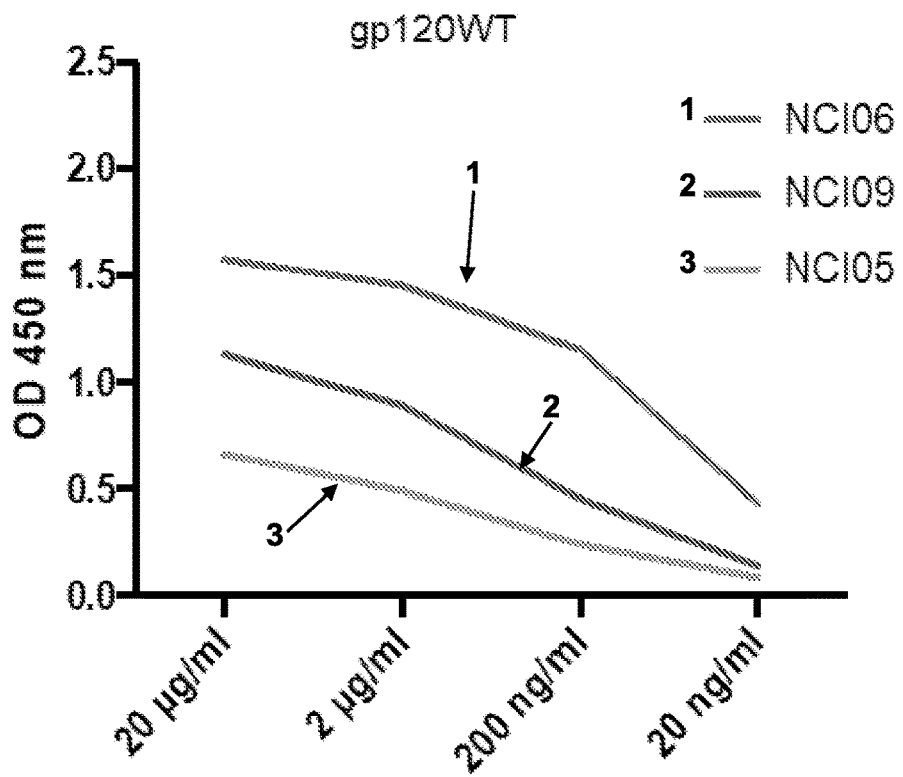
Figure 2L:
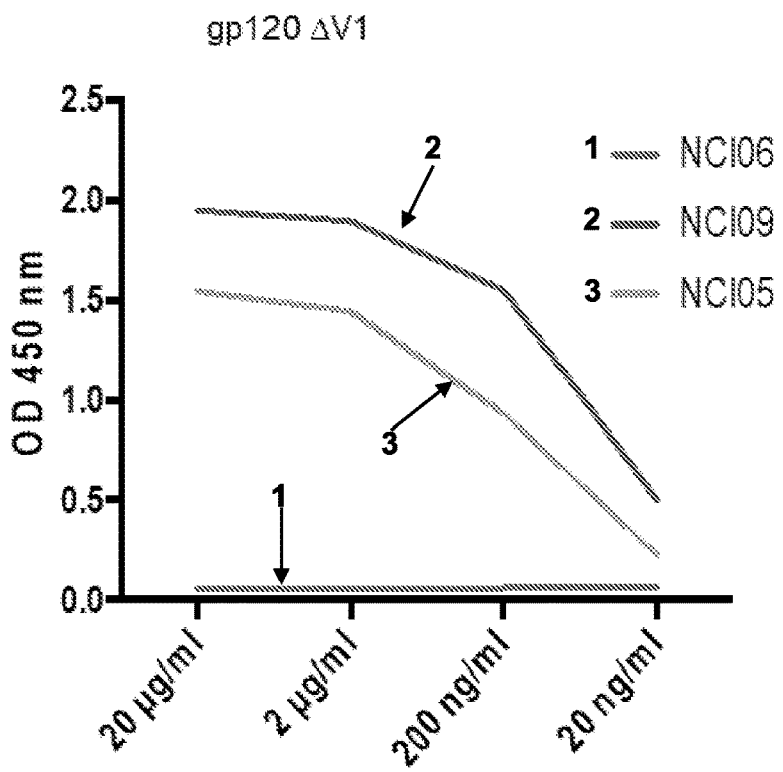

To test this hypothesis in vivo and investigate more directly the role of V1a and V2 in vaccine efficacy, structure-based design was used to delete V1 from models of the SIV trimer while preserving V2 folded conformations. The V1 origin and insertion (stem) to the holo V1/V2 domain connects the A and B β-strands (McLellan et al., Nature, 480, 336-343, 2011). The gp120ΔV1 was engineered by truncating V1 at its stem and energy minimized it using the Biased-Probability Monte Carlo (BPMC) conformational search as previously described (Abagyan et al., J Mol Biol, 235, 983-1002, 1994; Cardozo et al., Proteins, 23, 403-414, 1995), to determine that the conformational rearrangement in V2 resulted in stable, low energy α-helix at its core (FIG. 2C). A prior study has shown that an alternative α-helical conformation to that inferred in most Env crystallography structures may be the target of protective Abs in the RV144 trial (Aiyegbo et al., PLOS One, 12, e0170530, 2017), which suggests that the V1 loop may enforce a particular, probably β-strand conformation, perhaps as a way of masking the V2 sites of vulnerability. However, since a β-strand is observed for this segment in the HIV trimer crystallographically, we could not rule out the relevance of the β-strand conformation. Accordingly, gp120 $ΔV1_{gpg}$ was engineered as control by inserting the Gly-Pro-Gly β-turn at the excision point, which should minimally perturb the crystallographically-evident V1/V2 Greek key β-sheet fold (FIG. 2D).

Figure 3A:
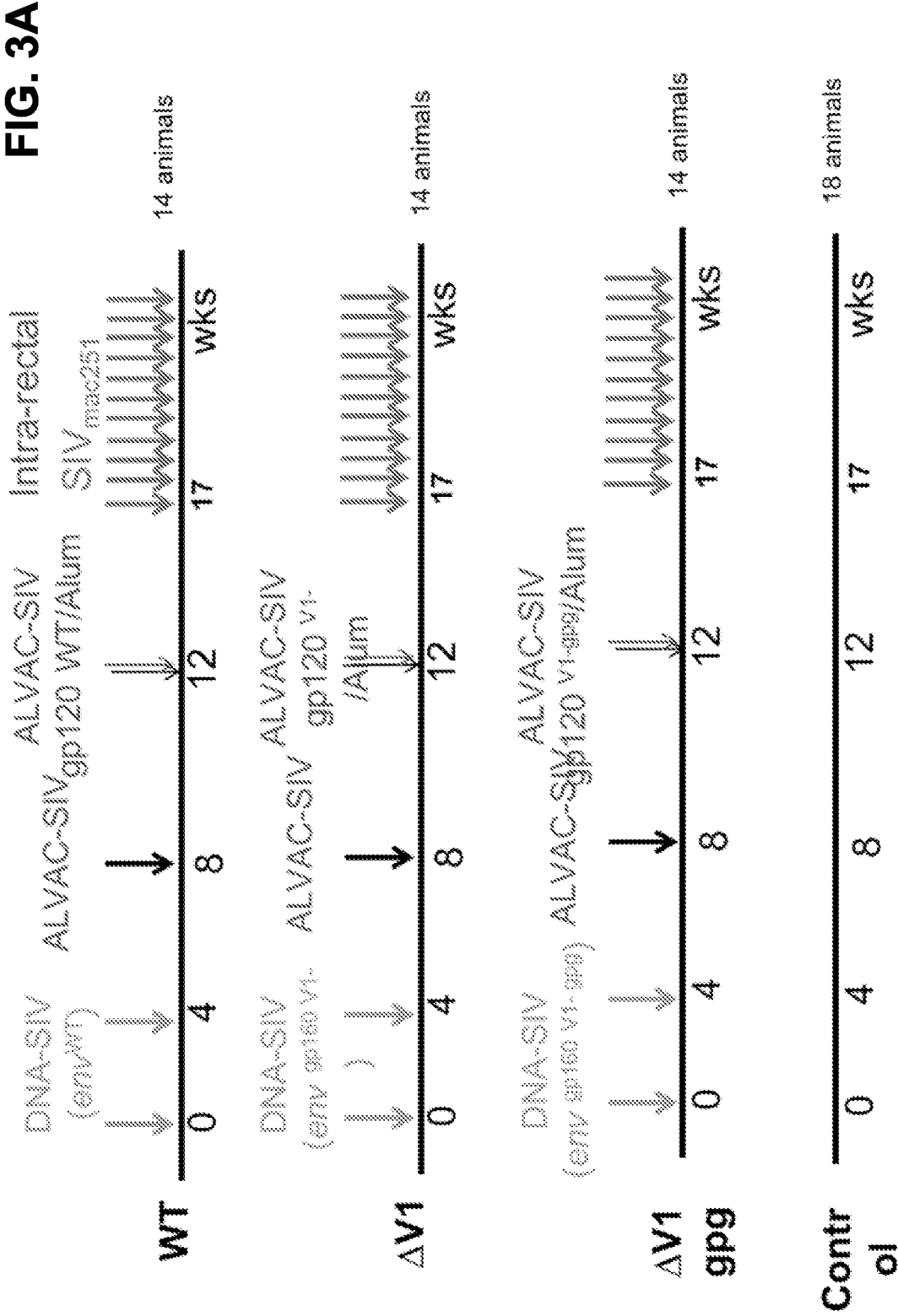
FIGS. 3A-3N.

The two M766 ($SIV_{mac251}$)-based gp120 immunogens deleted in V1 ($gp120_{ΔV1}$ and $gp120_{ΔV1gpg}$) were engineered and expressed in CHO cells together with the wild type gp120 (gp120WT) (FIG. 2E). Both purified monomeric $gp120_{ΔV1}$ and $gp120_{ΔV1gpg}$ were not recognized in western blot by the anti V1 antibodies NCI06, and ITS41, as expected (FIGS. 2F-2G) but reacted to a polyclonal anti SIV gp120 rabbit serum (FIG. 2H) as well to the mAb NCI05 and NCI09 (FIGS. 2I-2J). Both $gp120_{ΔV1}$ and gp120 ΔV1gpg proteins bound better than the $gp120_{WT}$ in ELISA to both NCI05 and NCI09 mAbs and to the simian CD4 molecule indicative that V1 deletion increased V2 and CD4 accessibility. matching $SIV_{mac251M766}$-based gp160 DNA ΔV1 and $gp160_{ΔV1gpg}$ constructs were also engineered and tested in a study in macaques with a short and simpler immunization regimen than the previously established 52% vaccine efficacy baseline DNA/ALVAC/gp120 protocol with the intent to amplifying differences in the vaccination outcomes. Three groups of 14 macaques were each vaccinated with two inoculations of SIV $gp160_{WT}$, or $gp160_{ΔV1}$ or $gp160_{ΔV1gpg}$ together with SIVp57 Gag DNA to produce pseudo-virions at 0 and 4 weeks, followed by one boost at week 8 with ALVAC-SIV (that expressed the gp120 wild type and an additional boost at week 12 with ALVAC-SIV together with the $gp120_{WT}$, or $gp120_{ΔV1}$ or $gp120_{ΔV1gpg}$ in alum (FIG. 3A).

Figure 3B:
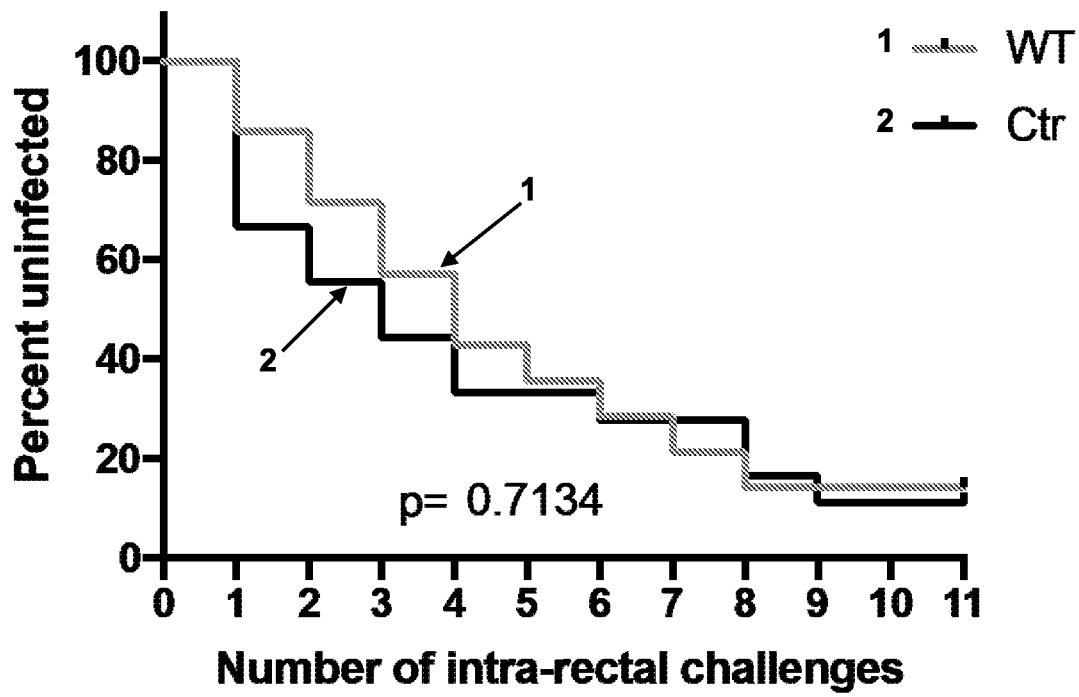
(FIG. 3E) Titers of antibody response cyclic V2. F: Amino acid sequence of the Diagnostic Peptide that recognize the second V2 α4β7 site $DP2_{\alpha4\beta7}$ of $SIV_{mac251}$ and $SIV_{SME543}$ and of the epitopes recognized by NCI09 and NI05.
(FIG. 3F) sequences of $DP2\alpha4\beta7_{251}$ (SEQ ID NO: 22), $DP2\alpha4\beta7_{E543}$ (SEQ ID NO: 23), NCI09 (SEQ ID NO: 18), and NCI05 (SEQ ID NO: 35). Binding of the $DP2_{\alpha4\beta7251}$ and $DP2_{\alpha4\beta E453}$ to (FIG. 3G) NCI05 and (FIG. 3H) NCI09. Binding of sera from the immunized groups to (FIG. 3I) $DP2_{\alpha4\beta7251}$ or (FIG. 3J) $DP2_{\alpha4\beta E453}$.
(FIG. 3K) correlation of the serum immune response to $DP2_{\alpha4\beta E453}$ and the time of $SIV_{mac251}$ acquisition C. Serum neutralizing antibodies to the Tier 2 $SIV_{mac251CS.41}$ pseudovirus at week 17 were higher in the in the ΔV1 envelope immunogens group (FIG. 3M) and correlated with faster acquisition of $SIV_{mac251}$ (FIG. 3N). Inhibition of V2 binding to α4β7 by the sera of immunized animals (1:200 dilution) in an adhesion assay.
Figure 3C:
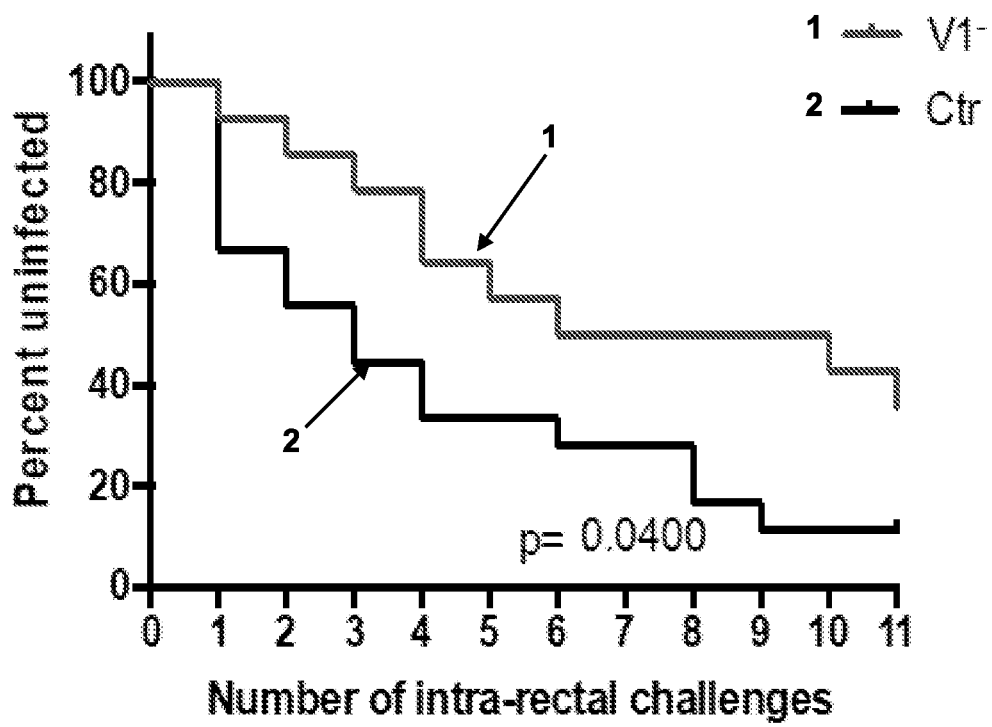
Figures 3F, 3G:
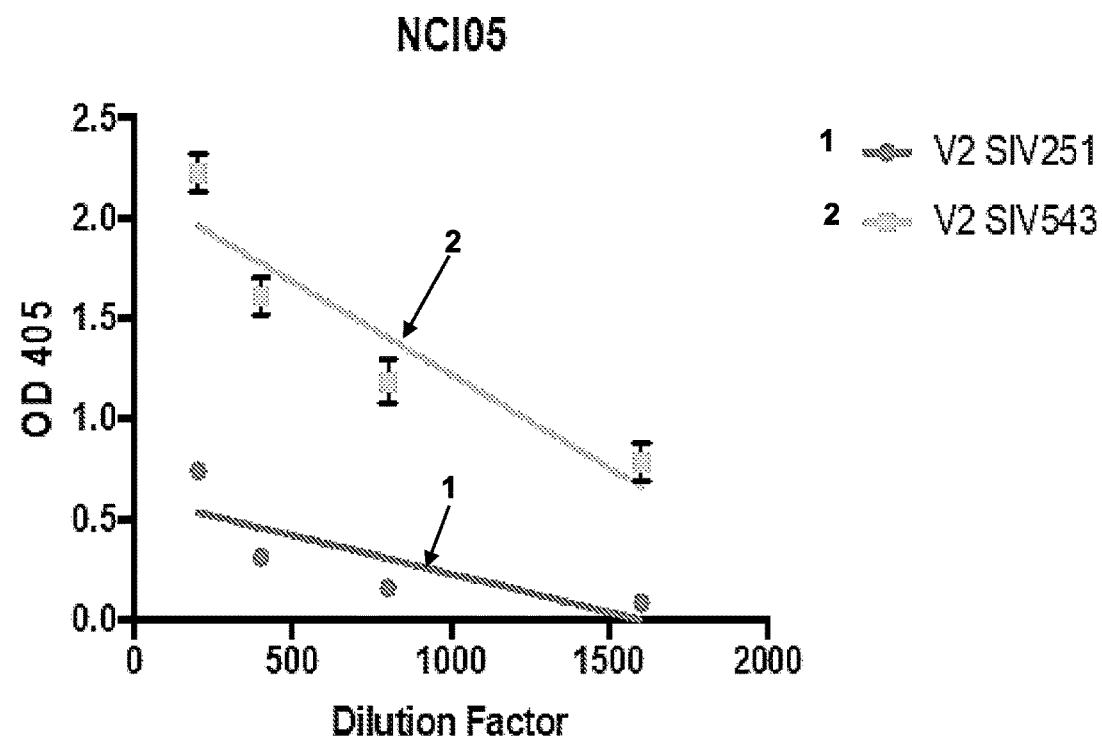
Figure 3H:
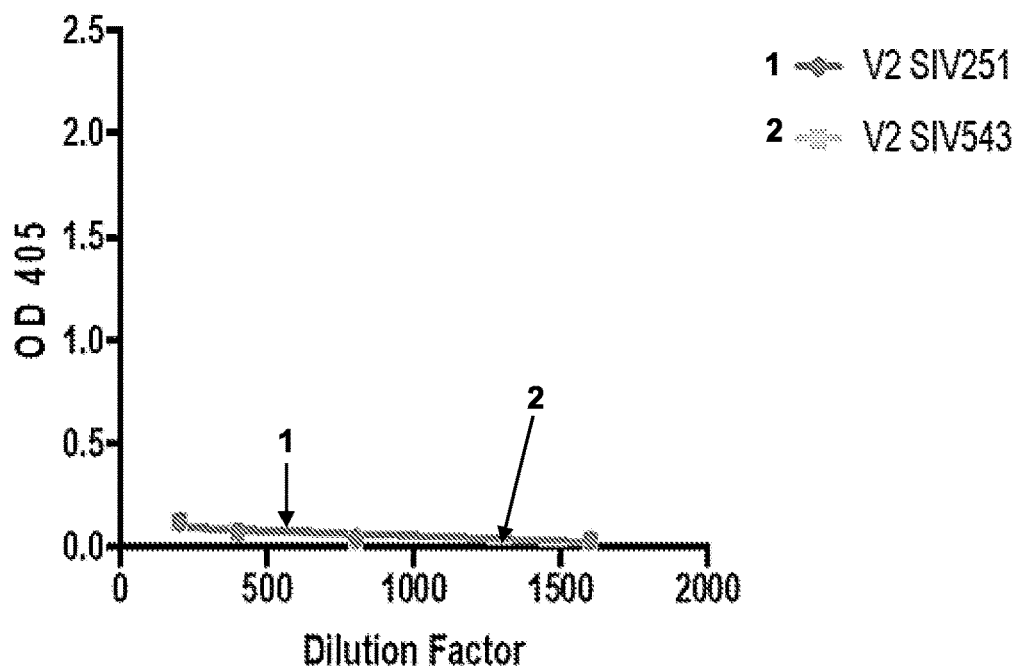
Figure 3I:
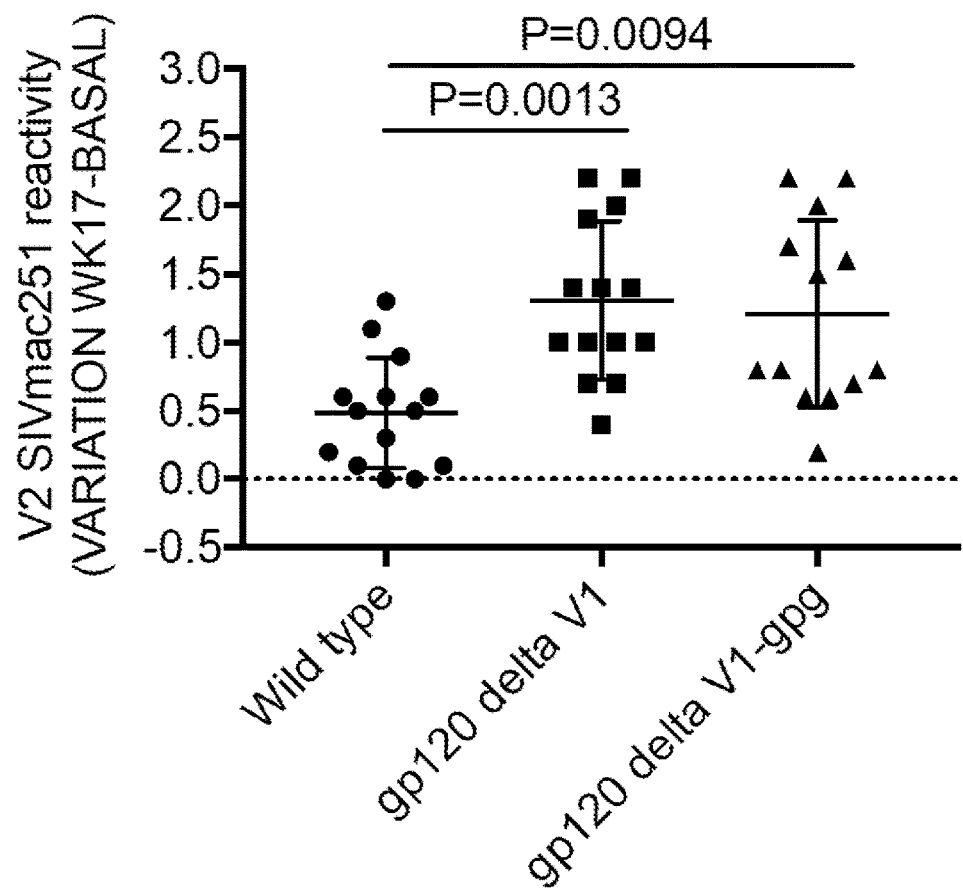
Figures 3J, 3K:
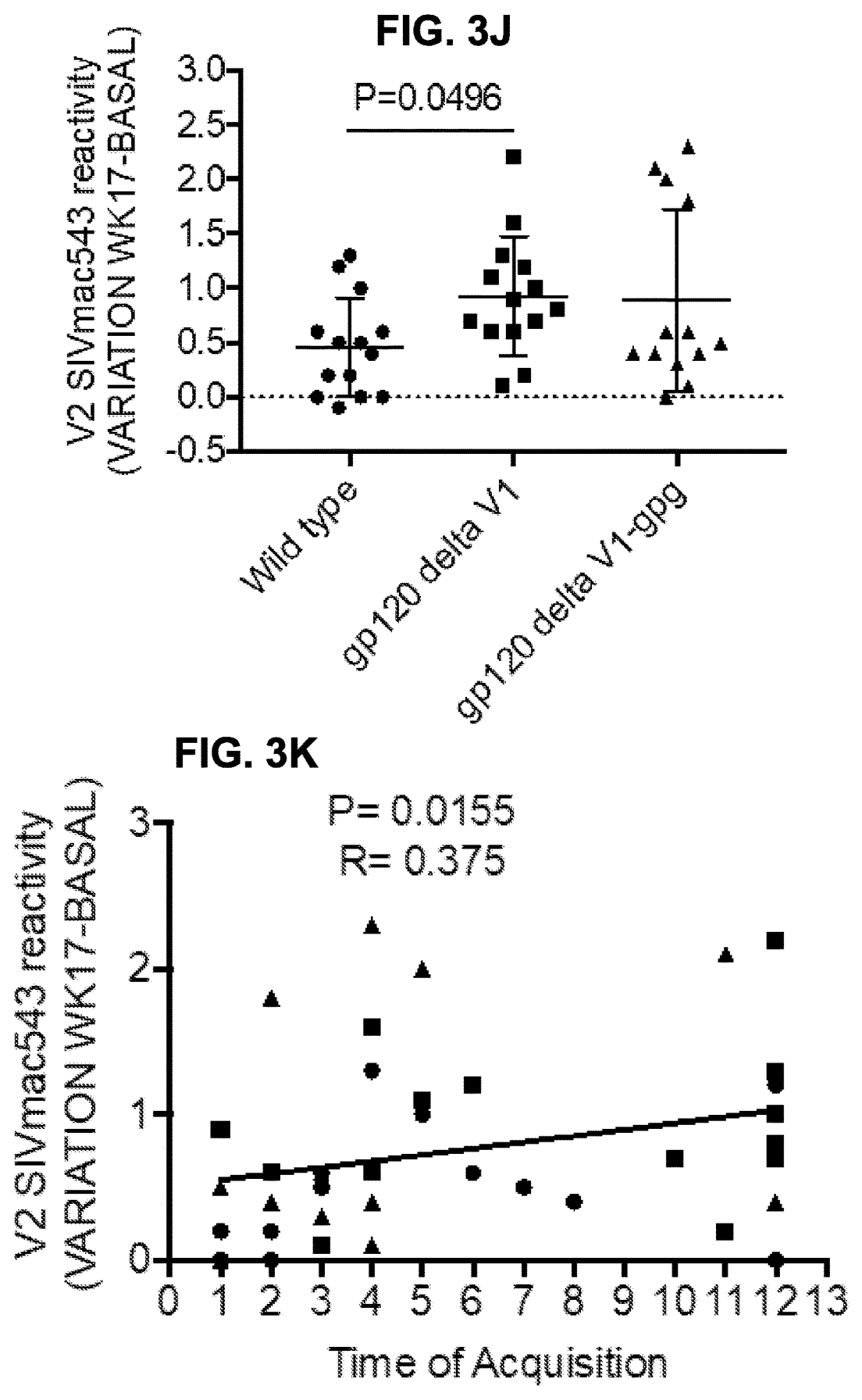
Figure 3L:
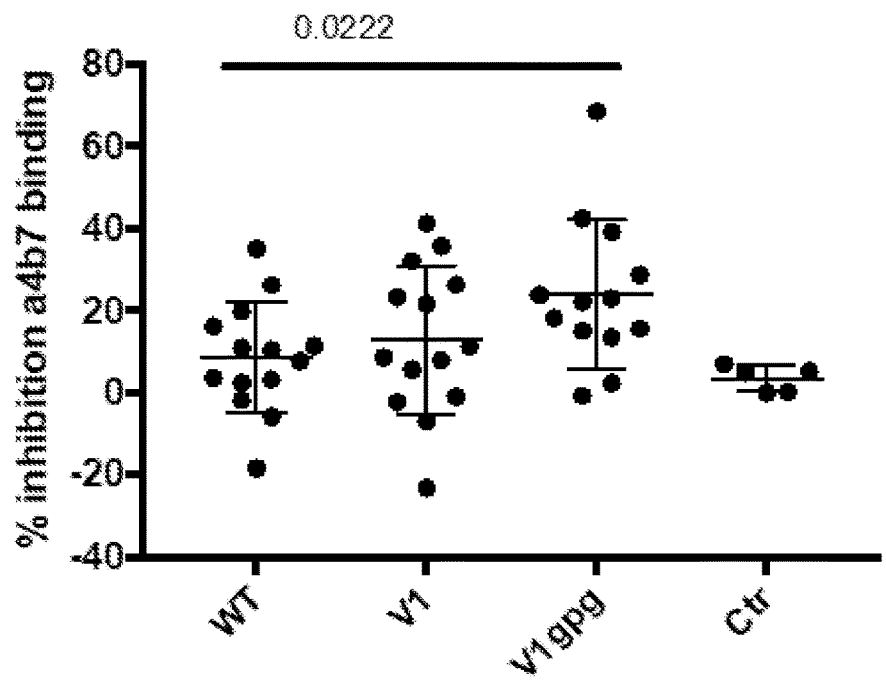
Figure 3M:
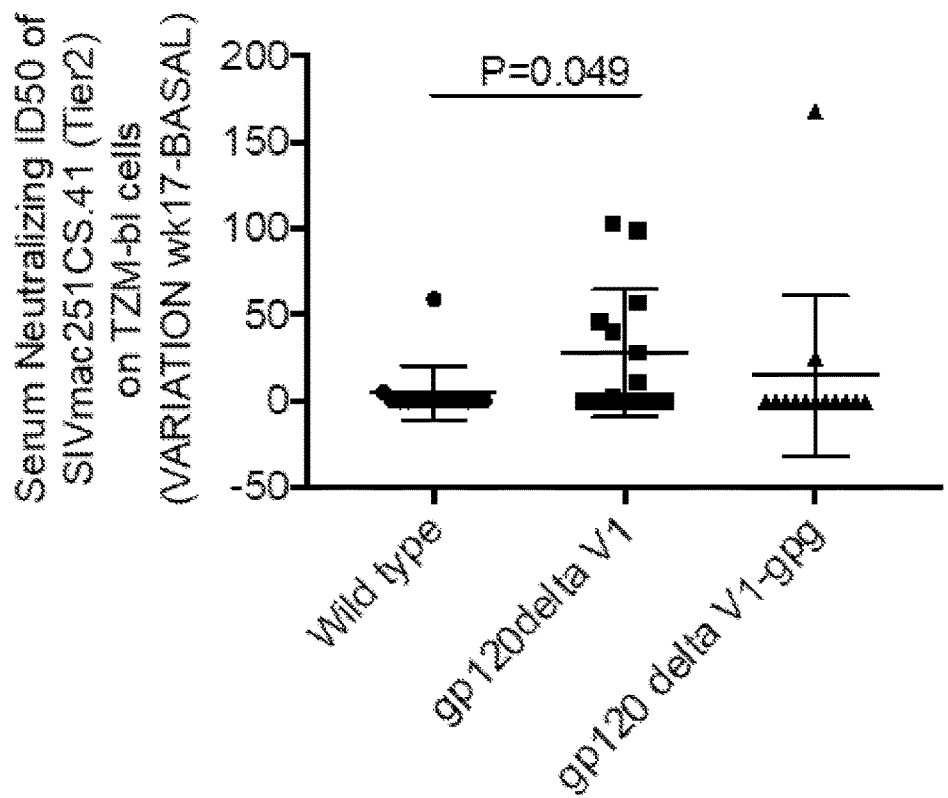
Figure 3N:
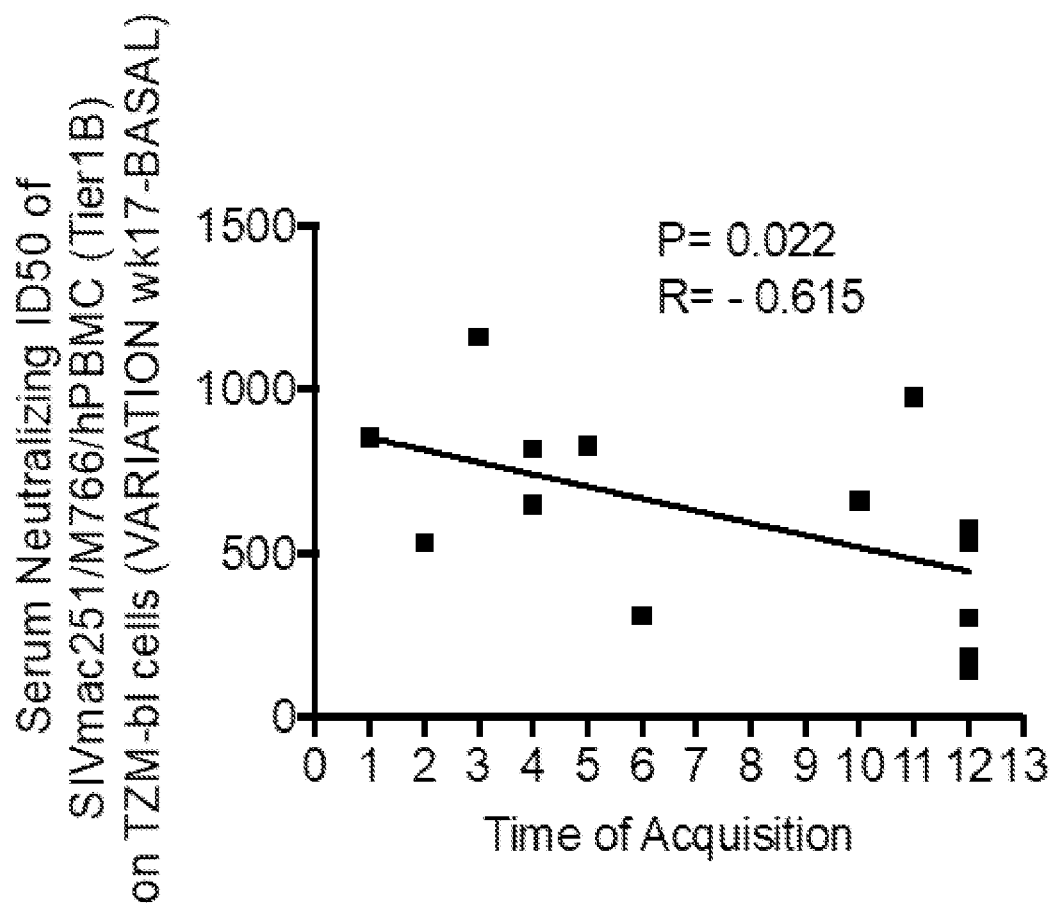

Vaccinated macaques together with an additional unimmunized control group of 18 macaques were exposed weekly to a total of 11 low doses of $SIV_{mac251}$ by the intrarectal route beginning at five weeks after the last immunization (week 17). Strikingly a significant decrease in the risk of $SIV_{mac251}$ acquisition was observed only in in the group of macaques immunized with the gp160 DNAΔV1 and the gp120 protein immunogens engineered to maintain predominantly the α-helix V2 conformation (FIG. 3C) but not with the WT or the ΔV1gpg envelope immunogens (FIGS. 3B-3D). Analyses of serum antibody titers to the $SIV_{766}$gp120 envelope protein demonstrated no significant differences in the three immunized groups (FIG. 13A) and, as expected, the sera of animals vaccinated with the ΔV1 and ΔV1gpg envelope immunogens did not recognize overlapping peptides in the V1 region (FIG. 13B). Importantly the antibody titers to the $SIV_{mac251}$ cyclic V2 peptide were higher in both groups immunized with the ΔV1 or ΔV1gpg than the wild type envelope immunogens (FIG. 3E). Prior results indicated that an HIV peptide correlating with protection in the RV144 study adopted an α-helical conformation. Therefore, diagnostic peptides were designed that included the second binding site of V2 to α47, encompassing the amino acid sequence of $SIV_{mac251}$, DKTKEYNETWYSTD (SEQ ID NO: 22, designated as DP2α4β7$_{251}$) and of $SIV_{SME543}$ DKKIEYNETWYSRD (SEQ ID NO: 23, designated as DP2α4β7$_{E543}$) (FIG. 3F). As expected, both DP2α4β7$_{251}$ and DP2α4β7$_{E543}$ bound NCI05 (FIG. 3G) but not NCI09 (FIG. 3H). The sera of macaques immunized with the ΔV1 or ΔV1gpg immunogens had significantly higher reactivity to DP2α4β7$_{251}$ than those immunized with WT (FIG. 3I). In contrast, reactivity to the DP2α4β7$_{E543}$ was significantly higher only in the ΔV1 group (FIG. 3J) and interestingly this response inversely correlated with the risk of $SIV_{mac251}$ acquisition, despite its difference in amino acid sequence from the challenge virus (FIG. 3K). Analysis of the ability of the sera from the immunized macaques to inhibit the binding of cyclic V2 to α4β7 revealed that it was highest in the group immunized with the ΔV1gpg envelope immunogens and this activity did not correlate with $SIV_{mac251}$ acquisition (FIG. 3L). Animals immunized with the ΔV1 also exhibited the highest-level neutralizing antibodies against the Tier 2 $SIV_{mac251CS.41}$ (FIG. 3M), surprisingly, however, this response was associated with an increased risk of virus acquisition (FIG. 3N).

DISCUSSION

Viruses, including the Western Equine Encephalitis, Polio, Hepatitis C, Influenza viruses, and SARS-Coronavirus (Sautto et al., Antiviral Res., 96, 82-89, 2012; To et al., Clin Vaccine Immunol., 19:1012-1018, 2012; Zhong et al., Biochem Biopphys Res Commun, 390:1056-1060, 2009; Tripp et al., J Virol Methods, 128:21-28, 2005; Dulbecco et al., Virology, 2, 162-205, 1956; Nicasio et al., Viruses, 4, 1731-1752, 2012) use several strategies to escape the host B-cell immune responses to viral surface proteins. These include antibody interference mediated by non-protective antibodies inhibiting immunoglobulin binding to distant, protective epitopes. The molecular mechanisms underlying antibody interference include steric hindrance that directly inhibits antibody access to the epitope or allosteric inhibition when antibody binding induce conformational changes that alter distant epitopes recognition (Klionsky et al., Autophagy, 12, 1-222, 2016; Sautto et al., Antiviral Res, 96, 82-89, 2012). Interference of antibodies to the HIV gp41 has been observed (Verrier et al. J Virol, 75, 9177-9186, 2001), but little is known about interfering antibodies that target apical gp120 domains and in particular the V1/V2 gp120 domains that constituted the correlate of risk of HIV acquisition in RV144. By using protein engineering and vaccine efficacy, measured as the risk of SIV acquisition as a read out, data presented in this example shows that SIV uses a similar mechanism for V1 to interfere with antibodies to V2. These results show that V1 has evolved in SIV, and likely HIV, to protect at least two viral vulnerability sites, the V2c by steric hindrance and the V2b by allosteric inhibition, possibly by creating a V1/V2 domain in a Greek-key β-sheet fold that presents non-protective epitopes to the host immune system.

Materials and Methods:

Animals studies: All animals used in the study were colony-bred rhesus macaques (*Macaca mulatta*), obtained from either Covance Research Products (Alice, TX) or Morgan Island. The animals were housed and handled in accordance with the standards of the Association for the Assessment and Accreditation of Laboratory Animal Care International.

The first cohort of animals consisted of a total of 78 vaccinated animals and 53 controls and the vaccine immunogens are previously reported (Vaccari et al., Nat Med, 22, 762-770, 2016; Vaccari et al., Nat Med, 24, 847-856, 2018). As a source for the molecular cloning of monoclonal antibodies we used the PBMCs of animal P770, a colony-bred Rhesus macaque (*Macaca mulatta*) included in the study described in (Klionsky et al., Autophagy, 12, 1-222, 2016). Briefly, P770 was immunized at weeks 0, 4, 12, and 24 with intramuscular inoculations of $10^8$ plaque-forming units (PFU) of ALVAC (vCP2432) expressing SIV genes gag-pro and gp120TM (Sanofi Pasteur). The sequence of the SIV genes was that of M766r, a mucosally transmitted founder variant of $SIV_{mac251}$. At weeks 12 and 24, the animal was administered in the thigh opposite as that of vector immunization a protein boost of 200 μg each of monomeric $SIV_{mac251}$-M766 gp120-gD and $SIV_{smE660}$ gp120-gD CG7V both formulated in alum. Four weeks after the final immunization, the animal underwent a challenge phase of 10 low-dose intrarectal 120 $TCID_{50}$ $SIV_{mac251}$ administrations and resulted uninfected. At week 53, P770 underwent a second round of 9 immunizations (referred to in the text as hyperimmunizations) administered every five weeks up to week 93. At week 131, the animal was challenged weekly for ten weeks using 120 $TCID_{50}$ of the same $SIV_{mac251}$ challenge stock used at week 28 and resulted (FIG. 7A).

The second cohort of animal included 3 groups of 14 animals each that were vaccinated intramuscularly with SIVp57Gag DNA (1 mg) together with either $SIVgp160_{WT}$, or ΔV1 or $ΔV1_{gpg}$ at week 0,1. At week 8 and 12 all animals received an intramuscular immunization of $10^8$ pfu of ALVAC-SIV (vCP 23.). At week 12 animals received also on the contralateral tight either $SIVgp120_{WT}$, or ΔV1 or ΔV1gpg, all formulated in alum. At five weeks after the last immunization (week 17) all vaccinated animals, together with another group of 18 naïve animals as controls, were exposed to one weekly dose of $SIV_{mac251}$ (1:200 dilution; $TCID_{50}$) for a total of 11 weeks.

Cloning of monoclonal antibodies from animal the vaccinated protected animal 770: The protein scaffold 1J08, which was previously demonstrated to present the SIV Env V1V2 domain in the conformation naturally found on the native V1V2 protomer basing on stable expression, clash score and solvent accessibility, was used to identify V1V2-specific B cell clones and produced as described in (Vaccari et al., Nat Med, 22, 762-770, 2016). The expression vector pVRC8400 encoding the C-terminal His-tagged, avi-tagged 1J08-scaffolded $SIV_{mac251}$-M766r or $SIV_{smE543}$ V1V2 sequences (GenScript) was used to transfect 293Freestyle (293F) cells with 293fectin transfection reagent (Invitrogen) following the company's instructions. 6 days post-transfection, cell culture supernatants were harvested and filtered through 0.22 μm filter and supplemented with protease inhibitor tablets (Roche). The constructs were passed through a Ni-Sepharose excel affinity media (GE Healthcare) and further purified with size exclusion chromatography (SEC) on a HiLoad 16/600 200 pg Superdex column (GE Healthcare).

The mAbs NCI05 and NCI09 were cloned from the hyperimmunized protected Rhesus macaque P770 following the methods described in (Vaccari et al., Nat Med, 22, 762-770, 2016). Briefly, frozen P770 PBMCs from week 85 (two weeks after the 7$^{th}$ hyperimmunization) were thawed and stained to allow the identification of CD20+, CD3−, CD4−, CD8−, CD14−, IgG+, IgM-memory B cells. After staining, the cells were washed twice with PBS and resuspended in 200 μl of PBS containing 1J08 $SIV_{mac251}$-M766 V1V2 conjugated to APC and 1J08 $SIV_{smE543}$ V1V2 conjugated to PE and incubated in the dark for 15 minutes at room temperature. The cells were then washed in PBS, analyzed and sorted with a modified 3-laser FACSAria cell sorter using the FACSDiva software (BD Biosciences). Cells that resulted positive for binding to $SIV_{smE543}$/V1V2 only or $SIV_{smE543}$ and $SIV_{mac251}$/V1V2 were singularly sorted into well of 96-well plates containing lysis solution. Flow cytometric data was analyzed with FlowJo 9.7.5.

Total RNA was reverse transcribed in each well, and rhesus immunoglobulin heavy (H), light kappa (LK) and light lambda (LA) chains variable domain genes amplified by nested PCR. Positive amplification products as analyzed on 2% agarose gel (Embi-Tec) were sequenced, and those that were identified as carrying Igγ and IgLκ or IgLλ sequences were re-amplified with sequence-specific primers carrying unique restriction sites using the first-round nested PCR products as template. Resulting PCR products were run on a 1% agarose gel, purified with QIAGEN Gel Extraction Kit® (QIAGEN) and eluted with 25 μl of nuclease-free water (Quality Biological). Purified PCR products were then digested and ligated into rhesus Igγ, IgLκ and IgLλ expression vectors containing a multiple cloning site upstream of the rhesus Igγ, Igκ or Igλ constant regions. Full-length IgG were expressed as by co-transfecting 293F cells with equal amounts of paired heavy and light chain plasmids then purified using Protein A Sepharose beads (GE Healthcare) according to the manufacturer's instructions.

Monoclonal antibody binding and competition assays: The ITS41 mAbs were previously isolated from a $SIV_{smE660}$-infected rhesus macaque (Mason et al., PLOS Pathog 12, e1005537 (2016). ITS41.01 bind to a V1 epitope 1 as previously reported (Gottardo et al., PLOS One 8, e75665, 2013). The monoclonal NCI04, NCI06, NCI05, and NCI09 antibodies were generated as described in the present example. Binding of SIV-specific mAbs to viral proteins or synthetic peptides was measured by enzyme-linked immunosorbent assay (ELISA). Plates were coated overnight at 4° C. with 50 μl, 100 ng/well of antigen in PBS, then blocked with 300 μl/well of 1% PBS-BSA for 1 hour at 37° C. When cyclic V2 (cV2) was tested, plates were coated at 4° C. overnight with 200 ng/well of streptavidin (Sigma-Aldrich) in bicarbonate buffer, pH 9.6, then incubated with biotinylated cV2 peptide (produced by JPT Peptide Technologies and kindly provided by Dr. Rao, Military HIV Research Program) for 1 h at 37° C. and blocked with 0.5% milk in 1×PBS, 0.1% Tween 20, pH 7.4 overnight at 4° C. Coated, blocked plates were incubated with 40 µl/well of serial dilutions of mAbs in 1% PBS-BSA for 1 hour at 37° C. 40 µl/well of a polyclonal preparation of Horseradish peroxidase-conjugated goat anti-monkey IgG antibody (Abcam) at 1:30,000 incubated for 1 hour at 37° C. Plates were washed between each step with 0.05% Tween 20 in PBS. Plates were developed using either 3,3',5,5'-tetramethylbenzidine (TMB) (Thermo Scientific) and read at 450 nm. When testing binding to linear peptides, cyclic V2 or 1J08 V1V2 scaffolds, a ratio of the molecular weights of these constructs to the native glycoprotein monomer was calculated to obtain coating with the same number of epitopes/well. Competition assays of anti-V2 mAbs were performed by enzyme-linked immunosorbent assay (ELISA) as described in Mason 2016 (PLOS Pathog, 12, e1005537, 2016) and Sautto 2012 Sautto et al., Antiviral Res, 96, 82-89, 2012). Briefly, plates were coated with 100 ng/well of purified proteins $SIV_{mac251}$-M766/gp120 (Advanced BioScience Laboratories, Inc.), $SIV_{smE660}$ 1J08 V1V2 scaffold (Mason et al., PLOS Pathog, 12, e1005537, 2016, Fazi et al., J Biol Chem, 277, 5290-5298, 2002) and blocked with 1% PBS/BSA. Serial dilutions of unbiotinylated competitor mAb in 1% PBS-BSA were then added to the wells for 15 mins prior to addition of biotinylated probe mAbs at a concentration to yield ~50% saturating OD450. After incubation with streptavidin-HRP (KPL) for 1 hr at 37° C., signal was developed through incubation with 3,3',5,5' tetramethylbenzidine (TMB) substrate (Thermo Fisher Scientific) and Optical density (OD) read at 450 nm. Two negative (1% PBS/BSA or serial dilutions of anti-CD4bs ITS01) and one positive (serial dilutions of unbiotinylated probe mAb) control of competition were included in each assay.

Neutralization activity of monoclonal antibodies. SIV pseudoviruses were produced as previously described (Tassaneetrithep et al., PLOS One, 9, e108446, 2014). Briefly, a luciferase reporter plasmid containing essential HIV genes was used in combination with a plasmid encoding for SIV gp160 to yield pseudoviruses exposing SIV Env on their surface. Plasmids encoding SIV gp160, clones $SIV_{smE660.CP3C}$, $SIV_{smE660.CR54}$, $SIV_{mac251.H9}$ and $SIV_{mac251.30}$ were kindly provided by David Montefiori. Single-round infection of TZM-bl was detected quantitatively in relative light units (RLU). Virus neutralization was measured as the 50% inhibitory concentration of mAb necessary to cause a 50% reduction in RLU as compared to virus control wells after subtraction of background RLU.

Figure 4A:
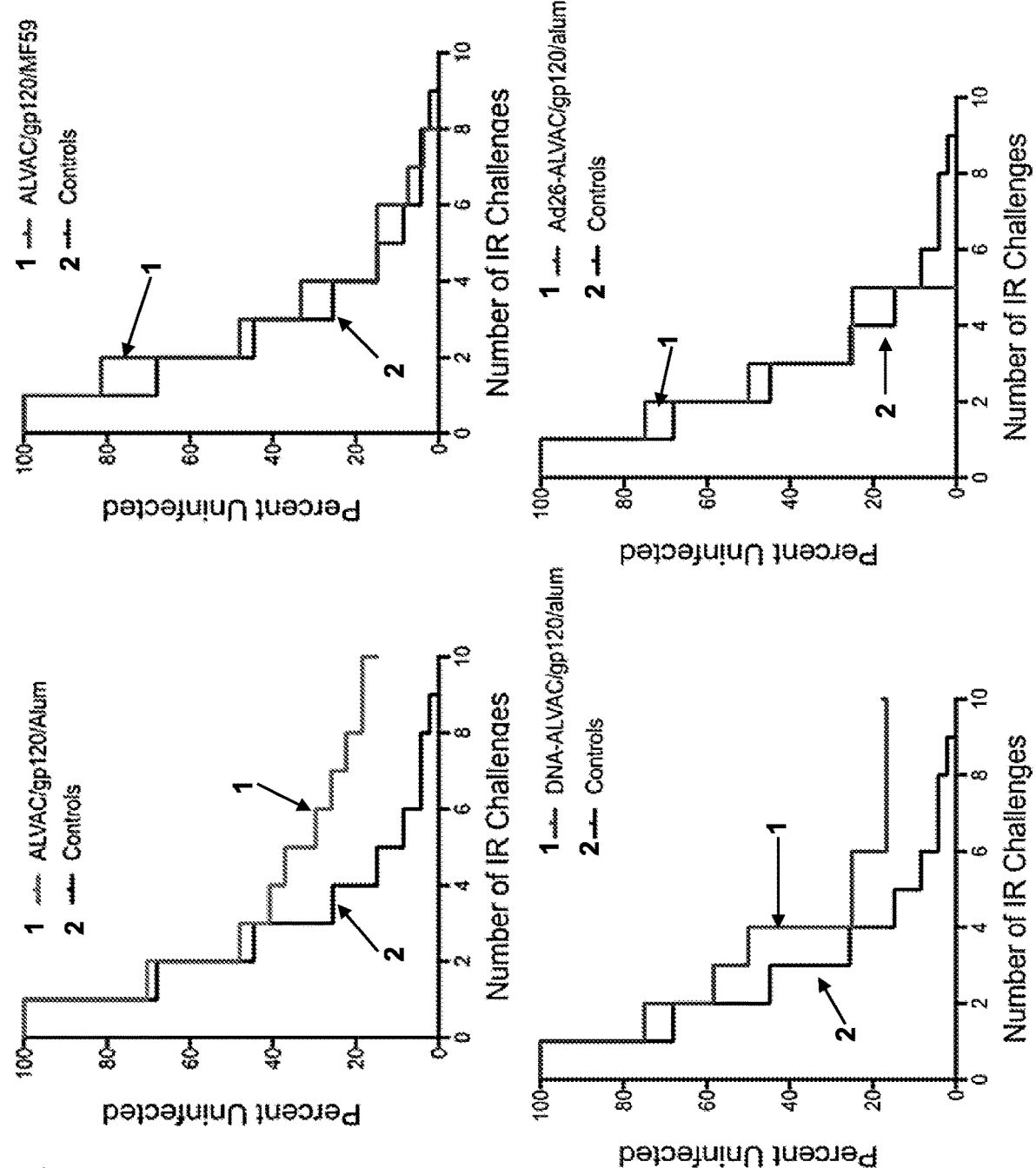

Adhesion assay and peptide arrays: A static adhesion assay was used to characterize the interaction between gp120 and $\alpha_4\beta_7$ based on a previously described method developed by Peachman and colleagues in which RPMI8866 cells, which express $\alpha_4\beta_7$ on the cell surface, were allowed to adhere to the recombinant Env proteins, V1/V2 scaffolds, or synthetic V2 cyclic peptides (FIG. 4A). The $\alpha_4\beta_7$-expressing RPMI8866 cell line was derived from a human B cell lymphoma, and expresses $\alpha_4\beta_7$, but no detectable CD4 or CCR5. Cells were grown in media containing retinoic acid, which increased levels of both expression and clustering of $\alpha_4\beta_7$ (FIG. 5B). In some assays, anti-integrin and anti-gp120 mAbs or sera were included as adhesion inhibitors. This cell-based assay measured adhesion between two multivalent surfaces. For the serum peptide arrays: sera were collected at 1 week after the last immunization for linear mapping, diluted to 1:20, and added to plates coated with peptides encompassing the entire $SIV_{K6W}$ gp120 amino acid sequence as previously described (Pegu et al., J Virol, 87, 1708-1719, 2013).

Antibody binding measured by surface plasmon resonance. To characterize the interaction between gp120 and $\alpha_4\beta_7$ a novel surface-plasmon resonance (SPR) based assay was developed that utilized dextran surfaces coated with recombinant envelope (Env) proteins, V1/V2 scaffolds, or synthetic V2 cyclic peptides. The analyte that we reacted with these surfaces was a recombinant soluble $\alpha_4\beta_7$ heterodimer in which the carboxy-terminal transmembrane and cytoplasmic tail domains of both chains were removed and replaced by short peptides that function as an "$\alpha_4$ chain acid-$\beta_7$ chain base coiled-coil clasp" (Nishiuchi et al., Matrix Biol, 25, 189-197, 2006). This acid-base clasp was joined by a disulfide bond that served to stabilize the heterodimer. In one iteration of this assay, short linear peptides derived from V2 we employed as competitive inhibitors.

Structural Analysis. The variable region of the NCI09 heavy chain was synthesized and cloned into a pVRC8400 vector containing an HRV3C cleavage site in the hinge region as previously described (McLellan Nature 2011). Heavy and light chain plasmids were co-expressed in 1 liter of Expi293F cells. IgG was purified from the supernatant through binding to a protein A Plus Agarose (Pierce) column and eluting with IgG Binding Buffer (Thermo Fisher). Antibodies were buffer-exchanged to PBS and then 10 mg of IgG was cleaved with HRV3C protease. The digested IgG was then passed over a 2 ml protein A Plus column to remove the Fc fragment. The Fab was further purified over a Superdex 200 gel filtration column in buffer containing 5 mM HEPES 7.5, 50 mM NaCl, and 0.02% $NaN_3$. To form NCI09-V2 peptide complexes, 5 mg of purified fab at a concentration of 2 mg/ml was incubated at room temperature for 30 minutes with a five-fold molar excess of SIV V2 peptide, synthesize by GenScript, and the complex was then concentrated down to 10 mg/ml using 10,000 MWCO Ultra centrifugal filter units (EMD Millipore). Antibody-peptide complexes were then screened against 576 crystallization conditions using a Mosquito crystallization robot mixing 0.1 µl of protein complex with 0.1 µl of the crystallization screening reservoir. Larger crystals were then grown by the vapor diffusion method in a sitting drop at 20° C. by mixing 1 µl of protein complex with 1 µl of reservoir solution (22% (w/v) PEG 4000, 0.1 M Na Acetate pH 4.6). Crystals were flash frozen in liquid nitrogen supplemented with 20% ethylene glycol as a cryoprotectant. Data were collected at 1.00 Å using the SER-CAT beamline ID-22 of the Advanced Photon Source, Argonne National Laboratory. Diffraction data were processed with HKL2000 (HKL Research). A molecular replacement solution was obtained with Phenix (phenix-online.org) contained one Fab molecule per asymmetric unit in space group P212121. Model building was carried out using COOT software (mrc-lmb.cam.ac.uk/personal/pemsley/coot/), and was refined with Phenix. Final data collection and refinement statistics are shown in Table S1. The Ramachandran plot determined by Molprobity (molprobity.biochem.duke.edu) shows 98.2% of all residues in favored regions and 100% of all residues in allowed regions for the complex structure.

α-helix peptide design. Peptide specific for the epitopes in the region near the α4β7 receptor site in the V2 loop of SIVmac251 and SIVmac543/E660, but distinct from the epitope targeted by NCI09 were designed by ab initio (computational chemistry) folding ab of overlapping fragments of amino acid length 5 to 17 from that region from position 167 in the V2 loop to position 184. Initial folding was performed as previously described using a method verified by NMR (Abagyan et al., J mol. Biol., 235 (3): 983-1002, 1994; Aiyegbo et al., PloS one.; 12 (1): e0170530, 2017; Totrov et al., Biopolymers, 60 (2): 124-33, 2001). Optimal characteristics were a) an alpha-helical lowest energy conformation and b) helical stability, assessed by the energy spectrum of the folding. The optimal fragment from SIVmac543/E660 was 14 amino acids in length with sequence DKKIEYNETWYSRD (SEQ ID NO: 24) and the equivalent fragment from 251, DKTKEYNETWYSTD (SEQ ID NO: 25), which also had optimal alpha-helical structure, was also used. Peptides were synthesized commercially (Genewiz Inc) with an N-terminal biotin attached. ELISA assays were performed as previously described (Almond Adv Virol., 2012:803535, 2012; Cardozo et al., Vaccine, 32 (39): 4916-24, 2014).

Statistical analysis. Fisher Exact Test was used for all pairwise comparisons. Wilcoxon rank sum and Kruskal-Wallis tests was used to compare populations of continuous data for groups of 2 and >3, respectively. ANOVA was used to determine the significance of titers or the reduction in viral load over time in well controlled animals, if applicable. Threshold: 2-sided alpha-level of 0.05, with Bonferroni correction made for multiple comparisons.

Challenge exposure of vaccinated macaques: The numbers of macaques were chosen based on the assumption that the probability of infection in each naïve control is 30% at each challenge exposure. In this case, each comparison of the 12 animals in one vaccinated group versus the 18 in the control group will have approximately 48% power if the vaccine has 50% efficacy, 70% power if it has 60% efficacy, and 90% power if it reaches the anticipated 70% efficacy.

Evaluation of immune responses: Distributions of serum IgG log-transformed titers to gp70-V1/V2 proteins typically result in standard deviations of 0.19. If one vaccine regimen has an expected mean log titer 0.12 (0.63 SD) greater than the other two, with 12 animals in each group, and if the log titers are normally distributed, the best regimen has 84% probability of being superior. The actual empirical distributions were negatively skewed, increasing the probability of the superior regimen to 90%.

Example 2

V1-Deleted HIV-1 Env Proteins for Human Immunization

The results presented in Example 1 show that immunization with the identified gp120 V1-deletion in the context of the DNA/ALVAC/gp120/platform in an SIV model reduces $SIV_{mac251}$ acquisition to a greater degree than the prior best performing regimen in a stringent, highly translational macaque model. This example illustrates HIV-1 Env immunogens containing the V1 deletion identified in Example 1 for use in humans.

A large number of reports suggest that the SIV and HIV envelopes are architecturally identical (e.g., Julien et al., Science, 342, 1477-1483, 2013; Chuang et al., J Virol, 91, e02268-16, 2017), therefore V1-deletion in an HIV envelope is expected to achieve the same bioactivity as observed in the SIV model.

Of the diverse HIV strains available, the A244 HIV gp120 protein was selected for three reasons:
1) A244 protein was used in the RV144 study;
2) mAbs CH58 and CH59 from a protected individual in the RV144 study targeting V2b/c were specific for A244 (Liao et al., Immunity, 38 (1): 176-86, 2013);
3) molecular modeling shows high similarity between the SIV gp120 used in Example 1 and A244 gp120 V2 regions (FIG. 14A).

Although the V1 loop is shorter in A244 than $SIV_{mac251}$, the disulfide bridge at positions 131 and 157 (Hxbc2 numbering) that is both the origin and insertion of V1 and therefore defines it, is conserved in nearly all HIV and SIV strains. Therefore, the V1-deleted V2 domain and the rest of gp120 in A244 and $SIV_{mac251}$ or $SIV_{SM/E660}$ are architecturally identical, because the V1-defining disulfide bridge normalizes any dramatic structural changes transmitted to the rest of the protein by V1 deletion between 131 and 157. Deletion of the V1 loop of A244 is believed to unmask V2b and V2c in similar manner as in the $SIV_{mac251}$ construct, since it connects directly to V2b and lies directly over V2c. In support of this concept, the bioequivalence of this envelope region of the A244 and $SIV_{mac251}$ was established by a preliminary probe bearing the HIV equivalents of the NCI05 and NCI09 V2 target sites. It was found that macaque sera from an animal vaccinated with a protective vaccine (that used alum as an adjuvant for the protein boost, Vaccari et al., Adjuvant-dependent innate and adaptive immune signatures of risk of $SIV_{mac251}$ acquisition. Nat Med 22, 762-770, 2016) recognized an HIV equivalent V2c peptide better than the sera of animals immunized with a non-protective vaccine (that used MF59 as an adjuvant in the protein boost) (FIG. 14B). These data support a structural and immunological equivalence of V1-deletion and the key V2 sites in SIV and HIV-1 A244. Accordingly, the probability is high that A244 V1V2 architecture and antigenicity of the V1V2 domain is identical to $SIV_{mac251}$ and $SIV_{SM\ E660}$ despite different sequence, and all that is needed to produce an A244 HIV-1 ΔV1 immunogen with equivalent antigenicity and immunogenicity to $SIV_{mac251M766}$ ΔV1 is fine-tuning by the same protein engineering techniques used to successfully design $SIV_{mac251M766}$ ΔV1.

To show that the V1-deleted HIV A244 will recapitulate the antigenicity of the ΔV1-deleted SIV envelope immunogens, gp120 from the A244 strain was modified with the 137-152 deletion and expressed in 293 or CHO cells as assessed for PG9 and CH58 binding by ELISA (FIG. 15). The sequence of the V1-deleted A244 gp120 is provided as SEQ ID NO: 1. The PG9 antibody specifically binds to a conformational epitope of the gp120 V1/V2 domain, whereas CH58 antibody is specific for a conformational epitope of the V2 domain. The ELISA binding data shows that the ΔV1 modification disrupted PG9 binding to both A244 and SIV gp120, but had no effect on CH58 binding to these proteins. Thus, A244 gp120 with the 137-152 deletion recapitulated the antigenicity of the ΔV1-deleted SIV envelope.

Exemplary sequences are provided as follows:
A244 gp120 with V1 137-152 deletion: SEQ ID NO: 1
MN gp120 with V1 137-152 deletion: SEQ ID NO: 2
96ZM651 gp120 with V1 137-152 deletion: SEQ ID NO: 3
A244 Env with ΔV1 137-152 deletion and without signal peptide: SEQ ID NO: 4
MN Env with ΔV1 137-152 deletion and without signal peptide: SEQ ID NO: 5

96ZM651 Env with ΔV1 137-152 deletion and without signal peptide: SEQ ID NO: 66

Full-length A244 Env with the ΔV1 137-152 deletion: SEQ ID NO: 6

Full-length MN Env with ΔV1 137-152 deletion: SEQ ID NO: 7

Full-length 96ZM651 Env with ΔV1 137-152 deletion SEQ ID NO: 67.

It will be apparent that the precise details of the methods or compositions described may be varied or modified without departing from the spirit of the described embodiments. We claim all such modifications and variations that fall within the scope and spirit of the claims below.

It is claimed:

1. A recombinant gp120 protein comprising a deletion consisting of deletion of HIV-1 Env residues 137-152 according to the HXBc2 numbering system, wherein the recombinant gp120 protein comprises or consists of an amino acid sequence at least 90% identical to any one of SEQ ID NOs: 1-3, and wherein the recombinant gp120 protein elicits an immune response to HIV-1.

2. The recombinant gp120 protein of claim 1, comprising or consisting of HIV-1 Env residues 31-507, with the deletion of residues 137-152, according to the HXBc2 numbering system.

3. The recombinant gp120 protein of claim 1, comprising or consisting of the amino acid sequence set forth as any one of SEQ ID NOs: 1-3.

4. A recombinant gp140 protein, a recombinant gp145 protein, or a recombinant gp160 protein comprising the recombinant gp120 protein of claim 1, wherein the recombinant gp140 protein, the recombinant gp145 protein, or the recombinant gp160 protein elicits an immune response to HIV-1.

5. A recombinant HIV-1 Env ectodomain trimer, comprising protomers comprising the recombinant gp120 protein of claim 1 and a gp41 ectodomain, wherein the HIV-1 Env ectodomain trimer elicits an immune response to HIV-1.

6. The recombinant HIV-1 Env ectodomain trimer of claim 5, wherein the recombinant gp120 protein comprises or consists of HIV-1 Env residues 31-507, with the deletion of residues 137-152, according to the HXBc2 numbering system, and the gp41 ectodomain comprises or consists of HIV-1 Env residues 512-664 according to the HXBc2 numbering system.

7. A recombinant HIV-1 Env ectodomain trimer comprising protomers comprising a recombinant gp120 protein and a gp41 ectodomain, wherein the recombinant gp120 protein comprises a deletion consisting of deletion of HIV-1 Env residues 137-152 according to the HXBc2 numbering system, the HIV-1 Env ectodomain trimer elicits an immune response to HIV-1, and wherein the protomers of the HIV-1 Env ectodomain trimer comprise or consist of an amino acid sequence at least 90% identical to any one of SEQ ID NOs: 4-5 and 66.

8. The recombinant HIV-1 Env ectodomain trimer of claim 7, wherein the protomers of the HIV-1 Env ectodomain trimer comprise or consist of the amino acid sequence set forth as any one of SEQ ID NOs: 4-5 and 66.

9. The recombinant HIV-1 Env ectodomain trimer of claim 5, wherein the protomers of the recombinant HIV-1 Env ectodomain trimer comprise a C-terminal fusion to a trimerization domain by a peptide linker, or directly fused to the trimerization domain.

10. The recombinant HIV-1 Env ectodomain trimer of claim 5, wherein the recombinant HIV-1 Env ectodomain trimer is soluble.

11. The recombinant HIV-1 Env ectodomain trimer of claim 5, wherein the protomers of the recombinant HIV-1 Env ectodomain trimer are each fused c-terminally to a transmembrane domain.

12. The recombinant gp120 protein of claim 1, further comprising one or more additional amino acid substitutions or deletions, or a recombinant gp140 protein, a recombinant gp145 protein, a recombinant gp160 protein, or a recombinant HIV-1 Env ectodomain trimer comprising the recombinant gp120 protein of claim 1 and further comprising the one or more additional amino acid substitutions or deletions.

13. The recombinant gp120 protein of claim 1, wherein the immune response inhibits HIV-1 infection, or a recombinant gp140 protein, a recombinant gp145 protein, a recombinant gp160 protein, or a recombinant HIV-1 Env ectodomain trimer comprising the recombinant gp120 protein of claim 1 that induces an immune response inhibits HIV-1 infection.

14. An immunogenic conjugate comprising the recombinant gp120 protein of claim 1 conjugated to a heterologous carrier, or a recombinant gp140 protein, a recombinant gp145 protein, a recombinant gp160 protein, or a recombinant HIV-1 Env ectodomain trimer comprising the recombinant gp120 protein of claim 1 and conjugated to a heterologous carrier.

15. A virus-like particle comprising the recombinant gp120 protein of claim 1 or a virus like particle comprising a recombinant gp140 protein, a recombinant gp145 protein, a recombinant gp160 protein, or a recombinant HIV-1 Env ectodomain trimer comprising the recombinant gp120 protein of claim 1.

16. An immunogenic composition for use to elicit an immune response to HIV-1 in a subject, comprising the recombinant gp120 protein of claim 1, or an immunogenic composition comprising a recombinant gp140 protein, a recombinant gp145 protein, a recombinant gp160 protein, or a recombinant HIV-1 Env ectodomain trimer comprising the recombinant gp120 protein of claim 1, and a pharmaceutically acceptable carrier.

17. The immunogenic composition of claim 16, further comprising an adjuvant.

18. A method for eliciting an immune response to HIV-1 in a subject, comprising administering to the subject an effective amount of the recombinant gp120 protein of claim 1 or a recombinant gp140 protein, a recombinant gp145 protein, a recombinant gp160 protein, or a recombinant HIV-1 Env ectodomain trimer comprising the recombinant gp120 protein of claim 1, to elicit the immune response.

19. The method of claim 18, wherein the immune response treats or inhibits an HIV-1 infection in the subject.

* * * * *

SEQUENCE LISTING

```
<160> NUMBER OF SEQ ID NOS: 68

<210> SEQ ID NO 1
<211> LENGTH: 476
<212> TYPE: PRT
<213> ORGANISM: Human immunodeficiency virus type 1

<400> SEQUENCE: 1

Asn Leu Trp Lys Trp Gly Thr Leu Ile Leu Gly Leu Val Ile Ile Cys
1               5                   10                  15

Ser Ala Ser Asp Asn Leu Trp Val Thr Val Tyr Tyr Gly Val Pro Val
            20                  25                  30

Trp Arg Asp Ala Asp Thr Thr Leu Phe Cys Ala Ser Asp Ala Lys Ala
        35                  40                  45

Gln Glu Thr Glu Ala His Asn Val Trp Ala Thr His Ala Cys Val Pro
    50                  55                  60

Thr Asp Pro Asn Pro Gln Glu Leu His Leu Glu Asn Val Thr Glu Asn
65                  70                  75                  80

Phe Asn Met Trp Lys Asn Asn Met Val Glu Gln Met Gln Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Ala Asn Leu Glu Val Arg Asn
        115                 120                 125

Cys Ser Phe Asn Met Thr Thr Glu Leu Arg Asp Lys Lys Gln Lys Val
    130                 135                 140

His Ala Leu Phe Tyr Lys Leu Asp Ile Val Pro Ile Glu Asp Asn Thr
145                 150                 155                 160

Ser Ser Ser Lys Tyr Arg Leu Ile Asn Cys Asn Thr Ser Val Ile Lys
                165                 170                 175

Gln Ala Cys Pro Lys Ile Ser Phe Asp Pro Ile Pro Ile His Tyr Cys
            180                 185                 190

Thr Pro Ala Gly Tyr Ala Ile Leu Lys Cys Asn Asp Lys Asn Phe Asn
        195                 200                 205

Gly Thr Gly Pro Cys Lys Asn Val Ser Ser Val Gln Cys Thr His Gly
    210                 215                 220

Ile Lys Pro Ala Val Ser Thr Gln Leu Leu Leu Asn Gly Ser Leu Ala
225                 230                 235                 240

Glu Glu Glu Ile Ile Ile Arg Ser Glu Asn Leu Thr Asn Asn Ala Lys
                245                 250                 255

Thr Ile Ile Val His Leu Asn Lys Ser Val Glu Ile Asn Cys Thr Arg
            260                 265                 270

Pro Ser Asn Asn Thr Arg Thr Ser Ile Asn Ile Gly Pro Gly Gln Val
        275                 280                 285

Phe Tyr Arg Thr Gly Asp Ile Ile Gly Asp Ile Arg Lys Ala Tyr Cys
    290                 295                 300

Glu Ile Asn Gly Ala Lys Trp Asn Glu Val Leu Lys Lys Val Thr Glu
305                 310                 315                 320
```

```
Lys Leu Lys Glu His Phe Asn Asn Lys Thr Ile Ile Phe Gln Pro Pro
            325                 330                 335

Ser Gly Gly Asp Leu Glu Ile Thr Met His His Phe Asn Cys Arg Gly
        340                 345                 350

Glu Phe Phe Tyr Cys Asn Thr Thr Arg Leu Phe Asn Asn Thr Cys Met
            355                 360                 365

Glu Asn Glu Thr Met Glu Gly Cys Asn Gly Thr Ile Ile Leu Pro Cys
        370                 375                 380

Lys Ile Lys Gln Ile Ile Asn Met Trp Gln Ala Gly Gln Ala Met
385                 390                 395                 400

Tyr Ala Pro Pro Ile Ser Gly Arg Ile Asn Cys Val Ser Asn Ile Thr
            405                 410                 415

Gly Ile Leu Leu Thr Arg Asp Gly Leu Asn Asn Thr Asn Glu Thr
        420                 425                 430

Phe Arg Pro Gly Gly Gly Asn Ile Lys Asp Asn Trp Arg Ser Glu Leu
            435                 440                 445

Tyr Lys Tyr Lys Val Val Gln Ile Glu Pro Leu Gly Ile Ala Pro Thr
        450                 455                 460

Arg Ala Lys Arg Val Val Glu Arg Glu Lys Arg
465                 470                 475

<210> SEQ ID NO 2
<211> LENGTH: 480
<212> TYPE: PRT
<213> ORGANISM: Human immunodeficiency virus type 1

<400> SEQUENCE: 2

His Trp Trp Gly Trp Gly Thr Met Leu Leu Gly Leu Leu Met Ile Cys
1               5                   10                  15

Ser Ala Thr Glu Lys Leu Trp Val Thr Val Tyr Tyr Gly Val Pro Val
            20                  25                  30

Trp Lys Glu Ala Thr Thr Thr Leu Phe Cys Ala Ser Asp Ala Lys Ala
        35                  40                  45

Tyr Asp Thr Glu Val His Asn Val Trp Ala Thr His Ala Cys Val Pro
    50                  55                  60

Thr Asp Pro Asn Pro Gln Glu Val Gln Leu Val Asn Val Thr Glu Asp
65                  70                  75                  80

Phe Asn Met Trp Lys Asn Asn Met Val Glu Gln Met His Glu Asp Ile
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asp Leu Arg Asn Glu Met Lys Asn
        115                 120                 125

Cys Ser Phe Asn Ile Thr Thr Ser Ile Arg Asp Lys Met Gln Lys Glu
    130                 135                 140

Tyr Ala Leu Leu Tyr Lys Leu Asp Ile Val Ala Ile Asp Lys Asp Asn
145                 150                 155                 160

Thr Ser Tyr Arg Leu Ile Ser Cys Asn Thr Ser Val Ile Thr Gln Ala
                165                 170                 175

Cys Pro Lys Val Ser Phe Glu Pro Ile Pro Ile His Tyr Cys Ala Pro
            180                 185                 190

Ala Gly Phe Ala Ile Leu Lys Cys Asn Asp Lys Asn Phe Thr Gly Lys
        195                 200                 205

Gly Pro Cys Lys Asn Val Ser Thr Val Gln Cys Thr His Gly Ile Arg
    210                 215                 220
```

Pro Val Val Ser Thr Gln Leu Leu Leu Asn Gly Ser Leu Ala Glu Glu
225                 230                 235                 240

Glu Val Val Ile Arg Ser Glu Asn Phe Thr Asn Asn Ala Lys Thr Ile
            245                 250                 255

Ile Val His Leu Asn Glu Ser Val Gln Ile Asn Cys Thr Arg Pro Tyr
        260                 265                 270

Asn Asn Arg Arg Thr Arg Ile His Ile Gly Pro Gly Arg Ala Phe Tyr
    275                 280                 285

Thr Thr Lys Asn Ile Lys Gly Thr Ile Arg Gln Ala His Cys Thr Ile
290                 295                 300

Ser Ser Ala Lys Trp Asn Asp Thr Leu Arg Gln Ile Val Ser Lys Leu
305                 310                 315                 320

Lys Glu Gln Phe Lys Asn Lys Thr Ile Val Phe Lys Gln Ser Ser Gly
                325                 330                 335

Gly Asp Pro Glu Ile Val Met His Ser Phe Asn Cys Gly Gly Glu Phe
            340                 345                 350

Phe Tyr Cys Asn Thr Ser Ser Leu Phe Asn Ser Thr Trp Asn Gly Asn
        355                 360                 365

Asn Thr Trp Asn Thr Thr Gly Ser Asn Ser Asn Ile Thr Leu Gln
    370                 375                 380

Cys Lys Ile Lys Gln Ile Ile Asn Met Trp Gln Glu Val Gly Lys Ala
385                 390                 395                 400

Met Tyr Ala Pro Pro Ile Glu Gly Gln Ile Arg Cys Ser Ser Asn Ile
                405                 410                 415

Thr Gly Leu Leu Leu Thr Arg Asp Gly Gly Asn Asp Thr Asp Thr Asn
            420                 425                 430

Asn Thr Glu Ile Phe Arg Pro Gly Gly Gly Asp Met Arg Asp Asn Trp
        435                 440                 445

Arg Ser Glu Leu Tyr Lys Tyr Lys Val Val Thr Ile Glu Pro Leu Gly
    450                 455                 460

Val Ala Pro Thr Lys Ala Lys Arg Arg Val Val Gln Arg Glu Lys Arg
465                 470                 475                 480

<210> SEQ ID NO 3
<211> LENGTH: 484
<212> TYPE: PRT
<213> ORGANISM: Human immunodeficiency virus type 1

<400> SEQUENCE: 3

Arg Trp Trp Thr Trp Gly Ile Leu Gly Phe Trp Met Leu Met Ile Cys
1               5                   10                  15

Asn Val Trp Gly Asn Leu Trp Val Thr Val Tyr Tyr Gly Val Pro Val
            20                  25                  30

Trp Lys Glu Ala Lys Thr Thr Leu Phe Cys Ala Ser Asp Ala Lys Ser
        35                  40                  45

Tyr Glu Lys Glu Val His Asn Val Trp Ala Thr His Ala Cys Val Pro
    50                  55                  60

Thr Asp Pro Asn Pro Gln Glu Ile Val Leu Gly Asn Val Thr Glu Asn
65                  70                  75                  80

Phe Asn Met Trp Lys Asn Asp Met Val Asp Gln Met His Glu Asp Ile
                85                  90                  95

Ile Ser Leu Trp Asp Gln Ser Leu Lys Pro Cys Val Lys Leu Thr Pro
            100                 105                 110

```
Leu Cys Val Thr Leu Asn Cys Thr Glu Val Asn Val Asp Met Lys Asn
            115                 120                 125
Cys Ser Phe Asn Ile Thr Thr Glu Leu Lys Asp Lys Lys Asn Val
    130                 135                 140
Tyr Ala Leu Phe Tyr Lys Leu Asp Ile Val Ser Leu Asn Glu Thr Asp
145                 150                 155                 160
Asp Ser Glu Thr Gly Asn Ser Ser Lys Tyr Tyr Arg Leu Ile Asn Cys
                165                 170                 175
Asn Thr Ser Ala Leu Thr Gln Ala Cys Pro Lys Val Ser Phe Asp Pro
            180                 185                 190
Ile Pro Ile His Tyr Cys Ala Pro Ala Gly Tyr Ala Ile Leu Lys Cys
        195                 200                 205
Asn Asn Lys Thr Phe Asn Gly Thr Gly Pro Cys His Asn Val Ser Thr
    210                 215                 220
Val Gln Cys Thr His Gly Ile Lys Pro Val Val Ser Thr Gln Leu Leu
225                 230                 235                 240
Leu Asn Gly Ser Leu Ala Glu Glu Gly Ile Ile Arg Ser Glu Asn
                245                 250                 255
Leu Thr Asn Asn Val Lys Thr Ile Ile Val His Leu Asn Arg Ser Ile
            260                 265                 270
Glu Ile Val Cys Val Arg Pro Asn Asn Asn Thr Arg Gln Ser Ile Arg
        275                 280                 285
Ile Gly Pro Gly Gln Thr Phe Tyr Ala Thr Gly Asp Ile Ile Gly Asp
    290                 295                 300
Ile Arg Gln Ala His Cys Asn Ile Ser Arg Thr Asn Trp Thr Lys Thr
305                 310                 315                 320
Leu Arg Glu Val Arg Asn Lys Leu Arg Glu His Phe Pro Asn Lys Asn
                325                 330                 335
Ile Thr Phe Lys Pro Ser Ser Gly Gly Asp Leu Glu Ile Thr Thr His
            340                 345                 350
Ser Phe Asn Cys Arg Gly Glu Phe Phe Tyr Cys Asn Thr Ser Gly Leu
        355                 360                 365
Phe Ser Ile Asn Tyr Thr Glu Asn Asn Thr Asp Gly Thr Pro Ile Thr
    370                 375                 380
Leu Pro Cys Arg Ile Arg Gln Ile Ile Asn Met Trp Gln Glu Val Gly
385                 390                 395                 400
Arg Ala Met Tyr Ala Pro Pro Ile Glu Gly Asn Ile Ala Cys Lys Ser
                405                 410                 415
Asp Ile Thr Gly Leu Leu Leu Val Arg Asp Gly Gly Ser Thr Asn Asp
            420                 425                 430
Ser Thr Asn Asn Asn Thr Glu Ile Phe Arg Pro Ala Gly Gly Asp Met
        435                 440                 445
Arg Asp Asn Trp Arg Ser Glu Leu Tyr Lys Tyr Lys Val Val Glu Ile
    450                 455                 460
Lys Pro Leu Gly Ile Ala Pro Thr Glu Ala Lys Arg Arg Val Val Glu
465                 470                 475                 480
Arg Glu Lys Arg

<210> SEQ ID NO 4
<211> LENGTH: 828
<212> TYPE: PRT
<213> ORGANISM: Human immunodeficiency virus type 1
```

<400> SEQUENCE: 4

```
Asn Leu Trp Lys Trp Gly Thr Leu Ile Leu Gly Leu Val Ile Ile Cys
1               5                   10                  15

Ser Ala Ser Asp Asn Leu Trp Val Thr Val Tyr Tyr Gly Val Pro Val
            20                  25                  30

Trp Arg Asp Ala Asp Thr Thr Leu Phe Cys Ala Ser Asp Ala Lys Ala
        35                  40                  45

Gln Glu Thr Glu Ala His Asn Val Trp Ala Thr His Ala Cys Val Pro
50                  55                  60

Thr Asp Pro Asn Pro Gln Glu Leu His Leu Glu Asn Val Thr Glu Asn
65                  70                  75                  80

Phe Asn Met Trp Lys Asn Asn Met Val Glu Gln Met Gln Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Ala Asn Leu Glu Val Arg Asn
        115                 120                 125

Cys Ser Phe Asn Met Thr Thr Glu Leu Arg Asp Lys Lys Gln Lys Val
130                 135                 140

His Ala Leu Phe Tyr Lys Leu Asp Ile Val Pro Ile Glu Asp Asn Thr
145                 150                 155                 160

Ser Ser Ser Lys Tyr Arg Leu Ile Asn Cys Asn Thr Ser Val Ile Lys
                165                 170                 175

Gln Ala Cys Pro Lys Ile Ser Phe Asp Pro Ile Pro Ile His Tyr Cys
            180                 185                 190

Thr Pro Ala Gly Tyr Ala Ile Leu Lys Cys Asn Asp Lys Asn Phe Asn
        195                 200                 205

Gly Thr Gly Pro Cys Lys Asn Val Ser Ser Val Gln Cys Thr His Gly
210                 215                 220

Ile Lys Pro Ala Val Ser Thr Gln Leu Leu Leu Asn Gly Ser Leu Ala
225                 230                 235                 240

Glu Glu Glu Ile Ile Arg Ser Glu Asn Leu Thr Asn Asn Ala Lys
                245                 250                 255

Thr Ile Ile Val His Leu Asn Lys Ser Val Glu Ile Asn Cys Thr Arg
            260                 265                 270

Pro Ser Asn Asn Thr Arg Thr Ser Ile Asn Ile Gly Pro Gly Gln Val
        275                 280                 285

Phe Tyr Arg Thr Gly Asp Ile Ile Gly Asp Ile Arg Lys Ala Tyr Cys
290                 295                 300

Glu Ile Asn Gly Ala Lys Trp Asn Glu Val Leu Lys Lys Val Thr Glu
305                 310                 315                 320

Lys Leu Lys Glu His Phe Asn Asn Lys Thr Ile Ile Phe Gln Pro Pro
                325                 330                 335

Ser Gly Gly Asp Leu Glu Ile Thr Met His His Phe Asn Cys Arg Gly
            340                 345                 350

Glu Phe Phe Tyr Cys Asn Thr Thr Arg Leu Phe Asn Asn Thr Cys Met
        355                 360                 365

Glu Asn Glu Thr Met Glu Gly Cys Asn Gly Thr Ile Ile Leu Pro Cys
370                 375                 380

Lys Ile Lys Gln Ile Ile Asn Met Trp Gln Arg Ala Gly Gln Ala Met
385                 390                 395                 400
```

-continued

Tyr Ala Pro Pro Ile Ser Gly Arg Ile Asn Cys Val Ser Asn Ile Thr
                405                 410                 415
Gly Ile Leu Leu Thr Arg Asp Gly Gly Leu Asn Asn Thr Asn Glu Thr
            420                 425                 430
Phe Arg Pro Gly Gly Gly Asn Ile Lys Asp Asn Trp Arg Ser Glu Leu
        435                 440                 445
Tyr Lys Tyr Lys Val Val Gln Ile Glu Pro Leu Gly Ile Ala Pro Thr
    450                 455                 460
Arg Ala Lys Arg Arg Val Val Glu Arg Glu Lys Arg Ala Val Gly Ile
465                 470                 475                 480
Gly Ala Met Ile Phe Gly Phe Leu Gly Ala Ala Gly Ser Thr Met Gly
                485                 490                 495
Ala Ala Ser Ile Thr Leu Thr Val Gln Ala Arg Gln Leu Leu Ser Gly
            500                 505                 510
Ile Val Gln Gln Gln Ser Asn Leu Leu Arg Ala Ile Glu Ala Gln Gln
        515                 520                 525
His Leu Leu Gln Leu Thr Val Trp Gly Ile Lys Gln Leu Gln Ala Arg
    530                 535                 540
Val Leu Ala Val Glu Arg Tyr Leu Lys Asp Gln Lys Leu Leu Gly Leu
545                 550                 555                 560
Trp Gly Cys Ser Gly Lys Ile Ile Cys Thr Thr Ala Val Pro Trp Asn
                565                 570                 575
Ser Thr Trp Ser Asn Arg Ser Phe Glu Glu Ile Trp Asn Asn Met Thr
            580                 585                 590
Trp Ile Glu Trp Glu Arg Glu Ile Ser Asn Tyr Thr Asn Gln Ile Tyr
        595                 600                 605
Glu Ile Leu Thr Gln Ser Gln Asn Gln Gln Asp Arg Asn Glu Lys Asp
    610                 615                 620
Leu Leu Glu Leu Asp Lys Trp Ala Ser Leu Trp Lys Trp Phe Asp Ile
625                 630                 635                 640
Thr Asn Trp Leu Trp Tyr Ile Lys Ile Phe Ile Met Ile Val Gly Gly
                645                 650                 655
Leu Ile Gly Leu Arg Ile Ile Phe Ala Val Leu Ser Ile Val Asn Arg
            660                 665                 670
Val Arg Gln Gly Tyr Ser Pro Leu Ser Leu Gln Ile Pro Thr His His
        675                 680                 685
Gln Arg Glu Pro Asp Arg Pro Glu Arg Ile Glu Glu Gly Gly Gly Glu
    690                 695                 700
Gln Gly Arg Asp Lys Ser Val Arg Leu Val Ser Gly Phe Leu Ala Leu
705                 710                 715                 720
Thr Trp Asp Asp Leu Arg Ser Leu Cys Leu Phe Ser Tyr His Arg Leu
                725                 730                 735
Arg Asp Phe Ile Ser Ile Ala Ala Arg Thr Val Glu Leu Leu Gly His
            740                 745                 750
Ser Ser Leu Lys Gly Leu Arg Arg Gly Trp Glu Gly Leu Lys Tyr Leu
        755                 760                 765
Gly Asn Leu Ile Leu Tyr Trp Gly Gln Glu Leu Lys Ile Ser Ala Ile
    770                 775                 780
Ser Leu Leu Asn Ala Thr Ala Ile Ala Val Ala Gly Trp Thr Asp Arg
785                 790                 795                 800
Val Ile Glu Val Ala Gln Gly Ala Trp Arg Ala Ile Leu His Ile Pro
                805                 810                 815

-continued

```
Arg Arg Ile Arg Gln Gly Leu Glu Arg Thr Leu Leu
                820                 825
```

<210> SEQ ID NO 5
<211> LENGTH: 824
<212> TYPE: PRT
<213> ORGANISM: Human immunodeficiency virus type 1

<400> SEQUENCE: 5

```
His Trp Trp Gly Trp Gly Thr Met Leu Leu Gly Leu Leu Met Ile Cys
1               5                   10                  15

Ser Ala Thr Glu Lys Leu Trp Val Thr Val Tyr Tyr Gly Val Pro Val
                20                  25                  30

Trp Lys Glu Ala Thr Thr Thr Leu Phe Cys Ala Ser Asp Ala Lys Ala
            35                  40                  45

Tyr Asp Thr Glu Val His Asn Val Trp Ala Thr His Ala Cys Val Pro
        50                  55                  60

Thr Asp Pro Asn Pro Gln Glu Val Gln Leu Val Asn Val Thr Glu Asp
65                  70                  75                  80

Phe Asn Met Trp Lys Asn Asn Met Val Glu Gln Met His Glu Asp Ile
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asp Leu Arg Asn Glu Met Lys Asn
        115                 120                 125

Cys Ser Phe Asn Ile Thr Thr Ser Ile Arg Asp Lys Met Gln Lys Glu
    130                 135                 140

Tyr Ala Leu Leu Tyr Lys Leu Asp Ile Val Ala Ile Asp Lys Asp Asn
145                 150                 155                 160

Thr Ser Tyr Arg Leu Ile Ser Cys Asn Thr Ser Val Ile Thr Gln Ala
                165                 170                 175

Cys Pro Lys Val Ser Phe Glu Pro Ile Pro Ile His Tyr Cys Ala Pro
            180                 185                 190

Ala Gly Phe Ala Ile Leu Lys Cys Asn Asp Lys Asn Phe Thr Gly Lys
        195                 200                 205

Gly Pro Cys Lys Asn Val Ser Thr Val Gln Cys Thr His Gly Ile Arg
    210                 215                 220

Pro Val Val Ser Thr Gln Leu Leu Leu Asn Gly Ser Leu Ala Glu Glu
225                 230                 235                 240

Glu Val Val Ile Arg Ser Glu Asn Phe Thr Asn Asn Ala Lys Thr Ile
                245                 250                 255

Ile Val His Leu Asn Glu Ser Val Gln Ile Asn Cys Thr Arg Pro Tyr
            260                 265                 270

Asn Asn Arg Arg Thr Arg Ile His Ile Gly Pro Gly Arg Ala Phe Tyr
        275                 280                 285

Thr Thr Lys Asn Ile Lys Gly Thr Ile Arg Gln Ala His Cys Thr Ile
    290                 295                 300

Ser Ser Ala Lys Trp Asn Asp Thr Leu Arg Gln Ile Val Ser Lys Leu
305                 310                 315                 320

Lys Glu Gln Phe Lys Asn Lys Thr Ile Val Phe Lys Gln Ser Ser Gly
                325                 330                 335

Gly Asp Pro Glu Ile Val Met His Ser Phe Asn Cys Gly Gly Glu Phe
            340                 345                 350

Phe Tyr Cys Asn Thr Ser Ser Leu Phe Asn Ser Thr Trp Asn Gly Asn
        355                 360                 365
```

```
Asn Thr Trp Asn Asn Thr Thr Gly Ser Asn Ser Asn Ile Thr Leu Gln
    370                 375                 380

Cys Lys Ile Lys Gln Ile Ile Asn Met Trp Gln Glu Val Gly Lys Ala
385                 390                 395                 400

Met Tyr Ala Pro Pro Ile Glu Gly Gln Ile Arg Cys Ser Ser Asn Ile
                405                 410                 415

Thr Gly Leu Leu Leu Thr Arg Asp Gly Gly Asn Asp Thr Asp Thr Asn
                420                 425                 430

Asn Thr Glu Ile Phe Arg Pro Gly Gly Gly Asp Met Arg Asp Asn Trp
            435                 440                 445

Arg Ser Glu Leu Tyr Lys Tyr Lys Val Val Thr Ile Glu Pro Leu Gly
        450                 455                 460

Val Ala Pro Thr Lys Ala Lys Arg Arg Val Val Gln Arg Glu Lys Arg
465                 470                 475                 480

Ala Ala Ile Gly Ala Leu Phe Leu Gly Phe Leu Gly Ala Ala Gly Ser
                485                 490                 495

Thr Met Gly Ala Ala Ser Met Met Leu Thr Val Gln Ala Arg Gln Leu
                500                 505                 510

Leu Ser Gly Ile Val Gln Gln Gln Asn Asn Leu Leu Arg Ala Ile Glu
            515                 520                 525

Ala Gln Gln His Met Leu Gln Leu Thr Val Trp Gly Ile Lys Gln Leu
        530                 535                 540

Gln Ala Arg Val Leu Ala Val Glu Arg Tyr Leu Arg Asp Gln Gln Leu
545                 550                 555                 560

Leu Gly Ile Trp Gly Cys Ser Gly Lys Leu Ile Cys Thr Thr Thr Val
                565                 570                 575

Pro Trp Asn Ala Ser Trp Ser Asn Lys Ser Gln Glu Asp Ile Trp Asn
            580                 585                 590

Asn Met Thr Trp Met Gln Trp Glu Arg Glu Ile Asp Asn Tyr Thr Ser
        595                 600                 605

Thr Ile Tyr Glu Leu Leu Glu Lys Ser Gln Asn Gln Gln Glu Lys Asn
    610                 615                 620

Glu Gln Glu Leu Leu Glu Leu Asp Lys Trp Ala Ser Leu Trp Asn Trp
625                 630                 635                 640

Phe Asp Ile Thr Asn Trp Leu Trp Tyr Ile Lys Ile Phe Ile Met Ile
                645                 650                 655

Val Gly Gly Leu Ile Gly Leu Arg Ile Val Phe Ala Val Leu Ser Ile
                660                 665                 670

Val Asn Arg Val Arg Gln Gly Tyr Ser Pro Leu Ser Leu Gln Thr Arg
    675                 680                 685

Pro Pro Val Pro Arg Gly Pro Asp Arg Pro Glu Gly Thr Glu Glu Glu
        690                 695                 700

Gly Gly Glu Arg Asp Arg Asp Thr Ser Gly Arg Leu Val Asp Gly Phe
705                 710                 715                 720

Leu Ala Ile Ile Trp Val Asp Leu Arg Ser Leu Leu Phe Ser Tyr
                725                 730                 735

His Arg Leu Arg Asp Leu Leu Leu Ile Ala Ala Arg Ile Val Glu Leu
            740                 745                 750

Leu Gly Arg Arg Gly Trp Glu Ile Leu Lys Tyr Trp Trp Asn Leu Leu
        755                 760                 765

Gln Tyr Trp Ser Gln Glu Leu Lys Asn Ser Ala Val Ser Leu Leu Asn
    770                 775                 780
```

```
Ala Thr Ala Val Ala Val Glu Gly Thr Asp Arg Val Ile Glu Val
785                 790                 795                 800

Leu Gln Arg Ala Gly Arg Ala Ile Leu His Ile Pro Thr Arg Ile Arg
            805                 810                 815

Gln Gly Leu Glu Arg Ala Leu Leu
            820

<210> SEQ ID NO 6
<211> LENGTH: 839
<212> TYPE: PRT
<213> ORGANISM: Human immunodeficiency virus type 1

<400> SEQUENCE: 6

Met Arg Val Lys Glu Thr Gln Met Thr Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala Gln Glu Thr Glu Ala
    50                  55                  60

His Asn Val Trp Ala Thr His Ala Cys Val Pro Thr Asp Pro Asn Pro
65                  70                  75                  80

Gln Glu Leu His Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Asn Leu Glu Val Arg Asn Cys Ser Phe Asn Met
    130                 135                 140

Thr Thr Glu Leu Arg Asp Lys Lys Gln Lys Val His Ala Leu Phe Tyr
145                 150                 155                 160

Lys Leu Asp Ile Val Pro Ile Glu Asp Asn Thr Ser Ser Ser Lys Tyr
                165                 170                 175

Arg Leu Ile Asn Cys Asn Thr Ser Val Ile Lys Gln Ala Cys Pro Lys
            180                 185                 190

Ile Ser Phe Asp Pro Ile Pro Ile His Tyr Cys Thr Pro Ala Gly Tyr
        195                 200                 205

Ala Ile Leu Lys Cys Asn Asp Lys Asn Phe Asn Gly Thr Gly Pro Cys
    210                 215                 220

Lys Asn Val Ser Ser Val Gln Cys Thr His Gly Ile Lys Pro Ala Val
225                 230                 235                 240

Ser Thr Gln Leu Leu Leu Asn Gly Ser Leu Ala Glu Glu Glu Ile Ile
                245                 250                 255

Ile Arg Ser Glu Asn Leu Thr Asn Asn Ala Lys Thr Ile Ile Val His
            260                 265                 270

Leu Asn Lys Ser Val Glu Ile Asn Cys Thr Arg Pro Ser Asn Asn Thr
        275                 280                 285

Arg Thr Ser Ile Asn Ile Gly Pro Gly Gln Val Phe Tyr Arg Thr Gly
    290                 295                 300

Asp Ile Ile Gly Asp Ile Arg Lys Ala Tyr Cys Glu Ile Asn Gly Ala
305                 310                 315                 320

Lys Trp Asn Glu Val Leu Lys Lys Val Thr Glu Lys Leu Lys Glu His
                325                 330                 335
```

```
Phe Asn Lys Thr Ile Ile Phe Gln Pro Pro Ser Gly Gly Asp Leu
            340                 345                 350

Glu Ile Thr Met His His Phe Asn Cys Arg Gly Glu Phe Phe Tyr Cys
                355                 360                 365

Asn Thr Thr Arg Leu Phe Asn Asn Thr Cys Met Glu Asn Glu Thr Met
370                 375                 380

Glu Gly Cys Asn Gly Thr Ile Ile Leu Pro Cys Lys Ile Lys Gln Ile
385                 390                 395                 400

Ile Asn Met Trp Gln Arg Ala Gly Gln Ala Met Tyr Ala Pro Pro Ile
                405                 410                 415

Ser Gly Arg Ile Asn Cys Val Ser Asn Ile Thr Gly Ile Leu Leu Thr
                420                 425                 430

Arg Asp Gly Gly Leu Asn Asn Thr Asn Glu Thr Phe Arg Pro Gly Gly
                435                 440                 445

Gly Asn Ile Lys Asp Asn Trp Arg Ser Glu Leu Tyr Lys Tyr Lys Val
            450                 455                 460

Val Gln Ile Glu Pro Leu Gly Ile Ala Pro Thr Arg Ala Lys Arg Arg
465                 470                 475                 480

Val Val Glu Arg Glu Lys Arg Ala Val Gly Ile Gly Ala Met Ile Phe
                485                 490                 495

Gly Phe Leu Gly Ala Ala Gly Ser Thr Met Gly Ala Ala Ser Ile Thr
                500                 505                 510

Leu Thr Val Gln Ala Arg Gln Leu Leu Ser Gly Ile Val Gln Gln Gln
            515                 520                 525

Ser Asn Leu Leu Arg Ala Ile Glu Ala Gln Gln His Leu Leu Gln Leu
            530                 535                 540

Thr Val Trp Gly Ile Lys Gln Leu Gln Ala Arg Val Leu Ala Val Glu
545                 550                 555                 560

Arg Tyr Leu Lys Asp Gln Lys Leu Leu Gly Leu Trp Gly Cys Ser Gly
                565                 570                 575

Lys Ile Ile Cys Thr Thr Ala Val Pro Trp Asn Ser Thr Trp Ser Asn
                580                 585                 590

Arg Ser Phe Glu Glu Ile Trp Asn Asn Met Thr Trp Ile Glu Trp Glu
            595                 600                 605

Arg Glu Ile Ser Asn Tyr Thr Asn Gln Ile Tyr Glu Ile Leu Thr Gln
            610                 615                 620

Ser Gln Asn Gln Gln Asp Arg Asn Glu Lys Asp Leu Leu Glu Leu Asp
625                 630                 635                 640

Lys Trp Ala Ser Leu Trp Lys Trp Phe Asp Ile Thr Asn Trp Leu Trp
                645                 650                 655

Tyr Ile Lys Ile Phe Ile Met Ile Val Gly Gly Leu Ile Gly Leu Arg
                660                 665                 670

Ile Ile Phe Ala Val Leu Ser Ile Val Asn Arg Val Arg Gln Gly Tyr
                675                 680                 685

Ser Pro Leu Ser Leu Gln Ile Pro Thr His His Gln Arg Glu Pro Asp
            690                 695                 700

Arg Pro Glu Arg Ile Glu Glu Gly Gly Gly Glu Gln Gly Arg Asp Lys
705                 710                 715                 720

Ser Val Arg Leu Val Ser Gly Phe Leu Ala Leu Thr Trp Asp Asp Leu
                725                 730                 735

Arg Ser Leu Cys Leu Phe Ser Tyr His Arg Leu Arg Asp Phe Ile Ser
                740                 745                 750
```

```
Ile Ala Ala Arg Thr Val Glu Leu Leu Gly His Ser Ser Leu Lys Gly
            755                 760                 765
Leu Arg Arg Gly Trp Glu Gly Leu Lys Tyr Leu Gly Asn Leu Ile Leu
        770                 775                 780
Tyr Trp Gly Gln Glu Leu Lys Ile Ser Ala Ile Ser Leu Leu Asn Ala
785                 790                 795                 800
Thr Ala Ile Ala Val Ala Gly Trp Thr Asp Arg Val Ile Glu Val Ala
                805                 810                 815
Gln Gly Ala Trp Arg Ala Ile Leu His Ile Pro Arg Arg Ile Arg Gln
            820                 825                 830
Gly Leu Glu Arg Thr Leu Leu
            835

<210> SEQ ID NO 7
<211> LENGTH: 835
<212> TYPE: PRT
<213> ORGANISM: Human immunodeficiency virus type 1

<400> SEQUENCE: 7

Met Arg Val Lys Gly Ile Arg Arg Asn Tyr Gln His Trp Trp Gly Trp
1               5                   10                  15
Gly Thr Met Leu Leu Gly Leu Leu Met Ile Cys Ser Ala Thr Glu Lys
            20                  25                  30
Leu Trp Val Thr Val Tyr Tyr Gly Val Pro Val Trp Lys Glu Ala Thr
        35                  40                  45
Thr Thr Leu Phe Cys Ala Ser Asp Ala Lys Ala Tyr Asp Thr Glu Val
    50                  55                  60
His Asn Val Trp Ala Thr His Ala Cys Val Pro Thr Asp Pro Asn Pro
65              70                  75                  80
Gln Glu Val Gln Leu Val Asn Val Thr Glu Asp Phe Asn Met Trp Lys
                85                  90                  95
Asn Asn Met Val Glu Gln Met His Glu Asp Ile Ile Ser Leu Trp Asp
            100                 105                 110
Gln Ser Leu Lys Pro Cys Val Lys Leu Thr Pro Leu Cys Val Thr Leu
        115                 120                 125
Asn Cys Thr Asp Leu Arg Asn Glu Met Lys Asn Cys Ser Phe Asn Ile
    130                 135                 140
Thr Thr Ser Ile Arg Asp Lys Met Gln Lys Glu Tyr Ala Leu Leu Tyr
145                 150                 155                 160
Lys Leu Asp Ile Val Ala Ile Asp Lys Asp Asn Thr Ser Tyr Arg Leu
                165                 170                 175
Ile Ser Cys Asn Thr Ser Val Ile Thr Gln Ala Cys Pro Lys Val Ser
            180                 185                 190
Phe Glu Pro Ile Pro Ile His Tyr Cys Ala Pro Ala Gly Phe Ala Ile
        195                 200                 205
Leu Lys Cys Asn Asp Lys Asn Phe Thr Gly Lys Gly Pro Cys Lys Asn
    210                 215                 220
Val Ser Thr Val Gln Cys Thr His Gly Ile Arg Pro Val Val Ser Thr
225                 230                 235                 240
Gln Leu Leu Leu Asn Gly Ser Leu Ala Glu Glu Val Val Ile Arg
                245                 250                 255
Ser Glu Asn Phe Thr Asn Asn Ala Lys Thr Ile Ile Val His Leu Asn
            260                 265                 270
Glu Ser Val Gln Ile Asn Cys Thr Arg Pro Tyr Asn Asn Arg Arg Thr
        275                 280                 285
```

-continued

```
Arg Ile His Ile Gly Pro Gly Arg Ala Phe Tyr Thr Thr Lys Asn Ile
        290                 295                 300

Lys Gly Thr Ile Arg Gln Ala His Cys Thr Ile Ser Ser Ala Lys Trp
305                 310                 315                 320

Asn Asp Thr Leu Arg Gln Ile Val Ser Lys Leu Lys Glu Gln Phe Lys
                325                 330                 335

Asn Lys Thr Ile Val Phe Lys Gln Ser Ser Gly Gly Asp Pro Glu Ile
                340                 345                 350

Val Met His Ser Phe Asn Cys Gly Gly Glu Phe Phe Tyr Cys Asn Thr
            355                 360                 365

Ser Ser Leu Phe Asn Ser Thr Trp Asn Gly Asn Asn Thr Trp Asn Asn
        370                 375                 380

Thr Thr Gly Ser Asn Ser Asn Ile Thr Leu Gln Cys Lys Ile Lys Gln
385                 390                 395                 400

Ile Ile Asn Met Trp Gln Glu Val Gly Lys Ala Met Tyr Ala Pro Pro
                405                 410                 415

Ile Glu Gly Gln Ile Arg Cys Ser Ser Asn Ile Thr Gly Leu Leu Leu
                420                 425                 430

Thr Arg Asp Gly Gly Asn Asp Thr Asp Thr Asn Asn Thr Glu Ile Phe
            435                 440                 445

Arg Pro Gly Gly Gly Asp Met Arg Asp Asn Trp Arg Ser Glu Leu Tyr
        450                 455                 460

Lys Tyr Lys Val Val Thr Ile Glu Pro Leu Gly Val Ala Pro Thr Lys
465                 470                 475                 480

Ala Lys Arg Arg Val Val Gln Arg Glu Lys Arg Ala Ala Ile Gly Ala
                485                 490                 495

Leu Phe Leu Gly Phe Leu Gly Ala Ala Gly Ser Thr Met Gly Ala Ala
            500                 505                 510

Ser Met Met Leu Thr Val Gln Ala Arg Gln Leu Leu Ser Gly Ile Val
        515                 520                 525

Gln Gln Gln Asn Asn Leu Leu Arg Ala Ile Glu Ala Gln Gln His Met
530                 535                 540

Leu Gln Leu Thr Val Trp Gly Ile Lys Gln Leu Gln Ala Arg Val Leu
545                 550                 555                 560

Ala Val Glu Arg Tyr Leu Arg Asp Gln Gln Leu Leu Gly Ile Trp Gly
                565                 570                 575

Cys Ser Gly Lys Leu Ile Cys Thr Thr Thr Val Pro Trp Asn Ala Ser
            580                 585                 590

Trp Ser Asn Lys Ser Gln Glu Asp Ile Trp Asn Asn Met Thr Trp Met
        595                 600                 605

Gln Trp Glu Arg Glu Ile Asp Asn Tyr Thr Ser Thr Ile Tyr Glu Leu
    610                 615                 620

Leu Glu Lys Ser Gln Asn Gln Gln Glu Lys Asn Glu Gln Glu Leu Leu
625                 630                 635                 640

Glu Leu Asp Lys Trp Ala Ser Leu Trp Asn Trp Phe Asp Ile Thr Asn
                645                 650                 655

Trp Leu Trp Tyr Ile Lys Ile Phe Ile Met Ile Val Gly Gly Leu Ile
                660                 665                 670

Gly Leu Arg Ile Val Phe Ala Val Leu Ser Ile Val Asn Arg Val Arg
            675                 680                 685

Gln Gly Tyr Ser Pro Leu Ser Leu Gln Thr Arg Pro Pro Val Pro Arg
        690                 695                 700
```

```
Gly Pro Asp Arg Pro Glu Gly Thr Glu Glu Gly Gly Glu Arg Asp
705                 710                 715                 720

Arg Asp Thr Ser Gly Arg Leu Val Asp Gly Phe Leu Ala Ile Ile Trp
            725                 730                 735

Val Asp Leu Arg Ser Leu Leu Leu Phe Ser Tyr His Arg Leu Arg Asp
        740                 745                 750

Leu Leu Leu Ile Ala Ala Arg Ile Val Glu Leu Leu Gly Arg Arg Gly
    755                 760                 765

Trp Glu Ile Leu Lys Tyr Trp Trp Asn Leu Leu Gln Tyr Trp Ser Gln
770                 775                 780

Glu Leu Lys Asn Ser Ala Val Ser Leu Leu Asn Ala Thr Ala Val Ala
785                 790                 795                 800

Val Ala Glu Gly Thr Asp Arg Val Ile Glu Val Leu Gln Arg Ala Gly
            805                 810                 815

Arg Ala Ile Leu His Ile Pro Thr Arg Ile Arg Gln Gly Leu Glu Arg
            820                 825                 830

Ala Leu Leu
        835

<210> SEQ ID NO 8
<211> LENGTH: 328
<212> TYPE: PRT
<213> ORGANISM: Human immunodeficiency virus type 1

<400> SEQUENCE: 8

Gln Val Tyr Asn Ile Thr Trp Glu Val Thr Asn Gly Asp Arg Glu Thr
1               5                   10                  15

Val Trp Ala Ile Ser Gly Asn His Pro Leu Trp Thr Trp Trp Pro Val
            20                  25                  30

Leu Thr Pro Asp Leu Cys Met Leu Ala Leu Ser Gly Pro Pro His Trp
        35                  40                  45

Gly Leu Glu Tyr Gln Ala Pro Tyr Ser Ser Pro Pro Gly Pro Pro Cys
    50                  55                  60

Cys Ser Gly Ser Ser Gly Ser Ser Ala Gly Cys Ser Arg Asp Cys Asp
65                  70                  75                  80

Glu Pro Leu Thr Ser Leu Thr Pro Arg Cys Asn Thr Ala Trp Asn Arg
                85                  90                  95

Leu Lys Leu Asp Gln Val Thr His Lys Ser Ser Glu Gly Phe Tyr Val
            100                 105                 110

Cys Pro Gly Ser His Arg Pro Arg Glu Ala Lys Ser Cys Gly Gly Pro
        115                 120                 125

Asp Ser Phe Tyr Cys Ala Ser Trp Gly Cys Glu Thr Thr Gly Arg Val
    130                 135                 140

Tyr Trp Lys Pro Ser Ser Ser Trp Asp Tyr Ile Thr Val Asp Asn Asn
145                 150                 155                 160

Leu Thr Thr Ser Gln Ala Val Gln Val Cys Lys Asp Asn Lys Trp Cys
                165                 170                 175

Asn Pro Leu Ala Ile Gln Phe Thr Asn Ala Gly Lys Gln Val Thr Ser
            180                 185                 190

Trp Thr Thr Gly His Tyr Trp Gly Leu Arg Leu Tyr Val Ser Gly Arg
        195                 200                 205

Asp Pro Gly Leu Thr Phe Gly Ile Arg Leu Arg Tyr Gln Asn Leu Gly
    210                 215                 220

Pro Arg Val Pro Ile Gly Pro Asn Pro Val Leu Ala Asp Gln Leu Ser
225                 230                 235                 240
```

```
Leu Pro Arg Pro Asn Pro Leu Pro Lys Pro Ala Lys Ser Pro Pro Ala
            245                 250                 255

Ser Val Lys Leu Thr Pro Leu Cys Val Thr Leu Asn Cys Ile Asp Leu
            260                 265                 270

Arg Asn Glu Ile Lys Asn Cys Ser Phe Asn Ile Thr Thr Ser Ile Arg
        275                 280                 285

Asp Lys Val Gln Lys Glu Tyr Ala Leu Phe Tyr Lys Leu Asp Ile Val
        290                 295                 300

Pro Ile Asp Asn Pro Lys Asn Ser Thr Asn Tyr Arg Leu Ile Ser Cys
305                 310                 315                 320

Asn Thr Ser Val Ile Thr Gln Ala
            325
```

<210> SEQ ID NO 9
<211> LENGTH: 2526
<212> TYPE: DNA
<213> ORGANISM: Human immunodeficiency virus type 1

<400> SEQUENCE: 9

```
atgagagtga aggagacaca gatgaattgg ccaaacttgt ggaaatgggg gactttgatc    60
cttgggttgg tgataatttg tagtgcctca gacaacttgt gggttacagt ttattatggg   120
gttcctgtgt ggagagatgc agataccacc ctattttgtg catcagatgc aaagcacat   180
gagacagaag tgcacaatgt ctgggccaca catgcctgtg tacccacaga ccccaaccca   240
caagaaatag acctggaaaa tgtaacagaa aattttaaca tgtggaaaaa taacatggta   300
gagcagatgc aggaggatgt aatcagttta tgggatcaaa gtctaaagcc atgtgtaaag   360
ttaactcctc tctgcgttac tttacattgt actaatgcta atttggaagt aagaaactgt   420
tcttttaata tgaccacaga actaagagat aagaagcaga aggtccatgc actttttat   480
aagcttgata tagtaccaat tgaagataat aacgataata gtaagtatag gttaataaat   540
tgtaatactt cagtcattaa gcaggcttgt ccaaagatat cctttgatcc aattcctata   600
cattattgta ctccagctgg ttatgcgatt ttaaagtgta atgataagaa tttcaatggg   660
acagggccat gtaaaaacgt cagctcagta caatgcacac atggaattaa gccagtggta   720
tcaactcaat tgctgttaaa tggcagtcta gcagaagaag ataataat cagatctgaa   780
gatctcacaa acaatgccaa aaccataata gtgcaccta taaatctgt agtaatcaat   840
tgtaccagac cctccaacaa tacaagaaca agtataacta taggaccagg acaagtattc   900
tatagaacag gagacataat aggagatata agaaaagcat attgtgagat taatggaaca   960
gaatggaata aagctttaaa acaggtaact gaaaagttaa aagagcactt taataataag  1020
ccaataatct ttcaaccacc ctcaggagga gatctagaaa ttacaatgca tcattttaat  1080
tgtagaggag aatttttcta ttgcaataca acacgactgt ttaataatac ttgcatagca  1140
aatggaacca tagaggggtg taatggcaat atcacacttc catgcaagat aaaacaaatt  1200
ataaacatgt ggcagggagc aggacaagca atgtatgctc ctcccatcag tggaacaatt  1260
aattgtgtat caaatattac aggaatacta ttgacaagag atggtggtgc tactaataat  1320
acgaataacg agaccttcag acctggagga ggaaatataa aggacaattg gagaaatgaa  1380
ttatataaat ataaagtagt acaaattgaa ccactaggag cagcacccac cagggcaaag  1440
agaagagtgg tggagagaga aaaaagagca gtgggaatag gagctatgat ctttgggttc  1500
ttaggagcag caggaagcac tatgggcgcg gcgtcaataa cgctgacggt acaggccaga  1560
```

-continued

```
caattattgt ctggtatagt gcaacagcaa agcaatttgc tgagggctat agaggcgcag    1620
cagcatctgt tgcaactcac agtctggggc attaaacagc tccaggcaag agtcctggct    1680
gtggaaagat acctaaagga tcaaaagttc ctaggacttt ggggctgctc tggaaaaatc    1740
atctgcacca ctgcagtgcc ctggaactcc acttggagta ataaatctct gaagagatt     1800 tggaacaaca tgacatggat agaatgggag agagaaatta gcaattacac aaaccaaata    1860
tatgagatac ttacaaaatc gcaggaccag caggacagga atgaaaagga tttgttagaa    1920
ttggataaat gggcaagtct gtggacttgg tttgacataa caaattggct gtggtatata    1980
aaaatattta taatgatagt gggaggttta ataggattaa gaataatttt tgctgtgctt    2040
tctatagtga atagagttag gcagggatac tcacctttgt ctttccagac cccttgccat    2100
catcagaggg aacccgacag acccgaaaga atcgaagaag aaggtggcga gcaaggcaga    2160
gacagatccg tgcgattagt gagcggattc ttagctcttg catgggacga tctacggagc    2220
ctgtgcctct tcagctacca ccgcttgaga gacttcatct tgattgcagc gaggactgtg    2280
gaacttctgg gacgcagcag tctcaaggga ctgacgggg gtggaagg cctcaaatat       2340 ctggggaatc ttctgttata ttggggtcag gaactaaaaa ttagtgctat ttctttgctt    2400
gatgctacag caatagcagt agcggggtgg acagataggg ttatagaagt agcacaagga    2460
gcttggaaag ccattctcca catacctaga agaatcagac agggcttaga aagggctttg    2520
caataa                                                              2526
```

```
<210> SEQ ID NO 10
<211> LENGTH: 856
<212> TYPE: PRT
<213> ORGANISM: Human immunodeficiency virus type 1

<400> SEQUENCE: 10

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190
```

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
        290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

```
Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
            645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
            675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
            755                 760                 765

His Arg Leu Arg Asp Leu Leu Leu Ile Val Thr Arg Ile Val Glu Leu
770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
            805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
            835                 840                 845

Gln Gly Leu Glu Arg Ile Leu Leu
    850                 855

<210> SEQ ID NO 11
<211> LENGTH: 4
<212> TYPE: PRT
<213> ORGANISM: Artificial Sequence
<220> FEATURE:
<223> OTHER INFORMATION: Furin cleavave site

<400> SEQUENCE: 11

Arg Glu Lys Arg
1

<210> SEQ ID NO 12
<211> LENGTH: 6
<212> TYPE: PRT
<213> ORGANISM: Artificial Sequence
<220> FEATURE:
<223> OTHER INFORMATION: Furin cleavave site

<400> SEQUENCE: 12

Arg Arg Arg Arg Arg Arg
1               5

<210> SEQ ID NO 13
<211> LENGTH: 10
<212> TYPE: PRT
<213> ORGANISM: Artificial Sequence
```

```
<220> FEATURE:
<223> OTHER INFORMATION: Peptide linker

<400> SEQUENCE: 13

Gly Gly Ser Gly Gly Gly Gly Ser Gly Gly
1               5                   10

<210> SEQ ID NO 14
<211> LENGTH: 27
<212> TYPE: PRT
<213> ORGANISM: Human immunodeficiency virus type I

<400> SEQUENCE: 14

Lys Ile Phe Ile Met Ile Val Gly Gly Leu Ile Gly Leu Arg Ile Val
1               5                   10                  15

Phe Ala Val Leu Ser Val Ile His Arg Val Arg
            20                  25

<210> SEQ ID NO 15
<211> LENGTH: 23
<212> TYPE: PRT
<213> ORGANISM: Artificial Sequence
<220> FEATURE:
<223> OTHER INFORMATION: transmembrane domain

<400> SEQUENCE: 15

Ile Leu Ala Ile Tyr Ser Thr Val Ala Ser Ser Leu Val Leu Leu Val
1               5                   10                  15

Ser Leu Gly Ala Ile Ser Phe
            20

<210> SEQ ID NO 16
<211> LENGTH: 29
<212> TYPE: PRT
<213> ORGANISM: Artificial Sequence
<220> FEATURE:
<223> OTHER INFORMATION: transmembrane domain

<400> SEQUENCE: 16

Ile Ile Thr Ile Gly Ser Ile Cys Met Val Val Gly Ile Ile Ser Leu
1               5                   10                  15

Ile Leu Gln Ile Gly Asn Ile Ile Ser Ile Trp Val Ser
            20                  25

<210> SEQ ID NO 17
<211> LENGTH: 26
<212> TYPE: PRT
<213> ORGANISM: Artificial Sequence
<220> FEATURE:
<223> OTHER INFORMATION: Foldon domain

<400> SEQUENCE: 17

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe
            20                  25

<210> SEQ ID NO 18
<211> LENGTH: 16
<212> TYPE: PRT
<213> ORGANISM: Human immunodeficiency virus type 1
```

-continued

<400> SEQUENCE: 18

Lys Phe Thr Met Thr Gly Leu Lys Arg Asp Lys Thr Lys Glu Tyr Asn
1               5                   10                  15

<210> SEQ ID NO 19
<211> LENGTH: 14
<212> TYPE: PRT
<213> ORGANISM: Human immunodeficiency virus type 1

<400> SEQUENCE: 19

Ile Ala Gln Asn Asn Cys Thr Gly Leu Glu Gln Glu Gln Met
1               5                   10

<210> SEQ ID NO 20
<211> LENGTH: 14
<212> TYPE: PRT
<213> ORGANISM: Human immunodeficiency virus type 1

<400> SEQUENCE: 20

Arg Cys Asn Lys Ser Glu Thr Asp Arg Trp Gly Leu Thr Lys
1               5                   10

<210> SEQ ID NO 21
<211> LENGTH: 4
<212> TYPE: PRT
<213> ORGANISM: Human immunodeficiency virus type 1

<400> SEQUENCE: 21

Gly Gly Gly Gly
1

<210> SEQ ID NO 22
<211> LENGTH: 14
<212> TYPE: PRT
<213> ORGANISM: Human immunodeficiency virus type 1

<400> SEQUENCE: 22

Asp Lys Thr Lys Glu Tyr Asn Glu Thr Trp Tyr Ser Thr Asp
1               5                   10

<210> SEQ ID NO 23
<211> LENGTH: 14
<212> TYPE: PRT
<213> ORGANISM: Human immunodeficiency virus type 1

<400> SEQUENCE: 23

Asp Lys Lys Ile Glu Tyr Asn Glu Thr Trp Tyr Ser Arg Asp
1               5                   10

<210> SEQ ID NO 24
<211> LENGTH: 14
<212> TYPE: PRT
<213> ORGANISM: Human immunodeficiency virus type 1

<400> SEQUENCE: 24

Asp Lys Lys Ile Glu Tyr Asn Glu Thr Trp Tyr Ser Arg Asp
1               5                   10

<210> SEQ ID NO 25
<211> LENGTH: 14
<212> TYPE: PRT
<213> ORGANISM: Human immunodeficiency virus type 1

```
<400> SEQUENCE: 25

Asp Lys Thr Lys Glu Tyr Asn Glu Thr Trp Tyr Ser Thr Asp
1               5                   10

<210> SEQ ID NO 26
<211> LENGTH: 14
<212> TYPE: PRT
<213> ORGANISM: Human immunodeficiency virus type 1

<400> SEQUENCE: 26

Val Thr Leu His Cys Thr Asn Ala Asn Leu Thr Asn Ala Asn
1               5                   10

<210> SEQ ID NO 27
<211> LENGTH: 14
<212> TYPE: PRT
<213> ORGANISM: Human immunodeficiency virus type 1

<400> SEQUENCE: 27

Val Thr Leu Asn Cys Thr Asp Leu Arg Asn Thr Thr Asn Thr
1               5                   10

<210> SEQ ID NO 28
<211> LENGTH: 14
<212> TYPE: PRT
<213> ORGANISM: Human immunodeficiency virus type 1

<400> SEQUENCE: 28

Val Thr Leu Asn Cys Thr Glu Val Asn Val Thr Arg Asn Val
1               5                   10

<210> SEQ ID NO 29
<211> LENGTH: 17
<212> TYPE: PRT
<213> ORGANISM: Human immunodeficiency virus type 1

<400> SEQUENCE: 29

Cys Ser Phe Asn Met Thr Thr Glu Leu Arg Asp Lys Lys Gln Lys Val
1               5                   10                  15

His

<210> SEQ ID NO 30
<211> LENGTH: 17
<212> TYPE: PRT
<213> ORGANISM: Human immunodeficiency virus type 1

<400> SEQUENCE: 30

Cys Ser Phe Asn Ile Thr Thr Ser Ile Arg Asp Lys Met Gln Lys Glu
1               5                   10                  15

Tyr

<210> SEQ ID NO 31
<211> LENGTH: 17
<212> TYPE: PRT
<213> ORGANISM: Human immunodeficiency virus type 1

<400> SEQUENCE: 31

Cys Ser Phe Asn Ile Thr Thr Glu Leu Lys Asp Lys Lys Lys Asn Val
1               5                   10                  15

Tyr
```

```
<210> SEQ ID NO 32
<211> LENGTH: 14
<212> TYPE: PRT
<213> ORGANISM: Human immunodeficiency virus type 1

<400> SEQUENCE: 32

Asp Lys Lys Gln Lys Val His Ala Leu Phe Tyr Lys Leu Asp
1               5                   10

<210> SEQ ID NO 33
<211> LENGTH: 14
<212> TYPE: PRT
<213> ORGANISM: Human immunodeficiency virus type 1

<400> SEQUENCE: 33

Asp Lys Met Gln Lys Glu Tyr Ala Leu Leu Tyr Lys Leu Asp
1               5                   10

<210> SEQ ID NO 34
<211> LENGTH: 14
<212> TYPE: PRT
<213> ORGANISM: Human immunodeficiency virus type 1

<400> SEQUENCE: 34

Asp Lys Lys Lys Asn Val Tyr Ala Leu Phe Tyr Lys Leu Asp
1               5                   10

<210> SEQ ID NO 35
<211> LENGTH: 15
<212> TYPE: PRT
<213> ORGANISM: Human immunodeficiency virus type 1

<400> SEQUENCE: 35

Arg Asp Lys Lys Lys Glu Tyr Asn Glu Thr Trp Tyr Ser Ala Asp
1               5                   10                  15

<210> SEQ ID NO 36
<211> LENGTH: 56
<212> TYPE: PRT
<213> ORGANISM: Human immunodeficiency virus type 1

<400> SEQUENCE: 36

Asn Glu Thr Ser Ser Cys Ile Ala Gln Asn Asn Cys Thr Gly Leu Glu
1               5                   10                  15

Gln Glu Gln Met Ile Ser Cys Lys Phe Thr Met Thr Gly Leu Lys Arg
                20                  25                  30

Asp Lys Thr Lys Glu Tyr Asn Glu Thr Trp Tyr Ser Thr Asp Leu Val
            35                  40                  45

Cys Glu Gln Gly Asn Ser Thr Asp
    50                  55

<210> SEQ ID NO 37
<211> LENGTH: 20
<212> TYPE: PRT
<213> ORGANISM: Human immunodeficiency virus type 1

<400> SEQUENCE: 37

Thr Gly Leu Glu Gln Glu Gln Met Ile Ser Cys Lys Phe Thr Met Thr
1               5                   10                  15

Gly Leu Lys Arg
            20

<210> SEQ ID NO 38
```

```
<211> LENGTH: 20
<212> TYPE: PRT
<213> ORGANISM: Human immunodeficiency virus type 1

<400> SEQUENCE: 38

Gln Met Ile Ser Cys Lys Phe Thr Met Thr Gly Leu Lys Arg Asp Lys
1               5                   10                  15

Thr Lys Glu Tyr
            20

<210> SEQ ID NO 39
<211> LENGTH: 20
<212> TYPE: PRT
<213> ORGANISM: Human immunodeficiency virus type 1

<400> SEQUENCE: 39

Phe Thr Met Thr Gly Leu Lys Arg Asp Lys Thr Lys Glu Tyr Asn Glu
1               5                   10                  15

Thr Trp Tyr Ser
            20

<210> SEQ ID NO 40
<211> LENGTH: 20
<212> TYPE: PRT
<213> ORGANISM: Human immunodeficiency virus type 1

<400> SEQUENCE: 40

Lys Arg Asp Lys Thr Lys Glu Tyr Asn Glu Thr Trp Tyr Ser Thr Asp
1               5                   10                  15

Leu Val Cys Glu
            20

<210> SEQ ID NO 41
<211> LENGTH: 20
<212> TYPE: PRT
<213> ORGANISM: Human immunodeficiency virus type 1

<400> SEQUENCE: 41

Glu Tyr Asn Glu Thr Trp Tyr Ser Thr Asp Leu Val Cys Glu Gln Gly
1               5                   10                  15

Asn Ser Thr Asp
            20

<210> SEQ ID NO 42
<211> LENGTH: 39
<212> TYPE: PRT
<213> ORGANISM: Human immunodeficiency virus type 1

<400> SEQUENCE: 42

Asn Lys Ser Glu Thr Asp Arg Trp Gly Leu Thr Lys Ser Ser Thr Thr
1               5                   10                  15

Ile Thr Thr Ala Ala Pro Thr Ser Ala Pro Val Ser Glu Lys Ile Asp
            20                  25                  30

Met Val Asn Glu Thr Ser Ser
        35

<210> SEQ ID NO 43
<211> LENGTH: 20
<212> TYPE: PRT
<213> ORGANISM: Human immunodeficiency virus type 1
```

```
<400> SEQUENCE: 43

Pro Cys Val Lys Leu Ser Pro Leu Cys Ile Thr Met Arg Cys Asn Lys
1               5                   10                  15

Ser Glu Thr Asp
            20

<210> SEQ ID NO 44
<211> LENGTH: 20
<212> TYPE: PRT
<213> ORGANISM: Human immunodeficiency virus type 1

<400> SEQUENCE: 44

Pro Cys Leu Ile Thr Met Arg Cys Asn Lys Ser Glu Thr Asp Arg Trp
1               5                   10                  15

Gly Leu Thr Lys
            20

<210> SEQ ID NO 45
<211> LENGTH: 20
<212> TYPE: PRT
<213> ORGANISM: Human immunodeficiency virus type 1

<400> SEQUENCE: 45

Arg Cys Asn Lys Ser Glu Thr Asp Arg Trp Gly Leu Thr Lys Ser Ser
1               5                   10                  15

Thr Thr Ile Thr
            20

<210> SEQ ID NO 46
<211> LENGTH: 20
<212> TYPE: PRT
<213> ORGANISM: Human immunodeficiency virus type 1

<400> SEQUENCE: 46

Thr Asp Arg Trp Gly Leu Thr Lys Ser Ser Thr Thr Ile Thr Thr Ala
1               5                   10                  15

Ala Pro Thr Ser
            20

<210> SEQ ID NO 47
<211> LENGTH: 20
<212> TYPE: PRT
<213> ORGANISM: Human immunodeficiency virus type 1

<400> SEQUENCE: 47

Thr Lys Ser Ser Thr Thr Ile Thr Thr Ala Ala Pro Thr Ser Ala Pro
1               5                   10                  15

Val Ser Glu Lys
            20

<210> SEQ ID NO 48
<211> LENGTH: 20
<212> TYPE: PRT
<213> ORGANISM: Human immunodeficiency virus type 1

<400> SEQUENCE: 48

Ile Thr Thr Ala Ala Pro Thr Ser Ala Pro Val Ser Glu Lys Ile Asp
1               5                   10                  15

Met Val Asn Glu
            20
```

<210> SEQ ID NO 49
<211> LENGTH: 20
<212> TYPE: PRT
<213> ORGANISM: Human immunodeficiency virus type 1

<400> SEQUENCE: 49

Thr Ser Ala Pro Val Ser Glu Lys Ile Asp Met Val Asn Glu Thr Ser
1               5                   10                  15

Ser Cys Ile Ala
            20

<210> SEQ ID NO 50
<211> LENGTH: 20
<212> TYPE: PRT
<213> ORGANISM: Human immunodeficiency virus type 1

<400> SEQUENCE: 50

Glu Lys Ile Asp Met Val Asn Glu Thr Ser Ser Cys Ile Ala Gln Asn
1               5                   10                  15

Asn Cys Thr Gly
            20

<210> SEQ ID NO 51
<211> LENGTH: 20
<212> TYPE: PRT
<213> ORGANISM: Human immunodeficiency virus type 1

<400> SEQUENCE: 51

Asn Glu Thr Ser Ser Cys Ile Ala Gln Asn Asn Cys Thr Gly Leu Glu
1               5                   10                  15

Gln Glu Gln Met
            20

<210> SEQ ID NO 52
<211> LENGTH: 20
<212> TYPE: PRT
<213> ORGANISM: Human immunodeficiency virus type 1

<400> SEQUENCE: 52

Ile Ala Gln Asn Asn Cys Thr Gly Leu Glu Gln Glu Gln Met Ile Ser
1               5                   10                  15

Cys Lys Phe Thr
            20

<210> SEQ ID NO 53
<211> LENGTH: 11
<212> TYPE: PRT
<213> ORGANISM: Human immunodeficiency virus type 1

<400> SEQUENCE: 53

Thr Gly Leu Lys Arg Asp Lys Thr Lys Glu Tyr
1               5                   10

<210> SEQ ID NO 54
<211> LENGTH: 20
<212> TYPE: PRT
<213> ORGANISM: Human immunodeficiency virus type 1

```
<400> SEQUENCE: 54

Pro Leu Cys Ile Thr Met Arg Cys Asn Lys Ser Glu Thr Asp Arg Trp
1               5                   10                  15

Gly Leu Thr Lys
            20

<210> SEQ ID NO 55
<211> LENGTH: 11
<212> TYPE: PRT
<213> ORGANISM: Human immunodeficiency virus type 1

<400> SEQUENCE: 55

Thr Gly Leu Lys Arg Asp Lys Lys Lys Glu Tyr
1               5                   10

<210> SEQ ID NO 56
<211> LENGTH: 15
<212> TYPE: PRT
<213> ORGANISM: Human immunodeficiency virus type 1

<400> SEQUENCE: 56

Glu Gln Glu Gln Met Ile Ser Cys Lys Phe Asn Met Thr Gly Leu
1               5                   10                  15

<210> SEQ ID NO 57
<211> LENGTH: 14
<212> TYPE: PRT
<213> ORGANISM: Human immunodeficiency virus type 1

<400> SEQUENCE: 57

Glu Gln Glu Met Ile Ser Cys Lys Phe Asn Met Thr Gly Leu
1               5                   10

<210> SEQ ID NO 58
<211> LENGTH: 15
<212> TYPE: PRT
<213> ORGANISM: Human immunodeficiency virus type 1

<400> SEQUENCE: 58

Met Ile Ser Cys Lys Phe Asn Met Thr Gly Leu Lys Arg Asp Lys
1               5                   10                  15

<210> SEQ ID NO 59
<211> LENGTH: 16
<212> TYPE: PRT
<213> ORGANISM: Human immunodeficiency virus type 1

<400> SEQUENCE: 59

Phe Lys Phe Asn Met Thr Gly Leu Lys Arg Asp Lys Lys Lys Glu Tyr
1               5                   10                  15

<210> SEQ ID NO 60
<211> LENGTH: 15
<212> TYPE: PRT
<213> ORGANISM: Human immunodeficiency virus type 1

<400> SEQUENCE: 60

Thr Gly Leu Lys Arg Asp Lys Lys Lys Glu Tyr Asn Glu Thr Trp
1               5                   10                  15

<210> SEQ ID NO 61
<211> LENGTH: 15
<212> TYPE: PRT
```

<210> SEQ ID NO 61
<211> LENGTH: 15
<212> TYPE: PRT
<213> ORGANISM: Human immunodeficiency virus type 1

<400> SEQUENCE: 61

Arg Asp Lys Lys Lys Glu Tyr Asn Glu Thr Trp Tyr Ser Ala Asp
1               5                   10                  15

<210> SEQ ID NO 62
<211> LENGTH: 15
<212> TYPE: PRT
<213> ORGANISM: Human immunodeficiency virus type 1

<400> SEQUENCE: 62

Lys Glu Tyr Asn Glu Thr Trp Tyr Ser Ala Asp Leu Val Cys Glu
1               5                   10                  15

<210> SEQ ID NO 63
<211> LENGTH: 15
<212> TYPE: PRT
<213> ORGANISM: Human immunodeficiency virus type 1

<400> SEQUENCE: 63

Glu Thr Trp Tyr Ser Ala Asp Leu Val Cys Glu Gln Gly Asn Asn
1               5                   10                  15

<210> SEQ ID NO 64
<211> LENGTH: 15
<212> TYPE: PRT
<213> ORGANISM: Human immunodeficiency virus type 1

<400> SEQUENCE: 64

Ser Ala Asp Leu Val Cys Glu Gln Gly Asn Asn Thr Gly Asn Glu
1               5                   10                  15

<210> SEQ ID NO 65
<211> LENGTH: 5
<212> TYPE: PRT
<213> ORGANISM: Human immunodeficiency virus type 1

<400> SEQUENCE: 65

Gly Gly Gly Gly Gly
1               5

<210> SEQ ID NO 66
<211> LENGTH: 836
<212> TYPE: PRT
<213> ORGANISM: Human immunodeficiency virus type 1

<400> SEQUENCE: 66

Arg Trp Trp Thr Trp Gly Ile Leu Gly Phe Trp Met Leu Met Ile Cys
1               5                   10                  15

Asn Val Trp Gly Asn Leu Trp Val Thr Val Tyr Gly Val Pro Val
                20                  25                  30

Trp Lys Glu Ala Lys Thr Thr Leu Phe Cys Ala Ser Asp Ala Lys Ser
            35                  40                  45

Tyr Glu Lys Glu Val His Asn Val Trp Ala Thr His Ala Cys Val Pro
        50                  55                  60

Thr Asp Pro Asn Pro Gln Glu Ile Val Leu Gly Asn Val Thr Glu Asn
65                  70                  75                  80

Phe Asn Met Trp Lys Asn Asp Met Val Asp Gln Met His Glu Asp Ile
                85                  90                  95

Ile Ser Leu Trp Asp Gln Ser Leu Lys Pro Cys Val Lys Leu Thr Pro
            100                 105                 110

-continued

```
Leu Cys Val Thr Leu Asn Cys Thr Glu Val Asn Val Asp Met Lys Asn
            115                 120                 125
Cys Ser Phe Asn Ile Thr Thr Glu Leu Lys Asp Lys Lys Asn Val
        130                 135                 140
Tyr Ala Leu Phe Tyr Lys Leu Asp Ile Val Ser Leu Asn Glu Thr Asp
145                 150                 155                 160
Asp Ser Glu Thr Gly Asn Ser Ser Lys Tyr Tyr Arg Leu Ile Asn Cys
                165                 170                 175
Asn Thr Ser Ala Leu Thr Gln Ala Cys Pro Lys Val Ser Phe Asp Pro
            180                 185                 190
Ile Pro Ile His Tyr Cys Ala Pro Ala Gly Tyr Ala Ile Leu Lys Cys
            195                 200                 205
Asn Asn Lys Thr Phe Asn Gly Thr Gly Pro Cys His Asn Val Ser Thr
        210                 215                 220
Val Gln Cys Thr His Gly Ile Lys Pro Val Val Ser Thr Gln Leu Leu
225                 230                 235                 240
Leu Asn Gly Ser Leu Ala Glu Glu Gly Ile Ile Arg Ser Glu Asn
                245                 250                 255
Leu Thr Asn Asn Val Lys Thr Ile Ile Val His Leu Asn Arg Ser Ile
            260                 265                 270
Glu Ile Val Cys Val Arg Pro Asn Asn Asn Thr Arg Gln Ser Ile Arg
        275                 280                 285
Ile Gly Pro Gly Gln Thr Phe Tyr Ala Thr Gly Asp Ile Ile Gly Asp
        290                 295                 300
Ile Arg Gln Ala His Cys Asn Ile Ser Arg Thr Asn Trp Thr Lys Thr
305                 310                 315                 320
Leu Arg Glu Val Arg Asn Lys Leu Arg Glu His Phe Pro Asn Lys Asn
                325                 330                 335
Ile Thr Phe Lys Pro Ser Ser Gly Gly Asp Leu Glu Ile Thr Thr His
            340                 345                 350
Ser Phe Asn Cys Arg Gly Glu Phe Phe Tyr Cys Asn Thr Ser Gly Leu
        355                 360                 365
Phe Ser Ile Asn Tyr Thr Glu Asn Asn Thr Asp Gly Thr Pro Ile Thr
370                 375                 380
Leu Pro Cys Arg Ile Arg Gln Ile Ile Asn Met Trp Gln Glu Val Gly
385                 390                 395                 400
Arg Ala Met Tyr Ala Pro Pro Ile Glu Gly Asn Ile Ala Cys Lys Ser
                405                 410                 415
Asp Ile Thr Gly Leu Leu Leu Val Arg Asp Gly Ser Thr Asn Asp
            420                 425                 430
Ser Thr Asn Asn Thr Glu Ile Phe Arg Pro Ala Gly Gly Asp Met
        435                 440                 445
Arg Asp Asn Trp Arg Ser Glu Leu Tyr Lys Tyr Lys Val Val Glu Ile
450                 455                 460
Lys Pro Leu Gly Ile Ala Pro Thr Glu Ala Lys Arg Arg Val Val Glu
465                 470                 475                 480
Arg Glu Lys Arg Ala Val Gly Ile Gly Ala Val Phe Leu Gly Phe Leu
                485                 490                 495
Gly Ala Ala Gly Ser Thr Met Gly Ala Ala Ser Ile Thr Leu Thr Ala
            500                 505                 510
Gln Ala Arg Gln Val Leu Ser Gly Ile Val Gln Gln Ser Asn Leu
        515                 520                 525
```

| | | | | | | | | | | | |
|---|---|---|---|---|---|---|---|---|---|---|---|
|Leu|Arg|Ala|Ile|Glu|Ala|Gln|Gln|His|Leu|Leu|Gln|Leu|Thr|Val|Trp
|   |530|   |   |   |535|   |   |   |540|   |   |

```
Leu Arg Ala Ile Glu Ala Gln Gln His Leu Leu Gln Leu Thr Val Trp
        530                 535                 540

Gly Ile Lys Gln Leu Gln Thr Arg Val Leu Ala Ile Glu Arg Tyr Leu
545                 550                 555                 560

Lys Asp Gln Gln Leu Leu Gly Leu Trp Gly Cys Ser Gly Lys Leu Ile
                565                 570                 575

Cys Thr Thr Ala Val Pro Trp Asn Ile Ser Trp Ser Asn Lys Ser Lys
                580                 585                 590

Thr Asp Ile Trp Asp Asn Met Thr Trp Met Gln Trp Asp Arg Glu Ile
        595                 600                 605

Ser Asn Tyr Thr Asn Thr Ile Tyr Arg Leu Leu Glu Asp Ser Gln Ser
        610                 615                 620

Gln Gln Glu Gln Asn Glu Lys Asp Leu Leu Ala Leu Asp Ser Trp Asn
625                 630                 635                 640

Asn Leu Trp Asn Trp Phe Asp Ile Thr Lys Trp Leu Trp Tyr Ile Lys
                645                 650                 655

Ile Phe Ile Met Ile Val Gly Gly Leu Ile Gly Leu Arg Ile Ile Phe
                660                 665                 670

Ala Val Leu Ser Ile Val Asn Arg Val Arg Gln Gly Tyr Ser Pro Leu
                675                 680                 685

Ser Phe Gln Thr Leu Ile Pro Asn Pro Arg Glu Pro Asp Arg Pro Gly
690                 695                 700

Arg Ile Glu Glu Glu Gly Gly Glu Gln Asp Lys Glu Arg Ser Val Arg
705                 710                 715                 720

Leu Val Ser Gly Phe Leu Ala Leu Ala Trp Asp Asp Leu Arg Ser Leu
                725                 730                 735

Cys Leu Phe Ser Tyr His Arg Leu Arg Asp Phe Ile Leu Val Thr Ala
                740                 745                 750

Arg Ala Val Glu Leu Leu Arg Arg Ser Ser Leu Lys Gly Leu Gln Arg
                755                 760                 765

Gly Trp Glu Ala Leu Lys Tyr Leu Gly Ser Leu Val Gln Tyr Trp Gly
770                 775                 780

Leu Glu Leu Lys Lys Ser Ala Ile Ser Leu Leu Asp Thr Ile Ala Ile
785                 790                 795                 800

Ala Val Ala Glu Gly Thr Asp Arg Ile Ile Glu Leu Ile Gln Gly Ile
                805                 810                 815

Cys Arg Ala Ile Arg Asn Val Pro Arg Arg Ile Arg Gln Gly Phe Glu
                820                 825                 830

Thr Ala Leu Leu
        835

<210> SEQ ID NO 67
<211> LENGTH: 847
<212> TYPE: PRT
<213> ORGANISM: Human immunodeficiency virus type 1

<400> SEQUENCE: 67

Met Arg Val Arg Glu Ile Leu Arg Asn Trp Gln Arg Trp Trp Thr Trp
1               5                   10                  15

Gly Ile Leu Gly Phe Trp Met Leu Met Ile Cys Asn Val Trp Gly Asn
                20                  25                  30

Leu Trp Val Thr Val Tyr Tyr Gly Val Pro Val Trp Lys Glu Ala Lys
            35                  40                  45

Thr Thr Leu Phe Cys Ala Ser Asp Ala Lys Ser Tyr Glu Lys Glu Val
        50                  55                  60
```

His Asn Val Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Glu Val Asn Val Asp Met Lys Asn Cys Ser Phe Asn Ile
    130                 135                 140

Thr Thr Glu Leu Lys Asp Lys Lys Asn Val Tyr Ala Leu Phe Tyr
145                 150                 155                 160

Lys Leu Asp Ile Val Ser Leu Asn Glu Thr Asp Asp Ser Glu Thr Gly
                165                 170                 175

Asn Ser Ser Lys Tyr Tyr Arg Leu Ile Asn Cys Asn Thr Ser Ala Leu
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
210                 215                 220

Asn Gly Thr Gly Pro Cys His Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Glu Gly Ile Ile Ile Arg Ser Glu Asn Leu Thr Asn Asn Val
            260                 265                 270

Lys Thr Ile Ile Val His Leu Asn Arg Ser Ile Glu Ile Val Cys Val
        275                 280                 285

Arg Pro Asn Asn Asn Thr Arg Gln Ser Ile Arg Ile Gly Pro Gly Gln
    290                 295                 300

Thr Phe Tyr Ala Thr Gly Asp Ile Ile Gly Asp Ile Arg Gln Ala His
305                 310                 315                 320

Cys Asn Ile Ser Arg Thr Asn Trp Thr Lys Thr Leu Arg Glu Val Arg
                325                 330                 335

Asn Lys Leu Arg Glu His Phe Pro Asn Lys Asn Ile Thr Phe Lys Pro
            340                 345                 350

Ser Ser Gly Gly Asp Leu Glu Ile Thr Thr His Ser Phe Asn Cys Arg
        355                 360                 365

Gly Glu Phe Phe Tyr Cys Asn Thr Ser Gly Leu Phe Ser Ile Asn Tyr
    370                 375                 380

Thr Glu Asn Asn Thr Asp Gly Thr Pro Ile Thr Leu Pro Cys Arg Ile
385                 390                 395                 400

Arg Gln Ile Ile Asn Met Trp Gln Glu Val Gly Arg Ala Met Tyr Ala
                405                 410                 415

Pro Pro Ile Glu Gly Asn Ile Ala Cys Lys Ser Asp Ile Thr Gly Leu
            420                 425                 430

Leu Leu Val Arg Asp Gly Gly Ser Thr Asn Asp Ser Thr Asn Asn Asn
        435                 440                 445

Thr Glu Ile Phe Arg Pro Ala Gly Gly Asp Met Arg Asp Asn Trp Arg
    450                 455                 460

Ser Glu Leu Tyr Lys Tyr Lys Val Val Glu Ile Lys Pro Leu Gly Ile
465                 470                 475                 480

Ala Pro Thr Glu Ala Lys Arg Arg Val Val Glu Arg Glu Lys Arg Ala
                485                 490                 495

Val Gly Ile Gly Ala Val Phe Leu Gly Phe Leu Gly Ala Ala Gly Ser
            500                 505                 510

Thr Met Gly Ala Ala Ser Ile Thr Leu Thr Ala Gln Ala Arg Gln Val
        515                 520                 525

Leu Ser Gly Ile Val Gln Gln Gln Ser Asn Leu Leu Arg Ala Ile Glu
    530                 535                 540

Ala Gln Gln His Leu Leu Gln Leu Thr Val Trp Gly Ile Lys Gln Leu
545                 550                 555                 560

Gln Thr Arg Val Leu Ala Ile Glu Arg Tyr Leu Lys Asp Gln Gln Leu
                565                 570                 575

Leu Gly Leu Trp Gly Cys Ser Gly Lys Leu Ile Cys Thr Thr Ala Val
            580                 585                 590

Pro Trp Asn Ile Ser Trp Ser Asn Lys Ser Lys Thr Asp Ile Trp Asp
        595                 600                 605

Asn Met Thr Trp Met Gln Trp Asp Arg Glu Ile Ser Asn Tyr Thr Asn
    610                 615                 620

Thr Ile Tyr Arg Leu Leu Glu Asp Ser Gln Ser Gln Gln Glu Gln Asn
625                 630                 635                 640

Glu Lys Asp Leu Leu Ala Leu Asp Ser Trp Asn Asn Leu Trp Asn Trp
                645                 650                 655

Phe Asp Ile Thr Lys Trp Leu Trp Tyr Ile Lys Ile Phe Ile Met Ile
            660                 665                 670

Val Gly Gly Leu Ile Gly Leu Arg Ile Ile Phe Ala Val Leu Ser Ile
        675                 680                 685

Val Asn Arg Val Arg Gln Gly Tyr Ser Pro Leu Ser Phe Gln Thr Leu
    690                 695                 700

Ile Pro Asn Pro Arg Glu Pro Asp Arg Pro Gly Arg Ile Glu Glu Glu
705                 710                 715                 720

Gly Gly Glu Gln Asp Lys Glu Arg Ser Val Arg Leu Val Ser Gly Phe
                725                 730                 735

Leu Ala Leu Ala Trp Asp Asp Leu Arg Ser Leu Cys Leu Phe Ser Tyr
            740                 745                 750

His Arg Leu Arg Asp Phe Ile Leu Val Thr Ala Arg Ala Val Glu Leu
        755                 760                 765

Leu Arg Arg Ser Ser Leu Lys Gly Leu Gln Arg Gly Trp Glu Ala Leu
    770                 775                 780

Lys Tyr Leu Gly Ser Leu Val Gln Tyr Trp Gly Leu Glu Leu Lys Lys
785                 790                 795                 800

Ser Ala Ile Ser Leu Leu Asp Thr Ile Ala Ile Ala Val Ala Glu Gly
                805                 810                 815

Thr Asp Arg Ile Ile Glu Leu Ile Gln Gly Ile Cys Arg Ala Ile Arg
            820                 825                 830

Asn Val Pro Arg Arg Ile Arg Gln Gly Phe Glu Thr Ala Leu Leu
        835                 840                 845

<210> SEQ ID NO 68
<211> LENGTH: 7
<212> TYPE: PRT
<213> ORGANISM: human immunodeficiency virus type I
<220> FEATURE:
<221> NAME/KEY: MISC_FEATURE
<222> LOCATION: (2)..(2)
<223> OTHER INFORMATION: X is any amino acid
<220> FEATURE:

-continued

```
<221> NAME/KEY: MISC_FEATURE
<222> LOCATION: (4)..(5)
<223> OTHER INFORMATION: X is any amino acid

<400> SEQUENCE: 68

Arg Xaa Lys Xaa Xaa Glu Tyr
1               5
```